(12) United States Patent
Weller et al.

(10) Patent No.: US 7,943,762 B2
(45) Date of Patent: May 17, 2011

(54) OLIGONUCLEOTIDE ANALOGS HAVING CATIONIC INTERSUBUNIT LINKAGES

(75) Inventors: Dwight D. Weller, Corvallis, OR (US);
Jed N. Hassinger, Philomath, OR (US);
Bao Zhong Cai, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 828 days.

(21) Appl. No.: 11/801,885

(22) Filed: May 10, 2007

(65) Prior Publication Data

US 2009/0088562 A1 Apr. 2, 2009

Related U.S. Application Data

(60) Provisional application No. 60/800,076, filed on May 11, 2006.

(51) Int. Cl.
*C12Q 1/68* (2006.01)
*C12P 19/34* (2006.01)
*C07H 21/02* (2006.01)
*C07H 21/04* (2006.01)
*C08B 3/00* (2006.01)

(52) U.S. Cl. ............ 536/31; 435/6; 435/91.1; 536/23.1; 536/24.5

(58) Field of Classification Search ............. 435/6, 91.1, 435/91.31; 536/23.1, 24.5, 31
See application file for complete search history.

(56) References Cited

U.S. PATENT DOCUMENTS

| | | | |
|---|---|---|---|
| 5,034,506 A | 7/1991 | Summerton et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,217,866 A | 6/1993 | Summerton et al. | |
| 5,506,337 A | 4/1996 | Summerton et al. | |
| 5,521,063 A | 5/1996 | Summerton et al. | |
| 5,576,302 A | 11/1996 | Cook et al. | |
| 5,580,767 A | 12/1996 | Cowsert et al. | |
| 5,698,685 A | 12/1997 | Summerton et al. | |
| 5,702,891 A | 12/1997 | Kolberg et al. | |
| 5,734,039 A | 3/1998 | Calabretta et al. | |
| 5,801,154 A | 9/1998 | Baracchini et al. | |
| 5,892,023 A | 4/1999 | Pirotzky et al. ............... 536/24.5 | |
| 5,955,318 A | 9/1999 | Simons et al. | |
| 6,060,456 A | 5/2000 | Arnold et al. | |
| 6,133,246 A | 10/2000 | McKay et al. | |
| 6,174,868 B1 | 1/2001 | Anderson et al. | |
| 6,228,579 B1 | 5/2001 | Zyskind et al. | |
| 6,239,265 B1 | 5/2001 | Cook | |
| 6,306,993 B1 | 10/2001 | Rothbard et al. | |
| 6,365,351 B1 | 4/2002 | Iversen | |
| 6,495,663 B1 | 12/2002 | Rothbard | |
| 6,677,153 B2 | 1/2004 | Iversen | |
| 6,784,291 B2 | 8/2004 | Iversen et al. | |
| 6,828,105 B2 | 12/2004 | Stein et al. | |
| 6,841,542 B2 | 1/2005 | Bartelmez et al. | |
| 7,049,431 B2 | 5/2006 | Iversen et al. | |
| 7,094,765 B1 | 8/2006 | Iversen et al. | |
| 7,115,374 B2 | 10/2006 | Linnen et al. | |
| 7,524,829 B2 * | 4/2009 | Stein et al. ................... | 514/44 R |
| 7,625,873 B2 | 12/2009 | Geller et al. | |
| 2003/0095953 A1 | 5/2003 | Cabot et al. ............... | 424/93.21 |
| 2003/0166588 A1 | 9/2003 | Iversen et al. | |
| 2003/0171335 A1 | 9/2003 | Stein et al. | |
| 2003/0224353 A1 | 12/2003 | Stein et al. | |
| 2004/0259108 A1 | 12/2004 | Linnen et al. | |
| 2005/0176661 A1 | 8/2005 | Vaillant et al. | |
| 2005/0234002 A1 | 10/2005 | Mourich et al. | |
| 2006/0148747 A1 | 7/2006 | Stein et al. | |
| 2006/0149046 A1 | 7/2006 | Arar | |
| 2006/0269911 A1 | 11/2006 | Iversen et al. | |
| 2007/0021362 A1 | 1/2007 | Geller et al. | |
| 2007/0037763 A1 | 2/2007 | Stein et al. | |
| 2007/0265214 A1 | 11/2007 | Stein et al. | |

FOREIGN PATENT DOCUMENTS

| | | | |
|---|---|---|---|
| WO | WO03033657 A2 | 4/2003 | |
| WO | WO2006/047683 A2 | 5/2006 | |

OTHER PUBLICATIONS

Agrawal et al. *Proc Natl Acad Sci U S A.*, 87(4):1401-5 (1990).
Akhtar, S., et al., *Nucleic Acids Res* 19(20):5551-9 (1991).
Anderson et al., *Antimicrobial Agents and Chemotherapy*, 40(9):2004-2011 (1996).
Anderson et al., *J. Neurochem.*, 73(2):867-873 (1999).
Arya, D. P. and T. C. Bruice, "Triple-helix formation of DNA oligomers with methylthiourea-linked nucleosides (DNmt): a kinetic and thermodynamic analysis.", *Proc Natl Acad Sci USA*, 96(8):4384-9 (1999).
Bailey et al., "Cationic oligonucleotides can mediate specific inhibition of gene expression in Xenopus oocytes." *Nucleic Acids Res*, 26(21):4860-7 (1998).
Banerjee, R. and A. Dasgupta (2001). "Interaction of picornavirus 2C polypeptide with the viral negative-strand RNA." *J Gen Virol* 82(Pt 11): 2621-7.
Banerjee, R. and A. Dasgupta (2001). "Specific interaction of hepatitis C virus protease/helicase NS3 with the 3'-terminal sequences of viral positive- and negative-strand RNA." *J Virol* 75(4): 1708-21.
Banerjee, R., A. Echeverri, et al. (1997). "Poliovirus-encoded 2C polypeptide specifically binds to the 3'-terminal sequences of viral negative-strand RNA." *J Virol* 71(12): 9570-8.
Banerjee, R., W. Tsai, et al. (2001). "Interaction of poliovirus-encoded 2C/2BC polypeptides with the 3' terminus negative-strand cloverleaf requires an intact stem-loop b." *Virology*, 280(1): 41-51.

(Continued)

*Primary Examiner* — Jane Zara
(74) *Attorney, Agent, or Firm* — Seed IP Law Group PLLC

(57) ABSTRACT

Morpholino oligomers containing both uncharged and cationic intersubunit linkages are provided. The oligomers are oligonucleotide analogs containing predetermined sequences of base-pairing moieties. The presence of the cationic intersubunit linkages in the oligomers, typically at a level of about 10-50% of total linkages, provides enhanced antisense activity, in various antisense applications, relative to the corresponding uncharged oligomers. Also provided are such oligomers conjugated to peptide transporter moieties, where the transporters are preferably composed of arginine subunits, or arginine dimers, alternating with neutral amino acid subunits.

16 Claims, 31 Drawing Sheets

OTHER PUBLICATIONS

Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).
Basler et al., *PNAS*, 97:12289-12294 (2000).
Blommers et al., *Nucleic Acids Res.*, 22(20):4187-94 (1994).
Bonham et al., *Nucleic Acids Res.*, 23(7):1197-203 (1995).
Borio et al., *JAMA*, 287(18):2391-2405 (2002).
Borriello et al., *J Immunol* 155(12):5490-7 (1995).
Boudvillain et al., *Biochemistry* 36(10):2925-31 (1997).
Branch, Andrea D., *TIBS*, 23:45-50 (1998).
Brasey et al., *J. Virol.*, 77(7):3939-3949 (2003).
Bray, M., K. Davis et al., "A mouse model for evaluation of prophylaxis and therapy of Ebola hemorrhagic fever.", *J Infect Dis.*, 178(3):651-61 (1998).
Burnett et al., *Nat. Rev. Drug Discovery*, 4:281-297 (2005).
Chambers et al., *Annu Rev Immunol*, 19:565-94, (2001).
Chirilla et al., *Biomaterials*, 23:321-342 (2002).
Clarke et al., *J. Infect. Diseases*, 181:S309-S316 (2000).
Connolly, B. M., K. E. Steele et al., "Pathogenesis of experimental Ebola virus infection in guinea pigs." *J Infect Dis.*, 179(Suppl 1):S203-S217 (1999).
Corey et al., Morpgolino Antisnese Oligonucleotides: Tools for Investigating Vertebrate Development, Genome Biology, 2(5):1015.1-1015.3 (2001).
Cross et al., "Solution structure of an RNA x DNA hybrid duplex containing a 3'-thioformacetal linker and an RNA A-tract." *Biochemistry*, 36(14): 4096-107 (1997).
Crooke, S. T. (2001). *Antisense Drug Technology: Principles, Strategies, and Applications*. New York, Marcel Dekker.
Dagle et al., "Targeted elimination of zygotic messages in *Xenopus laevis* embryos by modified oligonucleotides possessing terminal cationic linkages", *Nucleic Acids Res.*, 28(10): 2153-7 (2000).
Deas, T.S., et al., *Journal of Virology*, 79(8):4599-4609, (2005).
Dempcy, R. O., O. Almarsson et al., "Design and synthesis of deoxynucleic guanidine: a polycation analogue of DNA." *Proc Natl Acad Sci USA*, 91(17):7864-8 (1994).
Dempcy, R. O., J. Luo et al., "Design and synthesis of ribonucleic guanidine: a polycationic analog of RNA.", *Proc Natl Acad Sci USA*, 93(9):4326-30 (1996).
Ding, D., et al., *Nucleic Acids Res* 24(2):354-60, (1996).
Egholm et al., "PNA hybridizes to complementary oligonucleotides obeying the Watson-Crick hydrogen-bonding rules." *Nature*, 365(6446): 566-8 (1993).
Egli, M., G. Minasov et al., "Probing the influence of stereoelectronic effects on the biophysical properties of oligonucleotides: comprehensive analysis of the RNA affinity, nuclease resistance, and crystal structure of ten 2'-O-ribonucleic acid modifications.", *Biochemistry*, 44(25):9045-57 (2005).
Feldman et al., *Nat. Rev. Drug Discovery*, 3(8):677-685 (2003).
Feldman et al., *Current Topics Microbial. Immunol.*, 235:1-21 (1999).
Feldman et al., *Arch. Virol. Suppl.*, 7:81-100 (1993).
Felgner et al., *PNAS*, 84(21): 7413-7 (1987).
Freier, S.M., in Antisense Drug Technology: Principles, Strategies, and Applications, Ch. 5, pp. 107-118, (2001).
Gait et al., *J. Chem. Soc.*, 0(14)1684-1686 (1974).
Gee et al., *Antisense Nucleic Acid Drug Dev*, 8(2):103-11 (1998).
Geisbert and Hensley, *Expert Rev. Mol. Med.*, 6(20):1-24 (2004).
Geisbert and Hensley, *Lancet*, 362(9400):1953-1958 (2003).
Genbank Accession No. AF304460.
Green et al., *J. Am. Coll. Surg.*, 191:93-105 (2000).
Gupta, S., *Int J Oncol.*, 22(1):15-20 (2003).
Hanacek et al., *Journal of Virology*, 70:5203-5212 (1996).
Hanecak et al., *Journal of Virology*, 70(8):5203-5212 (1996).
Holland et al., Emerging Virus, Morse, S.S., Ed., Oxford University Press, New York and Oxford pp. 203-218 (1993).
Hudziak, R.M et al., Antisense Nucleic Acid Drug Dev., 10:163-176 (2000).
Hudziak, R.M et al., *Antisense Nucleic Acid Drug Dev.*, 6:267-272 (1996).
Jaeger, J.A., et al., Proc. Natl. Acad. Sci. USA 86:7706-7710, (1989).
Jahrling et al., *J. Infect. Dis.*, 179(Suppl 1):S222-S234 (1999).
Jen et al., *Stem Cells*, 18:307-319 (2000).
Johannes et al., *PNAS*, 96(23):13118-23 (1999).
Jubin, R., et al., Journal of Virology 74(22):10430-10437, (2000).
Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).
Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901 (2000).
Linkletter, B. A., I. E. Szabo et al., "Solid-phase synthesis of oligopurine deoxynucleic guanidine (DNG) and analysis of binding with DNA oligomers." *Nucleic Acids Res.*, 29(11): 2370-6 (2001).
Loke et al., *PNAS*, 86(10):3474-3478 (1989).
Lopez De Quinto S. et al., *Virology*, 255(2):324-336 (1999).
Lu et al., "Therapeutic dendritic-cell vaccine for chronic HIV-1 infection." *Nat Med.*, 10(12):1359-1365 (2004).
Markoff, L., *Adv. Virus Res.*, 59:177-228 (2003).
Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.
Meyer et al., *Curr. Top. Microbiol. Immunol.*, 262:139-157 (2002).
Micklefield, J., "Backbone modification of nucleic acids: synthesis, structure and therapeutic applications." *Curr Med Chem*, 8(10):1157-79 (2001).
Mohamadzadeh, M. and R. Luftig, *J Immune Based Ther Vaccines*, 2(1):1 (2004).
Moulton et al., Abstracts of Papers American Chemical Society National Meeting 226 (1-2): Biol 75 (Sep. 7-11, 2003).
Moulton, H. M. and J. D. Moulton, *Curr Opin Mol Ther.*, 5(2):123-32 (2003).
Moulton, H. M., et al., *Antisense Nucleic Acid Drug Dev.*, 13(1):31-43, (2003).
Moulton, H. M., M. H. Nelson, et al., *Bioconjug Chem* 15(2): 290-9 (2004).
National Center for Biotechnology Information Report No. AF029248 from NCBI Genome Database (2000).
National Center for Biotechnology Information Report No. NC_002645 from NCBI Genome Database (2001).
National Center for Biotechnology Information Report No. AY274119 from NCBI Genome Database (2003).
Nelson et al., "Arginine-rich peptide conjugation to morpholino oligomers: effects on antisense activity and specificity." *Bioconjug Chem.*, 16(4): 959-66 (2005).
Neuman, B.W., et al., Journal of Virology 78(11):5891-5899, (2004).
O'Ryan et al., in: Spector S, Lancz G, Eds., Clinical Virology Manual, New York, Elsevier Science pp. 361-396 (1992).
Orabona et al., "CD28 induces immunostimulatory signals in dendritic cells via CD80 and CD86.", 5(11):1134-1142 (2004).
Orr et al., *Current Opinion in Molecular Therapeuctics*, Current Drugs, 2(3):325-331 (2000).
Palu et al., *J. Biotech.*, 68:1-13 (1999).
Pardigon, N. and J. H. Strauss (1992). "Cellular proteins bind to the 3' end of Sindbis virus minus-strand RNA." *J Virol.*, 66(2): 1007-15.
Pardigon, N., E. Lenches, et al. (1993). "Multiple binding sites for cellular proteins in the 3' end of Sindbis alphavirus minus-sense RNA." *J Virol.*, 67(8): 5003-11.
Pari et al., *Antimicrobial Agents and Chemotherapy*, 39(5):1157-1161 (1995).
Partridge et al., Antisense Nucleic Acid Drug Development, 6(3):169-175 (1996).
Paul, A. V. (2002). Possible unifying mechanism of picornavirus genome replication. *Molecular Biology of Picornaviruses*. B. L. Semler and E. Wimmer. Washington, DC, ASM Press:227-246.
Peters and LeDuc, *J. Infect. Dis.*, 179(Suppl 1):ix-xvi (1999).

Polyak et al., *Journal of Virology*, 69(5):3211-3215 (1995).
Raviprakash, K., et al., Journal of Virology 69(1):69-74, (1995).
Roehl, H. H. and B. L. Semler (1995). "Poliovirus infection enhances the formation of two ribonucleoprotein complexes at the 3' end of viral negative-strand RNA." *J Virol.*, 69(5):2954-61.
Roehl, H. H., T. B. Parsley, et al. (1997). "Processing of a cellular polypeptide by 3CD proteinase is required for poliovirus ribonucleoprotein complex formation." *J Virol.* 71(1):578-85.
Rothbard et al., *J. Med. Chem.*, 45:3612-3618 (2002).
Salomon, B. and J. A. Bluestone, *Annu Rev Immunol.*, 19:225-52 (2001).
Sanchez et al., *Virus Res.*, 29(3):215-240 (1993).
Sankar e al., *European Journal of Biochemistry*, 184(1):39-45 (1989).
Shevac, E. M., "Animal Models for Autoimmune and Inflammatory Disease", Current Protocols in Immunology, John Wiley & Sons, Inc., S52 (2002).
Siprashvili, Z., et al., Human Gene Therapy 14:1225-1233, (2003).
Smith et al., *Current Opinion Molecular Therapeutcis*, 4(2):177-184 (2002).
Smith et al., *Emerg. Inf. Dis.*, 4:13-20 (1998).
Smith, R.M. and Wu, G.Y., Journal of Viral Hepatitis 11:115-123, (2004).
Stein et al., *Antisense Nucleic Acid Drug Development*, 11(5):317-325 (2001).
Stein, D., et al., *Antisense Nucleic Acid Drug Dev.*, 7(3):151-7, (1997).
Summerton et al., *Antisense & Nucleic Acid Drug Development*, 7:63-70 (1997).
Summerton et al., *Biochim et. Biophys. ACTA*, 1489:141-158 (1999).
Summerton, J. and D. Weller, "Morpholino antisense oligomers: design, preparation, and properties.", *Antisense Nucleic Acid Drug Dev.*, 7(3): 187-95 (1997).
Taylor et al., *Drug Discovery Today*, 4:562-567 (1999).
Thiel et al., *Journal of General Virology*, 82:1273-1281 (2001).
Toulme et al., Targeting RNA structures by antisense oligonucleotides. *Biochimie*, 78(7): 663-73 (1996).

Van der Merwe, P. A. and S. J. Davis, *Annu Rev Immunol.*, 21:659-84, (2003).
Vijayakrishnan et al., *Immunity*, 20(5):563-575 (2004).
Wages et al., *Biotechniques*, 23:1116-1121 (1997).
Wang et al., *Antimicrobial Agents Chemotherapy*, 45(4):1043-1052 (2001).
Warfield et al., *J. Exp. Med.*, 200(2):169-179 (2004).
Warfield, K. L., D. L. Swenson, et al., "Gene-Specific Countermeasures against Ebola Virus Based on Antisense Phosphorodiamidate Morpholino Oligomers." *PLoS Pathog* 2(1): e1 (2006).
Wasem, C., et al., *J Clin Invest* 111(8):1191-9, (2003).
Wei et al., *Nucleic Acids Res.*, 28:3065-3074 (2000).
Wender et al., *PNAS*, 97(24):13003-13008 (2000).
Wilson et al., *Mol. Cell Biol.*, 20(14):4990-4999 (2000).
Wu et al., *J. Biol. Chem.*, 267:12436-12439 (1992).
Xu et al., *Revue Scientifique Technique*, Office of International des Epizooties 10:2393-2408 (1991).
Xu, W. Y. (1991). "Viral haemorrhagic disease of rabbits in the People's Republic of China: epidemiology and virus characterisation." *Rev Sci Tech*, 10(2): 393-408.
Yakubov, L.A., et al., *Proc Natl Acad Sci U S A.*, 86(17):6454-8 (1989).
Zhang et al., *Antimicrobial Agents Chemotherapy*, 43(2):347-353 (1999).
Zuker, M., *Nucleic Acids Res.*, 31(13):3406-3415 (2003).
Agrawal et al., "Oligodeoxynucleoside phosphoramidates and phosphorothioates as inhibitors of human immunodeficiency virus," Proc. Natl. Acad. Sci. USA 85:7079-7083, 1988.
The International Search report and Written Opinion for PCT application PCT/US2007/011435, search report dated Sep. 29, 2008, 13 pages (2008).
Iversen et al., "Antisense antiviral compound and method for treating ssRNA viral infection," Office Action mailed Oct. 19, 2010, for U.S. Appl. No. 11/432,031, 25 pages.
Stein et al., "Antisense antiviral agent and method for treating ssRNA viral infection," Office Action mailed Feb. 17, 2010, for U.S. Appl. No. 11/431,968, 19 pages.

* cited by examiner

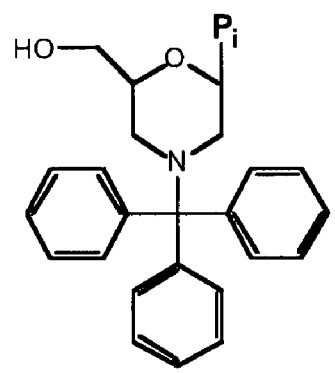
1a-e, where $P_i =$
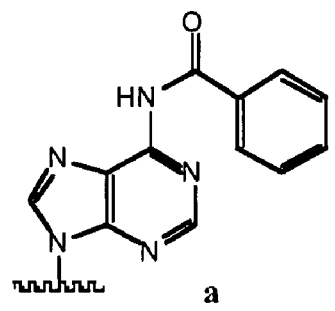
a
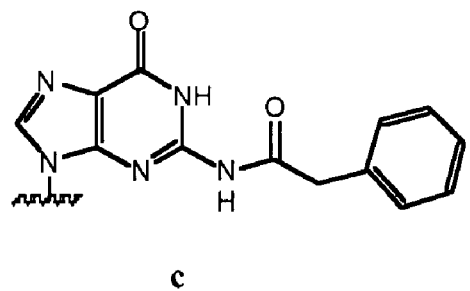
c
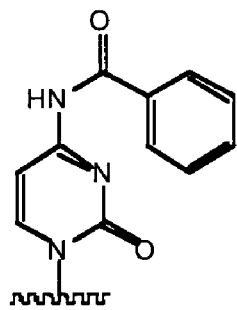
b
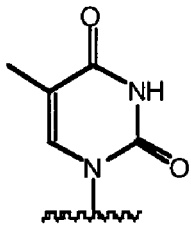
d
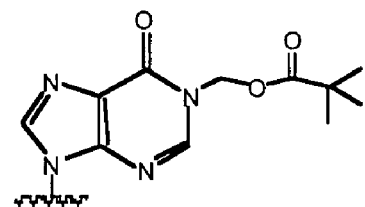
e
Fig. 2A 20a-e Y = H
21a-e Y = FMOC
20a-e Y = POClOEt 17a-e Y = H
18a-e Y = FMOC
19a-e Y = POClOEt

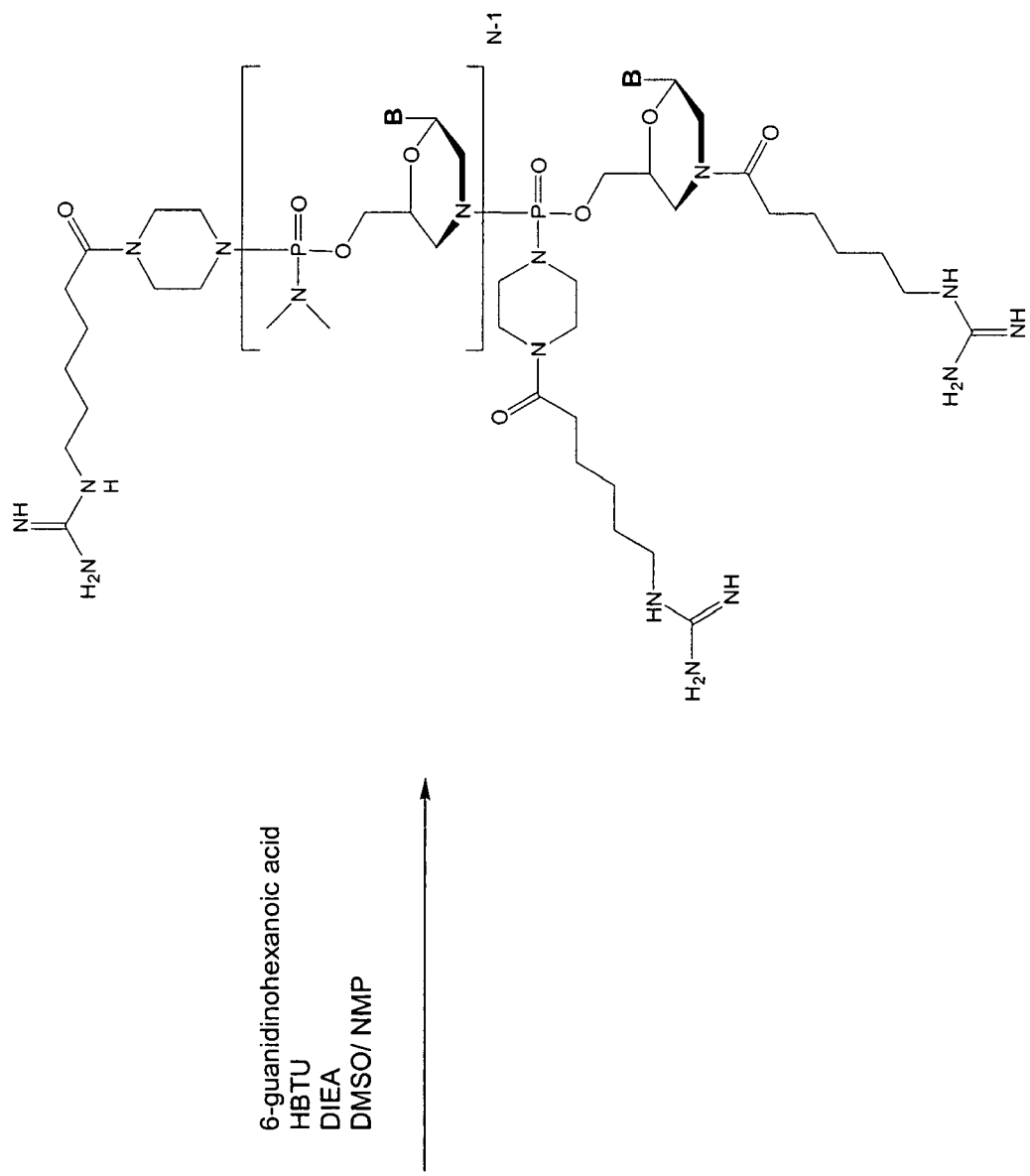
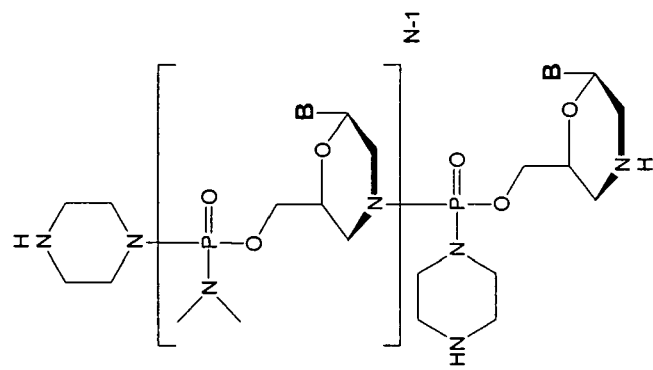
Fig. 2N

OLIGONUCLEOTIDE ANALOGS HAVING CATIONIC INTERSUBUNIT LINKAGES

This application claims priority to U.S. Patent Application No. 60/800,076 filed May 11, 2006, which is incorporated herein in its entirety by reference. U.S. Patent Application Nos. 60/799,976 filed May 11, 2006, 60/800,120 filed May 11, 2006, 60/800,145 filed May 11, 2006, Ser. No. 11/431,968 filed May 10, 2006, Ser. No. 11/432,031 filed May 10, 2006, Ser. No. 11/432,155 filed May 10, 2006, Ser. No. 11/432,216 filed May 10, 2006, Ser. No. 11/433,033 filed May 11, 2006, Ser. No. 11/433,213 filed May 11, 2006, Ser. No. 11/433,214 filed May 11, 2006, Ser. No. 11/433,257 filed May 11, 2006, Ser. No. 11/433,724 filed May 11, 2006, Ser. No. 11/433,840 filed May 11, 2006, Ser. No. 11/517,757 filed Sep. 8, 2006, Ser. No. 11/518,058 filed Sep. 8, 2006, Ser. No. 11/595,161 filed Nov. 8, 2006, and Ser. No. 11/715,572 filed Mar. 7, 2007, are also incorporated herein in their entirety by reference.

FIELD OF THE INVENTION

The present invention relates to oligonucleotide analogs (oligomers) useful as antisense compounds, and more particularly to oligomers containing cationic linkages, and the use of such oligomers in antisense applications. Particularly preferred are morpholino oligomers containing both uncharged linkages and cationic linkages, where both can be phosphorodiamidate linkages, and exemplary cationic linkages include a (1-piperazino) phosphinylideneoxy linkage and a (1-(4-(co-guanidino-alkanoyl))-piperazino) phosphinylideneoxy linkage.

REFERENCES

Arya, D. P. and T. C. Bruice (1999). "Triple-helix formation of DNA oligomers with methylthiourea-linked nucleosides (DNmt): a kinetic and thermodynamic analysis." *Proc Natl Acad Sci USA* 96(8): 4384-9.

Bailey, C. P., J. M. Dagle et al. (1998). "Cationic oligonucleotides can mediate specific inhibition of gene expression in *Xenopus oocytes*." *Nucleic Acids Res* 26(21): 4860-7.

Barawkar, D. A. and T. C. Bruice (1998). "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci USA* 95(19): 11047-52.

Bray, M., K. Davis et al. (1998). "A mouse model for evaluation of prophylaxis and therapy of Ebola hemorrhagic fever." *J Infect Dis* 178(3): 651-61. Connolly, B. M., K. E. Steele et al. (1999). "Pathogenesis of experimental Ebola virus infection in guinea pigs." *J Infect Dis* 179 Suppl 1: S203-17.

Crooke, S. T. (2001). *Antisense Drug Technology: Principles, Strategies, and Applications*. New York, Marcel Dekker.

Dempcy, R. O., O. Almarsson et al. (1994). "Design and synthesis of deoxynucleic guanidine: a polycation analogue of DNA." *Proc Natl Acad Sci USA* 91(17): 7864-8.

Dempcy, R. O., J. Luo et al. (1996). "Design and synthesis of ribonucleic guanidine: a polycationic analog of RNA." *Proc Natl Acad Sci USA* 93(9): 4326-30.

Egli, M., G. Minasov et al. (2005). "Probing the influence of stereoelectronic effects on the biophysical properties of oligonucleotides: comprehensive analysis of the RNA affinity, nuclease resistance, and crystal structure of ten 2'-O-ribonucleic acid modifications." *Biochemistry* 44(25): 9045-57.

Linkletter, B. A. and Bruice, T. C. (2000). "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901.

Linkletter, B. A., I. E. Szabo et al. (2001). "Solid-phase synthesis of oligopurine deoxynucleic guanidine (DNG) and analysis of binding with DNA oligomers." *Nucleic Acids Res* 29(11): 2370-6.

Micklefield, J. (2001). "Backbone modification of nucleic acids: synthesis, structure and therapeutic applications." *Curr Med Chem* 8(10): 1157-79.

Moulton, H. M., M. H. Nelson et al. (2004). "Cellular uptake of antisense morpholino oligomers conjugated to arginine-rich peptides." *Bioconjug Chem* 15(2): 290-9.

Nelson, M. H., D. A. Stein et al. (2005). "Arginine-rich peptide conjugation to morpholino oligomers: effects on antisense activity and specificity." *Bioconjug Chem* 16(4): 959-66.

Summerton, J. and D. Weller (1997). "Morpholino antisense oligomers: design, preparation, and properties." *Antisense Nucleic Acid Drug Dev* 7(3): 187-95.

Warfield, K. L., D. L. Swenson, et al. (2006). "Gene-Specific Countermeasures against Ebola Virus Based on Antisense Phosphorodiamidate Morpholino Oligomers." *PLoS Pathog* 2(1): el.

BACKGROUND OF THE INVENTION

Requirements for successful implementation of antisense therapeutic molecules, which are generally designed to bind to DNA or RNA of disease-causing proteins to prevent the production of such proteins, include (a) stability in vivo, (b) sufficient membrane permeability and cellular uptake, and (c) a good balance of binding affinity and sequence specificity. Many oligonucleotide analogs have been developed in which the phosphodiester linkages of native DNA are replaced by other linkages that are resistant to nuclease degradation (see e.g. Barawkar and Bruice 1998; Linkletter, Szabo et al. 2001; Micklefield 2001). Antisense oligonucleotides having various backbone modifications other than to the internucleoside linkage have also been prepared (Crooke 2001; Micklefield 2001). In addition, oligonucleotides have been modified by peptide conjugation in order to enhance cellular uptake (Moulton, Nelson et al. 2004; Nelson, Stein et al. 2005).

The performance of such nucleic acid analogs as antisense or antigene drugs has been hampered by certain characteristics of the various analogs. For example, analogs with negatively charged linkages, including phosphorothioate-linked analogs, suffer from considerable electrostatic repulsion between the negative charges of the oligomer and the DNA or RNA target. The phosphorothioates also exhibit non-specific binding to other cellular components such as proteins. These attributes limit the usefulness of antisense oligomers comprised of native RNA, native DNA, and negatively charged analogs as therapeutic agents (Crooke 2001). The nonionic methylphosphonate-linked oligonucleotide analogs can be transported into cells by passive diffusion and/or fluid phase endocytosis, but their use is hampered by stereoisomeric complexity and poor solubility (Crooke 2001; Micklefield 2001).

Several groups have reported the synthesis of positively charged oligonucleotides (Bailey, Dagle et al. 1998; Micklefield 2001; Egli, Minasov et al. 2005). For example, a class of guanidinium linked nucleosides (designated DNG), formed by replacement of the phosphate linkages in DNA and RNA by achiral guanidino groups, has been reported (Dempcy, Almarsson et al. 1994; Dempcy, Luo et al. 1996; Barawkar and Bruice 1998; Linkletter, Szabo et al. 2001). Oligomers linked with positively charged methylated thiourea linkages have also been reported (Arya and Bruice 1999). Replacement of some of these linkages with neutral urea linkages is reported to reduce the tendency of such positively charged oligomers towards non-sequence-specific binding (Linkletter and Bruice, 2000). However, there remains a need for oligonucleotide analogs with improved antisense or antigene performance, particularly in the area of stronger affinity for DNA and RNA, without compromising sequence selectivity.

SUMMARY

The invention provides, in one aspect, an oligomer comprising a backbone consisting of a sequence of morpholino ring structures joined by intersubunit linkages, where each such ring structure supports a base-pairing moiety, such that said oligomer can bind in a sequence-specific manner to a target nucleic acid, and where at least one intersubunit linkage between two consecutive such ring structures contains a pendant cationic group. The pendant group bears a distal nitrogen atom that can bear a positive charge at neutral or near-neutral (e.g. physiological) pH.

The intersubunit linkages are preferably phosphorus-containing linkages, having the structure:

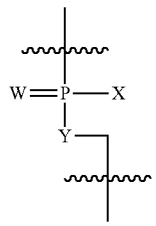

where
W is S or O, and is preferably O,
$X=NR^1R^2$ or $OR^6$,
  $Y=O$ or $NR^7$,
  and each said linkage in the oligomer is selected from:
  (a) uncharged linkage (a), where each of $R^1$, $R^2$, $R^6$ and $R^7$ is independently selected from hydrogen and lower alkyl;
  (b1) cationic linkage (b1), where $X=NR^1R^2$ and $Y=O$, and $NR^1R^2$ represents an optionally substituted piperazino group, such that $R^1R^2=$—CHRCHRN($R^3$)($R^4$)CHRCHR—,
where
  each R is independently H or $CH_3$,
  $R^4$ is H, $CH_3$, or an electron pair, and
  $R^3$ is selected from H, lower alkyl, C(=NH)NH$_2$, Z-L-NHC(=NH)NH$_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy) alkyl; and (b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl;

and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 80%, 10% to 50%, or 10% to 35% of the linkages may be cationic linkages.

Preferably, all cationic linkages in the oligomer are of the same type; i.e. all of type (b1), all of type (b2), or all of type (b3).

In one embodiment, at least one linkage is of type (b1), where, preferably, each R is H, $R^4$ is H, $CH_3$, or an electron pair, and $R^3$ is selected from H, lower alkyl, e.g. $CH_3$, C(=NH)NH$_2$, and C(O)-L-NHC(=NH)NH$_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g. —CH$_2$—CH$_2$—), alkoxy (—C—O—), and alkylamino (e.g. —CH$_2$—NH—), with the proviso that the terminal atoms in L (e.g., those adjacent to carbonyl or nitrogen) are carbon atoms. Although branched linkages (e.g. —CH$_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The morpholino subunits have the structure (i):

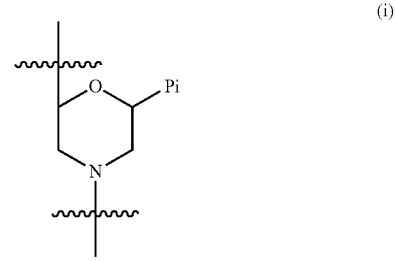

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

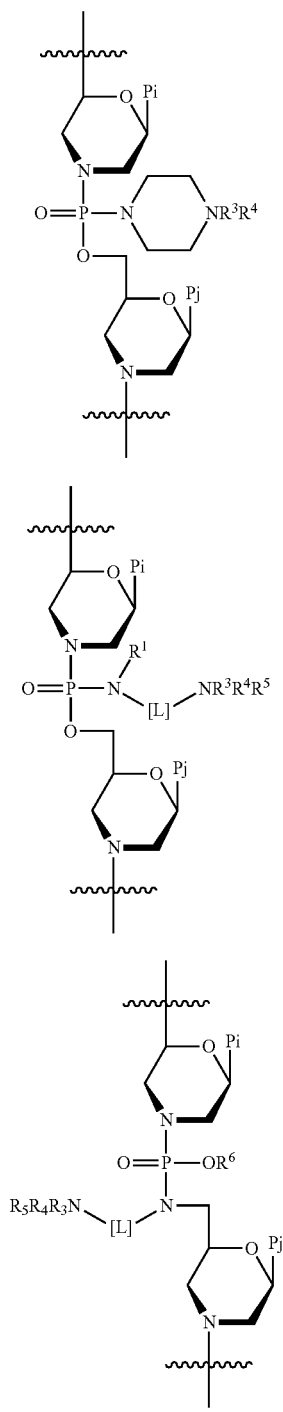

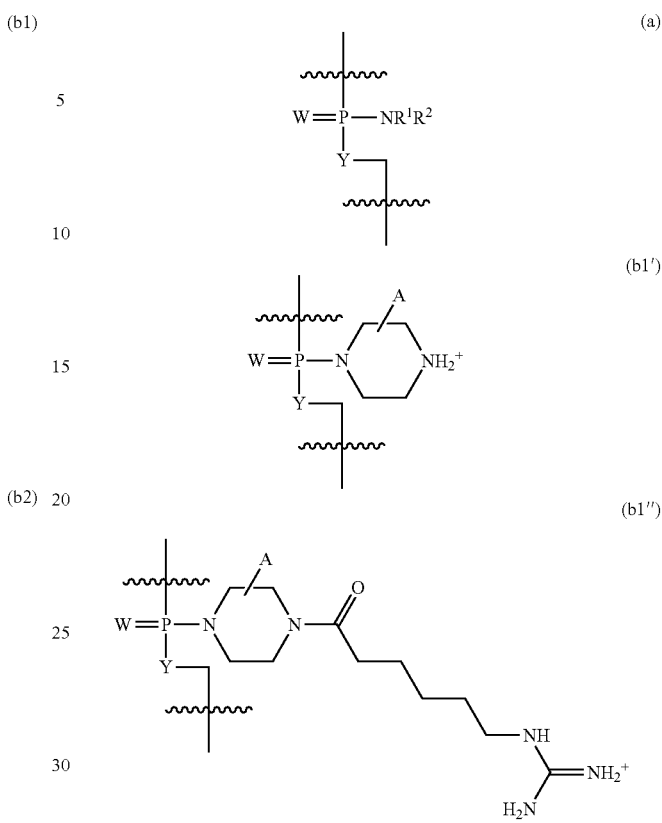

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, each A is hydrogen; that is, the nitrogen heterocycle is preferably unsubstituted. In further embodiments, at least 10% of the linkages are of type (b1') or (b1"); for example, 20% to 80%, 20% to 50%, or 20% to 30% of the linkages may be of type (b1') or (b1").

In other embodiments, the oligomer contains no linkages of type (b1'). Alternatively, the oligomer contains no linkages of type (b1) where each R is H, $R^3$ is H or $CH_3$, and $R^4$ is H, $CH_3$, or an electron pair.

In still further embodiments, the cationic linkages are of type (b2), where L is a linker up to 12 atoms in length having bonds selected from alkyl (e.g. —$CH_2$—$CH_2$—), alkoxy (—C—O—), and alkylamino (e.g. —$CH_2$—NH—), with the proviso that the terminal atoms in L (e.g., those adjacent to carbonyl or nitrogen) are carbon atoms.

The morpholino subunits may also be linked by non-phosphorus-based intersubunit linkages, as described further below, where at least one linkage is modified with a pendant cationic group as described above. For example, a 5'nitrogen atom on a morpholino ring could be employed in a sulfamide linkage (see e.g. FIG. 2G) or a urea linkage (where phosphorus is replaced with carbon or sulfur, respectively) and modified in a manner analogous to the 5'-nitrogen atom in structure (b3) above.

The subject oligomer may also be conjugated to a peptide transport moiety which is effective to enhance transport of the oligomer into cells. The transport moiety is preferably attached to a terminus of the oligomer, as shown, for example, in FIG. 1D, as well as FIGS. 2P-2Q.

Preferably, at least 5% of the linkages in an oligomer are selected from cationic linkages (b1), (b2), and (b3); in further embodiments, 10% to 35% of the linkages are selected from cationic linkages (b1), (b2), and (b3). As noted above, all of the cationic linkages in an oligomer are preferably of the same type or structure.

In further embodiments, the cationic linkages are selected from linkages (b1') and (b1") as shown below, where (b1') is referred to herein as a "Pip" linkage and (b1") is referred to herein as a "GuX" linkage:

Preferably, the transport moiety comprises 6 to 16 amino acids and is composed of subsequences selected from the group consisting of (X'Y'X'), (X'Y'), (X'Z'), and (X'Z'Z'), where (a) each X' subunit independently represents arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral linear amino acid —C(O)—$(CHR)_n$—NH—, where n is 1 to 7 and each R is independently H or methyl; and (c) each Z' subunit independently represents an α-amino acid having a neutral aralkyl side chain.

In selected embodiments, the peptide comprises a sequence which consists of at least two, or at least three, repeats of a single subsequence selected from (X'Y'X'), (X'Y'), (X'Z'), and (X'Z'Z'). For example, the peptide may comprise a sequence represented by one of $(X'Y'X')_p$, $(X'Y')_m$, and $(X'Z'Z')_p$, where p is 2 to 5 and m is 2 to 8.

Preferably, for each X', the side chain moiety is guanidyl; each Y' is —CO—$(CH_2)_n$—NH—, where n is 1 to 7; and each Z' is phenylalanine. In preferred embodiments of Y', n is 2 or 5, such that Y' is selected from a β-alanine subunit and a 6-aminohexanoic acid subunit.

Preferred peptides of this type include those comprising arginine dimers alternating with single Y' subunits, where Y' is preferably Ahx. Examples include peptides having the formula $(RY'R)_4$ or the formula $(RRY')_4$, where Y' is preferably Ahx. In one embodiment, Y' is a 6-aminohexanoic acid subunit and p is 4. In a further embodiment, each Z' is phenylalanine, and m is 3 or 4.

The conjugated peptide is preferably linked to a terminus of the oligomer via a linker Ahx-B, where Ahx is a 6-aminohexanoic acid subunit and B is a β-alanine subunit, as shown, for example, in FIG. 1D.

In a related aspect, the invention provides a method of enhancing antisense activity of an oligomer having a sequence of morpholino subunits, joined by intersubunit linkages, supporting base-pairing moieties, by modifying said oligomer to contain at least one cationic intersubunit linkage as disclosed herein. In one embodiment, said cationic intersubunit linkage(s) do not include linkages of type (b1') as depicted above. Enhancement of antisense activity may be evidenced by:

(i) a decrease in expression of an encoded protein, relative to that provided by a corresponding unmodified oligomer, when binding of the antisense oligomer to its target sequence is effective to block a translation start codon for the encoded protein, or (ii) an increase in expression of an encoded protein, relative to that provided by a corresponding unmodified oligomer, when binding of the antisense oligomer to its target sequence is effective to block an aberrant splice site in a pre-mRNA which encodes said protein when correctly spliced. Assays suitable for measurement of these effects are described further below. In one embodiment, modification provides this activity in a cell-free translation assay, or a splice correction translation assay in cell culture, as described herein. Preferably, activity is enhanced by a factor of at least two, more preferably by a factor of at least five, and most preferably by a factor of at least ten.

The compounds described herein may be used in methods of inhibiting production of a protein. Accordingly, a nucleic acid encoding such a protein is exposed to an antisense oligomer containing at least one cationic intersubunit linkage, and preferably containing 20% to 50% such cationic linkages, as disclosed herein, where the base pairing moieties Pi form a sequence effective to hybridize to a portion of the nucleic acid at a location effective to inhibit production of the protein. The location may be, for example, an ATG start codon of an mRNA, a splice site of a pre-mRNA, or a viral target sequence as described below.

Preferably, the oligomer has a $T_m$ with respect to binding to the target sequence of greater than about 50° C., and it is actively taken up by mammalian cells. The oligomer may be conjugated to a transport moiety as described herein to facilitate such uptake.

In one embodiment, the oligomer can be used in a method of reducing the risk of restenosis in a region of a patient's coronary vessel which has been treated by coronary angioplasty using a catheter with a distal-end expandable balloon, or which is at a junction formed in a coronary bypass operation. The method includes administering to the patient, by local administration directly to the vessel site of injury, an oligomer as described herein, containing at least one cationic intersubunit linkage, and preferably containing 20% to 50% such cationic linkages, having from 12 to 40 subunits, including a targeting base sequence that is complementary to a target sequence of at least 12 contiguous bases within the AUG start site region of human c-myc mRNA defined by SEQ ID NO: 59, in an amount effective to reduce the risk of restenosis in the patient. The compound is administered by one of:

(a) contacting the region of the vessel with a reservoir containing the antisense compound, and introducing the compound from the reservoir into the vessel by iontophoresis or electroporation;

(b) injecting the compound from the catheter directly into the region of the vessel, under pressure, through injectors contained on the surface of the catheter balloon, where said injectors are capable of penetrating the tunica media in the vessel;

(c) injecting into or contacting the region of the vessel, microparticles containing the antisense compound in entrapped form;

(d) contacting the region of the vessel with a hydrogel coating contained on the surface of the catheter balloon, and containing the antisense compound is diffusable form;

(e) contacting the region of the vessel with a stent having an outer surface layer containing the antisense compound in diffusable form; and (f) injecting the compound by intravascular administration, resulting in systemic delivery to the vascular tissues.

The antisense compound may have a targeting sequence having at least 90% homology to the sequence identified by SEQ ID NO: 43, and alternatively, at least 90% homology to a sequence selected from SEQ ID NOs: 60 and 61.

In another embodiment, the oligomer can be targeted against an mRNA sequence having its 5' end 1 to about 25 base pairs downstream of a normal splice acceptor junction in a preprocessed mRNA. Such targeting is effective to inhibit natural mRNA splice processing and produce splice variant mRNAs.

Suitable target proteins include, for example, transcription factors, particularly oncogenic or proto-oncogenic proteins such as myc, myb, rel, fos, jun, abl, bcl, and p53; matrix proteins, such as integrins and cathedrins; other tumor-expressed proteins, such as hCG; telomerases; receptor proteins; viral proteins, such as those expressed from the subgenomic spliced mRNAs of HIV, human papilloma virus, and human parvovirus B19; and immunomodulatory proteins such as, for example, CTLA-4, B7-2, PD-1, Foxp3, TGFbeta, and TNF receptor.

In another embodiment, the oligomer can be used for inhibiting replication of an RNA virus from the picornavirus, calicivirus, togavirus or flavivirus families, having a single-stranded, positive sense genome of less than 12 kb, and a first open reading frame that encodes a polyprotein containing multiple functional proteins. Accordingly, the virus, or, typically, a cell infected with the virus, is exposed to an oligomer as disclosed herein, containing at least one cationic intersubunit linkage, and preferably containing 20% to 50% such cationic linkages, and having a sequence of subunits supporting a targeting base sequence that is substantially complementary to a viral target sequence which spans the translation initiation region of the first open reading frame.

Exemplary targeting sequences have at least 90% homology to a sequence selected from the group consisting of:
  (i) SEQ ID NO. 62, for a polio virus of the Mahoney and Sabin strains,
  (ii) SEQ ID NO. 63, for a hepatitis A virus,
  (iii) SEQ ID NO. 64, for a rhinovirus 14,
  (iv) SEQ ID NO. 65, for a rhinovirus 16,
  (v) SEQ ID NO. 66, for a rhinovirus 1B, Other exemplary targeting sequences, directed against a calcivirus, have at least 90% homology to a sequence selected from the group consisting of:
  (i) SEQ ID NOs. 67, 68, and 69, for a serotype Pan-1 vesivirus,
  (ii) SEQ ID NO. 70, for a porcine calicivirus,
  (iii) SEQ ID NO. 71, for a Norwalk virus, and
  (iv) SEQ ID NO. 72, for a feline calicivirus.

For use in inhibition of hepatitis E virus, the targeting sequence has at least 90% homology to a sequence selected from the group consisting of SEQ ID NOs: 73 and 74. For use in inhibition of a hepatitis C flavivirus, the targeting sequence is complementary to a sequence of at least 12 contiguous bases of the HCV AUG start-site region identified by SEQ ID NO: 75. Exemplary targeting sequences include those having at least 90% homology to SEQ ID NOs. 18 and 76.

In a further embodiment, the oligomers can be used in inhibiting replication within a host cell of an RNA virus having a single-stranded, positive-sense genome and selected from one of the Flaviviridae, Picornoviridae, Caliciviridae, Togaviridae, Arteriviridae, Coronaviridae, Astroviridae or Hepeviridae families.

The method includes first identifying as a viral target sequence, a region within the 5'-terminal 40 bases of the positive strand of the infecting virus whose sequence is capable of forming internal stem-loop secondary structure. There is then constructed, by stepwise solid-phase synthesis, an oligomer having at least one cationic intersubunit linkage as described herein, and preferably containing 20% to 50% such cationic linkages, and having a targeting sequence of at least 12 subunits that is complementary to the virus-genome region capable of forming internal duplex structure, where the oligomer is able to form with the viral target sequence, a heteroduplex structure composed of the positive sense strand of the virus and the oligonucleotide compound, and characterized by a Tm of dissociation of at least 45° C. and disruption of such stem-loop structure.

The target sequence may be identified by analyzing the 5'-terminal sequences, e.g., the 5'-terminal 40 bases, by a computer program capable of performing secondary structure predictions based on a search for the minimal free energy state of the input RNA sequence.

In a related aspect, the oligomers can be used in methods of inhibiting in a mammalian host cell, replication of an infecting RNA virus having a single-stranded, positive-sense genome and selected from one of the Flaviviridae, Picornoviridae, Caliciviridae, Togaviridae, Arteriviridae, Coronaviridae, Astroviridae or Hepeviridae families. The method includes administering to the infected host cells, a virus-inhibitory amount of an oligomer as described herein, having a targeting sequence of at least 12 subunits that is complementary to a region within the 5'-terminal 40 bases of the positive-strand viral genome that is capable of forming internal stem-loop secondary structure. The compound is effective, when administered to the host cells, to form a heteroduplex structure (i) composed of the positive sense strand of the virus and the oligonucleotide compound, and (ii) characterized by a Tm of dissociation of at least 45° C. and disruption of such stem-loop secondary structure. The compound may be administered to a mammalian subject infected with the virus, or at risk of infection with the virus.

For treatment of a Flavivirus or Hepacivirus, the targeting sequence is complementary to a region associated with stem-loop secondary structure within one of the following sequences:
  (i) SEQ ID NO. 77, for St Louis encephalitis virus;
  (ii) SEQ ID NO. 78, for Japanese encephalitis virus;
  (iii) SEQ ID NO. 79, for a Murray Valley encephalitis virus;
  (iv) SEQ ID NO. 80, for a West Nile fever virus;
  (v) SEQ ID NO. 81, for a Yellow fever virus
  (vi) SEQ ID NO. 82, for a Dengue Type-2 virus;
  (vii) SEQ ID NO. 83, for a Hepatitis C virus;
  (viii) SEQ ID NO. 84, for a tick-borne encephalitis virus;
  (ix) SEQ ID NO. 85, for Omsk hemorrhagic fever virus; and
  (x) SEQ ID NO. 86, for Powassan virus.

Exemplary targeting sequences for these viruses include the following sequences, or portions of these sequences that overlap with one or more regions of duplex secondary structure in the associated target sequence:
  (i) SEQ ID NOS. 87 and 88, for St Louis encephalitis virus;
  (ii) SEQ ID NOS. 89 and 90, for Japanese encephalitis virus;
  (iii) SEQ ID NOS. 91 and 92, for a Murray Valley encephalitis virus;
  (iv) SEQ ID NOS. 93 and 94, for a West Nile fever virus;
  (v) SEQ ID NOS. 95 and 96, for a Yellow fever virus;
  (vi) SEQ ID NOS. 97, 98, for a Dengue virus;
  (vii) SEQ ID NOS. 99 and 100, for a Hepatitis C virus;
  (viii) SEQ ID NOS. 101 and 102, for a tick-borne encephalitis virus;
  (ix) SEQ ID NOS. 103 and 104, for Omsk hemorrhagic fever virus; and
  (x) SEQ ID NOS. 105 and 106, for Powassan virus.

For treatment of an Enterovirus, Rhinovirus, Hepatovirus or Aphthovirus, the targeting sequence is complementary to a region associated with stem-loop secondary structure within one of the following sequences:
  (i) SEQ ID NO. 107, for a polio virus of the Mahoney and Sabin strains;
  (ii) SEQ ID NO. 108, for a Human enterovirus A;
  (iii) SEQ ID NO. 109, for a Human enterovirus B;
  (iv) SEQ ID NO. 110, for a Human enterovirus C;
  (v) SEQ ID NO. 111, for a Human enterovirus D;
  (vi) SEQ ID NO. 112, for a Human enterovirus E;
  (vii) SEQ ID NO. 113, for a Bovine enterovirus;
  (viii) SEQ ID NO. 114, for Human rhinovirus 89;
  (ix) SEQ ID NO. 115, for Human rhinovirus B;

(x) SEQ ID NO. 116, for Foot-and-mouth disease virus; and (xi) SEQ ID NO. 117, for a hepatitis A virus.

Exemplary targeting sequences for these viruses include the following sequences, or portions of these sequences that overlap with one or more regions of duplex secondary structure in the associated target sequence:

(i) SEQ ID NOS. 118 and 119, for a polio virus of the Mahoney and Sabin strains;

(ii) SEQ ID NOS. 120 and 121, for a Human enterovirus A;

(iii) SEQ ID NOS. 122 and 123, for a Human enterovirus B;

(iv) SEQ ID NOS. 124 and 125, for a Human enterovirus C;

(v) SEQ ID NOS. 126 and 127, for a Human enterovirus D;

(vi) SEQ ID NOS. 128 and 129, for a Human enterovirus E;

(vii) SEQ ID NOS. 130 and 131, for a Bovine enterovirus;

(viii) SEQ ID NOS. 132 and 133, for Human rhinovirus 89;

(ix) SEQ ID NOS. 134 and 135, for Human rhinovirus B;

(x) SEQ ID NOS. 136 and 137, for Foot-and-mouth disease virus; and (xi) SEQ ID NOS. 138 and 139, for a hepatitis A virus.

For treatment of a Calicivirus or Norovirus, the targeting sequence is complementary to a region associated with stem-loop secondary structure within one of the following sequences:

(i) SEQ ID NO. 140, for a Feline Calicivirus;

(ii) SEQ ID NO. 141, for a Canine Calicivirus;

(iii) SEQ ID NO. 142, for a Porcine enteric calicivirus;

(iv) SEQ ID NO. 143, for Calicivirus strain NB; and (v) SEQ ID NO. 144, for a Norwalk virus.

Exemplary targeting sequences for these viruses include the following sequences, or portions of these sequences that overlap with one or more regions of duplex secondary structure in the associated target sequence:

(i) SEQ ID NOS. 145 and 146, for a Feline Calicivirus;

(ii) SEQ ID NOS. 147 and 148, for a Canine Calicivirus;

(iii) SEQ ID NOS. 149 and 150, for a Porcine enteric calicivirus;

(iv) SEQ ID NOS. 151 and 152, for Calicivirus strain NB; and (v) SEQ ID NOS. 153 and 154, for a Norwalk virus.

For treatment of the Hepevirus, Hepatitis E virus, the targeting sequence is complementary to a region associated with stem-loop secondary structure within the sequence identified as SEQ ID NO: 155. Exemplary targeting sequences include SEQ ID NOS: 156 and 157, or portions thereof that overlap with one or more regions of secondary structure in the associated target sequence.

For treatment of a Rubivirus or Alphavirus the targeting sequence is complementary to a region associated with stem-loop secondary structure within one of the following sequences:

(i) SEQ ID NO. 158, for Rubella virus;

(ii) SEQ ID NO. 159, for Eastern equine encephalitis virus;

(iii) SEQ ID NO. 160, for Western equine encephalitis virus; and (iv) SEQ ID NO. 161, for Venezuelan equine encephalitis virus.

Exemplary targeting sequences for each of these viruses are identified by the following sequence ID numbers, or portions of these sequences that overlap with one or more regions of duplex secondary structure in the associated target sequence:

(i) SEQ ID NOS. 162 and 163, for Rubella virus;

(ii) SEQ ID NOS. 164 and 165, for Eastern equine encephalitis virus;

(iii) SEQ ID NOS. 166 and 167, for Western equine encephalitis virus; and (iv) SEQ ID NOS. 168 and 169, for Venezuelan equine encephalitis virus For treatment of a Coronavirus or Arterivirus, the targeting sequence is complementary to a region associated with stem-loop secondary structure within one of the following sequences:

(i) SEQ ID NO. 170, for SARS coronavirus TOR2;

(ii) SEQ ID NO. 171, for Porcine epidemic diarrhea virus;

(iii) SEQ ID NO. 172, for Transmissible gastroenteritis virus;

(iv) SEQ ID NO. 173, for Bovine coronavirus;

(v) SEQ ID NO. 174, for Human coronavirus 229E;

(vi) SEQ ID NO. 175, for Murine hepatitis virus; and (vii) SEQ ID NO. 176, for Porcine reproductive and respiratory syndrome virus.

Exemplary targeting sequences for each of these viruses are identified by the following sequence ID numbers, or portions of these sequences that overlap with one or more regions of duplex secondary structure in the associated target sequence:

(i) SEQ ID NOS. 177 and 178, for SARS coronavirus TOR2;

(ii) SEQ ID NOS. 179 and 180, for Porcine epidemic diarrhea virus;

(iii) SEQ ID NOS. 181 and 182, for Transmissible gastroenteritis virus;

(iv) SEQ ID NOS. 183 and 184, for Bovine coronavirus;

(v) SEQ ID NOS. 185 and 186, for Human coronavirus 229E;

(vi) SEQ ID NOS. 187 and 188, for Murine hepatitis virus; and (vii) SEQ ID NOS. 189 and 190, for Porcine reproductive and respiratory syndrome virus.

For treatment of a Mamastrovirus, Human astrovirus, the targeting sequence is complementary to a region associated with stem-loop secondary structure within the sequence identified as SEQ ID NO: 191. Exemplary targeting sequences are SEQ ID NOS. 193 and 194, or portions of these sequences that overlap with one or more regions of duplex secondary structure in the associated target sequence.

For treatment of an Equine arteritis virus, the targeting sequence is complementary to a region associated with stem-loop secondary structure within the sequence identified as SEQ ID NO: 192. Exemplary targeting sequences are SEQ ID NOs. 195, 196, or portions of these sequences that overlap with one or more regions of duplex secondary structure in the associated target sequence.

In a method for selectively inhibiting HIV-1 replication in activated, HIV-infected human hematopoietic cells, e.g., macrophage or T lymphocyte cells, such activated, HIV-1 infected cells are exposed to an antisense oligomer as described herein, having at least one cationic intersubunit linkage as described herein, and preferably containing 20% to 50% such cationic linkages, and having a base sequence that is substantially complementary to a viral target sequence composed of at least 12 contiguous bases in a region of HIV-1 positive strand RNA identified by one of the sequences selected from the group consisting of SEQ ID NOs: 197-199, preferably.

In one embodiment, the oligomer is capable of hybridizing with a region of SEQ ID NO: 197, to inhibit the synthesis of the HIV Vif protein in the infected cells. The compound in this embodiment may have at least 12 contiguous bases from one of the sequences selected from the group consisting of SEQ ID NOs:200-203.

In another embodiment, the oligomer is capable of hybridizing with a region of SEQ ID NO:18, to inhibit the transcription of HIV mRNA transcripts. The compound in this embodiment may have at least 12 contiguous bases from the sequences identified as SEQ ID NOs:204 and 205.

In another embodiment, the oligomer is capable of hybridizing with a region of SEQ ID NO: 19, to inhibit reverse transcription of viral RNA by blocking the minus-strand transfer step. The compound in this embodiment may have at least 12 contiguous bases from the sequence identified as SEQ ID NO:206.

In another embodiment, the oligomer can be used in a method of inhibiting replication of a nidovirus in human cells, by exposing the cells to an oligomer as described herein, containing at least one cationic intersubunit linkage, and preferably containing 20% to 50% such cationic linkages, in an amount sufficient to inhibit nidovirus replication in the virus-infected cells. The oligomer has a sequence that is complementary to at least 8 bases contained in a sequence in a 5' leader sequence of the nidovirus' positive-strand genomic RNA from the group SEQ ID NOs: 207-209, each sequence of which includes an internal leader transcriptional regulatory sequence; and The oligomer is capable of forming with the nidovirus positive-strand genomic RNA a heteroduplex structure characterized by (1) a Tm of dissociation of at least 45° C., and (2) a disrupted base pairing between the transcriptional regulatory sequences in the 5' leader region of the positive-strand viral genome and negative-strand 3' subgenomic region.

The compound sequence may be complementary to at least a portion of the transcriptional regulatory sequence contained within one of the sequences SEQ ID NOS: 207-209. Exemplary compound sequences in this embodiment include SEQ ID NOs: 210-214. For use in inhibiting replication of human SARS virus, the compound may contain one of sequences SEQ ID NOs: 213 and 214. For use in inhibiting replication of human coronavius-229E or human coronavirus-OC43, the compound may contain one of the sequences SEQ ID NOS: 210 or 211, for the coronavirus-229E, and the sequence SEQ ID NO: 212, for the coronavirus-OC43.

For use in treating a nidovirus infection in a human subject, the compound may be administered orally to the subject, or by pulmonary delivery, to contact the compound with the virus-infected cells.

In another embodiment, the oligomer can be used in a method of inducing human dendritic cells to a condition of reduced capacity for antigen-specific activation of T cells, and, in mature dendritic cells, increased production of extracellular IL-10. The method includes exposing a population of human dendritic cells to an oligomer as described herein, containing at least one cationic intersubunit linkage, and preferably containing 20% to 50% such cationic linkages, and containing a base sequence effective to hybridize to an expression-sensitive region of a preprocessed or processed human CD-86 transcript identified, in its processed form, by SEQ ID NO: 215, to form, between the compound and transcript, a heteroduplex structure having a Tm of at least 45° C. The heteroduplex formation blocks expression of full-length CD86 in the cells, which in turn, produces inhibition of the expression of full-length CD86 on the surface of dendritic cells, and produces enhanced expression of extracellular IL-10 by mature dendritic cells.

Where the antisense oligomer is effective to hybridize to an expression-sensitive target region adjacent the start site of the processed human CD86 transcript, the oligomer may have a base sequence that is complementary to a target region containing at least 12 contiguous bases in a processed human CD86 transcript identified by SEQ ID NO: 216, where the compound is effective to block translation of the processed transcript. The antisense compound may have, for example, one of the base sequences identified by SEQ ID NOs: 48-50.

Where the antisense oligomer is effective to hybridize to a splice site of preprocessed human CD86, the compound may have a base sequence that is complementary to at least 12 contiguous bases of a splice site in a preprocessed human CD86 transcript, where the compound is effective to block processing of a preprocessed CD86 transcript to produce a full-length, processed CD 86 transcript. The splice site in the preprocessed CD86 transcript may have one of the sequences identified by SEQ ID NOs: 217-220. The antisense compound may have, for example, one of the base sequences identified by SEQ ID NOs: 51-54.

For use in inhibiting transplantation rejection in a human subject receiving an allograft tissue or organ, the oligomer is administered to the subject in an amount effective to inhibit the rate and extent of rejection of the transplant. The compound may be administered both prior to and following the allograft tissue or organ transplantation in the subject, and compound administration may be carried out for a selected period of 1-3 weeks. The compound may be further administered to the subject, as needed, to control the extent of transplantation rejection in the subject.

For use in treating an autoimmune condition in a human subject, the oligomer may be administered to the subject, in an amount effective to reduce the severity of the autoimmune condition. The compound may be administered over an extended period of time, as needed, to control the severity of the autoimmune condition in the subject.

In another embodiment, the oligomer can be used in a method of inhibiting replication within a host cell of an RNA virus having a single-stranded, negative sense genome and selected from the Orthomyxoviridae family including the Influenzavirus A, Influenzavirus B and Influenzavirus C genera. The host cell is contacted with an oligomer as described herein, containing at least one cationic intersubunit linkage, and preferably containing 20% to 50% such cationic linkages, and containing a base sequence effective to hybridize to a target region selected from the following: i) the 5' or 3' terminal 25 bases of a negative sense viral RNA segment of Influenzavirus A, Influenzavirus B and Influenzavirus C, ii) the terminal 30 bases of the 3' terminus of a positive sense cRNA of Influenzavirus A, Influenzavirus B and Influenzavirus C, and iii) the 50 bases surrounding the AUG start codon of an influenza viral mRNA.

The oligomer may be administered to a mammalian subject infected with the influenza virus, or at risk of infection with the influenza virus.

For treatment of Influenza A virus, the targeting sequence hybridizes to a region associated with one of the group of sequences identified as SEQ ID NOs: 221 and 222. Preferred targeting sequences are those complementary to either the minus strand target of SEQ ID NO: 222 or the positive-strand target of SEQ ID NO: 221. Exemplary antisense oligomers that target these two regions are listed as SEQ ID NOs: 223 and 224, respectively.

In another embodiment, one or more oligomers as described herein can be used in a method of in inhibiting replication within a host cell of an Ebola virus or Marburg virus, by contacting the cell with an oligomer as described herein, containing at least one cationic intersubunit linkage, and preferably containing 20% to 50% such cationic linkages, and having a targeting base sequence that is complementary to a target sequence composed of at least 12 contiguous bases within an AUG start-site region of a positive-strand mRNA identified by one of the Filovirus mRNA sequences selected from the group consisting of SEQ ID NOs: 250-255.

For treating an Ebola virus infection, the compound may have a targeting sequence that is complementary to a target sequence composed of at least 12 contiguous bases within the VP35 AUG start-site region identified by a target sequence selected from the group consisting of SEQ ID NOS:250. An exemplary targeting sequence is identified by SEQ ID NO: 1.

In another embodiment for treating an Ebola virus infection, the compound may have a targeting sequence that is complementary to a target sequence composed of at least 12 contiguous bases within the VP24 AUG or L AUG start-site regions identified by a target sequence selected from the group consisting of SEQ ID NOS:251 and 252, respectively. Exemplary targeting sequences include SEQ ID NO: 5 and 11, respectively.

For treating a Marburg virus infection, the compound may have a targeting sequence that is complementary to a target sequence composed of at least 12 contiguous bases within the VP35 AUG start-site region identified by a target sequence identified by SEQ ID NO: 253. An exemplary targeting sequence is selected from the group consisting of SEQ ID NOs: 256 and 257.

In another embodiment for treating a Marburg virus infection, the compound may have a targeting sequence that is complementary to a target sequence composed of at least 12 contiguous bases within the VP24 AUG or L AUG start-site regions identified by a target sequence selected from the group identified by SEQ ID NOs: 254 and 255, respectively. Exemplary targeting sequences are identified by SEQ ID NOs: 258-260.

The oligomers disclosed herein may also be used in a method of treating an Ebola or Marburg Filovirus infection in a subject, by administering to the subject, a therapeutically effective amount of an oligomer having a targeting sequence as described above; or in a method of vaccinating a mammalian subject against Ebola virus, by pretreating the subject with an oligomer as described herein and having a targeting sequence as described above, and exposing the subject to the Ebola virus, preferably in an attenuated form.

In another embodiment, an oligomer as described herein can be used in a method for treating loss of skeletal muscle mass in a human subject. The steps in the method entail
(a) measuring blood or tissue levels of myostatin in the subject,
(b) administering to the subject, a myostatin-expression-inhibiting amount of an oligomer as described herein, containing at least one cationic intersubunit linkage, and preferably containing 20% to 50% such cationic linkages, and having a base sequence effective to hybridize to an expression-sensitive region of processed or preprocessed human myostatin RNA transcript, identified, in its processed form, by SEQ ID NO: 225;
(c) by this administering, forming within target muscle cells in the subject, a base-paired heteroduplex structure composed of human myostatin RNA transcript and the antisense compound and having a Tm of dissociation of at least 45° C., thereby inhibiting expression of myostatin in said cells;
(d) at a selected time following administering the antisense compound, measuring a blood or tissue level of myostatin in the subject; and
(e) repeating the administering, using the myostatin levels measured in (d) to adjust the dose or dosing schedule of the amount of antisense compound administered, if necessary, so as to reduce measured levels of myostatin over those initially measured and maintain such levels of myostatin measured in step (d) within a range determined for normal, healthy individuals.

Where the antisense oligomer is effective to hybridize to a splice site of preprocessed human myostatin transcript, it has a base sequence that is complementary to at least 12 contiguous bases of a splice site in a preprocessed human myostatin transcript, and formation of the heteroduplex in step (c) is effective to block processing of a preprocessed myostatin transcript to produce a full-length, processed myostatin transcript. The splice site in the preprocessed myostatin transcript may have one of the sequences identified as SEQ ID NOs: 226-229. Exemplary antisense sequences are those identified by SEQ ID NOs: 230-233.

In another embodiment, an oligomer as described herein can be used in a method for inhibiting viral infection in mammalian cells by an Enterovirus or Rhinovirus in the Picornaviridae family. The method comprises exposing the cells to an antisense oligomer as described herein, containing at least one cationic intersubunit linkage, and preferably containing 20% to 50% such cationic linkages, and having a targeting sequence of at least 12 subunits complementary to SEQ ID NO: 55 or SEQ ID NO: 56 in the positive-sense strand of the virus, thereby to form a heteroduplex structure composed of the virus' positive sense strand and the oligomer, characterized by a Tm of dissociation of at least 45° C. The oligomer may have a sequence contained in SEQ ID NO: 234, such as one of the sequences identified by SEQ ID NOs: 235-237. Alternatively, the oligomer may have a sequence contained in SEQ ID NO: 238, such as one of the sequences identified by SEQ ID NOs: 239-245.

For use in treating a mammalian subject infected by an Enterovirus or Rhinovirus in the Picornaviridae family, the oligomer is administered to the subject in a pharmaceutically effective amount. Compound administration may be continued until a significant reduction in viral infection or the symptoms thereof is observed. For use in treating a mammalian subject at risk of infection by an Enterovirus or Rhinovirus in the Picornaviridae family, the oligomer is administered to the subject in an amount effective to inhibit infection of subject host cells by the virus.

In another embodiment, an oligomer as described herein can be used in a method for suppressing an immune response in a mammalian subject, e.g. for the treatment or prevention of an autoimmune condition or transplantation rejection, by administering to the subject a pharmaceutically effective amount of an oligomer as described herein, containing at least one cationic intersubunit linkage, and preferably containing 20% to 50% such cationic linkages, and having a targeting sequence of at least 12 subunits that is complementary to at least 12 subunits of a target sequence identified by SEQ ID NO: 246, spanning the splice junction between intron 1 and exon 2 of preprocessed T cell antigen-4 (CTLA-4) mRNA of the subject. The compound is capable of reacting with the preprocessed CTLA-4 mRNA in mammalian cells to form a heteroduplex (i) characterized by a Tm of dissociation of at least 45° C., and (ii) effective to increase the ratio of processed mRNA encoding ligand-independent CTLA-4 to processed mRNA encoding full-length CTLA-4 in the cells.

For the prevention of transplantation rejection in a human subject scheduled to receive a allogeneic organ transplantation, compound administration may be initiated at least one week before the scheduled transplantation. For the treatment of an autoimmune condition, the compound administration may be continued until a desired improvement in autoimmune condition is observed.

BRIEF DESCRIPTION OF THE FIGURES

FIG. 2A shows representative morpholino subunits 1a-e with protected recognition moieties Pi of A, C, G, T, and I.

FIG. 2N illustrates the introduction of guanidinium groups into morpholino oligomers by incorporation of guanidino acids at both backbone and terminal positions.

FIG. 2O illustrates the introduction of peptides into the backbone morpholino oligomers.

FIG. 11A shows concentration dependent effects up to 10 µM, and FIG. 11B shows concentration dependent effects up to 100 µM.

DETAILED DESCRIPTION

I. Definitions

Figure 1C:
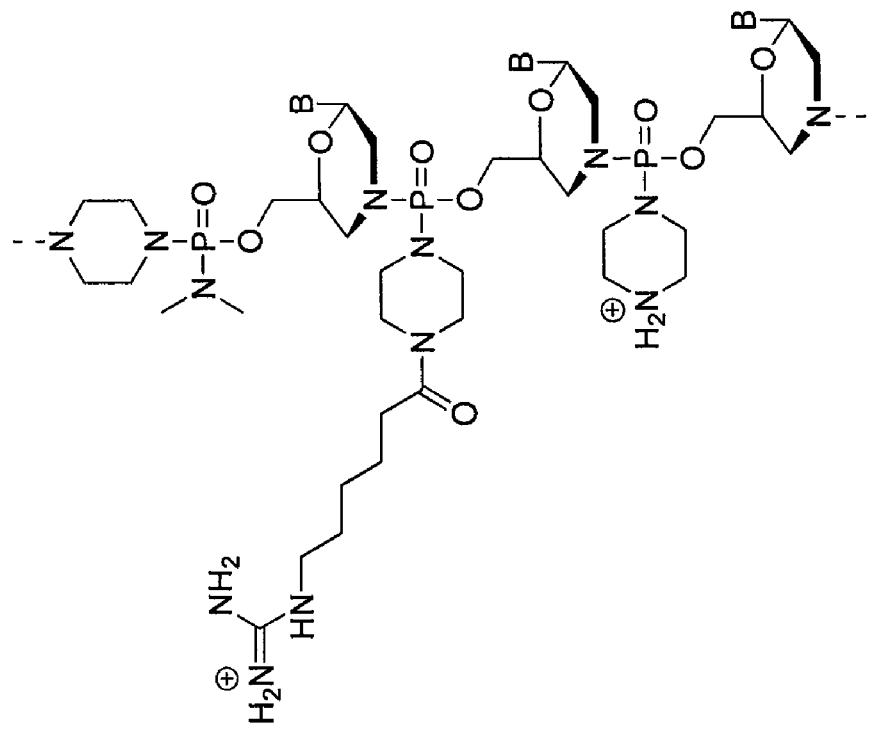
FIGS. 1B and 1C illustrate exemplary cationic linkage structures of the invention, where each B is independently a base-pairing moiety.

The terms below, as used herein, have the following meanings, unless indicated otherwise:

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligomer is composed of morpholino subunit structures linked together by (thio)phosphoramidate or (thio)phosphorodiamidate linkages, joining the morpholino nitrogen of one subunit to the 5' exocyclic carbon of an adjacent subunit, each subunit including a purine or pyrimidine base-pairing moiety effective to bind, by base-specific hydrogen bonding, to a base in a polynucleotide. Morpholino oligomers (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

A "phosphoramidate" group comprises phosphorus having three attached oxygen atoms and one attached nitrogen atom, while a "phosphorodiamidate" group (see e.g. FIGS. 1A-B) comprises phosphorus having two attached oxygen atoms and two attached nitrogen atoms. In the uncharged or the cationic intersubunit linkages of the oligomers described herein, one nitrogen is always pendant to the backbone chain. The second nitrogen, in a phosphorodiamidate linkage, is typically the ring nitrogen in a morpholino ring structure (again, see FIGS. 1A-B).

In a thiophosphoramidate or thiophosphorodiamidate linkage, one oxygen atom, typically the oxygen pendant to the backbone in the oligomers described herein, is replaced with sulfur. The terms "charged", "uncharged", "cationic" and "anionic" as used herein refer to the predominant state of a chemical moiety at near-neutral pH, e.g. about 6 to 8. Preferably, the term refers to the predominant state of the chemical moiety at physiological pH, that is, about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms, or 1-2 carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and preferably non-polar groups such as methyl, ethyl, methoxy, ethoxy, hydroxy, or fluoro.

An oligonucleotide or antisense oligomer "specifically hybridizes" to a target polynucleotide if the oligomer hybridizes to the target under physiological conditions, with a Tm greater than 37° C. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987).

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either a cytosine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "amino acid subunit" is preferably an α-amino acid residue (—CO—CHR—NH—); it may also be a β- or other amino acid residue (e.g. —CO—CH$_2$CHR—NH—), where R is a side chain.

The term "naturally occurring amino acid" refers to an amino acid present in proteins found in nature. The term "non-natural amino acids" refers to those amino acids not present in proteins found in nature; examples include beta-alanine (β-Ala) and 6-aminohexanoic acid (Ahx).

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Structural Features of Subject Oligomers

A. Oligomers with Cationic Intersubunit Linkages

The invention provides, in one aspect, an oligomer comprising a backbone consisting of a sequence of morpholino ring structures joined by intersubunit linkages, where each such ring structure supports a base-pairing moiety, such that said oligomer can bind in a sequence-specific manner to a target nucleic acid, and where at least one intersubunit linkage between two consecutive such ring structures contains a pendant cationic group. The pendant group bears a distal nitrogen atom that can bear a positive charge at neutral or near-neutral (e.g. physiological) pH.

The intersubunit linkages are preferably phosphorus-containing linkages, having the structure:

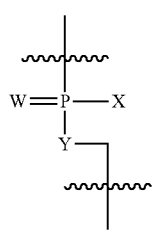

where
W is S or O, and is preferably O,
X=NR$^1$R$^2$ or OR$^6$,
Y=O or NR$^7$,
and each said linkage in the oligomer is selected from:
(a) uncharged linkage (a), where each of R$^1$, R$^2$, R$^6$ and R$^7$ is independently selected from hydrogen and lower alkyl;

(b1) cationic linkage (b1), where X=NR$^1$R$^2$ and Y=O, and NR$^1$R$^2$ represents an optionally substituted piperazino group, such that R$^1$R$^2$=—CHRCHRN(R$^3$)(R$^4$)CHRCHR—, where
each R is independently H or CH$_3$,
R$^4$ is H, CH$_3$, or an electron pair, and
R$^3$ is selected from H, lower alkyl, e.g. CH$_3$, C(=NH)NH$_2$, Z-L-NHC(=NH)NH$_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where X=NR$^1$R$^2$ and Y=O, R$^1$=H or CH$_3$, and R$^2$=LNR$^3$R$^4$R$^5$, where L, R$^3$, and R$^4$ are as defined above, and R$^5$ is H, lower alkyl, or lower (alkoxy) alkyl; and (b3) cationic linkage (b3), where Y=NR$^7$ and X=OR$^6$, and R$^7$=LNR$^3$R$^4$R$^5$, where L, R$^3$, R$^4$ and R$^5$ are as defined above, and R$^5$ is H or lower alkyl;

and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 80%, 10% to 50%, or 10% to 35% of the linkages may be cationic linkages.

In one embodiment, at least one linkage is of type (b1), where, preferably, each R is H, R$^4$ is H, CH$_3$, or an electron pair, and R$^3$ is selected from H, lower alkyl, e.g. CH$_3$, C(=NH)NH$_2$, and C(O)-L-NHC(=NH)NH$_2$. The latter two embodiments of R$^3$ provide a guanidino moiety, either attached directly to the piperazine ring, or pendant to a linker group L, respectively. For ease of synthesis, the variable Z in R$^3$ is preferably C(O) (carbonyl), as shown.

The linker group L, as noted above, contains bonds in its backbone selected from alkyl (e.g. —CH$_2$—CH$_2$—), alkoxy (—C—O—), and alkylamino (e.g. —CH$_2$—NH—), with the proviso that the terminal atoms in L (e.g., those adjacent to carbonyl or nitrogen) are carbon atoms. Although branched linkages (e.g. —CH$_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The morpholino subunits have the structure (i):

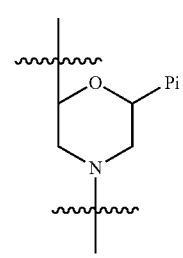

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

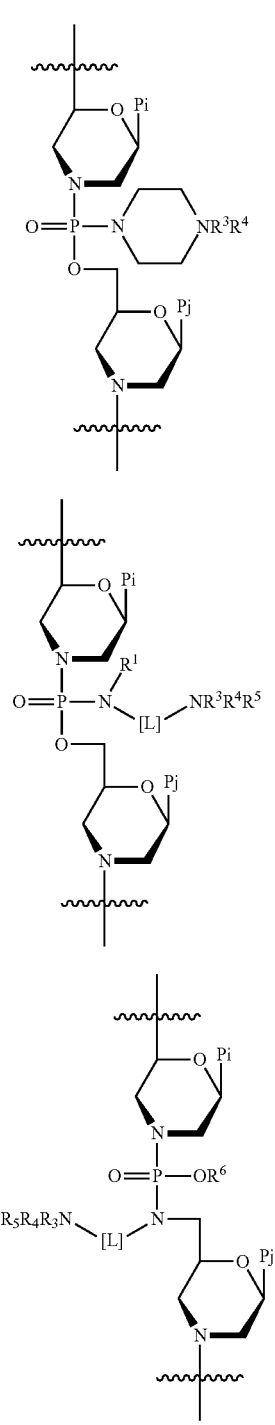

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1') is referred to herein as a "Pip" linkage and (b1") is referred to herein as a "GuX" linkage:

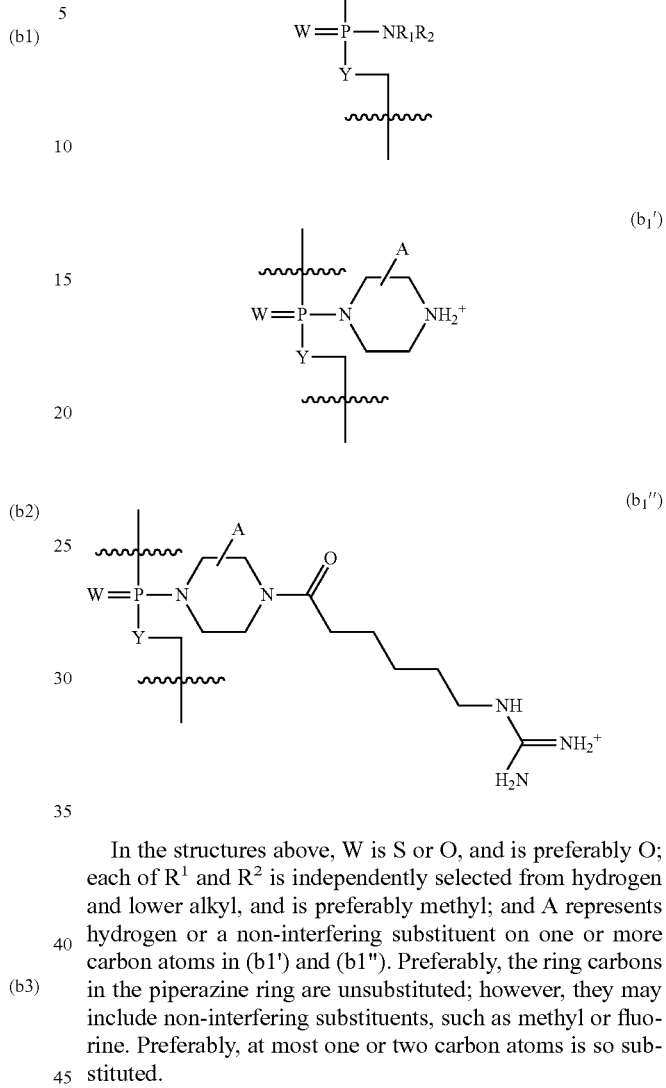

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 20% to 80%, 20% to 50%, or 20% to 30% of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage (see e.g. FIG. 2G) or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 5, 10, 20, 30, 40, 50, 60, 70, 80 or 90 percent cationic linkages. In selected embodiments, about 10 to 80, 20 to 80, 20 to 60, 20 to 50, 20 to 40, or about 20 to 35 percent of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 15 to 25 subunits. For example, an oligomer of the invention having 19-20 subunits, a useful length for an antisense oligomer, may ideally have two to seven, e.g. four to six, or three to five, cationic linkages, and the remainder uncharged linkages. An oligomer having 14-15 subunits may ideally have two to five, e.g. 3 or 4, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

As noted above, the substantially uncharged oligonucleotide may be modified, in accordance with an aspect of the invention, to include one or more charged linkages, e.g. up to about 1 per every 2-5 uncharged linkages, typically 3-5 per every 10 uncharged linkages. Optimal improvement in antisense activity is seen where up to about half of the backbone linkages are cationic. Some, but not maximum enhancement is typically seen with a small number e.g., 10-20% cationic linkages; where the number of cationic linkages exceeds 50-60%, the sequence specificity of the antisense binding to its target may be compromised or lost.

Additional experiments conducted in support of the present invention indicate that the enhancement seen with added cationic backbone charges may, in some case, be further enhanced by distributing the bulk of the charges close of the "center-region" backbone linkages of the antisense oligonucleotide, e.g., in a 20mer oligonucleotide with 8 cationic backbone linkages, having 70%-100% of these charged linkages localized in the 10 centermost linkages.

B. Peptide Transporters

The subject oligomer may also be conjugated to a peptide transport moiety which is effective to enhance transport of the oligomer into cells. The transport moiety is preferably attached to a terminus of the oligomer, as shown, for example, in FIG. 1D, as well as FIGS. 2P-2Q.

Preferably, the transport moiety comprises 6 to 16 amino acids and is composed of subsequences selected from the group represented by (X'Y'X'), (X'Y'), (X'Z'), and (X'Z'Z'), where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral linear amino acid —C(O)—(CHR)$_n$—NH—, where n is 1 to 7 and each R is independently H or methyl; and (c) each Z' subunit independently represents an α-amino acid having a neutral aralkyl side chain.

As used herein, a carrier protein is "composed of the subsequences selected from the group represented by X'Y'X', X'Y', X'Z'Z' and X'Z'" if substantially all of its amino acids can be represented by a non-overlapping series of the subsequences, or positional variations thereof, e.g., (X'X'Y')$_n$, (X'Y'X')$_n$, (Y'X'X')$_n$, (Y'X')$_n$, (X'Y')(X'X'Y')(X'Y')(X'X'Y'), (X'Y')$_n$(X'X'Y')$_m$, (X'FF)$_n$ or (FFX')$_n$. The protein may accommodate a small number, e.g., 1-3, of neutral amino acids other than Y.

In selected embodiments, the peptide comprises a sequence which consists of at least two, or at least three, repeats of a single subsequence selected from (X'Y'X'), (X'Y'), (X'Z'), and (X'Z'Z'). For example, the peptide may comprise a sequence represented by one of (X'Y'X')$_p$, (X'Y')$_m$, and (X'Z'Z')$_p$, where p is 2 to 5 and m is 2 to 8.

In selected embodiments, for each X', the side chain moiety is independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-aminopyrimidonyl, and it is preferably selected from guanidyl and amidinyl.

In preferred embodiments, for each X', the side chain moiety is guanidyl, as in the amino acid subunit arginine (Arg). In further embodiments, each Y' is —CO—(CH$_2$)$_n$—R—NH—, where n is 1 to 7 and R is H. For example, when n is 5 and R is H, Y' is a 6-aminohexanoic acid subunit, abbreviated herein as Ahx; when n is 2 and R is H, Y' is a β-alanine subunit. The aralkyl side chain of the Z' subunit is preferably benzyl (—CH$_2$C$_6$H$_6$) or phenethyl (—CH$_2$CH$_2$C$_6$H$_6$), which are preferably not further substituted but may include a non-interfering substituent as defined herein. Preferably, the side chain is benzyl (—CH$_2$C$_6$H$_6$), such that each Z' is phenylalanine (F).

Preferred peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In one embodiment, Y' is a 6-aminohexanoic acid subunit, R is arginine, and p is 4. In a further embodiment, the peptide comprises a sequence represented by (X'Z'Z')$_p$, where R is arginine, each Z' is phenylalanine, and p is 3 or 4.

Figure 1B:
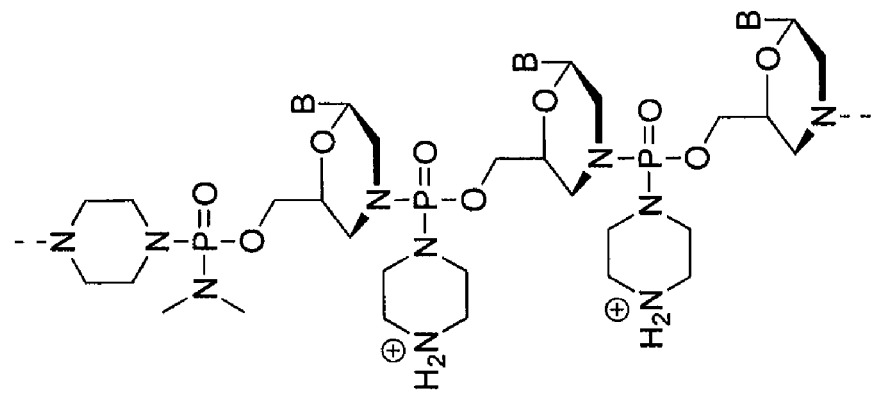
Figure 1A:
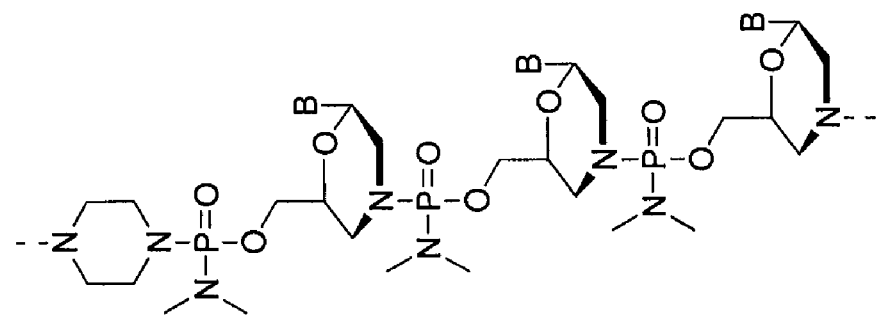
FIG. 1A illustrates an exemplary uncharged linkage structure.
Figure 1D:
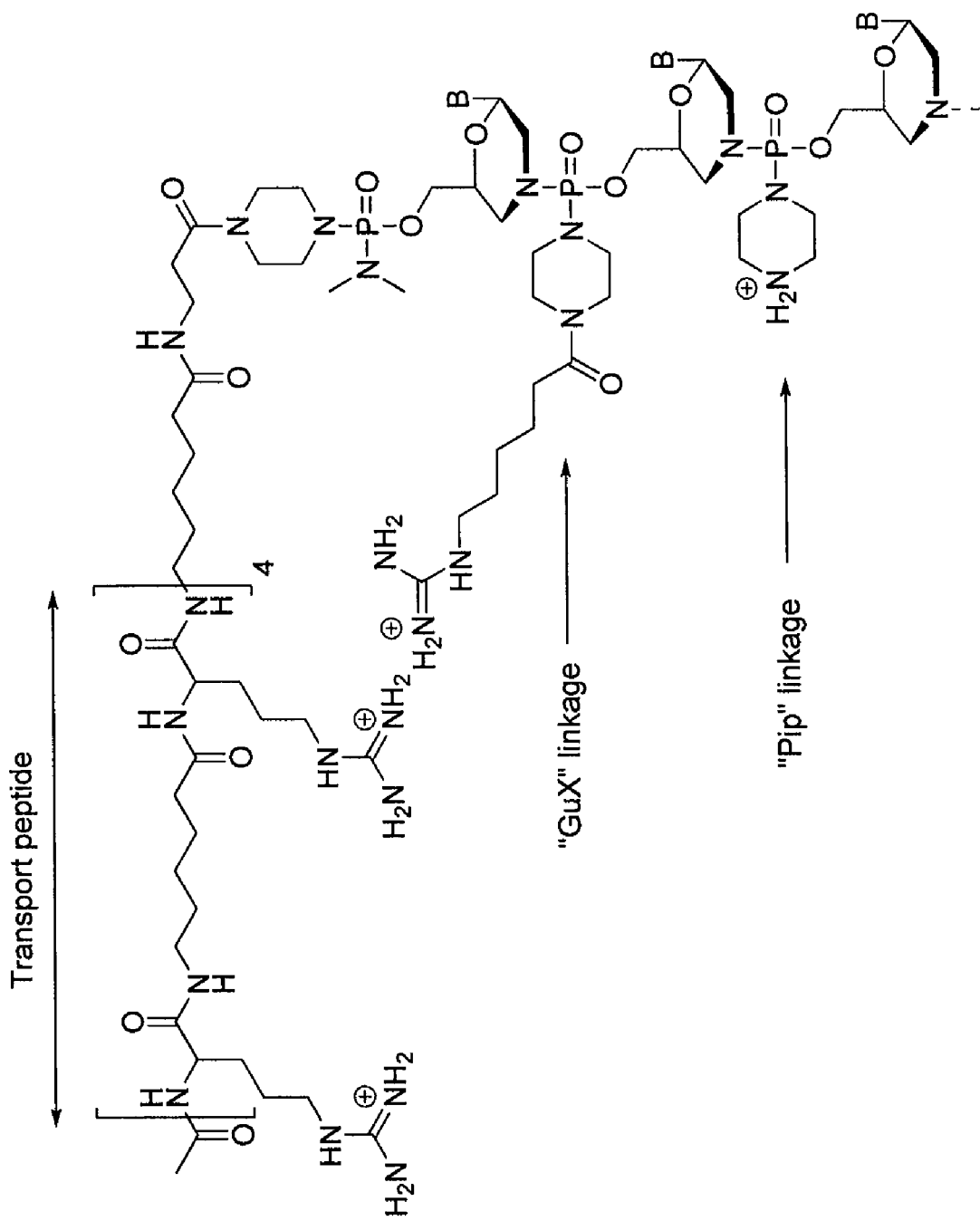
FIG. 1D illustrates a morpholino oligomer containing exemplary cationic intersubunit linkages and conjugated at a terminus to an arginine-rich peptide transport moiety. (Though multiple cationic linkage types are illustrated in FIGS. 1C and 1D, an oligomer will typically include one type of cationic linkage.)

The conjugated peptide is preferably linked to a terminus of the oligomer via a linker Ahx-B, where Ahx is a 6-aminohexanoic acid subunit and B is a β-alanine subunit, as shown, for example, in FIG. 1D.

The Y' subunits are either contiguous, in that no X' subunits intervene between Y' subunits, or interspersed singly between X' subunits. However, the linking subunit may be between Y' subunits. In one embodiment, the Y' subunits are at a terminus of the transporter; in other embodiments, they are flanked by X' subunits.

In further preferred embodiments, each Y' is —CO—(CH$_2$), CHR—NH—, where n is 1 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx.

Another preferred embodiment includes arginine subunits alternating with single Y' subunits ((RY')$_m$), where Y' is selected from β-alanine and Ahx; an example is given as SEQ ID NO: 285 below.

The nucleic acid analog is preferably linked to the transporter peptide at the C-terminus, as shown, for example, in FIG. 1D. A preferred linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense oligomer and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

Exemplary peptide transporters, including linkers (B or AhxB) are given below:

| Peptide | Sequence (N-terminal to C-terminal) | SEQ ID NO: |
| --- | --- | --- |
| (RRAhx)$_4$B | RRAhxRRAhxRRAhxRRAhxB | 278 |
| (RAhxR)$_4$AhxB | RAhxRRAhxRRAhxRRAhxRAhxB | 279 |
| (AhxRR)$_4$AhxB | AhxRRAhxRRAhxRRAhxRRAhxB | 280 |
| (RAhx)$_6$B | RAhxRAhxRAhxRAhxRAhxRAhxB | 281 |
| (RAhx)$_8$B | RAhxRAhxRAhxRAhxRAhxRAhxRAhxRAhxB | 282 |
| (RAhxR)$_3$AhxB | RAhxRRAhxRRAhxR AhxB | 283 |
| (RAhxRRBR)$_2$AhxB | RAhxRRBRRAhxRRBRAhxB | 284 |
| ((RB)3RAhx)2B | RBRBRBRAhxRBRBRBRAhxB | 285 |

III. Antisense Activity of Subject Oligomers

As shown herein, the partially cationic oligomers, such as +PMO, have higher affinity for DNA and RNA than do the corresponding neutral compounds, demonstrated by enhanced antisense activity in vitro and in vivo.

A. In Vitro Activity in Cell Free Assays

The oligomers of the invention were shown to provide superior antisense activity to fully uncharged oligomers when directed to a variety of different targets. In a first series of experiments, various PMO's (uncharged) and +PMO's (partially cationic) targeting different regions of EBOV (Ebola virus) mRNA, including the VP35 and L gene mRNA and two different regions of the VP24 mRNA, were prepared, as described in Materials and Methods. The sequences are shown as SEQ ID NOs: 1-15 in the Sequence Listing Table below, with the cationic (1-piperazino) phosphinylideneoxy linkage (as shown in FIG. 1B) at each position indicated with a "+" in the Sequence Listing table.

Cell free translation assays were performed using the appropriate EBOV:luciferase mRNA, prepared as described in Materials and Methods, as the input RNA. PMOs and +PMOs were evaluated for their ability to inhibit luciferase expression, based on luciferase light emission (n=3 per PMO concentration).

Figure 3:
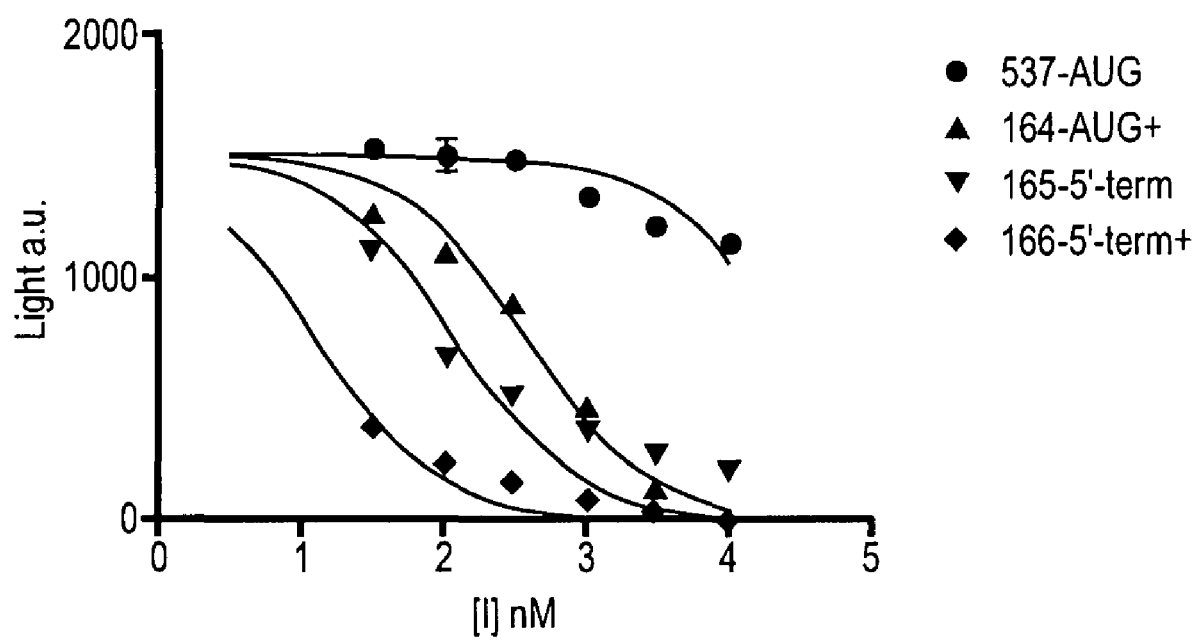
FIG. 3 shows the increased antisense activity of +PMO with cationic linkages targeting the EBOV VP24 mRNA compared to uncharged PMO in a cell free translation assay. +PMO used were VP24-8+ (SEQ ID NO:10) and VP245'trm6+ (SEQ ID NO:9) with 8 and 6 cationic linkages, respectively, compared to their uncharged PMO counterparts (SEQ ID NOs: 5 and 15, respectively).

The results for the oligomers targeting VP24:luciferase mRNA (SEQ ID NOs: 9 and 10) are shown in FIG. 3. Compared to the uncharged PMOs with the same base sequence (SEQ ID NOs: 15 and 5, respectively), the +PMOs with 6 to 8 cationic linkages demonstrated 10- to 100-fold increased antisense activity.

Figure 4:
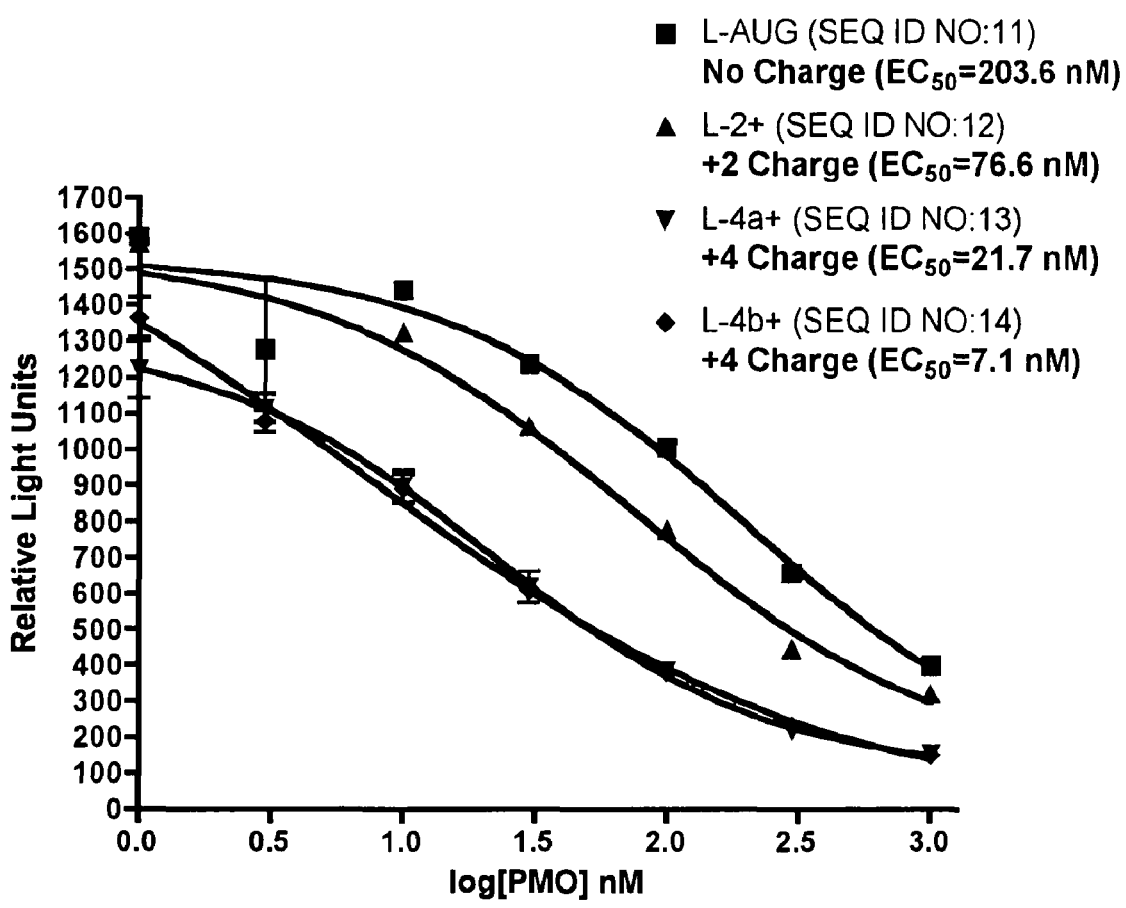
FIG. 4 shows the increased antisense activity of +PMO that target the L gene mRNA of EBOV in a cell free translation assay.

Results for similar assays employing PMOs and +PMOs targeting the VP35, VP24 and L gene mRNAs of EBOV, (SEQ ID NOS: 2-3, 6-8 and 12-14, respectively, having variable total charge and charge density as indicated in the Sequence Listing table) are shown in FIG. 4. Table 1 below lists the determined EC$_{50}$ values. In all cases, the incorporation of 2 to 4 cationic linkages in the backbone of these oligomers increased antisense activity approximately 2-30 fold.

TABLE 1

Specific inhibition of cell free translation using +PMO targeted to EBOV mRNA

| Name | SEQ ID NO | +Charge | EC$_{50}$ (nM) |
| --- | --- | --- | --- |
| VP35-AUG | 1 | 0 | 84.8 |
| VP35-2+ | 2 | 2 | 23.0 |
| VP35-4a+ | 3 | 4 | 18.7 |
| VP35-4b+ | 4 | 4 | 18.4 |
| VP24-AUG | 5 | 0 | 223.2 |
| VP24-2+ | 6 | 2 | 109.4 |
| VP24-4a+ | 7 | 4 | 47.6 |
| VP24-4b+ | 8 | 4 | 62.5 |
| L-AUG | 11 | 0 | 203.6 |
| L-2+ | 12 | 2 | 76.6 |
| L-4a+ | 13 | 4 | 21.7 |
| L-4b+ | 14 | 4 | 7.1 |

Figure 12:
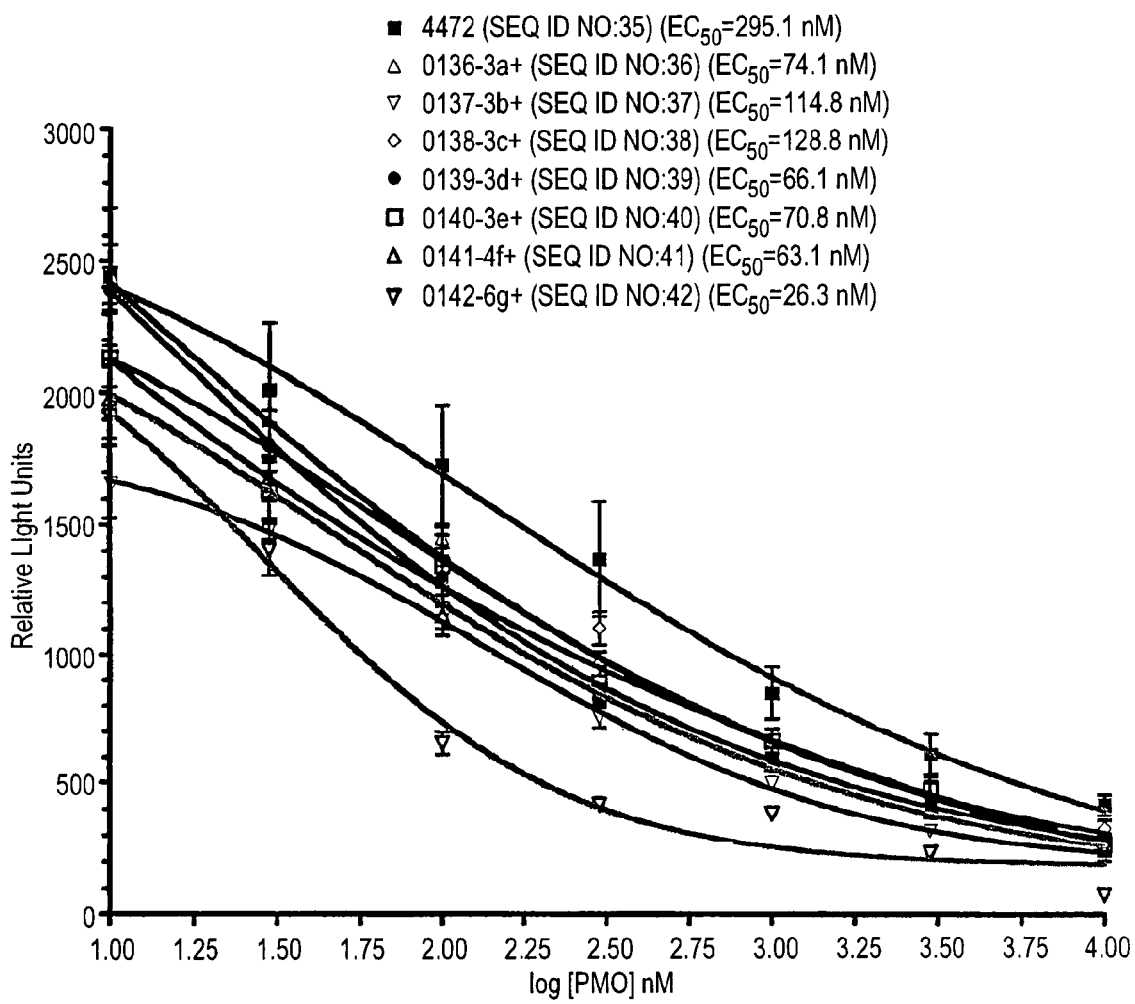
FIG. 12 is a graph of +PMO inhibition of cell free translation of the CYP3A2:luciferase fusion gene mRNA compared to the uncharged CYP3A2 PMO (SEQ ID NOs: 35-42). EC50 values for the various +PMO and PMO are also shown.

A further series of assays employed PMO and +PMO targeting the rat CYP3A2 gene start codon region (SEQ ID NOS: 35-42) to inhibit translation of a CYP3A2:luciferase fusion gene mRNA transcript. The number of cationic linkages charges in the CYP3A2+PMO series ranged from +3 to +6. The five +PMO with three cationic charges varied in the location within the oligomer of the cationic linkages. Results of the cell free translation assays are shown in FIG. 12, with the determined EC$_{50}$ values. It can be seen that the entire +PMO series demonstrated enhanced antisense activity, with as much as an 11 fold decrease in the EC$_{50}$ as compared to the uncharged PMO control (SEQ ID NO:35).

In a further experiment, a series of +PMO targeting the start codon region of hepatitis C virus (HCV; SEQ ID NOs: 19-35) were compared with the corresponding uncharged PMO (designated AVI-4065) in their ability to inhibit translation of an HCV:luciferase fusion gene transcript. As shown in the Sequence Table below, the number of cationic linkages in the HCV+PMO series ranged from +2 to +7. Cell free translation assays were performed using the HCV:luciferase mRNA as the input RNA, and the observed EC$_{50}$ values are given in Table 2 below. In all cases, relative to the uncharged AVI-4065 PMO, the addition of cationic linkages significantly lowered the observed EC$_{50}$.

TABLE 2

Specific inhibition of cell free translation using +PMO targeted to HCV mRNA

| Name | SEQ ID NO | +Charge | Description | $EC_{50}$ (nM) |
|---|---|---|---|---|
| AVI-4065 | 18 | 0 | ****************** | 850.8 |
| HCV-2a+ | 19 | +2 | ++************ | 471.0 |
| HCV-2b+ | 20 | 2 | **********+*+** | 724.4 |
| HCV-2c+ | 21 | 2 | +**************+ | 231.4 |
| HCV-2d+ | 22 | 2 | ***+**+**** | 326.3 |
| HCV-2e+ | 23 | 2 | ****++********* | 430.6 |
| HCV-2f+ | 24 | 2 | ***++********** | 656.3 |
| HCV-3g+ | 25 | 3 | *********+*+*+** | 228.9 |
| HCV-3h+ | 26 | 3 | ***+**+*+** | 583.5 |
| HCV-3i+ | 27 | 3 | +******+**+ | 427.7 |
| HCV-4j+ | 28 | 4 | ****+*+*+*+** | 315.3 |
| HCV-4k+ | 29 | 4 | +***+*+****+ | 193.1 |
| HCV-4l+ | 30 | 4 | +**+**+*+** | 314.5 |
| HCV-5m+ | 31 | 5 | ++++**+ | 146.0 |
| HCV-5n+ | 32 | 5 | +**+*++*+** | 212.0 |
| HCV-6o+ | 33 | 6 | +++++*+ | 161.7 |
| HCV-7p+ | 34 | 7 | +**+*++++*+ | 50.98 |

Figure 5:
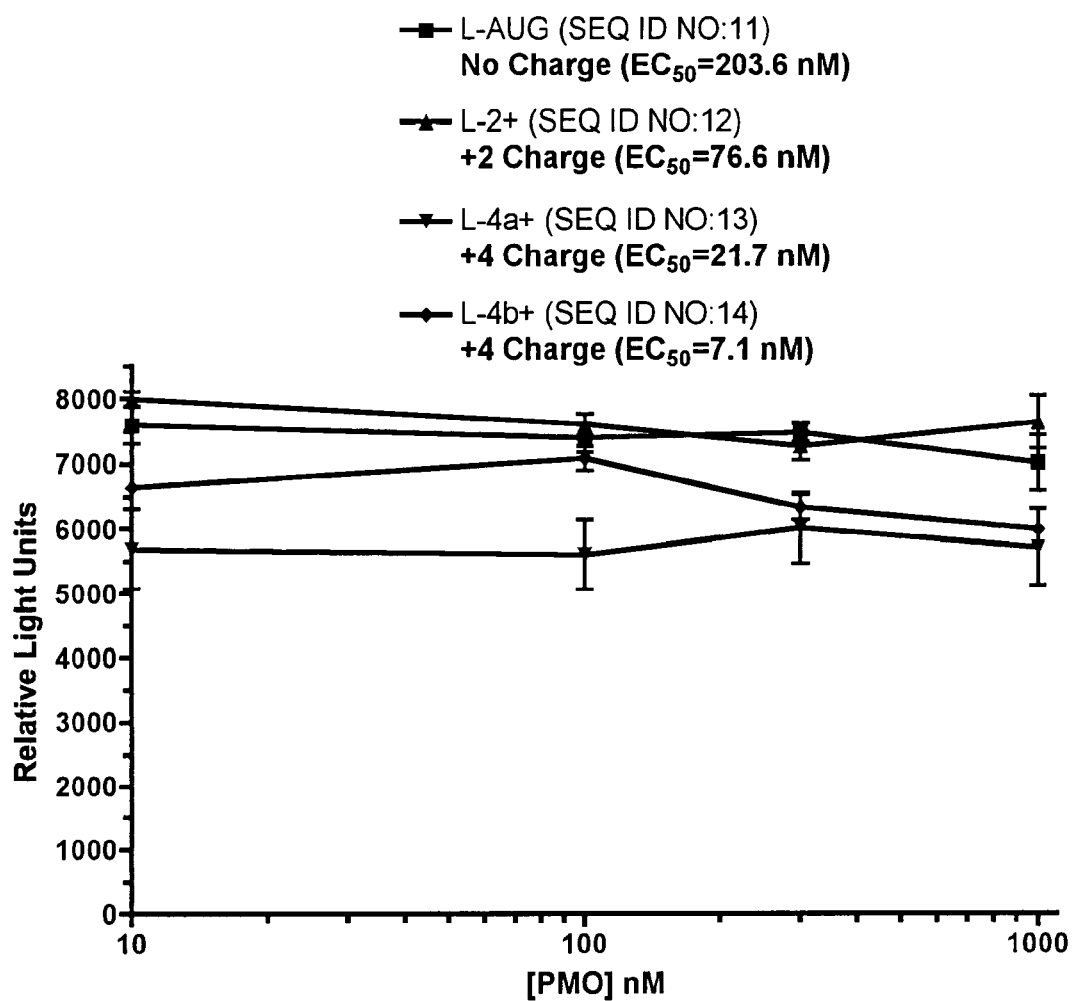
FIG. 5 shows the specificity of the +PMO that target the EBOV L gene mRNA when used in a cell free translation assay programmed with EBOV VP35:luciferase mRNA. The graph demonstrates no off-target antisense activity up to 1 mM +PMO concentration.

To evaluate the sequence specificity of the increased antisense activity of the +PMO, the +PMO were also used in cell free translation assays wherein the input mRNA did not encode a target for the +PMO. In this case, +PMO targeting the EBOV VP24 gene was used in an assay with EBOV L gene:luciferase mRNA. The results, presented in FIG. 5, demonstrate a high degree of specificity for the +PMO. +PMO concentrations higher than 30 μM were necessary before significant non-specific inhibition was observed.

B. In Vitro Activity in Cell Culture

As the data described above show, PMO+ oligomers provided a severalfold enhancement of antisense activity in cell-free assays over uncharged PMO oligomers. In an assay commonly used to assess transport and antisense activity in cell culture, HeLa cells are stably transfected with plasmid pLuc/705, which has a luciferase gene interrupted by a human β-globin intron mutated at nucleotide 705, thus causing incorrect splicing. Because the misspliced transcripts do not produce functional reporter proteins, no reporter signals are observed unless wild-type splicing is induced with a splice-correcting antisense oligomer. An antisense oligomer targeting the 705 splice site (having SEQ ID NO: 286), when delivered effectively, corrects splicing and allows luciferase expression. This assay measures the ability of oligomers to enter cells and nuclei, and subsequently block incorrect splicing of pre-mRNA, leading to expression of a reporter gene. Because oligomers must enter cells and cell nuclei to produce a signal in the assay, it is useful for measuring uptake and effectiveness of delivery moieties (when present) as well as antisense activity of the binding oligomers.

Morpholino oligomers having cationic linkages designated herein as "GuX" linkages or "Pip" linkages (see FIG. 1), in differing amounts and distribution, were evaluated in such an assay. The latter oligomers (having "Pip" linkages) are also referred to as PMO+ or PMO Plus, while the former oligomers (having "GuX" linkages) are referred to as PMO GuX.

The distribution of charges in the oligomers was as shown below:

| | | | | | | | | | | | | | | | | | 705 control PMO |
|---|---|---|---|---|---|---|---|---|---|---|---|---|---|---|---|---|---|
| C | C | T | C | T | T | A | C | C | T | C | A | G | T | T | A | C | A |
| | | | | | + | + | + | + | + | + | + | | | | | | 8+-Centralized |
| + | + | + | + | + | + | + | + | | | | | | | | | | 8+-Polarized |
| + | | + | | + | | + | | + | | | + | + | | + | | | 8+-Dispersed |
| | + | | | + | | + | | + | | | | | + | | + | | 6+-Dispersed |
| | + | | | | + | | | | + | | | + | | | | | 4+-Dispersed |

Figure 7:
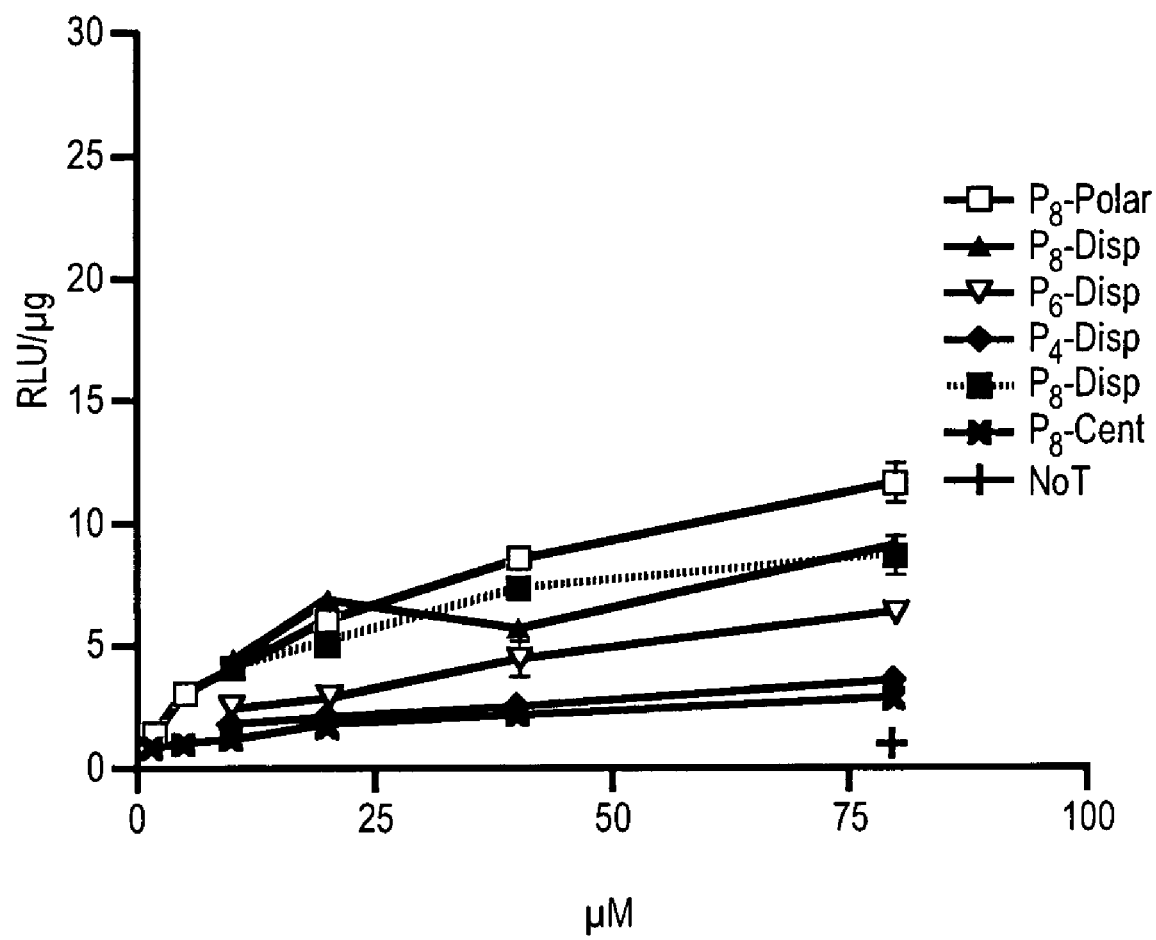
FIG. 7 shows the increased antisense activity of +PMO, with different distributions of cationic "Pip" linkages (P8-centralized, P8-dispersed, P6-dispersed, P4-dispersed, and P8-polarized; relative to uncharged PMO ("705"; SEQ ID NO: 286) in a splice correction translation assay in cell culture, described in Materials and Methods.
Figure 8:
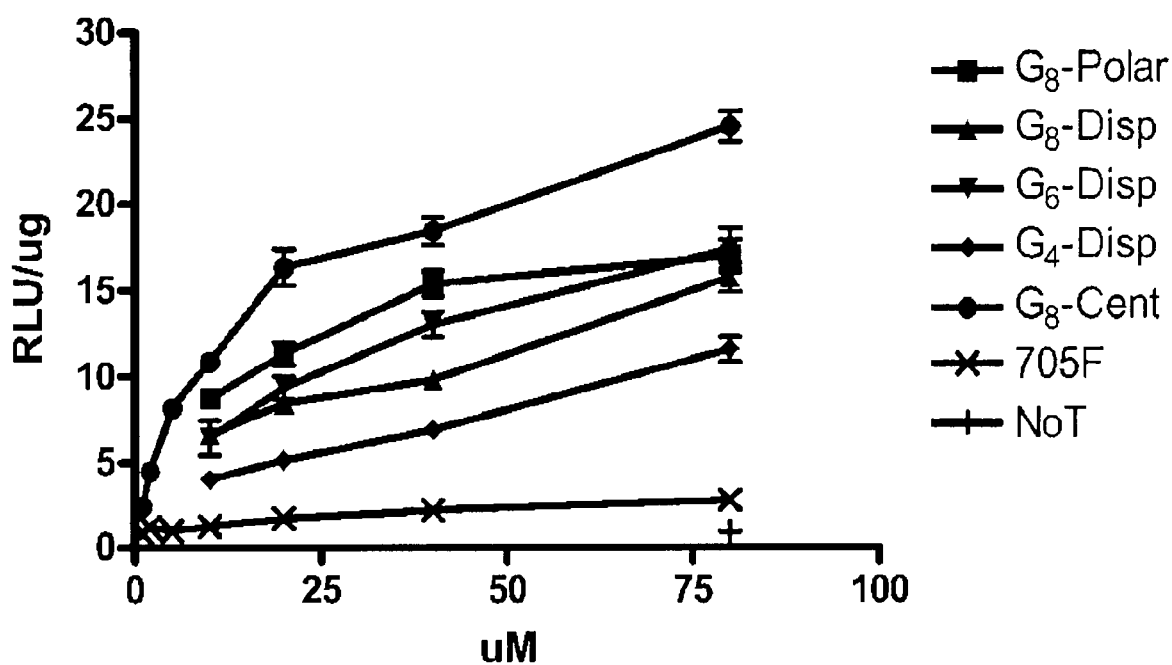
FIG. 8 shows the increased antisense activity of +PMO-GuX, with different distributions of cationic "GuX" linkages (G8-centralized, G8-dispersed, G6-dispersed, G4-dispersed, and G8-polarized; SEQ ID NOs: 48-52) relative to uncharged PMO (SEQ ID NO: 286) in a splice correction translation assay in cell culture, as described for FIG. 8.
Figure 10:
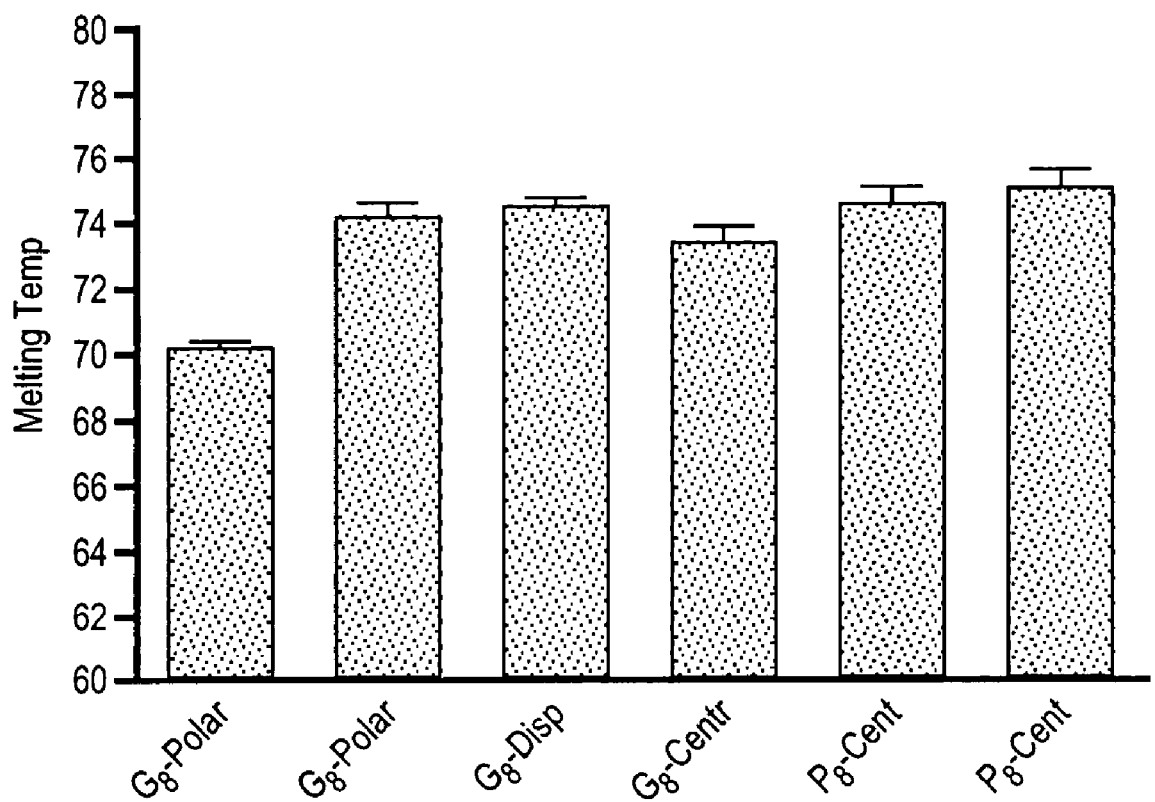
FIG. 10 shows binding affinities (Tm) of selected +PMO and +PMO-GuX oligomers from FIGS. 7 and 8 as compared with uncharged PMO of the same sequence.

As shown by the data in FIGS. 7 and 8, increasing the number of charges, up to eight, in the 18-mer increased the antisense activity in this assay relative to uncharged PMO. The data also suggest that the "centralized" position of the charges increased antisense activity relative to the "polarized" and "dispersed" distributions, and that the "GuX" linkages were significantly more effective than the "Pip" linkages. A comparison of binding affinities, based on Tm, shows that this pattern is not based simply on binding affinity (FIG. 10), although all charged PMO's had higher Tm's than the uncharged PMO.

Figure 9:
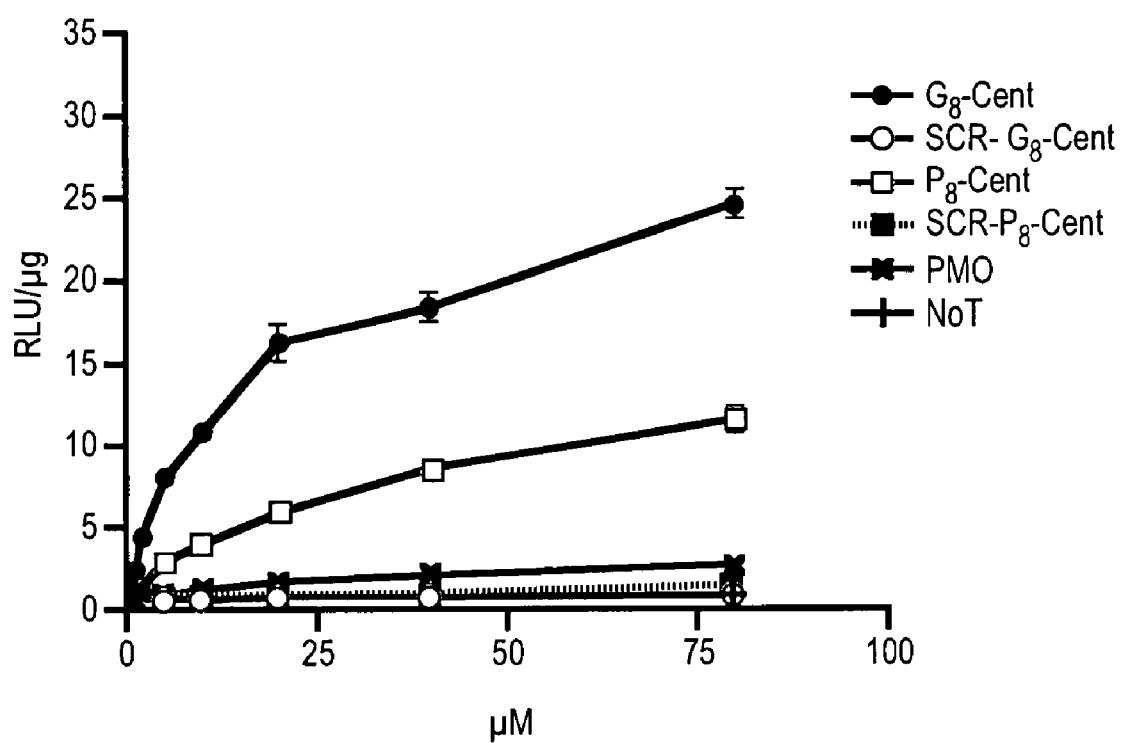
FIG. 9 compares antisense activities of "P8-centralized" Pip-modified +PMO (see FIG. 7) and "G8-centralized" GuX-modified +PMO-GuX (see FIG. 8) with scrambled sequence counterparts (SCR) and uncharged PMO in a in a splice correction translation assay in cell culture, as described for FIG. 8.

The data in FIG. 9 incorporate scrambled controls into the assays of FIGS. 7-8. As shown, the scrambled controls (SCR-$G_8$-Cent and SCR-$P_8$-Cent) showed essentially no antisense activity in the assay.

Figure 11A:
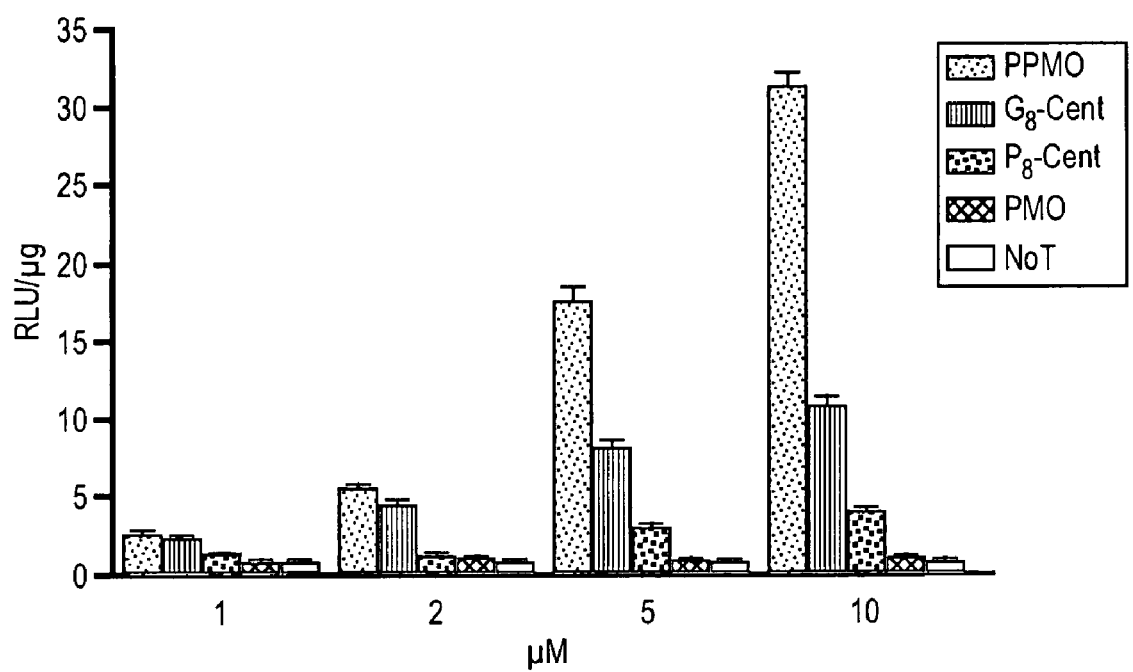
FIGS. 11A-B shows the increased uptake/antisense activity of +PMO, +PMO-GuX, and peptide-conjugated uncharged PMO ("PPMO") relative to unconjugated uncharged PMO (SEQ ID NO: 286) in a splice correction translation assay in cell culture, as described for FIG. 7.
Figure 11B:
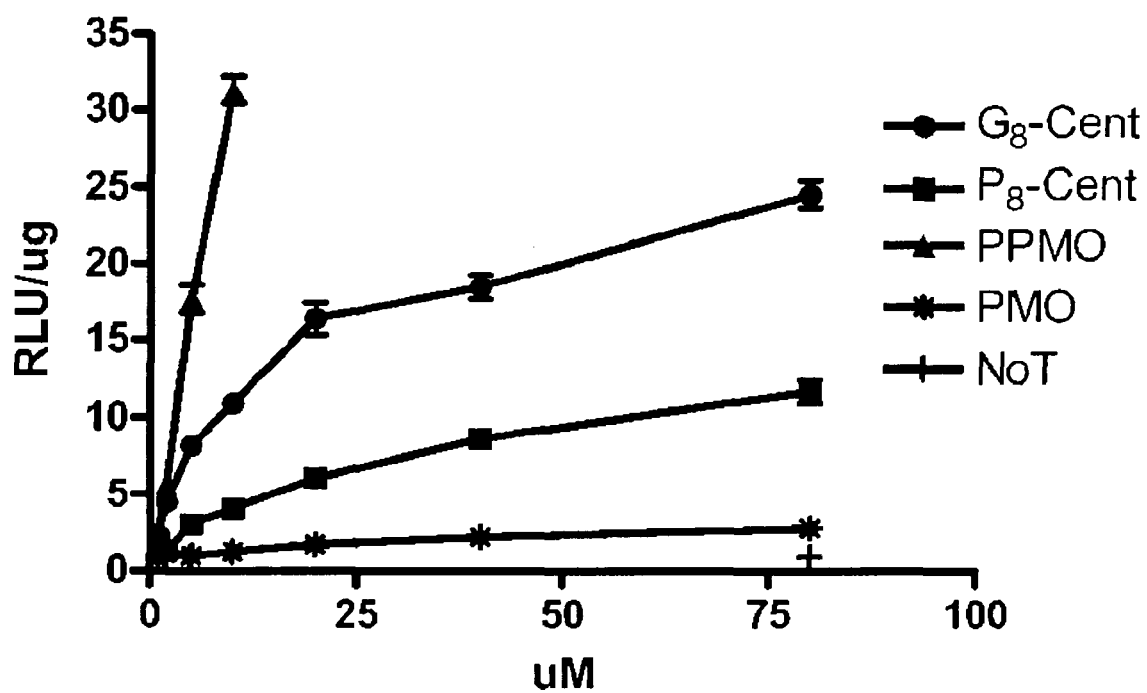

The data in FIGS. 11A-B compare the "$G_8$-Centralized" and "$P_8$-Centralized" charged oligomers with the 705 control PMO conjugated to a transport peptide having the formula $(RXR)_4$, where R is arginine and X is 6-aminohexanoic acid (see e.g. FIG. 1D). This conjugation has a dramatic effect on antisense activity, which is believed to be due in large part to enhanced transport into the cells.

C. In Vivo Activity: Increased Antiviral Efficacy of Ebola Virus-Specific +PMOs in Rodents To determine the in vivo efficacy of the Ebola virus-specific +PMOs, mice were treated with two 50 μg doses of three individual +PMOs and one uncharged PMO targeting the VP24 gene mRNA (VP24-AUG, VP24-2+, VP24-4a+ and VP24-4b+; SEQ ID NOS: 5-8, respectively) at 24 and 4 hours before challenge with 1000 plaque-forming units (pfu) of mouse-adapted Ebola virus. Survival was determined over a period of 14 days, with ten mice in each treatment group.

Figure 6:
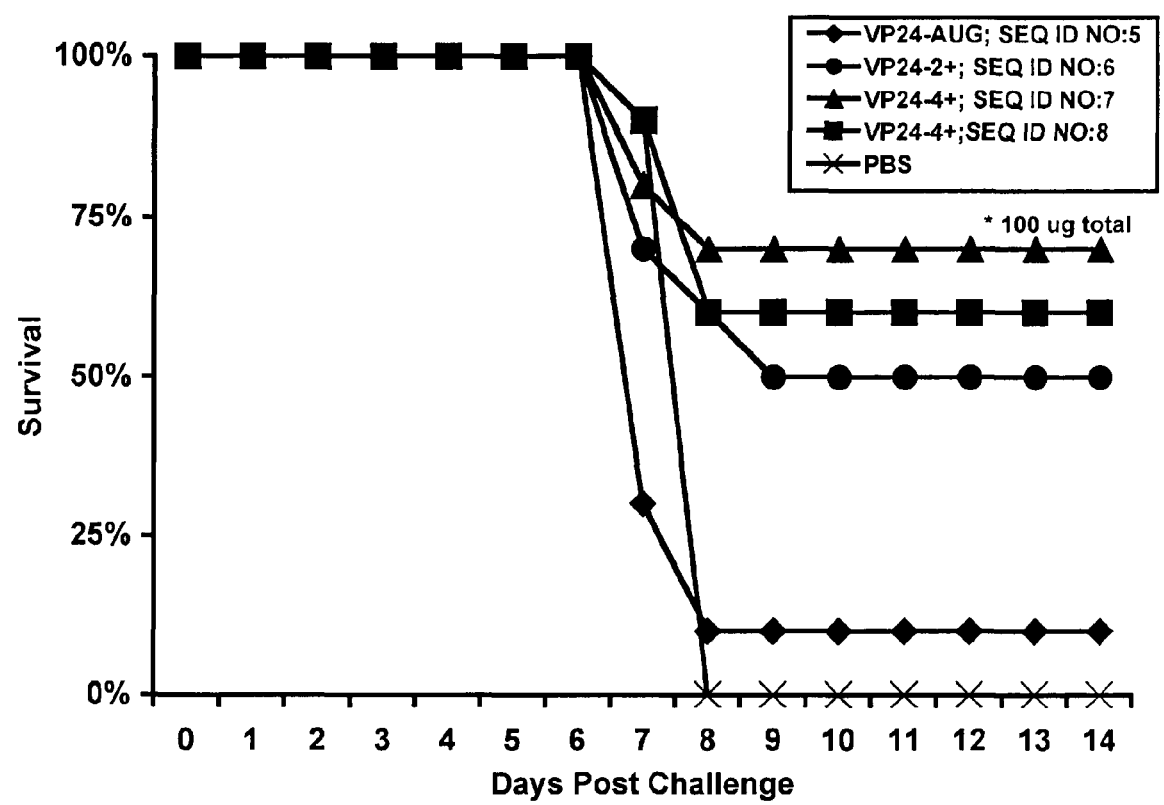
FIG. 6 is a plot of treatment efficacy, expressed as a percentage of mouse survivors over a 14 day period post-infection, for three different +PMO that target the EBOV VP24 gene (VP24-2+, VP24-4a+ and VP24-4b+; SEQ ID NOs: 6-8, respectively) compared to the uncharged PMO control (VP-24; SEQ ID NO: 5) and a phosphate buffered saline negative treatment control (PBS).

The VP24+PMOs exhibited a wide range of efficacy against lethal EBOV infection, with the +PMO containing four positive charges providing the most protection (70% survival), as shown in FIG. 6. The two +PMO with two positive charges demonstrated intermediate effect (50-60% survival), and the uncharged PMO provided the least protection, with only 10% survival. The negative control group received PBS and no survivors were observed. A similar beneficial effect was seen with +PMO targeting VP35 mRNA.

+PMO provided improved protection against a lethal Ebola virus challenge in a Hartley guinea pig model system. A three drug combination of uncharged PMO (SEQ ID NOs: 1, 5 and 11) or peptide-conjugated versions of this same three PMO provided no protection against a lethal Ebola virus challenge in the guinea pig model system. The same three drug combination in the +PMO form (SEQ ID NOs: 287, 288 and 289) provided protection to 75% of the challenged guinea pigs. Furthermore, the use of PMO+ allowed a two drug combination therapy (SEQ ID NOs: 288 and 289) to provide protection to 80% of the Ebola virus challenged guinea pigs.

Experiments in non-human primates (rhesus macaques) similar to those described previously (Warfield, Swenson et al. 2006) were conducted using +PMO compounds in the two drug combination form (SEQ ID NOs: 288 and 289). The Ebola virus-infected animals were treated with +PMO post-infection at 20 mg/kg daily for 10 days. The treatment provided protection to 75% of the animals, all of whom were challenged with 1000 pfu of Ebola virus.

IV. Preparation of Oligomers having Cationic Intersubunit Linkages

Figure 2B:
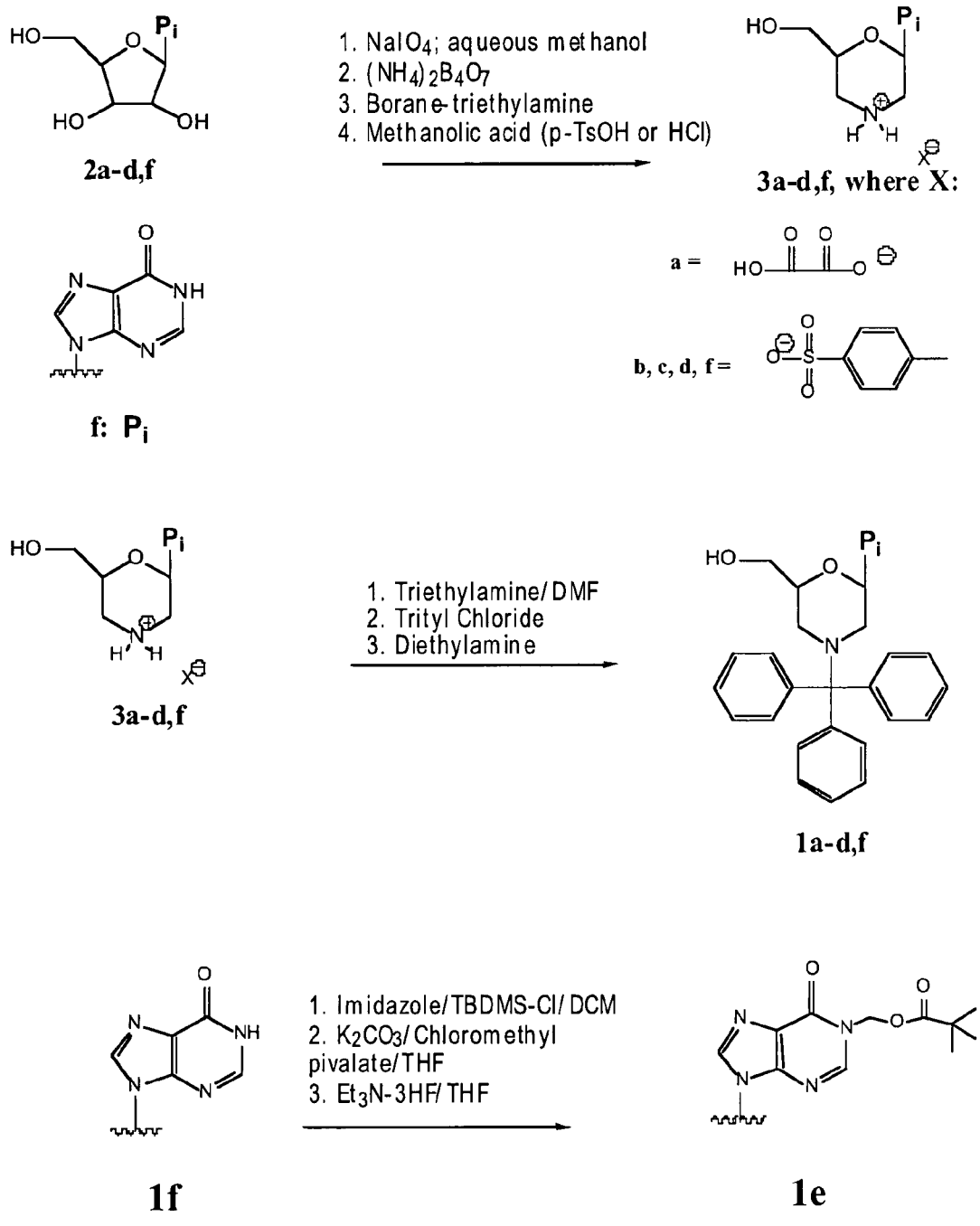
FIG. 2B shows synthetic schemes for preparation of the subunits of FIG. 2A from the corresponding ribonucleosides.
Figure 2C:
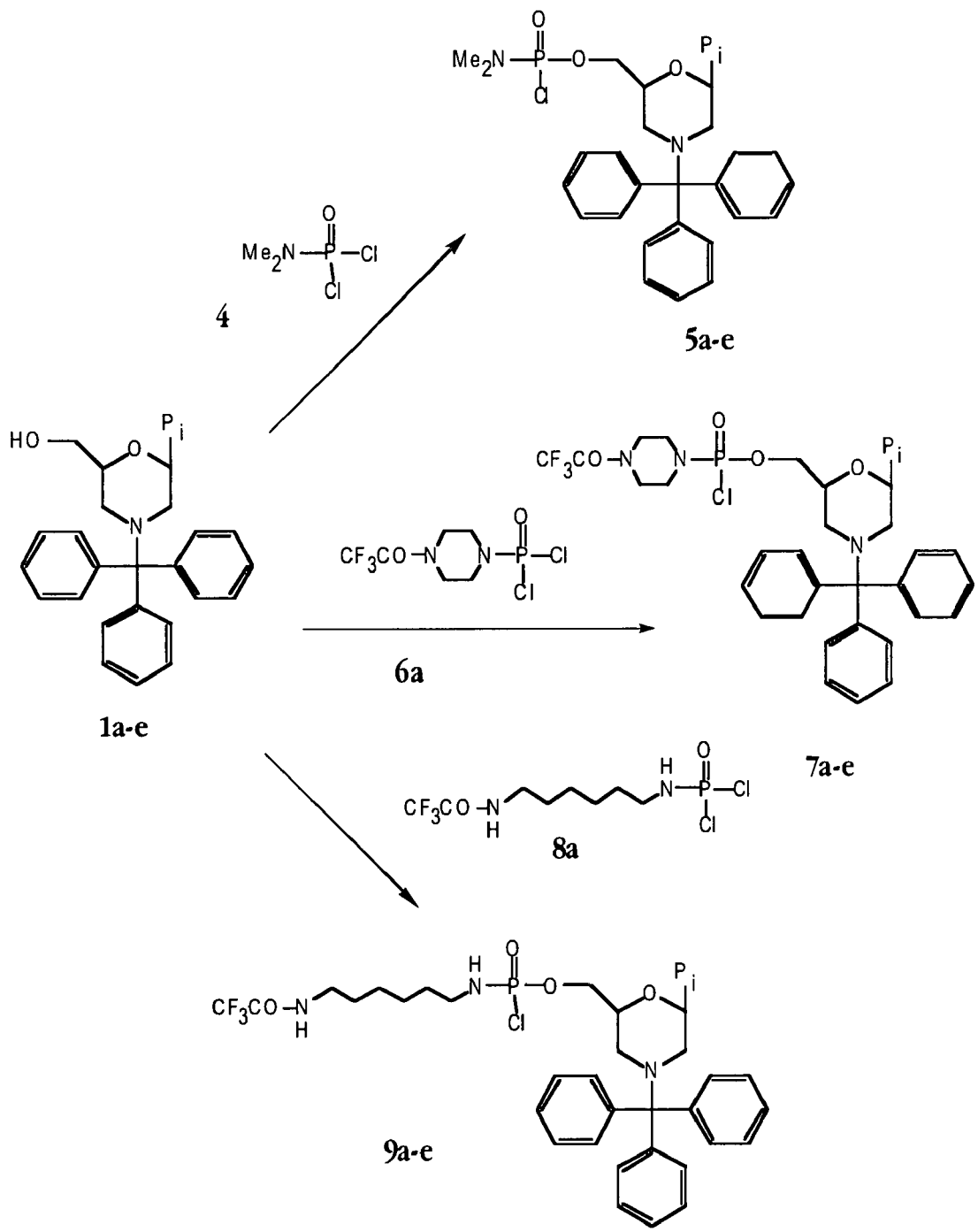
FIG. 2C illustrates the preparation of activated, protected subunits for preparation of linkage type (a) (uncharged) and linkage types (b1) and (b2) (charged) as designated herein.
Figure 2D:
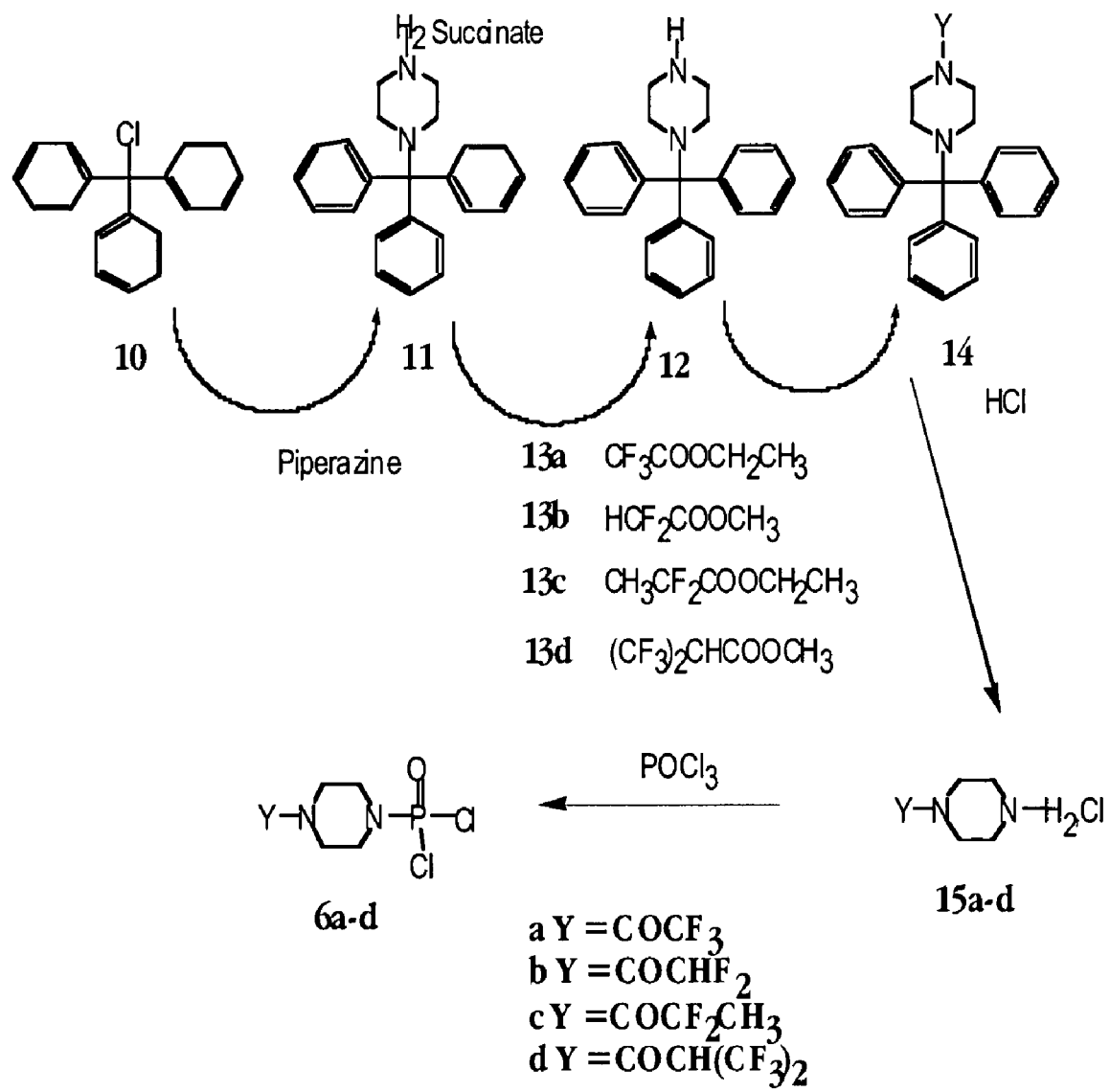
FIG. 2D is a schematic of a synthetic pathway that can be used to make morpholino subunits containing the (1-piperazino) phosphinylideneoxy ("Pip") linkage.
Figure 2E:
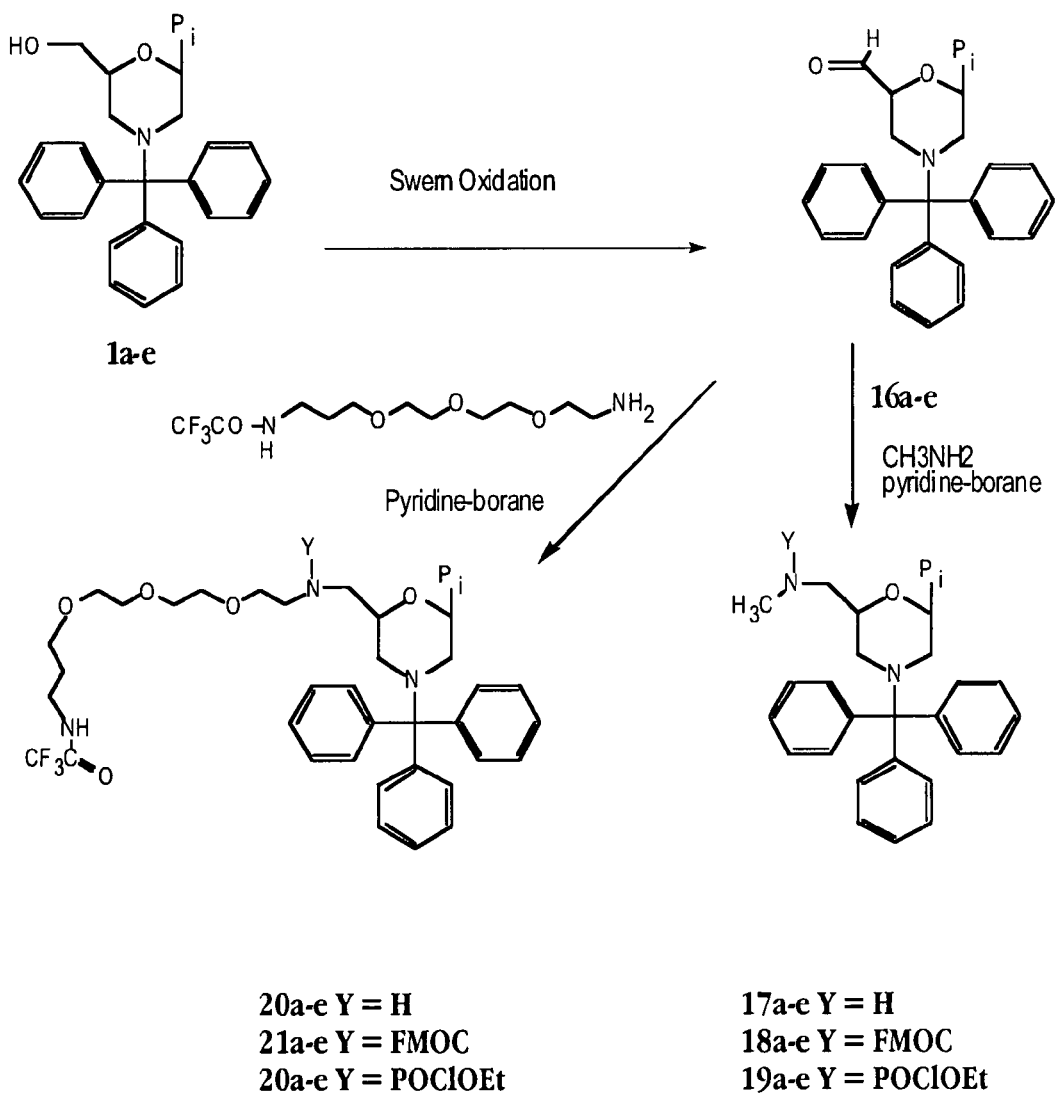
FIGS. 2E and 2F illustrate the preparation of activated, protected subunits for preparation of linkages of type (b3) (charged) as designated herein.
Figure 2F:
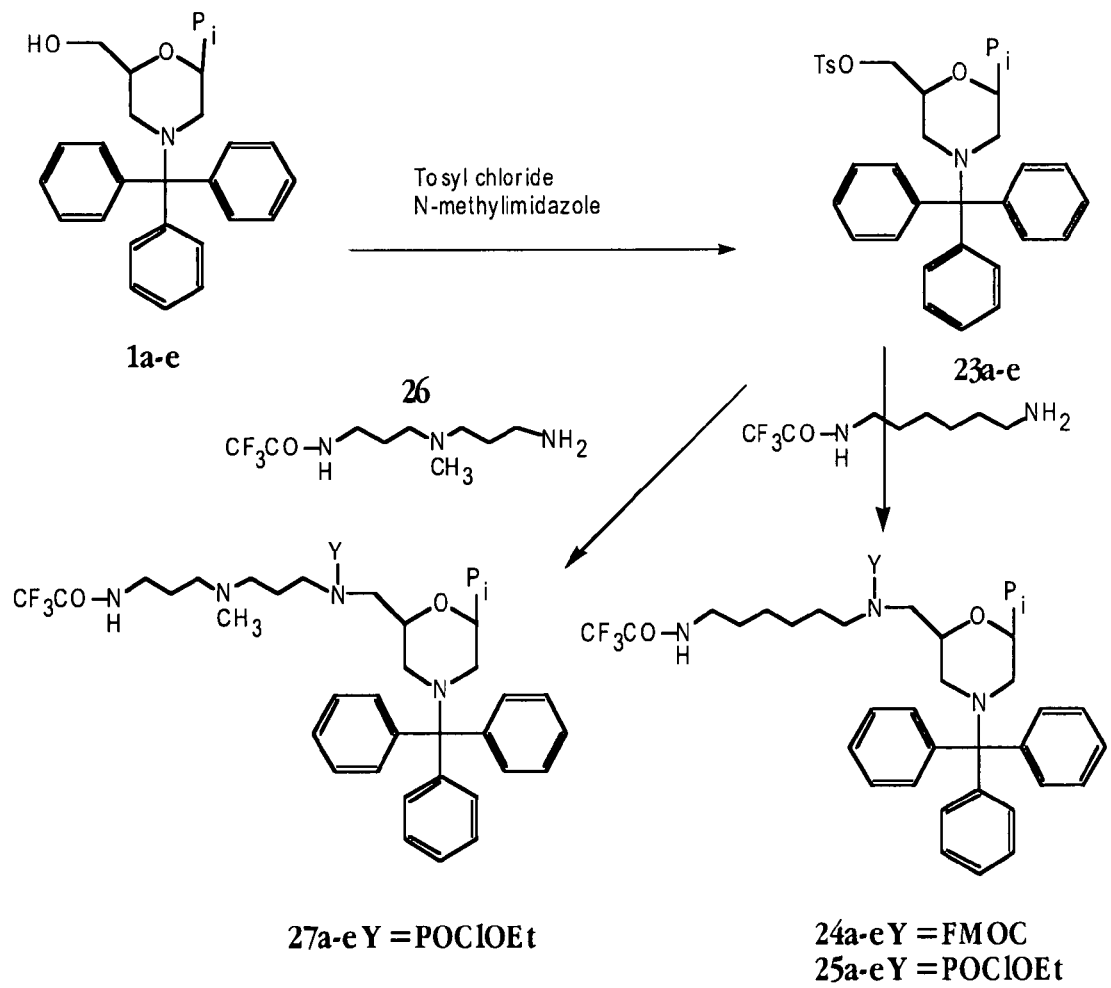
Figure 2G:
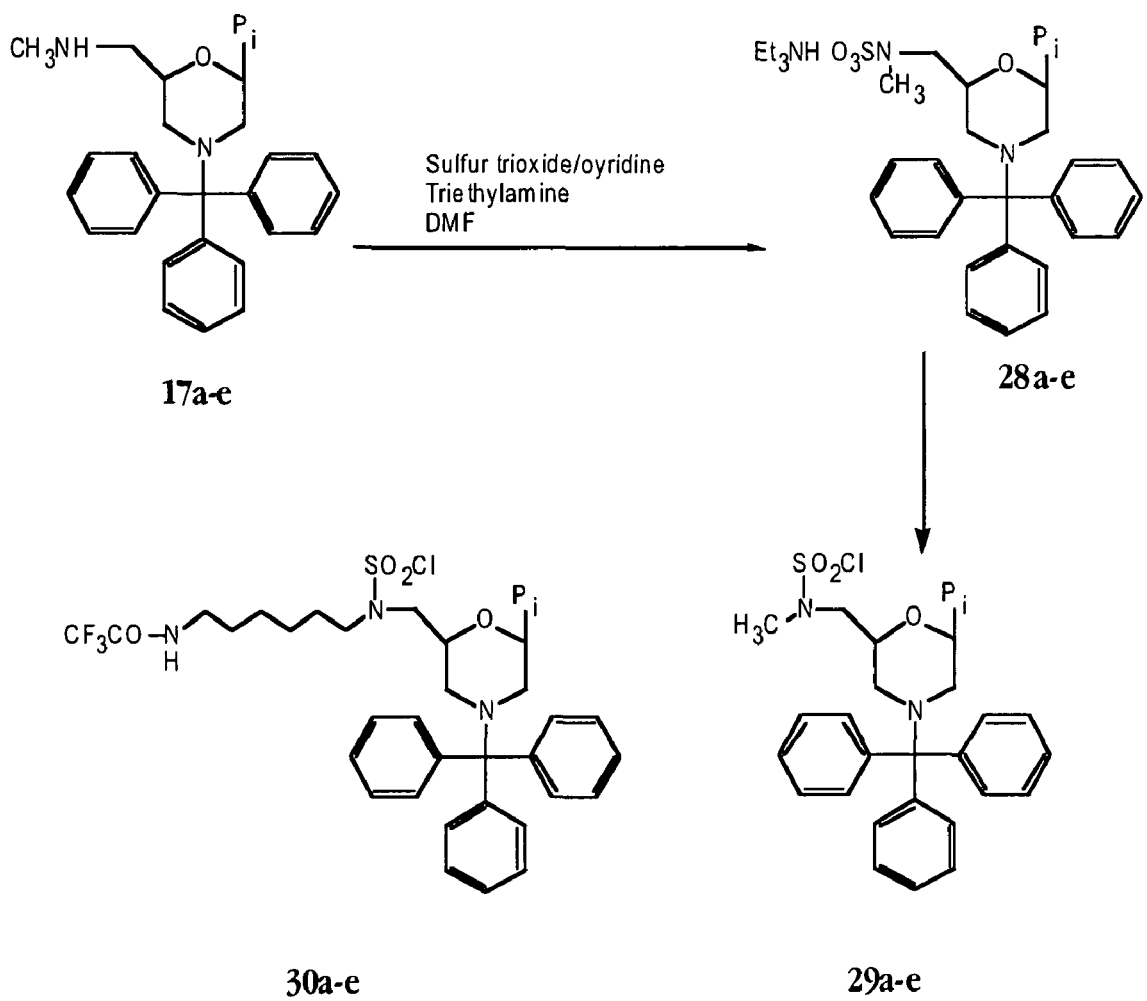
FIG. 2G illustrates the preparation of subunits that can be used to prepare linkages analogous to type (b3) (charged) but based on non-phosphorus-containing linkages, specifically sulfonamide linkages.
Figure 2H:
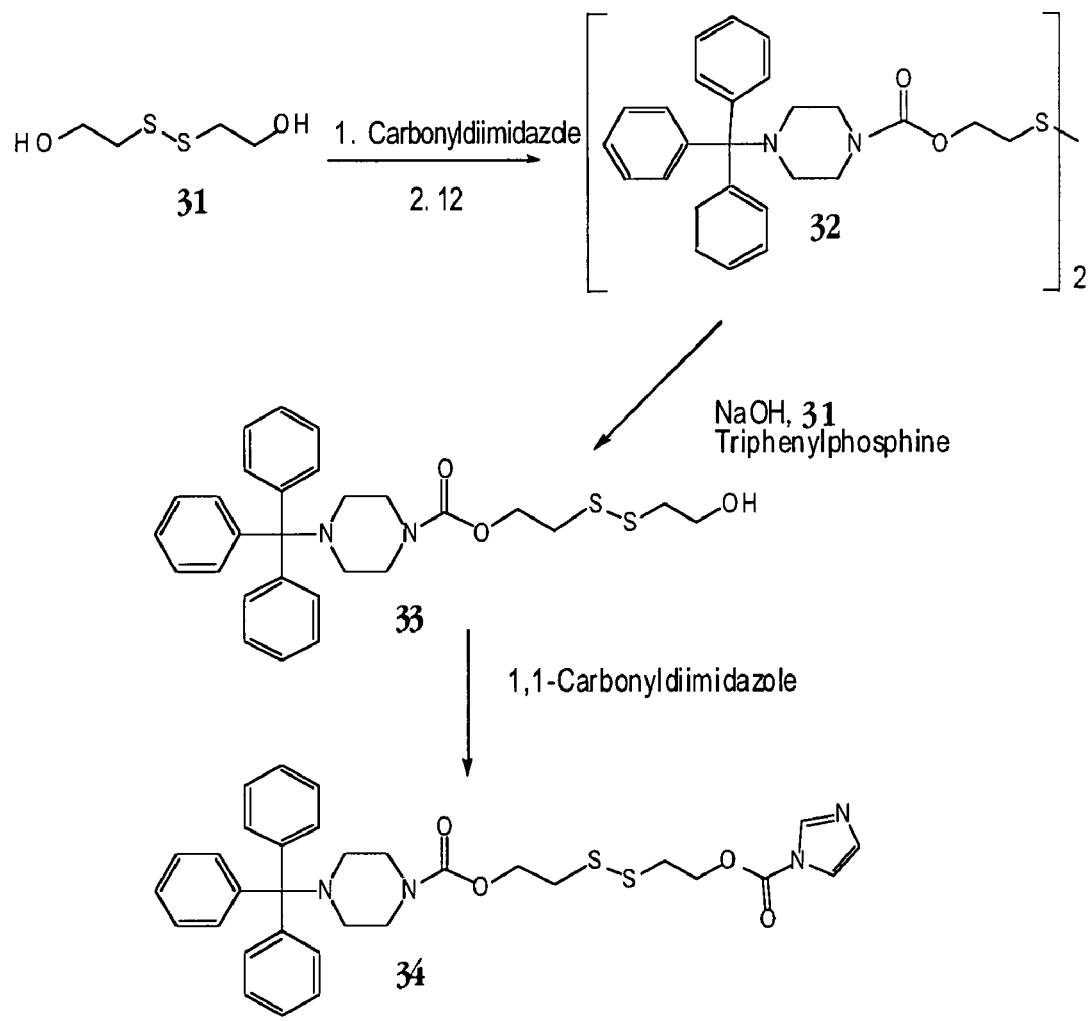
FIG. 2H illustrates preparation of a disulfide anchor, for use in modification of a synthesis resin used for stepwise preparation of a morpholino oligomer, allowing facile release of the oligomer by treatment with a thiol.
Figure 2I:
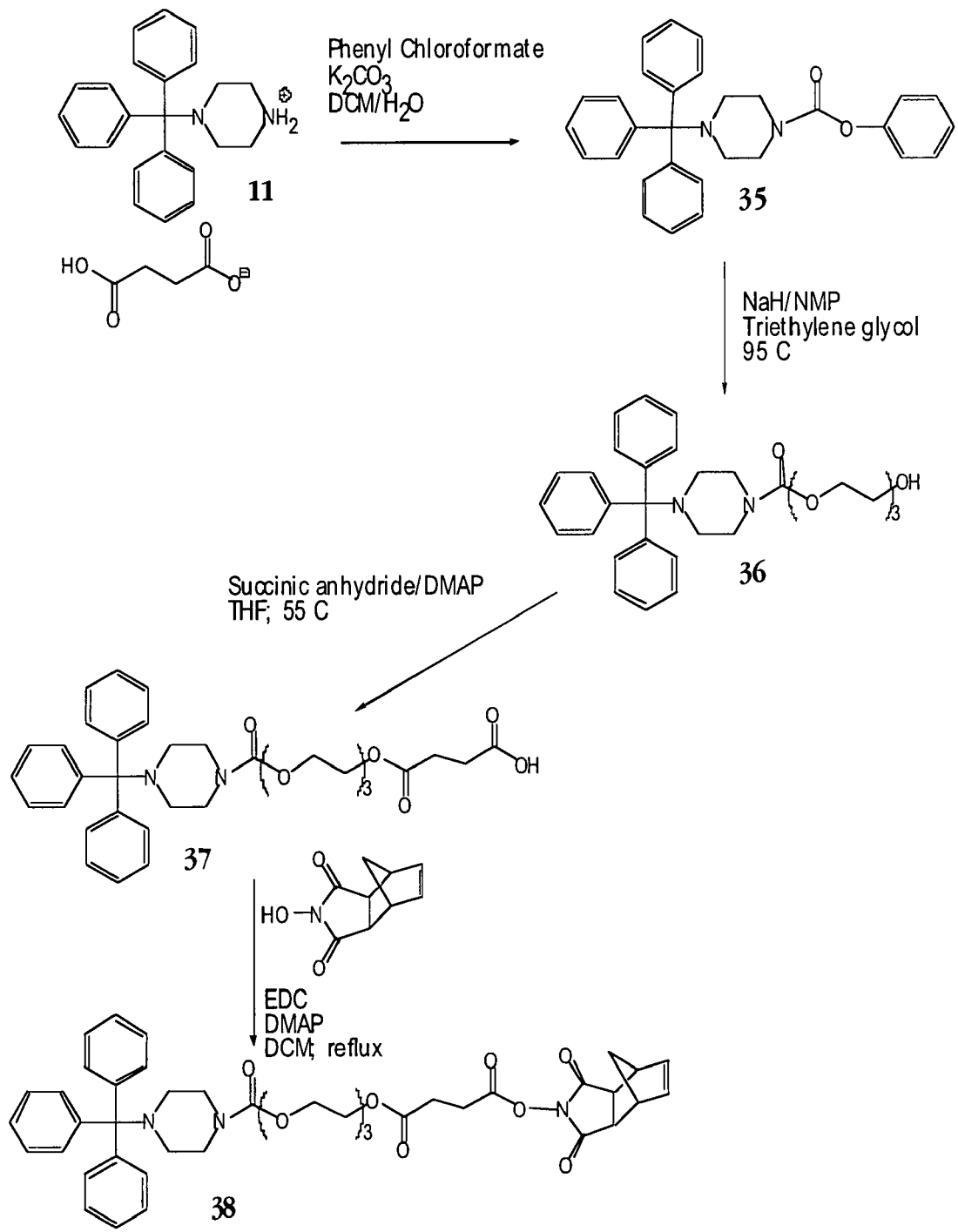
FIG. 2I illustrates the introduction a triethylene glycol containing moiety ("Tail") which increases aqueous solubility of synthetic antisense oligomers.
Figure 2J:
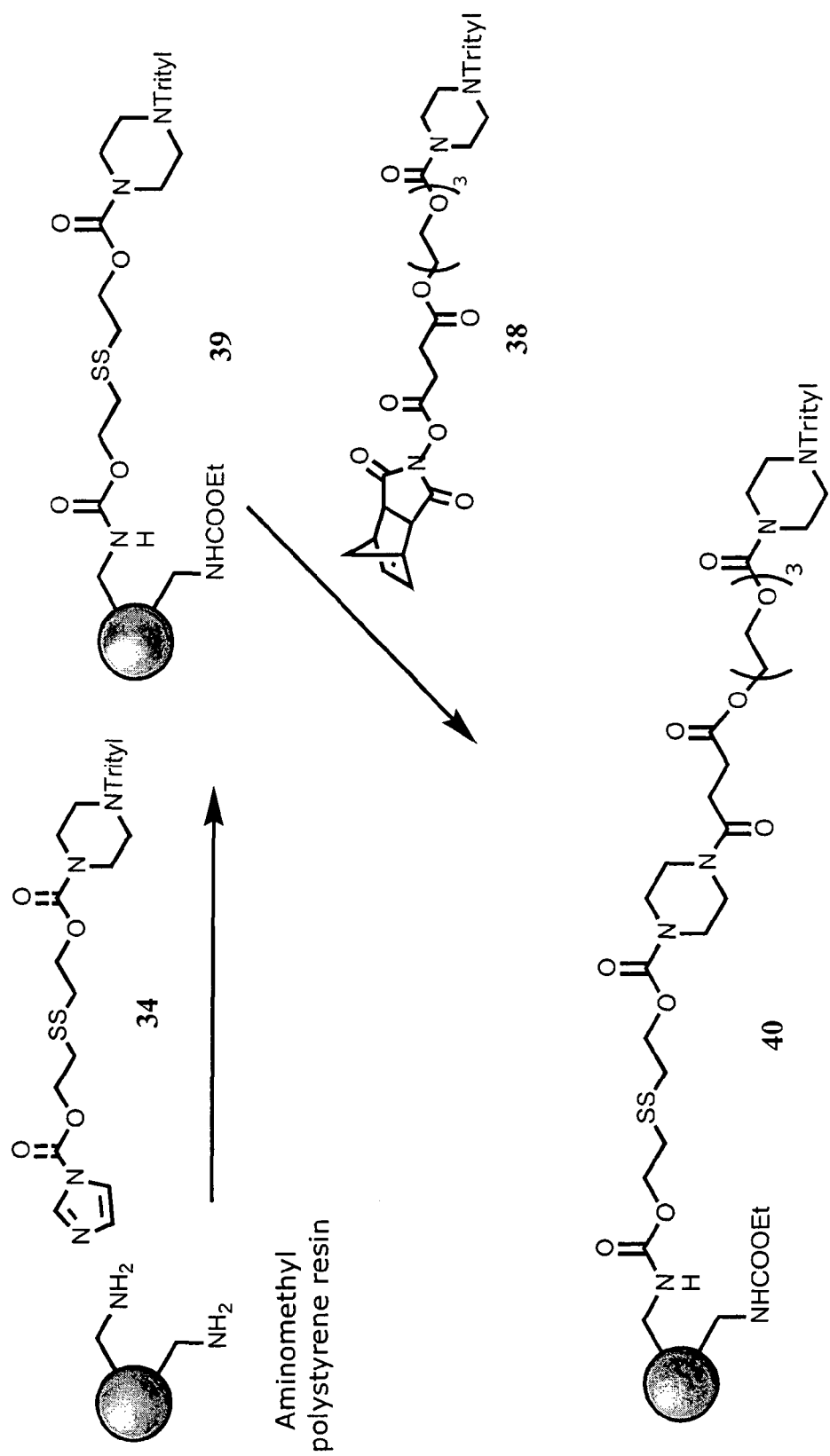
FIG. 2J illustrates the preparation of resins useful for the solid phase synthesis of morpholino oligomers.
Figure 2K:
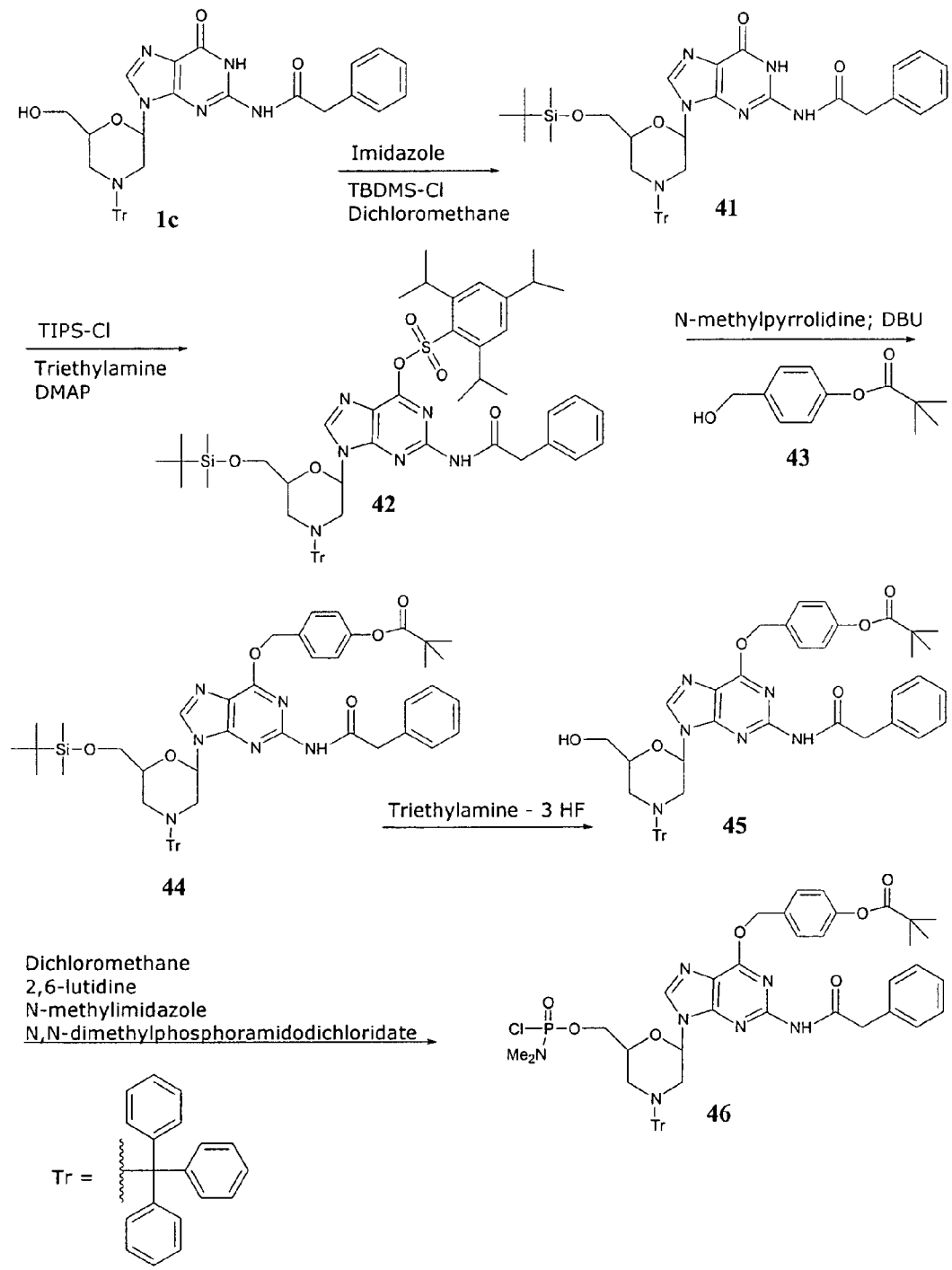
FIG. 2K illustrates the preparation of N2,O6-protected morpholino G Subunit for large scale oligomer synthesis
Figure 2L:
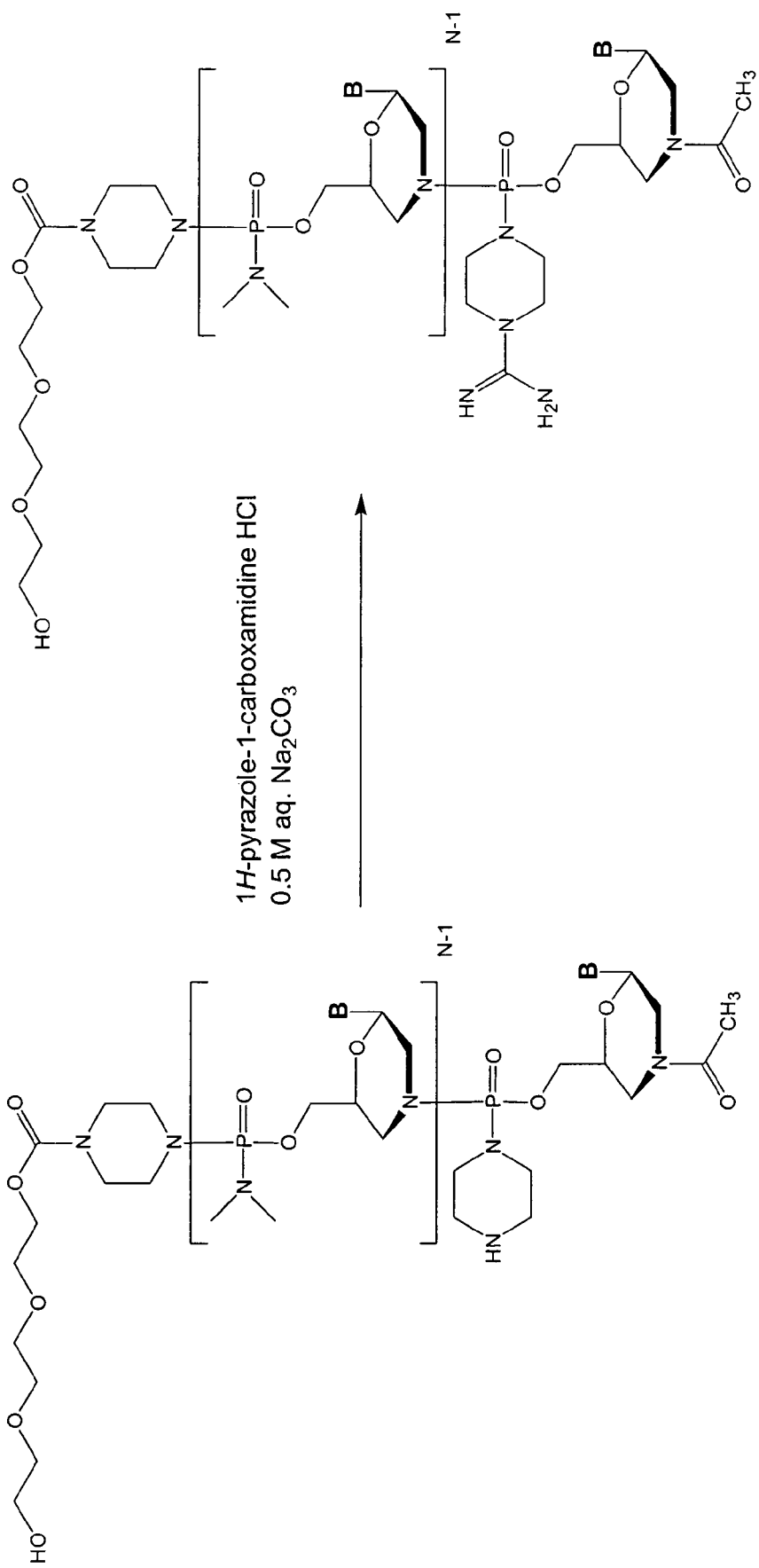
FIG. 2L illustrates the introduction of guanidinium groups by direct guanylation of amines on the morpholino oligomer.
Figure 2M:
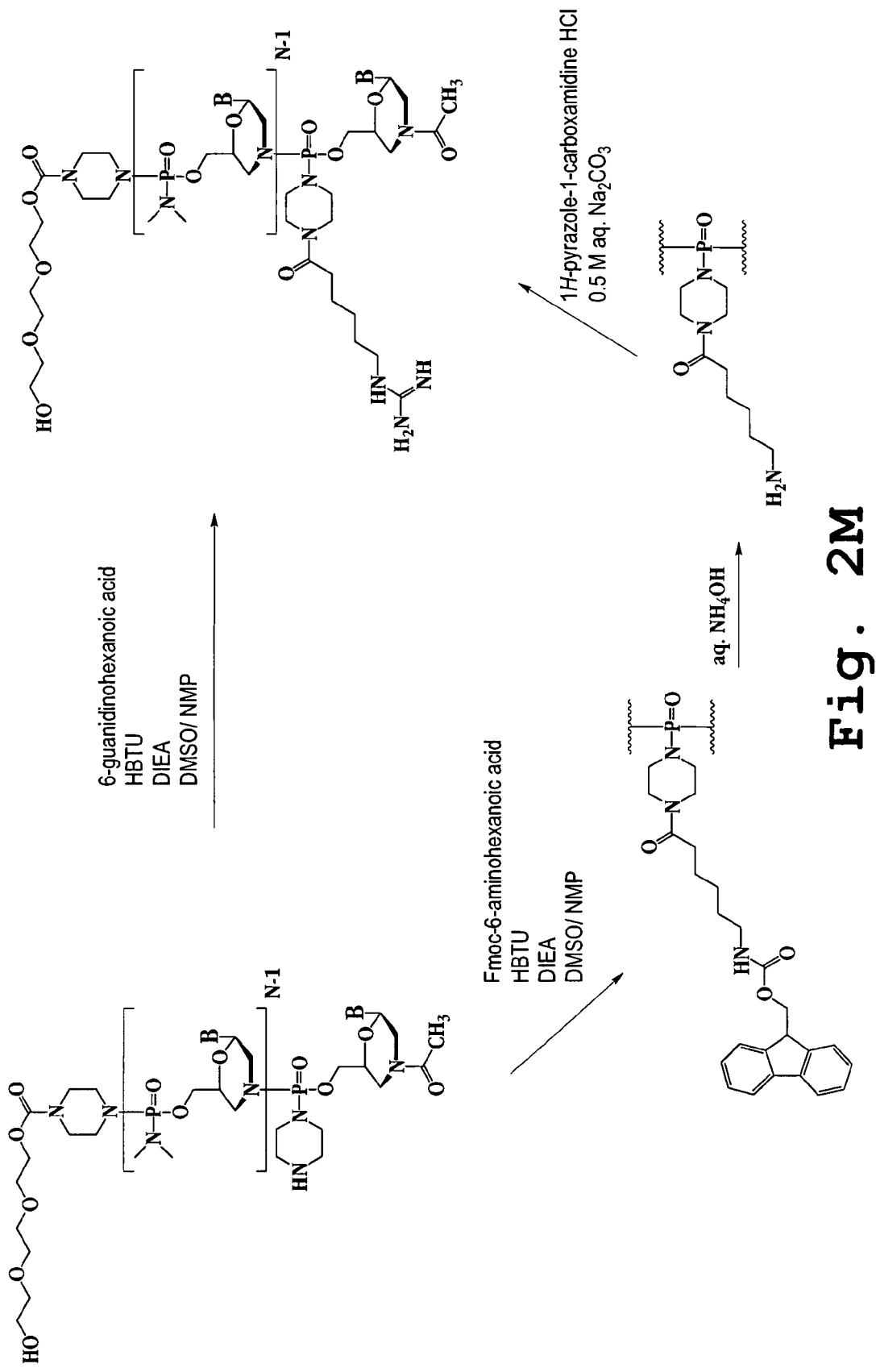
FIG. 2M illustrates the introduction of guanidinium groups into morpholino oligomers by incorporation of amino acids and guanidino acids.
Figure 20:
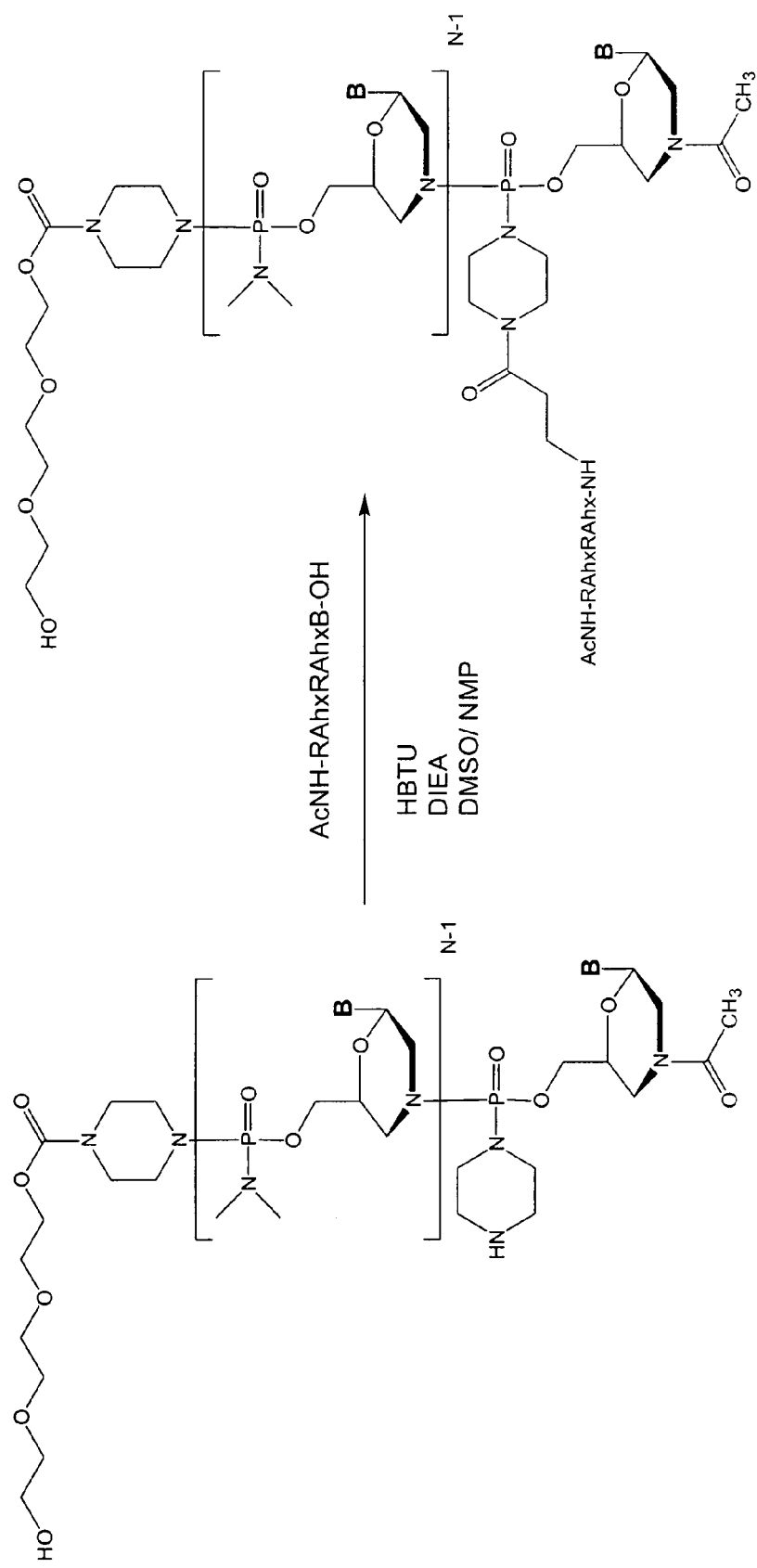
Figure 2P:
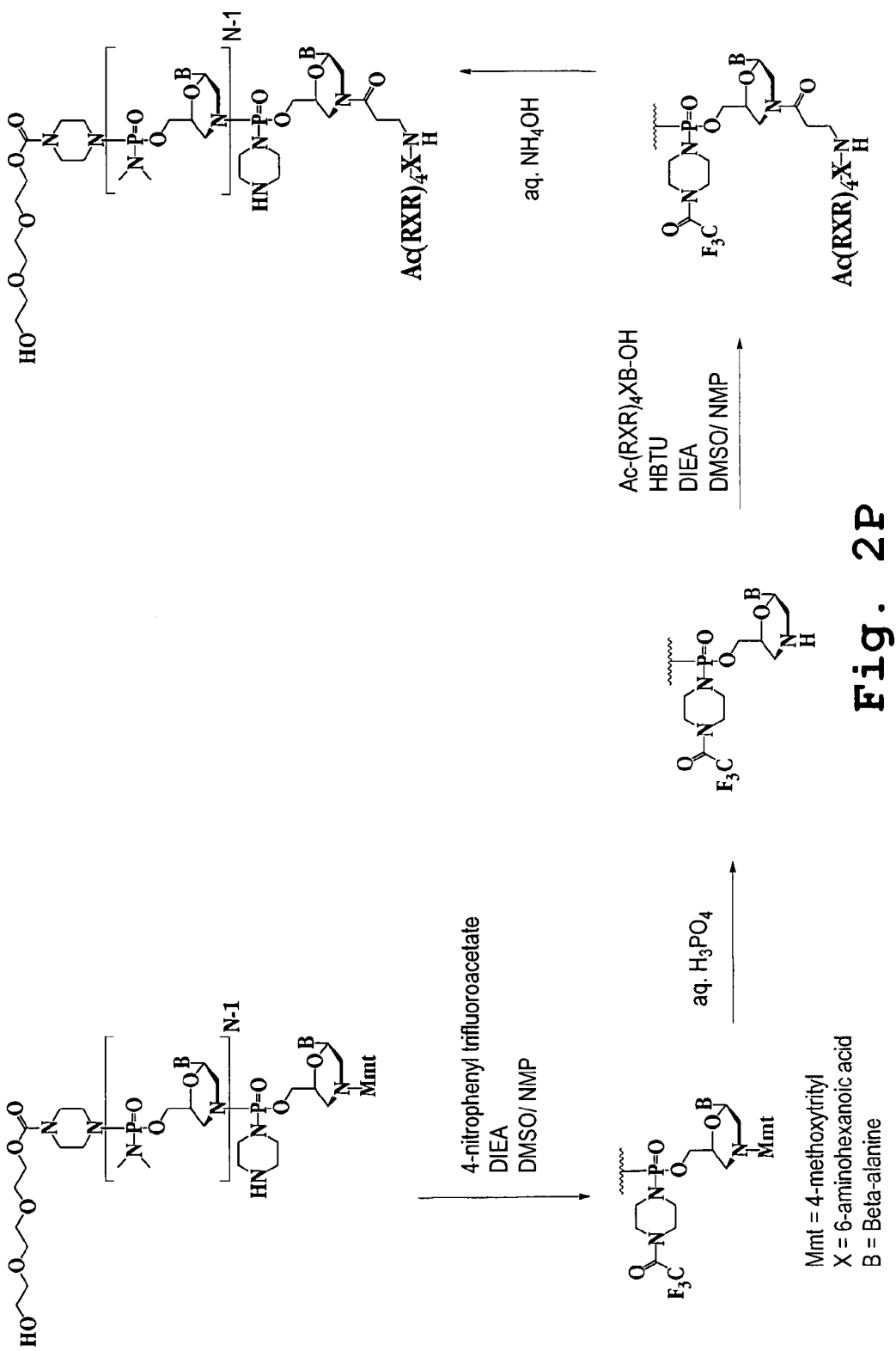
FIG. 2P illustrates the introduction of a transport peptides at the 3'-terminus of morpholino oligomers having charged groups of linkage type b1 in the backbone.
Figure 2Q:
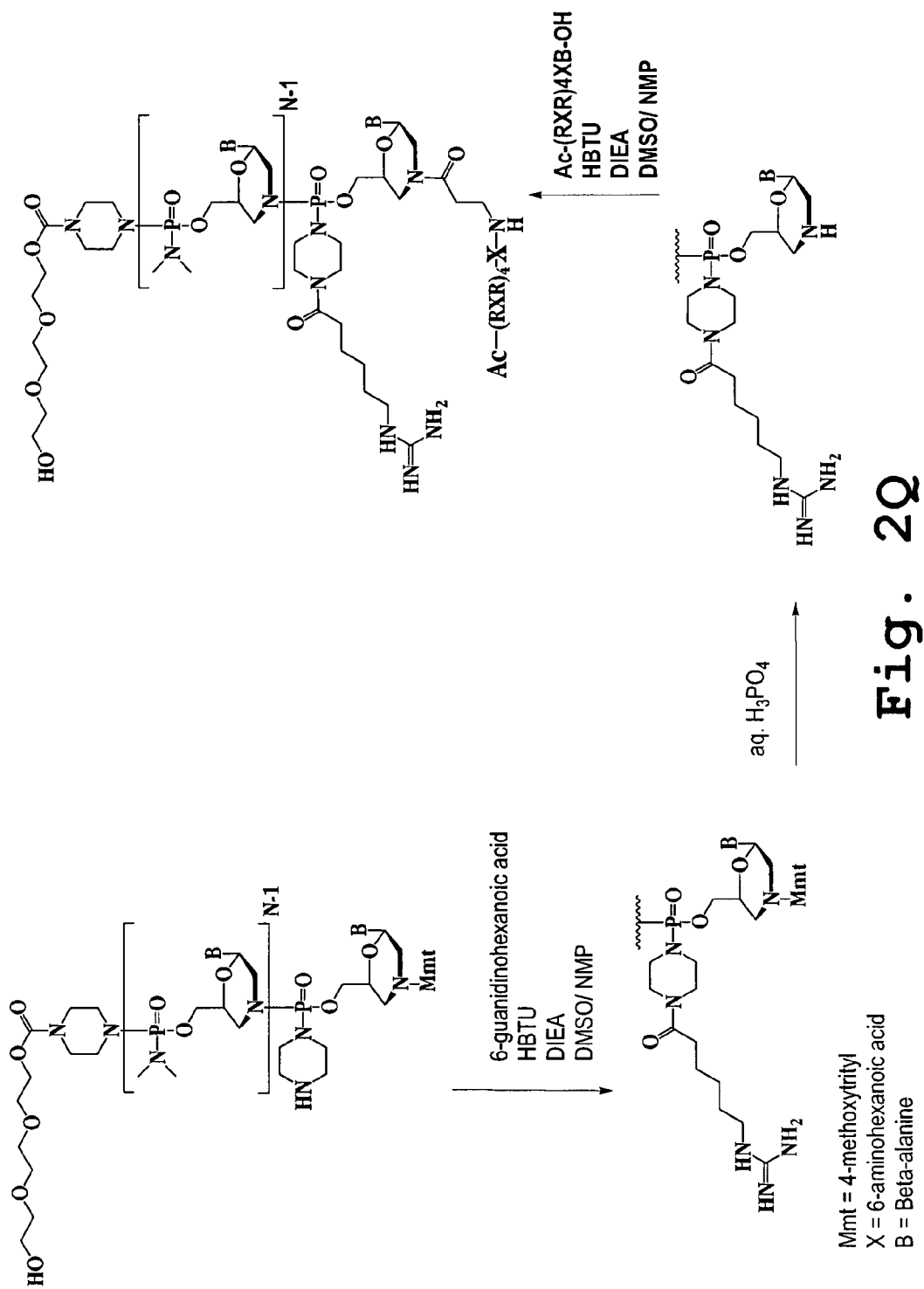
FIG. 2Q illustrates the introduction of a transport peptides at the 3'-terminus of morpholino oligomers having GuX linkages in the backbone.
Figure 2R:
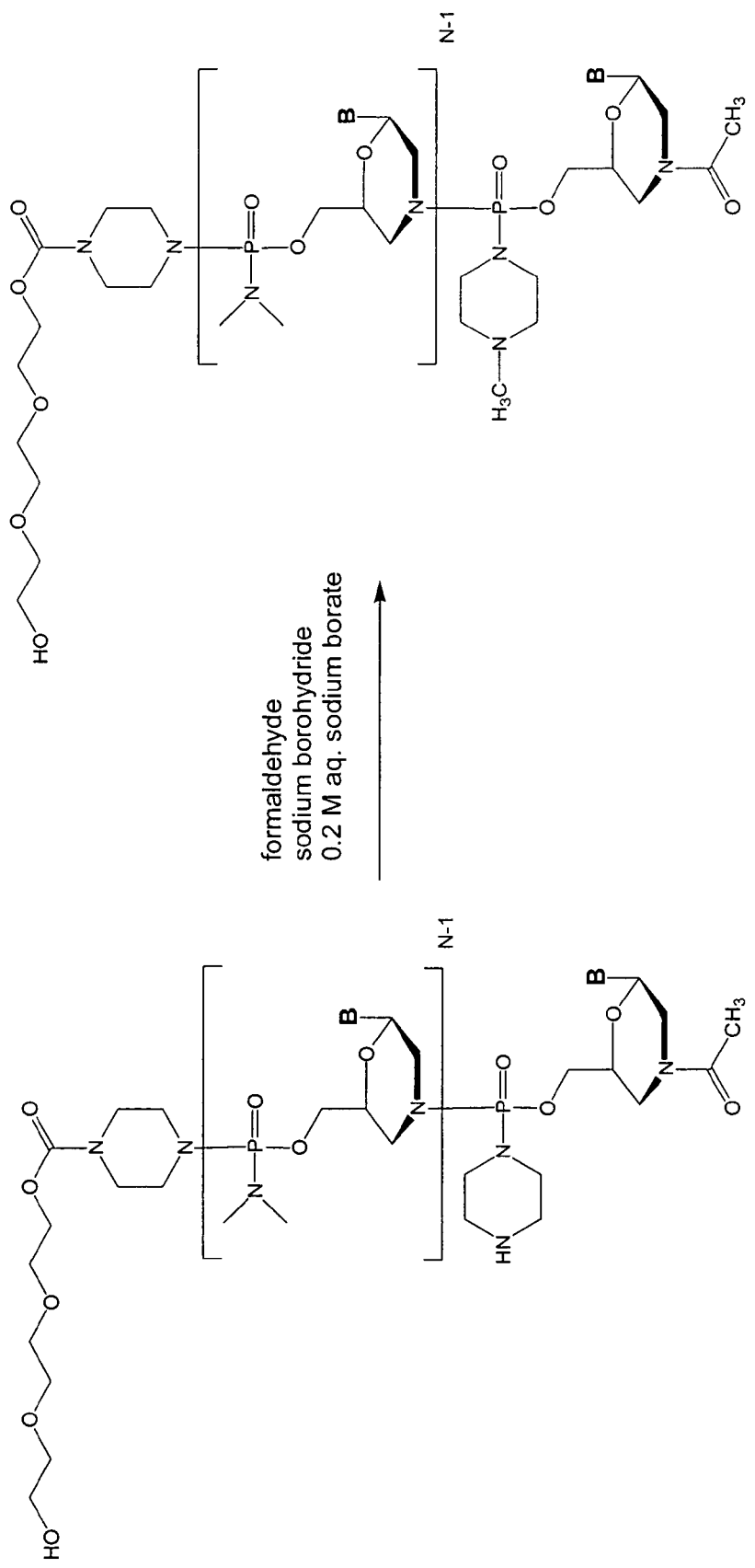
FIG. 2R illustrates the reductive alkylation of amines of morpholino oligomers.

FIGS. 2A through 2R illustrate the preparation of morpholino subunits having suitably protected base-pairing groups, and the conversion of these subunits into morpholino oligomers having cationic linkages. Further experimental detail is provided in Materials and Methods, below. The charged-linkage subunits can be used in standard stepwise oligomer synthesis, as described, for morpholino oligomers, in U.S. Pat. No. 5,185,444 or in Summerton and Weller, 1997 (cited above).

FIG. 2A shows representative morpholino subunits 1a-e with base-pairing moieties Pi of A, C, G, T, and I. These subunits can be prepared from the corresponding ribonucleosides as illustrated in FIG. 2B and described in Example 1. Suitable protecting groups are used for the nucleoside bases, where necessary; for example, benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base as shown in FIG. 2B. Although an unprotected hypoxanthine subunit, as in 1f, may be employed, yields in activation reactions are far superior when the base is protected.

Treatment of the 5'-hydroxy (1) with a reactive acid chloride, such as N,N-dimethylphosphoramidodichloridate (4), provides type (a) (uncharged linkage) activated subunits 5a-e, as shown in FIG. 2C and described in Example 2. Although the unprotected hypoxanthine containing subunit, as in 1f, may be employed, yields in activation reactions are far superior when the base is protected.

FIG. 2C also illustrates the use of alternate reactive acid chlorides, such as 6a, to convert 5'-hydroxy subunits 1a-e into type (b1) (charged linkage) activated subunits 7a-e.

Similarly, an acyclic reactive acid chloride, such as 8a, can be used to convert 5'-hydroxy subunits 1a-e into type (b2) (charged linkage) activated subunits 9a-e. These charged-linkage subunits may be incorporated into phosphorodiamidate-linked morpholino oligomers and, upon treatment with the usual reagents that remove the base protecting groups, preferably ammonia, produce oligomers containing type (b1) and (b2) cationic phosphorodiamidate linkages.

A schematic of a synthetic pathway that can be used to make morpholino subunits containing the (1-piperazino) phosphinylideneoxy linkage (type b1'; "Pip") is shown in FIG. 2D and described in Example 3. Reaction of piperazine and trityl chloride 10 gives trityl piperazine, which can be isolated as the succinate salt 11. Reaction with ethyl trifluoroacetate 13a in the presence of a weak base, e.g. diisopropylethylamine, provides 1-trifluoroacetyl-4-trityl piperazine 14, which upon treatment with HCl provide the detritylated salt 15 in good yield. Introduction of the dichlorophosphoryl moiety on the free eing nitrogen was performed with phosphorus oxychloride in toluene, yielding the piperazine-P(O)Cl$_2$ moiety 6a. This reagent can be reacted with 5'-hydroxy morpholino subunits to produce activated subunits containing the protected (1-piperazino) phosphinylideneoxy linkage, which can be incorporated into oligomers using the oligomer synthesis protocol below.

Selectively protected acyclic amines, suitable for incorporation into morpholino subunits for the preparation of type (b2) cationic linkages, may be prepared by methods analogous to that described and illustrated for the cyclic amines; see Example 4. Alternatively, treatment of a solution of a diamine with 1.6 equivalents of the reactive ester 13a-d provides a solution with <5% of the free diamino species. The solution was used directly for activation with POCl$_3$ and activation of the morpholino subunits 1a-e. A person skilled in the art would find it possible to prepare oligomers with more complex cationic sides chains using the methods above.

Subunits for the introduction of type (b3) cationic linkages, i.e. having a nitrogen at the 5'-position, into oligomers may be prepared, as shown in FIG. 2E and described in Example 5, by oxidation of a morpholino subunit to the corresponding aldehyde (16a-e) and reductive amination with a suitably protected diamine, which affords a representative 5'-aminomorpholino subunit 20a-e. It is often preferable to isolate the amine as the 9-fluorenylmethyloxycarbonyl (FMOC) derivative 21a-e following treatment with FMOC chloride. The free amine can be easily regenerated when needed by treatment with triethylamine or 1,8-diazabicyclo[5.4.0]undec-7-ene (DBU). Activation of the amine with ethyl phosphorodichloridate gives type (b3) activated subunits 22a-e, which can be incorporated into oligomers in the same manner as type (a), (b1) and (b2) subunits. A method for the preparation of variants of 22a-e, containing various side chains on the 5'-nitrogen, involves alkylation of an activated 5'-morpholino subunit with suitably protected amines. As shown in FIG. 2F for two examples, and described in Example 6, hexamethylene diamine was first protected, then reacted with 5'-O-p-toluenesulfonated subunit 23a-e. Using the methods in FIGS. 2E and 2F and in the corresponding Examples, a person skilled in the art could prepare a wide range of 5'-amino substituted subunits suitable for incorporation into cationic morpholino oligomers.

As noted above, cationic linkages may also be prepared from non-phosphorus-containing linkages. For example, subunits capable of providing sulfonamide linkages with pendant cationic groups may be introduced from the amine used in (b3) type linkages, as shown in FIG. 2G and described in Example 7. Reaction of the aminated subunits with sulfurtrioxide/pyridine in N,N-dimethylformamide containing triethylamine provides a sulfamic acid that was treated with phosgene in dichloromethane containing pyridine to give the activated sulfamoyl chloride containing subunit.

Morpholino oligomers can be prepared from such subunits in a stepwise manner on a solid support, preferably an aminomethyl polystyrene solid support, e.g. as described in U.S. Pat. No. 5,185,444 or in Summerton and Weller, 1997 (cited above). The resin is preferably modified by reaction with a disulfide "anchor", which allows production of the morpholino oligomer on the support and facile release upon treatment with a thiol, as shown in FIG. 2H and described in Example 8.

In some cases it is advantageous to introduce a triethylene glycol containing moiety ("tail") which increases aqueous solubility of the morpholino oligomers. One method for accomplishing this is illustrated in FIG. 2I and described in Example 9.

In a typical synthesis, the disulfide anchor 34 is reacted as shown in FIG. 2J with aminomethylpolystyrene resin in 1-methyl-2-pyrrolidinone (NMP) to give resin-anchor 39, suitable for incorporation of activated subunits. Optionally, the Tail moiety can be introduced onto the 5'-terminus of the oligomer by reaction of the disulfide anchor-resin with 38 to produce Tail-resin 40. Use of resin 40 will cause the $HOCH_2CH_2OCH_2CH_2OCH_2CH_2OC(O)$ group (=EG3) to become attached to the 5'-terminus of the oligomer.

The activated subunits, containing the appropriate inter-subunit linkage type, are introduced stepwise by solid phase synthesis on resin 39 containing anchor or, optionally, the Tail resin 40. A cycle of solid phase synthesis performed using an automated synthesizer consists of washing the resin with NMP or dichloromethane (DCM), followed by treatment with 11% cyanoacetic acid in 20% acetonitrile/DCM (v/v). After neutralization with a 5% solution of diisopropylethylamine (DIEA) in 20% isopropanol/DCM, the resin is reacted with a 0.2 M solution of the activated subunit in 1,3-dimethyl-2-imidazolidinone (DMI) (or Tail in NMP) containing 0.4 M 4-ethylmorpholine. After washing with neutralization solution, the cycle may be repeated to introduce the next subunit. Optionally, following the final subunit addition, the trityl group at the end of the resin is removed and methoxytrityl chloride introduced to prepare the 3'-methoxytritylated oligomer. The more labile methoxytrityl species provides benefit in the aqueous detritylation step which follows "trityl-ON/trityl-OFF" purification of the crude oligomers.

The reactor design used for the preparation of the bulk resins 39 and 40 was employed for larger scale synthesis of morpholino oligomers. On the large scale, the detritylation steps performed when phosphorodiamidate linkages had been introduced onto the resin used a solution of 4-cyanopyridinium trifluoroacetate in 20% trifluoroethanol/DCM. This provided less hydrolysis of the somewhat acid labile phosphorodiamidate linkages than did carboxylic acid based detritylation reagents. Additionally, the use of doubly protected G subunit was found to be advantageous. FIG. 2K illustrates synthesis of the N2,O6-protected G species 46 that was employed.

The synthesized oligomers were released from the solid support by treatment with a solution of 1,4-dithiothreitol and triethylamine in NMP. The solution was treated with concentrated ammonia and held at 45° C. The mixture was sealed in a pressure vessel and heated at 45° C. for 16-24 hours. The solution was diluted with 0.28% aqueous ammonia and passed through ion exchange resin to capture the crude methoxytritylated oligomer. The product was eluted with a salt gradient to recover the later-eluting, methoxytrityl or trityl containing product and the product containing fractions pooled. For preparation of 3'-unsubstituted (3'-H) oligomers requiring no further modification, the solution was treated with acid to pH=2.5 to demethoxytritylate the oligomer. The demethoxytritylation mixture was immediately neutralized with concentrated ammonia, and the solution passed through reversed phase resin. The product was recovered by elution with 45% acetonitrile/0.28% aqueous ammonia and isolated as a white powder after lyophilization. Further purification of the product may be performed on cation exchange resins as described in the methods section. Alternatively, it was advantageous to retain the 3'-methoxytrityl/trityl group in order to perform modification of the backbone amine moieties independent of the 3'-terminus of the oligomer, as described below. It this case, the above procedure was followed except that the aqueous acid treatment was omitted.

Amine groups introduced into a morpholino oligomer as part of cationic linkages may be further modified. This concept allows an oligomer to be constructed from a relatively simple modified subunit, but with functionality sufficient to allow the introduction of complex moieties in any location along the backbone of the morpholino oligomers.

(Note that, for reasons of synthesis, the 5' terminal linkage of an oligomer does not typically comprise a linkage of type (b1) described herein. As shown, for example, in FIGS. 2P-2Q, the preferred stepwise resin-supported synthesis of the oligomers provides a piperazine ring on the phosphorus atom at the 5'terminus; the presence of a second piperazine ring on the phosphorus would be constrained for steric reasons.)

An important modification is the incorporation of guanidinium groups into the oligomer. This may be done in two ways. In the first, the amine moiety on the backbone of the oligomer was directly converted into a guanidinium species by reaction with 1H-pyrazole-1-carboxamidine hydrochloride (M S Bernatowicz, Y Wu, G R Matsueda, J. Org. Chem., 1992, 57(8), 2497-2502) in sodium carbonate buffered aqueous solution, as in FIG. 2L, which also shows the EG3 Tail at the 5'-terminus. In the second, a substance containing both carboxyl and guanidinium groups, e.g., 6-guanidinohexanoic acid was activated with 2-(1-H-benzotriazol-1-yl)-1,1,3,3-tetramethylaminium hexafluorophosphate (HBTU) and reacted with the amine containing oligomer (FIG. 2M). In a similar fashion, 4-guanidinobutanoic acid, 3-guanidinopropanoic acid, and guanidinoacetic acid may be introduced. In a hybrid of these approaches, the amine moiety was reacted with a protected FMOC amino acid, e.g., FMOC 6-aminohexanoic acid to introduce a protected primary amine containing side chain, which after treatment with ammonia to remove the FMOC group was guanylated as above. Fully guanylated species were separated from partially guanylated oligomers by cation chromatography at the appropriate pH.

The termini of the oligomer can also eb substituted with guanidinium moieties by these methods, as illustrated in FIG. 2N, which also shows a representative oligomer created from resin 39, without addition of the PEG Tail.

Another modification of note is the incorporation of peptides along the backbone. Small peptides are readily available from commercial sources, for example, Bachem Calif., Inc. 3132 Kashiwa Street Torrance, Calif. 90505 USA, and AnaSpec, Inc. 2149 O'Toole Ave., San Jose, Calif. 95131. The incorporation of the peptide followed classic 2-(1-H-benzotriazol-1-yl)-1,1,3,3-tetramethylaminium hexafluorophosphate (HBTU) chemistry, as illustrated in FIG. 2O. Guanidinium groups on the oligomer or peptide do not interfere.

Oligomers may also be conjugated at the 3'-terminus to arginine rich peptides, useful to enhance delivery of the products into cells. In this case, protection of primary and secondary amine moieties along the backbone of 3'-methoxtritylated/tritylated oligomers was performed by trifluoroacetylation, as shown in FIG. 2P. The terminal methoxytrityl group was removed and the peptide conjugated using HBTU. The conjugation reaction was worked up by treatment with ammonia to remove the trifluoroacetyl groups. The conjugate was purified by cation exchange chromatography. When the backbone amine functions are fully guanylated, the peptide may be introduced without interference from these side chains, as shown in FIG. 2Q.

Methylation of the piperazine of the b1 linkage series may be accomplished by treating the morpholino oligomer with formaldehyde and sodium borohydride in aqueous solution as illustrated in FIG. 2R. Other aldehydes may be used to incorporate alternative groups.

V. Applications of Morpholino Oligomers Containing Cationic Linkages

The compounds described herein may be used in methods of inhibiting production of a protein. Accordingly, a nucleic acid encoding such a protein is exposed to an antisense oligomer containing at least one cationic intersubunit linkage, and preferably containing 20% to 50% such cationic linkages, as disclosed herein, where the base pairing moieties Pi form a sequence effective to hybridize to a portion of the nucleic acid at a location effective to inhibit production of the protein. The location may be, for example, an ATG start codon of an mRNA, a splice site of a pre-mRNA, or a viral target sequence as described below.

In general, for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107.

Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

Preferably, the oligomer is actively taken up by mammalian cells. The oligomer may be conjugated to a transport moiety as described herein to facilitate such uptake.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., *Leukemia* 10(12):1980-1989, 1996; Lappalainen et al., *Antiviral Res.* 23:119, 1994; Uhlmann et al., *Antisense Oligonucleotides: A New Therapeutic Principle*, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., *J. Biol. Chem.* 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

A. Antisense Compounds for Treating Restenosis

The compounds of the present invention are useful in treatment of vascular proliferative disorders such as restenosis. Areas of vessel injury include, for example, restenosis or renarrowing of the vascular lumen following vascular intervention, such as coronary artery balloon angioplasty, with or without stent insertion. Restenosis is believed to occur in about 30% to 60% of lesions treated by angioplasty and about 20% of lesions treated with stents within 3 to 6 months following the procedure. (See, e.g., Devi, N. B. et al., *Cathet Cardiovasc Diagn* 45(3):337-45, 1998). Stenosis can also occur after a coronary artery bypass operation, wherein heart surgery is done to reroute, or "bypass," blood around clogged arteries and improve the supply of blood and oxygen to the heart. In such cases, the stenosis may occur in the transplanted blood vessel segments, and particularly at the junction of replaced vessels. Stenosis can also occur at anastomotic junctions created for dialysis.

The oligomers of the invention can therefore be used in compositions and methods for treating restenosis. In particular, cationic linkages contained in an antisense morpholino oligomer composition directed against c-myc to reduce the risk of restenosis in transluminal angioplasty, such as percutaneous transluminal coronary angioplasty (PTCA) (see e.g. PCT Pubn. No. WO/2000/044897). Compared to morpholino oligomers with only uncharged linkages, those containing cationic linkages interspersed throughout the antisense c-myc compound are expected to provide greater efficacy at lower doses in the treatment of restenosis.

Thus, the method includes administering to the patient, by local administration directly to the vessel site of injury, or by systemic delivery via intravascular administration, an oligomer as described herein, containing at least one cationic intersubunit linkage, and preferably containing 20% to 50% such cationic linkages, having from 12 to 40 subunits, including a targeting base sequence that is complementary to a target sequence of at least 12 contiguous bases within the AUG start site region of human c-myc mRNA defined by SEQ ID NO:

59 (Human c-myc, −100 to +25 relative to ATG: CGCCGCT-GCC AGGACCCGCT TCTCTGAAAG GCTCTCCTTG CAGCTGCTTA GACGCTGGAT TTTTTTCGGG TAGTG-GAAAA CCAGCAGCCT CCCGCGACGA TGCCCCT-CAA CGTTAGCTTC ACCAA), in an amount effective to reduce the risk of restenosis in the patient. The compound is administered by one of:

(a) contacting the region of the vessel with a reservoir containing the antisense compound, and introducing the compound from the reservoir into the vessel by iontophoresis or electroporation;

(b) injecting the compound from the catheter directly into the region of the vessel, under pressure, through injectors contained on the surface of the catheter balloon, where said injectors are capable of penetrating the tunica media in the vessel;

(c) injecting into or contacting the region of the vessel, microparticles containing the antisense compound in entrapped form;

(d) contacting the region of the vessel with a hydrogel coating contained on the surface of the catheter balloon, and containing the antisense compound is diffusable form;

(e) contacting the region of the vessel with a stent having an outer surface layer containing the antisense compound in diffusable form; and (f) injecting the compound by intravascular administration resulting in systemic delivery to the vascular tissues.

The antisense compound may have a targeting sequence having at least 90% homology to the sequence identified by SEQ ID NO: 43 (ACGTTGAGGGGCATCGTCGC), and alternatively, at least 90% homology to a sequence selected from SEQ ID NOs: 60 (GGAGGCTGCTGGTTTTCCAC) and 61 (GGCATCGTCGCGGGAGGCTC).

The amount of antisense compound administered may be between about 0.5 and 30 mg. The compound may be derivatized with a moiety that enhances the solubility of the compound in aqueous medium, and the compound is administered from a solution containing at least about 30 mg/ml of the antisense compound.

The compound is designed to hybridize to c-myc mRNA under physiological conditions with a Tm substantially greater than 37° C., e.g., at least 50° C. and preferably 60-80° C. The compound preferably contains an internal 3-base triplet complementary to the AUG site, and bases complementary to one or more bases 5' and 3' to the start site. One preferred compound sequence is the 20-mer identified as SEQ ID NO: 43, where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions.

The oligomer is employed, for example, in a coated stent, or by an ex vivo soaking solution for treatment of saphenous veins, or otherwise delivered to the site of vascular injury. In another embodiment, the antisense compound forms part of a particle composition for use in restenosis treatment. One such particle is a biodegradable particle, e.g., a polylactate or polyglycolic particle, containing entrapped antisense compound. The particles are preferably in the 1-5 micron range, and are useful for delivery by direct particle delivery to an angioplasty vessel site, as described below, either by being impressed into the vessel walls by pressure from a balloon against the wall, or by release from a particle carrier, such as a stent.

The oligomer can also be employed by administering via systemic delivery to the site of vascular injury by intravascular injection.

Alternatively, the particles can be microbubbles containing the compound in entrapped form. The particles may be delivered directly to the vessel site, that is, by contacting the vessel walls with a directly with a suspension of the particles, with compound release from the particles, which may be facilitated by exposing the vessel region to ultrasonic energy.

Microbubble compositions have been found particularly useful in delivery of attached molecules, such as oligonucleotides, to areas of thrombosis or vessel injury, e.g. damaged endothelium, as well as to selected organs such as the liver and kidney. See, for example, PCT Pubn. No. WO 2000/02588, U.S. Pat. Nos. 6,245,247 and 7,094,765, and U.S. Appn. Pubn. No. 20030207907, which are incorporated herein by reference.

In still another embodiment, the particles are liposomes containing entrapped antisense compound. Because the liposome particles are applied directly to the vessel site, the liposomes may be conventional liposomes without surface modifications needed for achieving long circulation times.

B. Antiviral Applications

In another embodiment, oligomers of the invention can be used to inhibit the replication of an RNA virus having a single-stranded, positive-sense genome and selected from one of the Flaviviridae, Picornoviridae, Caliciviridae, Togaviridae, Arteriviridae, Coronaviridae, Astroviridae and Hepeviridae virus families.

B1. Targeting Stem-Loop Secondary Structure of ssRNA Viruses

One class of an exemplary antisense antiviral compound is a morpholino oligomer having cationic linkages, as described in the present invention, having a sequence of 12-40 subunits and a targeting sequence that is complementary to a region associated with stem-loop secondary structure within the 5'-terminal end 40 bases of the positive-sense RNA strand of the targeted virus. (See, e.g., PCT Pubn. No. WO/2006/033933 or U.S. Appn. Pubn. Nos. 20060269911 and 20050096291, which are incorporated herein by reference.)

The method includes first identifying as a viral target sequence, a region within the 5'-terminal 40 bases of the positive strand of the infecting virus whose sequence is capable of forming internal stem-loop secondary structure. There is then constructed, by stepwise solid-phase synthesis, an oligomer having at least one cationic intersubunit linkage as described herein, and preferably containing 20% to 50% such cationic linkages, and having a targeting sequence of at least 12 subunits that is complementary to the virus-genome region capable of forming internal duplex structure, where the oligomer is able to form with the viral target sequence, a heteroduplex structure composed of the positive sense strand of the virus and the oligonucleotide compound, and characterized by a Tm of dissociation of at least 45° C. and disruption of such stem-loop structure.

The target sequence may be identified by analyzing the 5'-terminal sequences, e.g., the 5'-terminal 40 bases, by a computer program capable of performing secondary structure predictions based on a search for the minimal free energy state of the input RNA sequence.

In a related aspect, the oligomers can be used in methods of inhibiting in a mammalian host cell, replication of an infecting RNA virus having a single-stranded, positive-sense genome and selected from one of the Flaviviridae, Picornoviridae, Caliciviridae, Togaviridae, Arteriviridae, Coronaviridae, Astroviridae or Hepeviridae families. The method includes administering to the infected host cells, a virus-inhibitory amount of an oligomer as described herein, having a targeting sequence of at least 12 subunits that is complementary to a region within the 5'-terminal 40 bases of the positive-strand viral genome that is capable of forming internal stem-loop secondary structure. The compound is effective, when administered to the host cells, to form a heteroduplex structure (i) composed of the positive sense strand of the virus and the oligonucleotide compound, and (ii) characterized by a Tm of dissociation of at least 45° C. and disruption of such stem-loop secondary structure. The compound may be administered to a mammalian subject infected with the virus, or at risk of infection with the virus.

For treatment of a Flavivirus or Hepacivirus, the targeting sequence is complementary to a region associated with stem-loop secondary structure within one of the following sequences:

(i) SEQ ID NO. 77, for St Louis encephalitis virus;
(ii) SEQ ID NO. 78, for Japanese encephalitis virus;
(iii) SEQ ID NO. 79, for a Murray Valley encephalitis virus;
(iv) SEQ ID NO. 80, for a West Nile fever virus;
(v) SEQ ID NO. 81, for a Yellow fever virus
(vi) SEQ ID NO. 82, for a Dengue Type-2 virus;
(vii) SEQ ID NO. 83, for a Hepatitis C virus;
(viii) SEQ ID NO. 84, for a tick-borne encephalitis virus;
(ix) SEQ ID NO. 85, for Omsk hemorrhagic fever virus; and
(x) SEQ ID NO. 86, for Powassan virus.

Exemplary targeting sequences for these viruses include the following sequences, or portions of these sequences that overlap with one or more regions of duplex secondary structure in the associated target sequence:

(i) SEQ ID NOS. 87 and 88, for St Louis encephalitis virus;
(ii) SEQ ID NOS. 89 and 90, for Japanese encephalitis virus;
(iii) SEQ ID NOS. 91 and 92, for a Murray Valley encephalitis virus;
(iv) SEQ ID NOS. 93 and 94, for a West Nile fever virus;
(v) SEQ ID NOS. 95 and 96, for a Yellow fever virus;
(vi) SEQ ID NOS. 97, 98, for a Dengue virus;
(vii) SEQ ID NOS. 99 and 100, for a Hepatitis C virus;
(viii) SEQ ID NOS. 101 and 102, for a tick-borne encephalitis virus;
(ix) SEQ ID NOS. 103 and 104, for Omsk hemorrhagic fever virus; and
(x) SEQ ID NOS. 105 and 106, for Powassan virus.

For treatment of an Enterovirus, Rhinovirus, Hepatovirus or Aphthovirus, the targeting sequence is complementary to a region associated with stem-loop secondary structure within one of the following sequences:

(i) SEQ ID NO. 107, for a polio virus of the Mahoney and Sabin strains;
(ii) SEQ ID NO. 108, for a Human enterovirus A;
(iii) SEQ ID NO. 109, for a Human enterovirus B;
(iv) SEQ ID NO. 110, for a Human enterovirus C;
(v) SEQ ID NO. 111, for a Human enterovirus D;
(vi) SEQ ID NO. 112, for a Human enterovirus E;
(vii) SEQ ID NO. 113, for a Bovine enterovirus;
(viii) SEQ ID NO. 114, for Human rhinovirus 89;
(ix) SEQ ID NO. 115, for Human rhinovirus B;
(x) SEQ ID NO. 116, for Foot-and-mouth disease virus; and
(xi) SEQ ID NO. 117, for a hepatitis A virus.

Exemplary targeting sequences for these viruses include the following sequences, or portions of these sequences that overlap with one or more regions of duplex secondary structure in the associated target sequence:

(i) SEQ ID NOS. 118 and 119, for a polio virus of the Mahoney and Sabin strains;
(ii) SEQ ID NOS. 120 and 121, for a Human enterovirus A;
(iii) SEQ ID NOS. 122 and 123, for a Human enterovirus B;
(iv) SEQ ID NOS. 124 and 125, for a Human enterovirus C;
(v) SEQ ID NOS. 126 and 127, for a Human enterovirus D;
(vi) SEQ ID NOS. 128 and 129, for a Human enterovirus E;
(vii) SEQ ID NOS. 130 and 131, for a Bovine enterovirus;
(viii) SEQ ID NOS. 132 and 133, for Human rhinovirus 89;
(ix) SEQ ID NOS. 134 and 135, for Human rhinovirus B;
(x) SEQ ID NOS. 136 and 137, for Foot-and-mouth disease virus; and
(xi) SEQ ID NOS. 138 and 139, for a hepatitis A virus.

For treatment of a Calicivirus or Norovirus, the targeting sequence is complementary to a region associated with stem-loop secondary structure within one of the following sequences:

(i) SEQ ID NO. 140, for a Feline Calicivirus;
(ii) SEQ ID NO. 141, for a Canine Calicivirus;
(iii) SEQ ID NO. 142, for a Porcine enteric calicivirus;
(iv) SEQ ID NO. 143, for Calicivirus strain NB; and
(v) SEQ ID NO. 144, for a Norwalk virus.

Exemplary targeting sequences for these viruses include the following sequences, or portions of these sequences that overlap with one or more regions of duplex secondary structure in the associated target sequence:

(i) SEQ ID NOS. 145 and 146, for a Feline Calicivirus;
(ii) SEQ ID NOS. 147 and 148, for a Canine Calicivirus;
(iii) SEQ ID NOS. 149 and 150, for a Porcine enteric calicivirus;
(iv) SEQ ID NOS. 151 and 152, for Calicivirus strain NB; and
(v) SEQ ID NOS. 153 and 154, for a Norwalk virus.

For treatment of the Hepevirus, Hepatitis E virus, the targeting sequence is complementary to a region associated with stem-loop secondary structure within the sequence identified as SEQ ID NO: 155. Exemplary targeting sequences include SEQ ID NOS: 156 and 157, or portions thereof that overlap with one or more regions of secondary structure in the associated target sequence.

For treatment of a Rubivirus or Alphavirus the targeting sequence is complementary to a region associated with stem-loop secondary structure within one of the following sequences:

(i) SEQ ID NO. 158, for Rubella virus;
(ii) SEQ ID NO. 159, for Eastern equine encephalitis virus;
(iii) SEQ ID NO. 160, for Western equine encephalitis virus; and
(iv) SEQ ID NO. 161, for Venezuelan equine encephalitis virus.

Exemplary targeting sequences for each of these viruses are identified by the following sequence ID numbers, or portions of these sequences that overlap with one or more regions of duplex secondary structure in the associated target sequence:

(i) SEQ ID NOS. 162 and 163, for Rubella virus;
(ii) SEQ ID NOS. 164 and 165, for Eastern equine encephalitis virus;
(iii) SEQ ID NOS. 166 and 167, for Western equine encephalitis virus; and
(iv) SEQ ID NOS. 168 and 169, for Venezuelan equine encephalitis virus For treatment of a Coronavirus or Arterivirus, the targeting sequence is complementary to a region associated with stem-loop secondary structure within one of the following sequences:

(i) SEQ ID NO. 170, for SARS coronavirus TOR2;
(ii) SEQ ID NO. 171, for Porcine epidemic diarrhea virus;
(iii) SEQ ID NO. 172, for Transmissible gastroenteritis virus;
(iv) SEQ ID NO. 173, for Bovine coronavirus;
(v) SEQ ID NO. 174, for Human coronavirus 229E;
(vi) SEQ ID NO. 175, for Murine hepatitis virus; and
(vii) SEQ ID NO. 176, for Porcine reproductive and respiratory syndrome virus.

Exemplary targeting sequences for each of these viruses are identified by the following sequence ID numbers, or portions of these sequences that overlap with one or more regions of duplex secondary structure in the associated target sequence:

(i) SEQ ID NOS. 177 and 178, for SARS coronavirus TOR2;
(ii) SEQ ID NOS. 179 and 180, for Porcine epidemic diarrhea virus;
(iii) SEQ ID NOS. 181 and 182, for Transmissible gastroenteritis virus;
(iv) SEQ ID NOS. 183 and 184, for Bovine coronavirus;
(v) SEQ ID NOS. 185 and 186, for Human coronavirus 229E;
(vi) SEQ ID NOS. 187 and 188, for Murine hepatitis virus; and
(vii) SEQ ID NOS. 189 and 190, for Porcine reproductive and respiratory syndrome virus.

For treatment of a Mamastrovirus, Human astrovirus, the targeting sequence is complementary to a region associated with stem-loop secondary structure within the sequence identified as SEQ ID NO: 191. Exemplary targeting sequences are SEQ ID NOS. 193 and 194, or portions of these sequences that overlap with one or more regions of duplex secondary structure in the associated target sequence.

For treatment of an Equine arteritis virus, the targeting sequence is complementary to a region associated with stem-loop secondary structure within the sequence identified as SEQ ID NO: 192. Exemplary targeting sequences are SEQ ID NOS. 195, 196, or portions of these sequences that overlap with one or more regions of duplex secondary structure in the associated target sequence.

B2. Targeting the First ORF of ssRNA Viruses

A second class of exemplary antisense antiviral compounds for use in inhibition of growth of viruses of the picornavirus, calicivirus, togavirus, coronavirus, and flavivirus families having a single-stranded, positive sense genome of less than 12 kb and a first open reading frame that encodes a polyprotein containing multiple functional proteins. In particular embodiments, the virus is an RNA virus from the coronavirus family or a West Nile, Yellow Fever or Dengue virus from the flavivirus family. The inhibiting compounds consist of antisense oligomers with interspersed cationic linkages, as described herein, having a targeting base sequence that is substantially complementary to a viral target sequence which spans the AUG start site of the first open reading frame of the viral genome. In one embodiment of the method, the oligomer is administered to a mammalian subject infected with the virus. See, e.g., PCT Pubn. No. WO/2005/007805 and US Appn. Pubn. No. 2003224353, which are incorporated herein by reference.

Exemplary antiviral compounds directed against a picornavirus include those having a targeting sequence having at least 90% homology to a sequence selected from the group consisting of: (i) SEQ ID NO. 62, for a polio virus of the Mahoney and Sabin strains, (ii) SEQ ID NO. 63, for a hepatitis A virus, (iii) SEQ ID NO. 64, for a rhinovirus 14, (iv) SEQ ID NO. 65, for a rhinovirus 16, and (v) SEQ ID NO. 66, for a rhinovirus 1B.

Exemplary antiviral compounds directed against a calicivirus include those having a targeting sequence having at least 90% homology to a sequence selected from the group consisting of: (i) SEQ ID NOs. 67, 68, and 69, for a serotype Pan-1 vesivirus, (ii) SEQ ID NO. 70, for a porcine calicivirus, (iii) SEQ ID NO. 71, for a Norwalk virus, and (iv) SEQ ID NO. 72, for a feline calicivirus.

For use in inhibition of a hepatitis C flavivirus, the targeting sequence is complementary to a sequence of at least 12 contiguous bases of the HCV AUG start-site region identified by SEQ ID NO: 75. Exemplary targeting sequences include those having at least 90% homology to SEQ ID NOs. 18 or 76.

Exemplary antiviral compounds directed against a togavirus include those having a targeting sequence having at least 90% homology to a sequence selected from the group consisting of SEQ ID NOs: 73 and 74, for hepatitis E virus.

The preferred target sequence is a region that spans the AUG start site of the first open reading frame (ORF1) of the viral genome. The first ORF generally encodes a polyprotein containing non-structural proteins such as polymerases, helicases and proteases. By "spans the AUG start site" is meant that the target sequence includes at least three bases on one side of the AUG start site and at least two bases on the other (a total of at least 8 bases). Preferably, it includes at least four bases on each side of the start site (a total of at least 11 bases).

More generally, preferred target sites include targets that are conserved between a variety of viral isolates. Other favored sites include the IRES (internal ribosome entry site), transactivation protein binding sites, and sites of initiation of replication. Complex and large viral genomes, which may provide multiple redundant genes, may be efficiently targeted by targeting host cellular genes coding for viral entry and host response to viral presence.

A variety of viral-genome sequences are available from well known sources, such as the NCBI Genbank databases. The AUG start site of ORF1 may also be identified in the gene database or reference relied upon, or it may be found by scanning the sequence for an AUG codon in the region of the expected ORF1 start site.

The general genomic organization of each of the four virus families is given below, followed by exemplary target sequences obtained for selected members (genera, species or strains) within each family.

Picornavirus. Typical of the picornavirus, the rhinovirus genome is a single molecule of single-stranded, positive sense, polyadenylated RNA of approximately 7.5 kb. The genome includes a long UTR, which is located upstream of the first polyprotein, and a single open reading frame (ORF) having a VPg (viral genome linked) protein covalently attached to its end. The ORF is subdivided into two segments, each of which encodes a polyprotein. The first segment encodes a polyprotein that is cleaved subsequently to form viral proteins VP 1 to VP4, and the second segment encodes a polyprotein which is the precursor of viral proteins including a Cis-pro, a protease, and a polymerase. The ORF terminates in a polyA termination sequence.

The target initial AUG start site is located between base positions 615-640; targeting this region is effective to inhibit translation of both polyprotein segments.

Calicivirus. The genome of a vesivirus, of the Calicivirus family, is a single molecule of infectious, single stranded, positive sense RNA of approximately 7.5 kb. The genome includes a UTR upstream of the first open reading frame (ORF1) which is unmodified. The 3' end of the genome is polyadenylated. The genome includes three open reading frames. The first open reading frame encodes a polyprotein, which is subsequently cleaved to form the viral non-structural proteins including a helicase, a protease, an RNA dependent RNA polymerase, and "VPg", a protein that becomes bound to the 5' end of the viral genomic RNA. The second open reading frame codes for the single capsid protein, and the third open reading frame codes for what is reported to be a structural protein that is basic in nature and probably able to associate with RNA.

The target initial AUG start site is located between base positions 7-35; targeting this region is effective in inhibiting the translation of first reading frame.

Togavirus. The genome of a rubella virus, of the Togavirus family, is a single linear molecule of single-stranded, positive-sense RNA of approximately 11.7 kb, which is infectious. The 5' end is capped with a 7-methylG molecule and the 3' end is polyadenylated. Full-length and subgenomic messenger RNAs have been demonstrated, and post translational cleavage of polyproteins occurs during RNA replication. The genome includes two open reading frames. The first open reading frame encodes a polyprotein which is subsequently cleaved into four functional proteins, nsP1 to nsP4. The second open reading frame encodes the viral capsid protein and three other viral proteins, PE2, 6K and E1.

The AUG start site for first open reading frame is located between base positions 10-40; targeting this region is effective to inhibit the translation of the first open reading frame.

Flavivirus. The hepatitis C virus genome is a single linear molecule of single-stranded, positive-sense RNA of about 11 kb. The 5' end is capped with a $m^7$GppAmp molecule, and the 3' end is not polyadenylated. The genome includes only one open reading frame, which encodes a precursor polyprotein separable into six structural and functional proteins. The initial AUG start site is located at base position 343.

GenBank references for exemplary viral nucleic acid sequences containing the ORF1 start site in the corresponding viral genomes are listed in Table 3, below. It will be appreciated that these sequences are only illustrative of other sequences in the ORF1 start-site region of members of the four virus families, as may be available from available gene-sequence databases of literature or patent resources.

Targeting sequences directed against a target region that spans the translation initiation site of the first open reading frame (ORF1) are selected by constructing a complementary sequence to one or more sequences spanning the AUG site in these target regions; see Table 3 below.

TABLE 3

Exemplary Antisense Sequences Targeting the ORF1 Translation Initiation Region

| Virus | GenBank Acc. No. | Targeted Region | Antisense Oligomer (5' to 3) | Seq. ID No. |
|---|---|---|---|---|
| Picornaviridae | | | | |
| Poliovirus Mahoney strain Sabin strain | NC002058 V01150 | 735-755 735-755 | CCTGAGCACCCATTATGATAC | 62 |
| Hepatitis A | M14707 | 731-754 | CCTTGTCTAGACATGTTCATTATT | 63 |
| Rhinovirus 14 | NC001490 | 621-640 | CTGAGCGCCCATGATCACAG | 64 |
| Rhinovirus 16 | NC001752 | 618-637 | TTGAGCGCCCATGATAACAA | 65 |
| Rhinovirus 1B | D00239 | 615-634 | CTGGGCACCCATGATGCCAA | 66 |
| Caliciviridae | | | | |
| Vesivirus (Pan-1) | AF091736 | 7-26 | GAGCCATAGCTCAAATTCTC | 67 |
| | | 1-21 | TAGCTCAAATTCTCATTTAC | 68 |
| | | 15-34 | GAGCGTTTGAGCCATAGCTC | 69 |
| Porcine | AF182760 | 6-25 | GACGGCAATTAGCCATCACG | 70 |
| Norwalk | AF093797 | 1-19 | CGACGCCATCATCATTCAC | 71 |
| Feline | AF479590 | 14-34 | CAGAGTTTGAGACATTGTCTC | 72 |
| Togaviridae | | | | |
| Hepatitis E | NC001434 | 6-28 | CCTTAATAAACTGATGGGCCTCC | 73 |
| | | 1-18 | CTGATGGGCCTCCATGGC | 74 |
| Flaviviridae | | | | |
| Hepatitis C | AF169005 | 348-330 | GTGCTCATGGTGCACGGTC-3 | 18 |
| | | | GGCCTTTCGCGACCCAACAC | 76 |

B3. Targeting Influenza Virus

A third class of exemplary antisense antiviral compounds are used in inhibition of growth of viruses of the Orthomyxoviridae family and in the treatment of a viral infection. The host cell is contacted with an oligomer as described herein, containing at least one cationic intersubunit linkage, and preferably containing 20% to 50% such cationic linkages, and containing a base sequence effective to hybridize to a target region selected from the following: i) the 5' or 3' terminal 25 bases of a negative sense viral RNA segment of Influenzavirus A, Influenzavirus B and Influenzavirus C, ii) the terminal 30 bases of the 3' terminus of a positive sense cRNA of Influenzavirus A, Influenzavirus B and Influenzavirus C, and iii) the 50 bases surrounding the AUG start codon of an influenza viral mRNA. (See, e.g., PCT Pubn. No. WO/2006/047683 or U.S. Appn. Pubn. No. 20070004661, which are incorporated herein by reference.)

The compounds are particularly useful in the treatment of influenza virus infection in a mammal. The oligomer may be administered to a mammalian subject infected with the influenza virus, or at risk of infection with the influenza virus.

For treatment of Influenza A virus, the targeting sequence hybridizes to a region associated with one of the group of sequences identified as SEQ ID NOs: 221-222. Preferred targeting sequences are those complementary to either the minus strand target of SEQ ID NO: 222 or the positive-strand target of SEQ ID NO: 221. Exemplary antisense oligomers that target these two regions are listed as SEQ ID NOs: 223 and 224, respectively.

These sequences will target most, if not all, influenza A virus strains because of the high degree of homology between strains at the respective targets.

Table 4 below shows exemplary targeting sequences, in a 5'-to-3' orientation, that are complementary to influenza A virus. The sequences listed provide a collection of targeting sequences from which targeting sequences may be selected, according to the general class rules discussed above.

TABLE 4

Exemplary Antisense Oligomer Sequences for Targeting Influenza A

| PMO | Target Nucleotides | GenBank Acc. No. | Targeting Antisense Oligomer (5' to 3') | SEQ. NO. |
|---|---|---|---|---|
| PB1-AUG | 13-33 | J02151 | GACATCCATTCAAATGGTTTG | 224 |
| (-)NP-3'trm | 1-22 | J02147 | AGCAAAAGCAGGGTAGATAATC | 223 |

B4. Targeting Viruses of the Picornaviridae Family

A fourth class of exemplary antisense antiviral compounds are used in inhibition of growth of viruses of the Picornaviridae family and in the treatment of a viral infection. The compounds are particularly useful in the treatment of Enterovirus and/or Rhinovirus infection in a mammal. The antisense antiviral compounds are partially positively charged morpholino oligomers having a sequence of 12-40 subunits, including at least 12 subunits having a targeting sequence that is complementary to a region associated with viral RNA sequences within one of two 32 conserved nucleotide regions of the viral 5' untranslated region identified by SEQ ID NOS: 55 and 56. (See, e.g., PCT Pubn. Nos. WO/2007/030576 and WO/2007/030691 or copending and co-owned provisional application Ser. Nos. 60/800,120 and 60/800,145, which are incorporated herein by reference.)

GenBank reference entries for exemplary viral nucleic acid sequences representing picornavirus genomic RNA are listed in Table 5 below. This table lists target regions for a 32-base sequence corresponding to nucleotides 443-474 of the poliovirus reference sequence (NC 002058) and contained in the 5' UTR region of several picoriviruses. All the viruses listed in Table 2 are human isolates and are organized into the Enterovirus and Rhinovirus genera as Human Enteroviruses A-D, Poliovirus, Rhinovirus A and Rhinovirus B according to convention as provided by the International Committee on Taxonomy of Viruses (ICTV).

There is a high degree of sequence conservation between viruses in the two genera, Enterovirus and Rhinovirus. The target sequence identified as SEQ ID NO: 56 (TCCTCCG-GCC CCTGAATGYG GCTAAYCYYA AC) represents a combined target sequence, where the letter "Y" in the sequence represents a pyrimidine base, i.e., may be either C or T.

TABLE 5

Exemplary Human Picornavirus Nucleic Acid Target Sequences; 5'-Region

| Virus | Ref. No. | GB No. | Region |
|---|---|---|---|
| Poliovirus-Mahoney strain | NC 002058 | V01149 | 443-474 |
| Enterovirus A (CV-A16) | NC 001612 | U05876 | 452-483 |
| Enterovirus 71 (HEV-71) | | U22521 | 448-479 |
| Enterovirus B (CV-B1) | NC 001472 | M16560 | 446-477 |
| Coxsackievirus B3 (CV-B3) | | M88483 | 447-478 |
| Coxsackievirus B2 (CV-B2) | | AF081485 | 448-479 |
| Coxsackievirus B4 (CV-B4) | | X05690 | 448-479 |
| Coxsackievirus B5 (CV-B5) | | X67706 | 448-479 |
| Coxsackievirus A9 (CV-A9) | | D00627 | 448-479 |
| Echovirus 4 (EV-4) | | X89534 | 331-362 |
| Echovirus 6 (EV-6) | | U16283 | 446-477 |
| Echovirus 11 (EV-11) | | X80059 | 449-480 |
| Echovirus 13 (EV-13) | | AF412361 | 259-290 |
| Echovirus 18 (EV-18) | | AF412366 | 259-290 |
| Echovirus 25 (EV-25) | | AY302549 | 466-477 |
| Enterovirus C (CV-A21) | NC 001428 | D00538 | 441-472 |

TABLE 5-continued

Exemplary Human Picornavirus Nucleic Acid Target Sequences; 5'-Region

| Virus | Ref. No. | GB No. | Region |
|---|---|---|---|
| Enterovirus D (HEV-70) | NC 001430 | D00820 | 446-477 |
| Rhinovirus A (HRV-89) | NC 001617 | M16248 | 442-473 |
| Rhinovirus B (HRV-14) | NC 001490 | K02121 | 453-484 |

Table 6 below shows exemplary targeting sequences that are complementary to a broad spectrum of picornaviruses, specifically members of the Enterovirus and Rhinovirus genera.

TABLE 6

Exemplary Antisense Oligomer Targeting Sequences

| Name | Target Nucleotides | GenBank Acc. No. | Targeting Antisense Oligomer (5' to 3') | SEQ. ID NO. |
|---|---|---|---|---|
| 5'-32 | 443-474 | | GTTGGGRTTRGCCGCATTCAGGGGCCG GAGGA | 234 |
| PV444 | 444-463 | V00149 | CCGCATTCAGGGGCCGGAGG | 235 |
| PV449 | 449-470 | V00149 | GGATTAGCCGCATTCAGGGCC | 236 |
| PV454 | 454-474 | V00149 | GTTGGGATTAGCCGCATTCAG | 237 |

Table 7 lists target regions for a second 32-base sequence from the poliovirus reference sequence (NC 002058) and contained in the 5' UTR region of several picoriviruses. The target sequence identified as SEQ ID NO: 55 (RYGGRAC-CRA CTACTTTGGG TGTCCGTGTT TC) represents a combined target sequence, where the positions indicated by the letter "R" may be either A or G, and the position indicated by the letter "Y" may be either C or T in these target regions.

TABLE 7

Exemplary Human Picornavirus Nucleic Acid Target Sequences; 3'-Region

| Virus | Ref. No. | GB No. | Region |
|---|---|---|---|
| Poliovirus-Mahoney strain | NC 002058 | V01149 | 531-562 |
| Enterovirus A (CV-A16) | NC 001612 | U05876 | 540-571 |
| Enterovirus 71 (HEV-71) | | U22521 | 536-567 |
| Enterovirus B (CV-B1) | NC 001472 | M16560 | 534-565 |
| Coxsackievirus B3 (CV-B3) | | M88483 | 535-566 |
| Coxsackievirus B2 (CV-B2) | | AF081485 | 536-567 |
| Coxsackievirus B4 (CV-B4) | | AF311939 | 537-568 |

TABLE 7-continued

Exemplary Human Picornavirus Nucleic Acid Target Sequences; 3'-Region

| Virus | Ref. No. | GB No. | Region |
|---|---|---|---|
| Coxsackievirus B5 (CV-B5) | | X67706 | 536-567 |
| Coxsackievirus A9 (CV-A9) | | D00627 | 536-567 |
| Echovirus 4 (EV-4) | | X89534 | 419-450 |
| Echovirus 6 (EV-6) | | U16283 | 534-565 |
| Echovirus 9 (EV-9) | | X92886 | 533-564 |
| Echovirus 11 (EV-11) | | X80059 | 537-568 |
| Echovirus 13 (EV-13) | | AY302539 | 535-566 |
| Echovirus 18 (EV-18) | | AF521513 | 94-125 |
| Echovirus 25 (EV-25) | | X90722 | 534-565 |
| Echovirus 30 (EV-30) | | AF311938 | 537-568 |
| Enterovirus C (CV-A21) | NC 001428 | D00538 | 529-560 |
| Enterovirus D (HEV-70) | NC 001430 | D00820 | 534-565 |
| Rhinovirus A (HRV-89) | NC 001617 | M16248 | 530-561 |
| Rhinovirus B (HRV-14) | NC 001490 | K02121 | 541-572 |

Targeting sequences designed to hybridize to these target resions are listed in Table 8.

TABLE 8

Exemplary Antisense Oligomer Targeting Sequences

| Name | Target Nucleotides | GenBank Acc. No. | Targeting Antisense Oligomer (5' to 3') | SEQ. ID NO. |
|---|---|---|---|---|
| 3'-37 | 526-562 | V00149 | AAAANGAAACACGGACACCCAAAG TAGTCGGTTCCGC | 238 |
| PV533 | 533-552 | V00149 | CACCCAAAGTAGTCGGTTCC | 239 |
| PV539 | 539-558 | V00149 | CACGGACACCCAAAGTAGTC | 240 |
| PV544 | 544-562 | V00149 | GGAAACACGGACACCCAAAG | 241 |
| PV548 | 548-567 | V00149 | AAAAGGAAACACGGACACCC | 242 |
| CVB3-548 | 548-568 | M88483 | ATGAAACACGGACACCCAAAG | 243 |
| EnteroX | 541-562 | V00149 | GAAACACGGACACCCAAAGTAG | 244 |
| HRV14-IRES | 551-574 | K02121 | GAGAAACACGGACACCCAAAGTAG | 245 |

B5. Targeting Viruses of the Flavivirus family

A fifth class of exemplary antisense antiviral compounds are used in inhibition of replication of a flavivirus in animal cells. An exemplary antisense oligomer of this class is a morpholino oligomer with cationic linkages, as described in the present invention, between 8-40 nucleotide bases in length and having a sequence of at least 8 bases complementary to a region of the virus' positive strand RNA genome that includes at least a portion of SEQ ID NO:57. See, for example, US Appn. Pubn. No. 20050096291, which is incorporated herein by reference.

The target sequences are those adjacent and including at least a portion, e.g., at least 2-8 bases, of the 5'-cyclization sequence (5'-CS) or 3'-CS sequences of the positive strand flaviviral RNA. A highly preferred target is the 3'-CS. GenBank references for exemplary viral nucleic acid sequences containing the 5'-CS and 3'-CS end terminal sequences in the corresponding viral genomes are listed in Table 1 below. The conserved regions of 5'-CS and 3'-CS are shown in bold in Table 9. Another group of exemplary target sequences are the complements of SEQ ID NOS: 267-277.

Targeting sequences directed against the 5'-CS and 3'-CS for selected viruses of the flavivirus genus are derived from sequences complementary and antiparallel to the sequences identified as SEQ ID NOS: 267-277 below.

TABLE 9

Exemplary 5'-CS and 3'-CS Target Sequences

| Virus | GenBank Acc. No. | 5'-CS Target Ncts. | SEQ ID NO. | Target Sequence (5' to 3') |
|---|---|---|---|---|
| St. Louis encephalitis | M16614 | 138-157 | 267 | GUCAAUAUGCUAAAACGCGG |
| Murray Valley encephalitis | AF161266 | 135-154 | | |
| West Nile | M12294 | 136-155 | | |
| Kunjin | D00246 | 115-134 | | |
| Japanese encephalitis | M18370 | 135-154 | 268 | AUCAAUAUGCUGAAACGCGG |
| Yellow fever | X03700 | 155-174 | 269 | GUCAAUAUGGUACGACGAGG |
| Dengue-Type 1 | M87512 | 115-135 | 270 | CUUUCAAUAUGCUGAAACGCG |
| Dengue-Type 2 | M19197 | 131-151 | | |
| Dengue-Type 4 | M14931 | 133-153 | | |
| Dengue-Type 3 | M93130 | 129-149 | 271 | CUAUCAAUAUGCUGAAACGCG |
| Tick borne encephalitis | U27495 | 108-129 | 272 | CAGCUUAGGAGAACAAGAGCUG |
| Powassen | L06436 | 81-102 | | |
| Louping III | Y07863 | 105-126 | | |
| Kyasanur Forest disease | X74111 | 94-115 | | |
| Alkhurma | AF331718 | 90-111 | | |
| West Nile | M12294 | 132-151 | 273 | GGCUGUCAAUAUGCUAAAAC |
| St. Louis encephalitis | M18370 | 10861-10882 | 274 | AACAGCAUAUUGACACCUGGGA |
| Japanese encephalitis | AF161266 | 10899-10920 | | |
| Murray Valley encephalitis | M12294 | 10853-10874 | | |
| West Nile | AY274505 | 10914-10934 | | |
| Kunjin | | | | |
| Yellow fever | X03700 | 10745-10767 | 275 | UGGGACCAUAUUGACGCCAGGGA |
| Dengue-Type 1 | M87512 | 10609-10630 | 276 | AAACAGCAUAUUGACGCUGGGA |
| Dengue-Type 2 | M19197 | 10595-10616 | | |
| Dengue-Type 3 | M93130 | 10588-10609 | | |
| Dengue-Type 4 | M14931 | 10540-10561 | | |
| Tick borne encephalitis | U27495 | 11057-11078 | 277 | CGGUUCUUGUUCUCCCUGAGCC |
| Powassen | L06436 | 10755-10776 | | |
| Louping III | Y07863 | 10787-10808 | | |

B6. Targeting Viruses of the Nidovirus family

A sixth class of exemplary antisense antiviral compounds are used in inhibition of replication of a nidovirus in virus-infected animal cells. An exemplary antisense oligomer of this class is a morpholino oligomer with cationic linkages, as described in the present invention, contains between 8-25 nucleotide bases, and has a sequence capable of disrupting base pairing between the transcriptional regulatory sequences in the 5' leader region of the positive-strand viral genome and negative-strand 3' subgenomic region (See, e.g., PCT Pubn. No. WO/2005/065268 or U.S. Appn. Pubn. No. 20070037763, which are incorporated herein by reference.)

Representative Nidoviruses are listed in Table 10, below. The term "Nidovirus" refers to viruses of the Nidovirales order which includes the families Coronaviridae and Arteriviridae. The term "coronavirus" is used herein to include all members of the Coronaviridae family including viruses of the Coronavirus and Torovirus genera. The term "arteriviris" includes members of the Arteriviridae family which includes the Arterivirus genera.

TABLE 10

Representative Nidoviruses

| Virus Name | Abbreviation |
|---|---|
| Canine coronavirus | CCoV |
| Feline coronavirus | FCoV |
| Human coronavirus 229E | HCoV-229E |
| Porcine epidemic diarrhea virus | PEDV |
| Transmissible gastroenteritis virus | TGEV |
| Porcine Respiratory Coronavirus | PRCV |
| Bovine coronavirus | BCoV |
| Human coronavirus OC43 | HCoV-OC43 |
| Murine hepatitis virus | MHV |
| Rat coronavirus | RCV |
| Infectious bronchitis virus | IBV |
| Turkey coronavirus | TCoV |
| Rabbit coronavirus | RbCoV |
| SARS coronavirus | SARS-CoV |
| Human torovirus | HuTV |
| Equine arteritis virus | EAV |
| Porcine reproductive and respiratory syndrome virus | PRRSV |
| Porcine hemagglutinating encephalomyelitis virus | PHEV |
| Simian hemorrhagic fever virus | SHFV |

The preferred target sequences are those nucleotide sequences adjacent and including at least a portion, e.g., at least 2-8 bases, of the leader TRS of the positive-RNA or the minus-strand body TRS of Nidovirus RNA. A variety of Nidovirus genome sequences are available from well known sources, such as the NCBI Genbank databases. GenBank references for exemplary viral nucleic acid sequences containing the leader TRS in the corresponding viral genomes are listed in Table 11 below; the bold nucleotides identify the core leader TRS.

TABLE 11

Exemplary TRS Target Sequences

| Virus | GenBank Acc. No. | Leader TRS | SEQ ID NO. | Target Sequence (5' to 3') |
|---|---|---|---|---|
| HCoV-229E | AF304460 | 55-78 | 207 | CUACUUUUCUCAACUAAACGAAAU |
| HCoV-OC43 | AY391777 | 51-74 | 208 | GAUCUUUUUGUAAUCUAAACUUUA |
| SARS-CoV | AY274119 | 53-76 | 209 | GAUCUGUUCUCUAAACGAACUUUA |

Exemplary targeting sequences directed against the leader TRS for selected Nidoviruses include SEQ ID NOs: 210-214.

More generally, exemplary targeting sequences include a sequence of at least 8 bases complementary to a region of the virus' negative strand, or, alternatively, positive-strand RNA genome, that includes at least a portion of the genome's negative strand leader TRS, or positive-strand leader TRS, respectively. The targeting sequence contains a sufficient number of bases in either of the TRSs to disrupt base pairing between the virus leader and body TRS sequences. The number of targeting sequences needed to disrupt this structure is preferably at least 2-4 bases complementary to the core leader or body TRS (shown in bold in Table 2), plus bases complementary to adjacent target-sequence bases.

B7. Targeting HIV-1

In a method for selectively inhibiting HIV-1 replication in activated, HIV-infected human hematopoietic cells, e.g., macrophage or T lymphocyte cells, such activated, HIV-1 infected cells are exposed to an antisense oligomer as described herein, having at least one cationic intersubunit linkage as described herein, and preferably containing 20% to 50% such cationic linkages, and having a base sequence that is substantially complementary to a viral target sequence composed of at least 12 contiguous bases in a region of HIV-1 positive strand RNA identified by one of the sequences selected from the group consisting of SEQ ID NOS: 197-199.

In one embodiment, the oligomer is capable of hybridizing with a region of SEQ ID NO:17, to inhibit the synthesis of the HIV Vif protein in the infected cells. The compound in this embodiment may have at least 12 contiguous bases from one of the sequences selected from the group consisting of SEQ ID NOs: 200-203.

In another embodiment, the oligomer is capable of hybridizing with a region of SEQ ID NO:198, to inhibit the transcription of HIV mRNA transcripts. The compound in this embodiment may have at least 12 contiguous bases from the sequences identified as SEQ ID NOs: 204 and 205.

In another embodiment, the oligomer is capable of hybridizing with a region of SEQ ID NO: 199, to inhibit reverse transcription of viral RNA by blocking the minus-strand transfer step. The compound in this embodiment may have at least 12 contiguous bases from the sequence identified as SEQ ID NO: 206.

B8. Targeting of Filoviruses

In another embodiment, one or more oligomers as described herein can be used in a method of in inhibiting replication within a host cell of an Ebola virus or Marburg virus, by contacting the cell with an oligomer as described herein, containing at least one cationic intersubunit linkage, and preferably containing 20% to 50% such cationic linkages, and having a targeting base sequence that is complementary to a target sequence composed of at least 12 contiguous bases within an AUG start-site region of a positive-strand mRNA, as described further below.

The filovirus viral genome is approximately 19,000 bases of single-stranded RNA that is unsegmented and in the antisense orientation. The genome encodes 7 proteins from monocistronic mRNAs complementary to the vRNA.

Target sequences are positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and VP 24, although L, nucleoproteins NP and VP30, are also contemplated. Among these early proteins are favored, e.g., VP35 is favored over the later expressed L polymerase.

In another embodiment, one or more oligomers as described herein can be used in a method of in inhibiting replication within a host cell of an Ebola virus or Marburg virus, by contacting the cell with an oligomer as described herein, containing at least one cationic intersubunit linkage, and preferably containing 20% to 50% such cationic linkages, and having a targeting base sequence that is complementary to a target sequence composed of at least 12 contiguous bases within an AUG start-site region of a positive-strand mRNA identified by one of the Filovirus mRNA sequences selected from the group consisting of SEQ ID NOS: 250-255.

For treating an Ebola virus infection, the compound may have a targeting sequence that is complementary to a target sequence composed of at least 12 contiguous bases within the VP35 AUG start-site region identified by a target sequence selected from the group consisting of SEQ ID NOS:250. An exemplary targeting sequence is identified by SEQ ID NO: 1.

In another embodiment for treating an Ebola virus infection, the compound may have a targeting sequence that is complementary to a target sequence composed of at least 12 contiguous bases within the VP24 AUG or L AUG start-site regions identified by a target sequence selected from the group consisting of SEQ ID NOS: 251 and 252, respectively. Exemplary targeting sequences include SEQ ID NO: 5 and 11, respectively.

For treating a Marburg virus infection, the compound may have a targeting sequence that is complementary to a target sequence composed of at least 12 contiguous bases within the VP35 AUG start-site region identified by a target sequence identified by SEQ ID NO: 253. An exemplary targeting sequence is selected from the group consisting of SEQ ID NOS: 256 and 257.

In another embodiment for treating a Marburg virus infection, the compound may have a targeting sequence that is complementary to a target sequence composed of at least 12 contiguous bases within the VP24 AUG or L AUG start-site regions identified by a target sequence selected from the group identified by SEQ ID NOS: 254 and 255, respectively. Exemplary targeting sequences are identified by SEQ ID NOS: 258-260.

The oligomers disclosed herein may also be used in a method of treating an Ebola or Marburg Filovirus infection in a subject, by administering to the subject, a therapeutically effective amount of an oligomer having a targeting sequence as described above; or in a method of vaccinating a mammalian subject against Ebola virus, by pretreating the subject with an oligomer as described herein and having a targeting sequence as described above, and exposing the subject to the Ebola virus, preferably in an attenuated form.

The Ebola virus RNA sequences (Zaire Ebola virus, Mayinga strain) can be obtained from GenBank Accession No. AF086833. The particular targeting sequences shown below were selected for specificity against the Ebola Zaire virus strain. Corresponding sequences for Ebola Ivory Coast, Ebola Sudan and Ebola Reston (GenBank Acc. No. AF522874) are readily determined from the known GenBank entries for these viruses. Preferably targeting sequences are selected that give a maximum consensus among the viral strains, particularly the Zaire, Ivory Coast, and Sudan strains, or base mismatches that can be accommodated by ambiguous bases in the antisense sequence, according to well-known base pairing rules.

GenBank references for exemplary viral nucleic acid sequences representing filovirus genomic segments are listed in Table 12 below. The nucleotide sequence numbers in Table 12 are derived from the GenBank reference for the positive-strand RNA of Ebola Zaire (AF086833) and Marburg virus (Z29337). Table 12 lists targets for exemplary Ebola viral genes VP35, VP24, and L. The target sequences for the AUG start codons of these genes are represented as SEQ ID NOS: 250-252. The corresponding set of target sequences for Marburg virus are shown as SEQ ID NOS: 253-255.

TABLE 12

Exemplary Filovirus Nucleic Acid Target Sequences

| Name | GenBank No. | Nucleotide Region | Sequence (5' to 3') | SEQ ID NO |
|---|---|---|---|---|
| VP35-AUG | AF086833 | 3029-3153 | AAUGAUGAAGAUUAAAACCUUCAUC AUCCUUACGUCAAUUGAAUUCUCUA GCACUCGAAGCUUAUUGUCUUCAAU GUAAAAGAAAAGCUGGUCUAACAAG AUGACAACUAGAACAAAGGGCAGGG | 250 |
| VP24-AUG | AF086833 | 10245-10369 | CGUUCCAACAAUCGAGCGCAAGGUU UCAAGGUUGAACUGAGAGUGUCUAG ACAACAAAAUAUUGAUACUCCAGAC ACCAAGCAAGACCUGAGAAAAAACC AUGGCUAAAGCUACGGGACGAUACA | 251 |
| L-AUG | AF086833 | 11481-11605 | GUAGAUUAAGAAAAAAGCCUGAGGA AGAUUAAGAAAAACUGCUUAUUGGG UCUUUCCGUGUUUUAGAUGAAGCAG UUGAAAUUCUUCCUCUUGAUAUUAA AUGGCUACACAACAUACCCAAUAC | 252 |
| VP35-AUG | Z29337 | 2844-2968 | CUAAAAAUCGAAGAAUAUUAAAGGU UUUCUUUAAUAUUCAGAAAAGGUUU UUUAUUCUCUUCUUUCUUUUUGCAA ACAUAUUGAAAUAAUAAUUUUCACA AUGUGGGACUCAUCAUAUAUGCAAC | 253 |
| VP24-AUG | Z29337 | 10105-10229 | UUCAUUCAAACACCCCAAAUUUUCA AUCAUACACAUAAUAACCAUUUUAG | 254 |

TABLE 12-continued

Exemplary Filovirus Nucleic Acid Target Sequences

| Name | GenBank No. | Nucleotide Region | Sequence (5' to 3') | SEQ ID NO |
|---|---|---|---|---|
| | | | UAGCGUUACCUUUCAAUACAAUCUA GGUGAUUGUGAAAAGACUUCCAAAC AUGGCAGAAUUAUCAACGCGUUACA | |
| L-AUG | Z29337 | 11379-11503 | UCAUUCUCUUCGAUACACGUUAUAU CUUUAGCAAAGUAAUGAAAAUAGCC UUGUCAUGUUAGACGCCAGUUAUCC AUCUUAAGUGAAUCCUUUCUUCAAU AUGCAGCAUCCAACUCAAUAUCCUG | 255 |

Targeting sequences are designed to hybridize to a region of the target sequence as listed in Table 13. Selected targeting sequences can be made shorter, e.g., 12 bases, or longer, e.g., 40 bases, and include a small number of mismatches, as long as the sequence is sufficiently complementary to allow hybridization with the target, and forms with either the virus positive-strand or minus-strand, a heteroduplex having a $T_m$ of 45° C. or greater.

Table 13 below shows exemplary targeting sequences, in a 5'-to-3' orientation, that target the Ebola Zaire virus (GenBank Acc. No. AF086833) according to the guidelines described above. Additional targeting sequences may be selected, according to the general class rules discussed above.

TABLE 13

Exemplary Antisense Oligomer Sequences Targeting Ebola Zaire

| Name | Target GenBank No. AF086833 | Sequence 5'-3' | SEQ ID NO |
|---|---|---|---|
| VP35'-AUG | 3133-3152 | CCTGCCCTTTGTTCTAGTTG | 1 |
| VP24-AUG | 10331-10349 | GCCATGGTTTTTTCTCAGG | 5 |
| VP24-5'trm | 10261-10280 | TTCAACCTTGAAACCTTGCG | 15 |

Table 14 below shows exemplary targeting sequences, in a 5'-to-3' orientation, that target the Marburg virus (GenBank Acc. No. Z29337) according to the guidelines described above. Additional targeting sequences may be selected, according to the general class rules discussed above.

TABLE 14

Exemplary Antisense Oligomer Sequences Targeting Marburg Virus

| Name | Target GenBank No. Z29337 | Sequence 5'-3' | SEQ ID NO |
|---|---|---|---|
| L-AUG | 11467-11485 | GCTGCATATTGAAGAAAGG | 259 |
| L + 7-AUG | 11485-11506 | CATCAGGATATTGAGTTGGATG | 260 |
| VP35-AUG | 2932-2952 | GTCCCACATTGTGAAAATTAT | 256 |
| VP35 + 7-AUG | 2950-2971 | CTTGTTGCATATATGATGAGTC | 257 |
| VP24 + 5-AUG | 10209-10231 | GTTGTAACGCGTTGATAATTCTG | 258 |

B9. Targeting of Arenaviruses

In another embodiment, an oligomer as described herein can be used in a method for inhibiting viral infection in mammalian cells by a species in the Arenaviridae family. In one aspect, the oligomers can be used in treating a mammalian subject infected with the virus.

Table 15 is an exemplary list of targeted viruses targeted by the invention as organized by their Old World or New World Arenavirus classification.

TABLE 15

Targeted Arenaviruses

| Family | Genus | Virus |
|---|---|---|
| Arenaviridae | Arenavirus | Old World Arenaviruses |
| | | Lassa virus (LASV) Lymphocytic choriomeningitis virus (LCMV) Mopeia virus (MOPV) New World Arenaviruses |
| | | Guanarito virus (GTOV) Junín virus (JUNV) Machupo virus (MACV) Pichinide virus (PICV) Pirital virus (PIRV) Sabiá virus (SABV) Tacaribe virus (TCRV) Whitewater Arroyo virus (WWAV) |

The genome of Arenaviruses consists of two single-stranded RNA segments designated S (small) and L (large). In virions, the molar ratio of S-to L-segment RNAs is roughly 2:1. The complete S-segment RNA sequence has been determined for several arenaviruses and ranges from 3,366 to 3,535 nucleotides. The complete L-segment RNA sequence has also been determined for several arenaviruses and ranges from 7,102 to 7,279 nucleotides. The 3' terminal sequences of the S and L RNA segments are identical at 17 of the last 19 nucleotides. These terminal sequences are conserved among all known arenaviruses. The 5'-terminal 19 or 20 nucleotides at the beginning of each genomic RNA are imperfectly complementary with each corresponding 3' end. Because of this complementarity, the 3' and 5' termini are thought to base-pair and form panhandle structures.

Replication of the infecting virion or viral RNA (vRNA) to form an antigenomic, viral-complementary RNA (vcRNA) strand occurs in the infected cell. Both the vRNA and vcRNA encode complementary mRNAs; accordingly, Arenaviruses are classified as ambisense RNA viruses, rather than negative- or positive-sense RNA viruses. The ambisense orientation of viral genes are on both the L- and S-segments. The NP and polymerase genes reside at the 3' end of the S and L vRNA segments, respectively, and are encoded in the conventional negative sense (i.e., they are expressed through transcription of vRNA or genome-complementary mRNAs). The genes located at the 5' end of the S and L vRNA segments, GPC and Z, respectively, are encoded in mRNA sense but there is no evidence that they are translated directly from genomic vRNA. These genes are expressed instead through transcription of genomic-sense mRNAs from antigenomes (i.e., the vcRNA), full-length complementary copies of genomic vRNAs that function as replicative intermediates. GenBank reference entries for exemplary viral nucleic acid sequences representing Arenavirus vRNA are listed in Table 2 below. Table 2 lists the antisense targets for a 19-base sequence corresponding to nucleotides 1-19 or 2-20 and contained in the 5'-terminal region of both the S- and L-segments of the listed Arenaviruses. All the viruses listed in Table 2 are human isolates The target sequence (SEQ ID NO: 261) is 5'-CG-CACMGDGG ATCCTAGGC-3', where the International Union of Pure and Applied Chemistry (IUPAC) nomenclature for incompletely specified bases are used in the description of the sequence (i.e., "M" for either C or A and "D" for either A, G or T).

There is a high degree of sequence conservation between Arenaviruses at the 5' terminus of the vRNA and vcRNA. Antisense targets include the 5' termini of either the S- or L-segment vRNA or vcRNA strands or the 5' termini of any of the four viral mRNAs. As such, the oligomers potentially disrupt viral replication, transcription or translation of viral RNA species.

The prototypic member of the Arenaviridae family is lymphocytic choriomeningitis virus (LCMV). Table 16 lists the corresponding target regions in a number of clinically relevant Arenaviruses and those present in the NCBI Reference Sequence database. The target sequence identified as SEQ ID NO: 261 represents a combined target sequence for each of these regions, where the positions indicated by the letter "M" may be either C or A and "D" is either A, G or T.

TABLE 16

Exemplary Human Arenavirus Nucleic Acid Target Regions

| Virus | Ref. No. | GB No. | Segment | Region |
|---|---|---|---|---|
| LASV | NC_004296 | J04324 | S | 1-19 |
| LASV | NC_004297 | U73034 | L | 1-19 |
| LCMV | NC_004294 | M20869 | S | 1-19 |
| LCMV | NC_004291 | J04331 | L | 1-19 |
| MOPV | NC_006575 | AY772170 | S | 1-19 |

TABLE 16-continued

Exemplary Human Arenavirus Nucleic Acid Target Regions

| Virus | Ref. No. | GB No. | Segment | Region |
|---|---|---|---|---|
| MOPV | NC_006574 | AY772169 | L | 1-19 |
| GTOV | NC_005077 | AY129247 | S | 1-19 |
| GTOV | NC_005082 | AY358024 | L | 1-19 |
| JUNV | NC_005081 | AY358023 | S | 1-19 |
| JUNV | NC_005080 | AY358022 | L | 1-19 |
| MACV | NC_005078 | AY129248 | S | 1-19 |
| MACV | NC_005079 | AY358021 | L | 1-19 |
| PICV | NC_006447 | K02734 | S | 1-19 |
| PICV | NC_006439 | AF427517 | L | 1-19 |
| PIRV | NC_005894 | AF485262 | S | 1-19 |
| PIRV | NC_005897 | AY494081 | L | 1-19 |
| SABV | NC_006317 | U41071 | S | 1-19 |
| SABV | NC_006313 | AY358026 | L | 1-19 |
| TCRV | NC_004293 | M20304 | S | 1-19 |
| TCRV | NC_004292 | J04340 | L | 1-19 |

Table 17 below shows exemplary targeting sequences, in a 5'-to-3' orientation, that are complementary to a broad spectrum of Arenaviruses. The CL-trm, LS-trm and SS-trm targeting oligomers (SED ID NOS: 262-264, respectively) were designed to target specifically Junin-Candid-1. As shown below, the targeting sequences represented by SEQ ID NOs: 265 and 266 incorporate inosine ("I") at two positions of sequence variability across a broad range of Arenavirus species.

TABLE 17

Exemplary Antisense Oligomer Targeting Sequences

| Name | Target Nucleotides | GenBank Acc. No. | Targeting Antisense Oligomer (5' to 3') | SEQ. ID NO. |
|---|---|---|---|---|
| CL-trm | 1-20 | NC_005080 | CGC CTA GGA TCC CCG GTG CG | 262 |
| LS-trm | 1-21 | NC_005080 | CGC CTA GGA TCC CCG GTG CGC | 263 |
| SS-trm | 1-20 | NC_005081 | GCC TAG GAT CCA CTG TGC GC | 264 |
| PanCL | 1-19 | N/A | GCC TAG GAT CCI CIG TGC G | 265 |
| PanLS | 1-20 | N/A | CGC CTA GGA TCC ICI GTG CG | 266 |

B9. General Aspects of Antiviral Applications

B9(a). Base Variations

The targeting sequence bases may be normal DNA bases or analogs thereof, e.g., uracil and inosine, that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

B9(b). Inhibition of Viral Replication

In one embodiment, antisense inhibition is effective in treating infection of a host animal by a virus, by contacting a cell infected with the virus with an antisense agent effective to inhibit the replication of the specific virus. The antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

B9(c). Administration Methods

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

B9(d). Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 1 ml range, preferably about 1 ml or less.

The sample may be treated to remove unwanted components and/or to treat the heteroduplex species in the sample to remove unwanted ssRNA overhang regions, e.g., by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

B9(e). Identification of an Infective Agent The specific virus causing an infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting broad families and/or genera of viruses. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

C. Improved Proliferation and Engraftment of Hematopoietic Stem Cells after Treatment with Antisense Oligomers that Target TGF-Beta In another embodiment, the present invention provides improved oligomers for the treatment of hematopoietic stem cells (HSCs) capable of rapid in vivo repopulation of the hematopoietic system. In addition, recent studies support the utility of HSCs as therapy for cardiovascular and peripheral vascular disease. However, these studies underscore the importance of the quality of the HSC population injected and their proliferative potential. HSC manipulation using antisense oligomers to TGF-beta increase the number of HSC precursors in circulation and enhance these cells reparative potential. An improvement in the potential of HSCs to home and attach to sites of injury coupled with improved HSC survival and proliferation represents an important therapeutic strategy for the care of patients with cardiovascular and peripheral vascular diseases.

Compositions of the invention comprise TGF-beta antisense oligomers interspersed with cationic linkages, as described in the present invention, that target either splice sites in the preprocessed RNA or the AUG start codon in the mRNA of the TGF-beta gene. Exemplary preferred antisense oligomers have a sequence presented as SEQ ID NO: 247 (GAGGGCGGCA TGGGGGAGGC), SEQ ID NO: 248 (GACCCATGGC AGCCCCCGTC G) or SEQ ID NO: 249 (GCAGCAGTTC TTCTCCGTGG). Treatment of CD34+ HSCs with such antisense agents is performed under culture conditions effective to block the expression of a functional TGF-beta and therefore block the effect of TGF-beta on replication and/or differentiation of the stem cells (see e.g. PCT Pubn. No. WO/2002/004479 or U.S. Appn. Pubn. No. 20030109465, which are incorporated herein by reference).

In a related method, the survival time of human stem cells in culture is prolonged, by exposing the cells ex vivo to a TGF-β blocking agent under culture conditions, and for a period of time, effective to preserve the viability and differentiation state of the stem cells. These cells may be maintained in vitro for an extended period of time, and they may be used for in vivo transfer into a subject in need of hematopoietic reconstitution, or the TGF-β blocking agent-treated stem cells may be cultured under conditions effective to result in rapid proliferation and differentiation of the cells into lineage committed progenitor cells and their progeny.

D. Modulation of Immune Response

The oligomers described herein may also be used to manipulate an immune response in a mammalian subject, for the treatment or prevention of an autoimmune condition or transplantation rejection. By manipulating the immune system's normal mechanism for the generation of immune tolerance to self antigens, the method is effective to alter the function and activity of T cells in a way that is advantageous in the treatment of transplantation rejection or autoimmune disorders, such as multiple sclerosis, lupis, myathenia gravis, inflammatory bowel disease and rheumatoid arthritis. The use of an antisense oligomer with cationic linkages as described herein, directed against CTLA-4, provides an improved means to alter T cell activation in response to an antigen presented by a mature dendritic cell. This allows the generation of a tolerized T cell population responding to transplanted tissue, when chronically activated as in an autoimmune condition, or by an immunogenic therapeutic protein.

For the prevention of transplantation rejection in a human subject scheduled to receive a allogeneic organ transplantation, compound administration may be initiated at least one week before the scheduled transplantation. The administering may be carried out by parenteral administration, at a dose level corresponding to between about 5 to 200 mg compound/day.

For the treatment of an autoimmune condition, the compound administration may be continued until a desired improvement in autoimmune condition is observed. The administering may be carried out by parenteral administration, at a dose level corresponding to between about 5 to 200 mg compound/day.

In preferred applications of the method, the subject is a human subject and the methods of the invention are applicable to treatment of any condition wherein either promoting immunological tolerance or enhancing immune activation would be effective to result in an improved therapeutic outcome for the subject under treatment.

The CTLA gene has four exons, designated exons 1-4, with an intron separating each exon pair. The introns are designated 1-3, where intron-1 is the intervening sequence between exons 1 and 2, intron-2, between exons 2 and 3, and intron-3, between exons 3 and 4. The full length CTLA isoform is encoded by all four exons, requiring excision of all three introns and preservation of all four exons. A ligand-independent form is of CTLA-4 is formed from exons 1, 3 and 4, requiring excision of intron 1 and adjacent exon 2, and introns 3 and 4. A secreted form of CTLA-4 is formed of exons 1, 2, and 4, requiring excision of intron 1, and a contiguous section of preprocessed mRNA containing intron 2, exon 3 and intron 3.

The targeting sequence of the oligomer is preferably complementary to at least 12 subunits of a target sequence identified by SEQ ID NO: 246, spanning the splice junction between intron 1 and exon 2 of preprocessed T cell antigen-4 (CTLA-4) mRNA of the subject.

The current antisense method is based upon the finding that CTLA-4 activity can be modulated in naïve and activated T cells by manipulating the relative ratios of specific spliced mRNA isoforms of the CTLA-4 gene to increase immunosuppression and immunologic tolerance. More specifically, it has been discovered that administration of an antisense compound that targets the splice region between intron-1 and exon-2 shifts the ratios of CTLA-4 mRNAs and CTLA-4 proteins from full length to ligand-independent forms, and that this shift is effective in treating an autoimmune condition or transplantation rejection, and in reducing the risk of transplantation rejection, on pretreating the subject prior to the transplantation operation.

In another embodiment, the present oligomers can be used to precisely and specifically alter the manner in which dendritic cells elicit antigen-specific immune responses from T cells. In particular, a diminution in the level of CD86 (B7-2) protein is achieved by antisense inhibition targeted to dendritic cells. Studies have shown that maturing DCs produce increased amounts of IL-10 as a result of diminished CD86 expression. Moreover, it was determined that the cytoplasmic region encoded by exon 10, in the murine homologe, is functionally linked to the regulation of this cytokine. Using antisense oligomers containing cationic linkages, as described in the present invention, targeted to the CD86 start codon or CD86 exon splice acceptor regions provides an improved means to precisely and specifically block T cell activation to an antigen presented by a mature dendritic cell (see e.g. PCT Pubn. No. WO/2005/072527). This allows the generation of a tolerized T cell and dendritic cell population responding to transplanted tissue, when chronically activated as in an autoimmune condition, or by an immunogenic therapeutic protein.

By manipulating the immune system's normal mechanism for the generation of immune tolerance to self antigens, the present method alters the function and activity of mature dendritic cells in a way that is advantageous in the treatment of transplantation rejection or autoimmune disorders, such as multiple sclerosis, lupis, myathenia gravis, inflammatory bowel disease and rheumatoid arthritis.

The antisense compound is targeted against an expression-sensitive region of a processed or preprocessed CD transcript, that is, a region which, when bound to the antisense compound, is effective to inhibit the expression of full-length CD86 in dendritic cells. In one general embodiment, the expression-sensitive region is one that includes or is adjacent the AUG start site of a processed transcript, where formation of an antisense-transcript heteroduplex is effective to inhibit translation of the transcript. Here the antisense compound has a base sequence that is complementary to a target region containing at least 12 contiguous bases in a processed human CD86 transcript (identified, in its processed form, by SEQ ID NO: 215), in the target region from about −20 to +30 bases with respect to the A nucleotide of the AUG start site at position 1, and which includes at least 6 contiguous bases of the sequence identified by SEQ ID NO: 216. Exemplary antisense sequences include those identified as SEQ ID NOS: 48-50.

In a more specific embodiment, the antisense compounds are designed to span or cover the three bases +12 to +14 bases (where the A nucleotide of the AUG start site represents +1). In this embodiment, the antisense compound may hybridize to a region spanning these bases, e.g., where the three bases are in the middle of the target region, or may hybridize to a region predominantly upstream of and including these bases, e.g., the target bases extending from −2 to +19 (SEQ ID NO: 50 below).

In another general embodiment, the expression-sensitive region is a splice-site target region that may include (i) an intron region adjacent, e.g., within 5 bases of, a splice-site donor or acceptor junction, (ii) a region spanning a donor or acceptor splice-site junction, or (iii) the exon region adjacent, e.g., within 5 bases of, a splice-site donor or acceptor junction. The target region preferably contains at least 12 contiguous bases in a preprocessed human CD86 transcript, and includes, in exemplary embodiment, at least 6 contiguous bases of one of the sequences identified by SEQ ID NOS: 217-220. Exemplary antisense sequences include those identified as SEQ ID NOS: 51-54.

Exemplary target sequences for the CD86 (B7-2) gene are listed in Table 18 below. The human CD86 AUG target and targeting sequences are derived from Genbank Accession No. NM006889. The human Exon 6 and 7 splice donor (sd) and splice acceptor (sa) target and targeting sequences are derived from Genbank Accession Nos. U17720 and U17721, respectively.

TABLE 18

Exemplary CD86 Target Sequences

| Oligomer Target | Sequence (5' to 3') | Nct. Range | SEQ ID NO. |
|---|---|---|---|
| CD86 AUG | CATTTGTGACAGCACTATGGGACT GAGT<u>AA</u>CATTCTCTTTGTGATG | 132-177 | 216 |
| CD86Ex6sa | AGCTTGAGGACCCTCAGCCTC | 170-190 | 217 |
| CD86Ex6sd | GCCTCGCAACTCTTATAAATGTG | 291-313 | 218 |
| CD86Ex7sa | GAACCAACACAATGGAGAGGGA | 274-295 | 219 |
| CD86Ex7sd | GAGTGAACAGACCAAGAAAAG | 298-319 | 220 |

TABLE 19

Exemplary CD86 Targeting Sequences

| Oligomer Target | Sequence (5' to 3') | SEQ ID NO. |
|---|---|---|
| CD86 AUG1 | GTTACTCAGTCCCATAGTGCTG | 48 |
| CD86 AUG2 | CCATAGTGCTGTCACAAATG | 49 |
| CD86 AUG3 | GAATGTTACTCAGTCCCATAG | 50 |
| CD86Ex6sa | GAGGCTGAGGGTCCTCAAGCT | 51 |
| CD86Ex6sd | CACATTTATAAGAGTTGCGAGGC | 52 |
| CD86Ex7sa | TCCCTCTCCATTGTGTTGGTTC | 53 |
| CD86Ex7sd | CTTTTCTTGGTCTGTTCACTC | 54 |

In a method of inducing immunological tolerance in vivo in a patient, the patient is administered a therapeutically effective amount of a CD86 antisense oligomer as described herein. The oligomers can be effective in the treatment of patients by modulating the immunological response to allogeneic transplantation, or elimination of chronically activated T cells in the case of autoimmune diseases.

In allogeneic transplantation, the patient is typically treated with the conjugate shortly before, e.g., a few days before, receiving the transplant, then treated periodically, e.g., once every 14 days, until immunological tolerance is established. Immunological tolerance can be monitored during treatment by testing patient T cells for reactivity with donor MHC antigens in a standard in vitro test, as detailed below.

For the treatment of an autoimmune disorder, such as multiple sclerosis, lupis, myathenia gravis, inflammatory bowel disease and rheumatoid arthritis, the patient is given an initial single dose of the CD86 antisense conjugate, then additional doses on a periodic basis, e.g., every 3-14 days, until improvement in the disorder is observed. As above, development of immunological tolerance can be monitored during treatment by testing T cells from a blood sample for their ability to react with a selected, relevant antigen in vitro.

Routes of antisense oligomer delivery include, but are not limited to, inhalation; transdermal delivery; various systemic routes, including oral and parenteral routes, e.g., intravenous, subcutaneous, intraperitoneal, or intramuscular delivery. In preferred applications of the method, the subject is a human subject and the methods of the invention are applicable to treatment of any condition wherein promoting immunological tolerance would be effective to result in an improved therapeutic outcome for the subject under treatment.

In another preferred application of the method, autologous dendritic cells isolated from a human subject can be treated ex vivo with the CD86 antisense compound in the presence of a selected, relevant antigen. This application of the method is particularly useful in treating an autoimmune disorder where the immune system is reacting inappropriately to specific antigens and these antigens can be used to condition the dendritic cells. An example is the immune-mediated destruction of myelin in multiple sclerosis (MS). Myelin basic protein (MBP) and proteolipid protein (PLP) are host proteins which are thought to be the key antigens in the etiology of this autoimmune disease (Shevac 2002).

In another embodiment of immune response modulation, the present compounds can be used to suppress the downregulation of central and peripheral immune responses. The Programmed Death 1 (PD-1) protein is markedly upregulated on the surface of exhausted virus-specific CD8+ T cells in many chronic viral infections including HCV and HIV infection. Targeting the splice junction regions of the PD-1 preprocessed RNA using antisense oligomers containing cationic linkages, as described in the present invention, provides a novel immunotherapeutic approach to reverse the suppression of cytotoxic T cell responses associated with many chronic viral infections and cancers.

In another embodiment, the expression of the TNF receptor (TNFR2) can be altered with antisense oligomers containing cationic linkages, as described in the present invention, to induce the expression of an alternatively spliced soluble TNF-α receptor 2 isoform (sTNFR2). This naturally occurring alternatively spliced isoform of the TNFR2 gene provides anti-inflamatory properties because it antagonizes TNF-alpha biological activity. Overexpression of the sTNFR2 isoform using antisense oligomers targeted to the exon 7 splice acceptor region of the human TNFR2 gene, using antisense oligomers as described in the present invention, provides an immunotherapeutic approach to inhibit inflammatory arthritis, specifically arthritis induced by TNF-alpha.

E. Treatment of Muscle Atrophy

In another embodiment, an oligomer as described herein can be used in a method for treating loss of skeletal muscle mass in a human subject. The steps in the method entail (a) measuring blood or tissue levels of myostatin in the subject, (b) administering to the subject, a myostatin-expression-inhibiting amount of an oligomer as described herein, containing at least one cationic intersubunit linkage, and preferably containing 20% to 50% such cationic linkages, and having a base sequence effective to hybridize to an expression-sensitive region of processed or preprocessed human myostatin RNA transcript, identified, in its processed form, by SEQ ID NO: 225;

(c) by this administering, forming within target muscle cells in the subject, a base-paired heteroduplex structure composed of human myostatin RNA transcript and the antisense compound and having a Tm of dissociation of at least 45° C., thereby inhibiting expression of myostatin in said cells;

(d) at a selected time following administering the antisense compound, measuring a blood or tissue level of myostatin in the subject; and (e) repeating the administering, using the myostatin levels measured in (d) to adjust the dose or dosing schedule of the amount of antisense compound administered, if necessary, so as to reduce measured levels of myostatin over those initially measured and maintain such levels of myostatin measured in step (d) within a range determined for normal, healthy individuals.

Where the antisense oligomer is effective to hybridize to a splice site of preprocessed human myostatin transcript, it has a base sequence that is complementary to at least 12 contiguous bases of a splice site in a preprocessed human myostatin transcript, and formation of the heteroduplex in step (c) is effective to block processing of a preprocessed myostatin transcript to produce a full-length, processed myostatin transcript. The splice site in the preprocessed myostatin transcript may have one of the sequences identified as SEQ ID NOs: 226-229. Exemplary antisense sequences are those identified by SEQ ID NOs: 230-233.

F. Further Applications of Splice-Region Antisense Targeting

The oligomers of the invention can be used in therapeutic compositions and methods for inhibiting expression of full-length proteins in cells, and in particular to antisense compositions targeted against an mRNA sequence having its 5' end 1 to about 25 base pairs downstream of a normal splice acceptor junction in a preprocessed mRNA. Such targeting is effective to inhibit natural mRNA splice processing and produce splice variant mRNAs. (See e.g. PCT Pubn. No. WO/2001/083740 or U.S. Appn. Pubn. No. 20060287268, which are incorporated herein by reference.)

Suitable target proteins include, for example, transcription factors, particularly oncogenic or proto-oncogenic proteins such as myc, myb, rel, fos, jun, abl, bcl, and p53; matrix proteins, such as integrins and cathedrins; other tumor-expressed proteins, such as hCG; telomerases; receptor proteins; viral proteins, such as those expressed from the subgenomic spliced mRNAs of HIV, human papilloma virus, and human parvovirus B19; and immunomodulatory proteins such as, for example, CTLA-4, B7-2, PD-1, Foxp3, TGF-beta, and TNF receptor. It is appreciated that inhibition or expression of modified forms of such proteins has numerous therapeutic applications. These include, but are not limited to, antitumor therapy, e.g. by targeting proteins, such as transcription factors, involved in various aspects of cell division and cell cycle regulation; antiviral therapy, by targeting proteins essential to replication or other vital functions of the infectious agent; inhibition of restenosis or other proliferative disorders, by inhibiting proteins which support cell proliferation at the site; and immunomodulation to either suppress an immune response associated with various autoimmune diseases or to enhance an immune response as in the case of chronic viral infections.

Transcription factors are typically multidomain proteins, having a DNA binding region and a protein-protein binding region. Interfering with one of these regions can produce a dominant negative protein, which counters the activity of the native protein by preserving one activity (such as protein binding) while inhibiting another activity critical to the proper function of the protein (such as DNA binding and transcriptional activation; or vice versa).

As noted above, functional domains of many of the target proteins noted above have been studied extensively and reported in the literature. Sequences of pre-mRNA, including locations of introns, exons, and AUG start codons, can be found in the GenBank sequence database or other published sources readily available to those of skill in the art.

Examples of antisense targeting downstream of splice acceptor domains are presented above, e.g. for methods of manipulating an immune response in a mammalian subject, i.e. by targeting CTLA-4 or CD86 expression.

In another embodiment, the present compounds can be used to suppress the downregulation of central and peripheral immune responses. The Programmed Death 1 (PD-1) protein is markedly upregulated on the surface of exhausted virus-specific CD8+ T cells in many chronic viral infections including HCV and HIV infection. Targeting the splice junction regions of the PD-1 preprocessed RNA using antisense oligomers interspersed with cationic linkages, as described in the present invention, provides a novel immunotherapeutic approach to reverse the suppression of cytotoxic T cell responses associated with many chronic viral infections and cancers.

In another embodiment, the expression of the TNF receptor (TNFR2) can be altered with antisense oligomers interspersed with cationic linkages, as described in the present invention, to induce the expression of an alternatively spliced soluble TNF-α receptor 2 isoform (sTNFR2). This naturally occurring alternatively spliced isoform of the TNFR2 gene provides anti-inflamatory properties because it antagonizes TNF-alpha biological activity. Overexpression of the sTNFR2 isoform using antisense oligomers targeted to the exon 7 splice acceptor region of the human TNFR2 gene, using antisense oligomers as described in the present invention, provides an immunotherapeutic approach to inhibit inflammatory arthritis, specifically arthritis induced by TNF-alpha.

G. Improved Pharmacokinetics of Various Drugs after Treatment with Antisense Oligomers that Target CYP3A4

In another embodiment, the oligomers of the present invention may be used to improve the pharmacokinetics of various drugs in patients by administering an antisense oligomer targeted to CYP3A4, a gene encoding a drug-metabolizing enzyme which reduces the half-life of the drug. The antisense oligomer is effective to reduce the production of the CYP3A4 enzyme in the subject, extending the drug's half-life and effectiveness and decreasing the drugs toxicity. (See e.g. PCT Pubn. No. WO/2001/087286 or U.S. Appn. Pubn. No. 20040229829, which are incorporated herein by reference.)

Compositions of the invention comprise CYP3A4 antisense oligomers interspersed with cationic linkages, as described in the current invention, that target the AUG start codon region in the mRNA or splice sites in the preprocessed RNA of the CYP3A4 gene. Exemplary preferred antisense oligomers have a sequence presented as the group consisting of SEQ ID NOs: 290-292.

EXPERIMENTAL

Materials and Methods (Subunits)

Unless otherwise noted, all chemicals were obtained from Sigma-Aldrich-Fluka. Benzoyl adenosine, benzoyl cytidine, and phenylacetyl guanosine were obtained from Carbosynth Limited, UK Unless otherwise indicated, mixtures of solvents are volume to volume (v/v). Optical Density is measured at 260 nm in water. Nomenclature of oligomer materials in this section uses the following format, where + indicates the b1 (piperazine) linkage; GuX indicates the 6-guanidinohexanoylpiperazine type b1 linkage; R is arginine; B is beta alanine; Ahx is 6-aminohexanoyl; GuAhx is 6-guanidinohexanoyl; Ahxpip is the 6-aminohexanoylpiperazine type b1 linkage; EG3 is the Tail; GuBu is 4-guanidinobutanoyl; GuBupip is 4-guanidinobutanoylpiperazine type b1 linkage; Ac is acetyl; TFApip is the trifluoroacetylpiperazine type b1 linkage; Gupip is the guanylpiperazine type b1 linkage; Gu is a guanyl (—C(NH)NH$_2$) group; Mepip is a 4-methylpiperazine type b1 linkage. Peptides are written N to C, but are linked by their C terminus to the oligomer 3'-terminus. Examples:

5'-(group)-NNNNNNNNNNNN-3'-(group): Uncharged backbone with type a linkages

5'-(EG$_3$)—NN+NNN+N+NNNNNN-3'-(H): Charged backbone with b1 (piperazine) linkages, a 5'-Tail moiety, and unsubstituted at 3'.

5'-(EG$_3$)-NN+NNN+N+NNNNNN-3'-(Ac(RAhxR)$_4$AhxB-): Charged backbone with b1 (piperazine) linkages, a 5'-Tail, and a peptide at the 3'-terminus, linked by the beta-alanine moiety.

5'-(GuAhx)-NN(GuX)NNN(GuX)N(GuX)NNNNNN-3'-(GuAhx): Charged backbone with b1 (6-guanidinohexanoylpiperazine) linkages and GuAhx groups on both termini. Although written differently, all charged positions contain a 6-guanidinohexanoyl moiety.

Example 1

Morpholino Subunits (See FIG. 2B)

General Preparation of morpholino salts 3a-d,f: To a cooled mixture of methanol (5-10 mL/g ribonucleosides 2) was added a warm aqueous solution of sodium meta-periodate (1.05 eq). At this stage, the composition of the reaction mixture will be from 15-40% water/methanol (v:v). To this mixture was added, in portions, solid 1a-d,f. Upon reaction completion (1-2 hr), the by-product sodium iodate cake was removed by filtration and reslurried with water/methanol to recover any product intermediate. To the pooled filtrates were added ammonium biborate (14-2.0 eq). After stirring at 20° C. for 45-120 min, the mixture was cooled, and borane-triethylamine (1.5-2.0 eq) was added. This mixture was adjusted to pH 3.5-4.0 with a methanolic solution of either p-toluenesulfonic acid (3b, c, d, f) or hydrochloric acid (3a) (4-5 eq). The mixture was held at pH 3.5-4.0 for 7-14 hr at <10° C. The p-toluenesulfonic acid salts of 3b, c, d, f were isolated by filtration and purified by recrystallization/reslurry.

The mixture containing 3a was neutralized to pH 7. The solution was concentrated by distillation to remove methanol, and the product was extracted into 1-butanol. This solution was adjusted to pH 4 with a methanolic solution of oxalic acid (0.5 eq). The oxalic acid salt of 3a was isolated by filtration and purified by reslurry. Yields for 3a-d,f=30-75%.

General Preparation of 1a-d,f: Compound 3a-d,f was dissolved/suspended in N,N-dimethylformamide (4-6 mL/g 3). To this mixture was added triethylamine (2.7-3.5 eq) and triphenylmethyl(trityl)chloride (1.1-1.5 eq). Upon reaction completion, the excess trityl chloride was quenched with diethylamine (0.5 eq). The crude products were isolated by either direct precipitation from ethyl acetate and water or through an extractive workup (water then ethyl acetate or dichloromethane) and precipitation. The products were purified by crystallization from toluene. Yields=75-90%

Preparation of 1e: Compound 1f was suspended in dichloromethane (8 mL/g 1f). To this suspension were added imidazole (1.3 eq) and t-butyldimethylchlorosilane (1.2 eq). Upon reaction completion (1-2 hr), the solution was washed successively with pH 3 citrate buffer and water. The resulting solution was concentrated to give a foam, which was dissolved in tetrahydrofuran (8 mL/g 1f). To this solution were added potassium carbonate (2.0 eq) and chloromethyl pivalate (1.5 eq) and the mixture was heated to reflux. Upon reaction completion (16 hr), the mixture was cooled and diluted with dichloromethane. The mixture was washed successively with $KH_2PO_4$ solution (pH 4.5) and water. The resulting solution was concentrated to give a foam. The foam was dissolved in tetrahydrofuran (4 mL/g 1f) and triethylamine trihydrofluoride (2.0 eq) was added. Upon reaction completion (16 hr), the solution was washed successively with saturated aqueous $NaHCO_3$ and water. The product was isolated by solvent exchange into toluene and precipitation into heptane. Yield=80% of 1e.

Example 2

Morpholino Subunits with Linkage Type (a) (See FIG. 2C)

General Preparation of 5a-e: Compound 1a-e was dissolved in dichloromethane (6 mL/g 1) and cooled to <5 C. To this solution were added 2,6-lutidine (1.6 eq), N-methylimidazole (0.3 eq), and N,N-dimethylphosphoramidodichloridate 4 (1.6 eq). Upon reaction completion (6-12 hr), this mixture was washed with a pH 3 citrate buffer. The crude product was isolated by precipitation into heptane. The final product was purified by silica gel chromatography (gradient of ethyl acetate/heptane). The pooled fractions containing product were combined, evaporated to a smaller volume, and isolated by precipitation from heptane. Yields=40-60%. During the chromatography of subunit 5e, as well as other subunits derived from this heterocyclic base, following ethyl acetate/heptane elution of the non-polar impurities, a gradient of (5% isopropanol/ethyl acetate) in dichloromethane was used to elute the product.

Example 3

Morpholino Subunits with Pro-Cationic Linkages Type (b1) (See FIG. D)

Preparation of N-trityl piperazine, succinate salt (11): To a cooled solution of piperazine (10 eq) in toluene/methanol (5:1 toluene/methanol (v:v); 5 mL/g piperazine) was added slowly a solution of trityl chloride 10 (1.0 eq) in toluene (5 mL/g trityl chloride). Upon reaction completion (1-2 hr), this solution was washed four times with water. To the resulting organic solution was added an aqueous solution of succinic acid (1.1 eq; 13 mL water/g succinic acid). This mixture was stirred for 90 min, and the solid product was collected by filtration. The crude solid was purified by two reslurries in acetone. Yield 70%.

Preparation of 1-trifluoroacetyl-4-trityl piperazine (14): To a slurry of 3.0 kg 11 in 18 L methanol (6 mL/g 11) was added 3.51 L diisopropylethylamine (3.0 eq) and 1.038 L ethyl trifluoroacetate 13a (1.3 eq). After overnight stirring, the organic mixture was distilled to dryness. The resulting oil was dissolved in 15 L dichloromethane (5 mL/g 11) and washed twice with 15 L 1M $KH_2PO_4$ and twice with 15 L de-ionized water. This solution was run through a 3.0 kg silica plug (1:1 silica:11), and washed with 9 L dichloromethane (3 ml/g 11, then concentrated to give a white foam. For 14a: Yield=2.9964 kg, 105%. $^{19}F$ NMR ($CDCl_3$) δ-68.7 (s).

For the preparation of 2,2-difluoropropionyl and hexafluoroisobutyryl amides, trityl piperazine succinate 11 in dichloromethane was reacted with an aqueous solution of potassium carbonate to remove succinic acid. The dichloromethane was evaporated and the tritylpiperazine free base 12 was treated with 2 eq of the ester 13c or 13d (both obtained from Synquest, Alachua, Fla., USA) without solvent in the presence of diisopropylethylamine (1.0 eq). The mixture was heated at 40° C. until complete. The mixture was dissolved in dichloromethane and passed through a plug of silica gel, eluting with ethyl acetate and heptane mixtures to provide the pure trityl piperazine amides.

Preparation of N-trifluoroacetyl piperazine, HCl salt (15): To a solution of 1.431 kg 14 in 7.16 L dichloromethane (5 mL/g 14) was added dropwise a solution of 3.37 L 2.0 M $HCl/Et_2O$ (2.0 eq). The reaction mixture was stirred for 1 hr, and the product was collected by filtration. The filter cake was washed with 2.0 L dichloromethane. The solids were dried at 40° C. in a vacuum oven for 24 hr. For 15a: Yield=724.2 g, 98.3%. $^{19}F$ NMR ($CDCl_3$) δ-68.2 (s); melting point=140° C. Recrystallization of a small sample from ethanol raised the melting point to 154-156° C.

Preparation of Activating Agent (6): To a cooled suspension of 15 (1.0 eq) in Toluene (10 mL/g 15) was added diisopropylethylamine (4.0 eq). The mixture was stirred in an ice bath for 1 hr and the salts were removed by filtration. The filter cake was washed twice with toluene (1.5 mL/g). The toluene solution of 15 free base (13 mL/g) was added slowly to a ice cooled solution of $POCl_3$ (1.2 eq) in toluene. The reaction mixture was stirred in an ice bath for 1 hr, then washed twice with 1 M $KH_2PO_4$ (13 mL/g) and once with and de-ionized water (13 mL/g). This solution was dried over $Na_2SO_4$ and distilled to dryness. The resulting amorphous solid was dissolved in dichloromethane (2 mL/g 15) and again distilled to dryness. For a 200 g batch of 15a the yield was of 6a was 226.9 g, 75%. $^{19}F$ NMR ($CDCl_3$) δ-68.85 (s); $^{31}P$ NMR ($CDCl_3$) δ 15.4 (s).

Preparation of Activated Subunits (7) (See FIG. 2C): To a cooled solution/slurry of morpholino subunit 1a-e (1.0 eq) in dichloromethane (5 mL/g subunit) were added successively 2,6-lutidine (1.6 eq), N-methylimidazole (0.3 eq), and 6a-d (1.6 eq) in dichloromethane (2 ml/g 6). The solution was allowed to warm to room temperature. After 3 hr, the solution was washed with 1M citric acid (pH 3). The organic layer was dried over $Na_2SO_4$, the solvents removed by distillation and toluene (5 mL/g) added. The product was precipitated by dropwise addition of the solution into heptanes (20 ml/g subunit) then collected by filtration. The crude product was purified by silica gel chromatography (gradient of ethyl acetate/heptane). The solvents were concentrated and replaced with toluene or ethyl benzene (5 ml/g subunit). The amorphous product was precipitated into heptane (20 ml/g subunit) then collected by filtration. Yield=50-70%. $^{19}F$ NMR ($CDCl_3$ shows one or two peaks with chemical shifts at about δ-68.8; 31P NMR ($CDCl_3$) typically shows two singlet peaks with chemical shifts at 13.0 to 13.4.

Example 4

Morpholino Subunits with Pro-Cationic Linkages Type (b2) (See FIG. 2C)

Primary Amine Containing Side Chain:
Hexamethylenediamine (100 g, 1 eq) was dissolved in methanol (1 L) and treated dropwise with a solution of ethyl trifluoroacetate (103 mL, 1 eq) in 150 mL methanol. Very slight warming of the solution occurs. The reaction was stirred for 30 min at room temperature after addition. TLC using chloroform/methanol/conc ammonia (8:3:1) shows the presence of amine. The solvents were removed by rotary evaporation, and the residue dissolved in toluene/ethyl acetate (1:3, 1 L) then washed four times with 10% saturated aqueous sodium chloride solution to effect complete removal of excess diamine. Evaporation yields 117 g crude amine which was used in the activation reaction as for the piperazine example above. Crude 8a was reacted with 1a using the conditions above to give 9a. The corresponding reaction with the other subunits produces 9b-e. The alternate amide protected amines were prepared and used in the same manner as previous examples, with amides from esters 13c,d formed by reaction of the amine with neat ester.

Secondary Amine Containing Side Chain:

N,N'-Dimethylethylenediamine (36.3 mL, 3 eq.) was mixed with trityl chloride (31.8 g, 1 eq.) in dichloromethane (300 mL). After 30 min the solvent was removed by evaporation and 300 mL toluene was added. The solution was washed three times with 300 mL water and finally with an equal volume of saturated aqueous sodium chloride. The foam formed on evaporation was used without purification.

The foam was dissolved in 400 mL methanol and 100 mL dichloromethane. Ethyl trifluoroacetate (17.5 mL) was added. After 30 min, the mixture was evaporated to dryness, 300 mL dichloromethane added, and the solution washed three times with an equal volume of water, and then once with saturated aqueous sodium chloride. After drying over sodium sulfate, the organic layer was evaporated to dryness. The product was purified by silica chromatography using 10% ethyl acetate heptane containing 1% lutidine to afford 24.8 g pure trityl amide.

The trityl amide was dissolved in dichloromethane (180 mL) and treated dropwise with 2 M HCl in ether (85 mL) and stirred at room temperature for 3 hr. The precipitated solid was filtered and dried overnight under high vacuum. The recovered product (10.06 g) was suspended in 100 mL dichloromethane and treated with diisopropylethylamine (25.0 mL) at which time a solution formed. This mixture was added to phosphorus oxychloride (4.6 mL) in toluene (100 mL) with stirring at 0° C. in an ice bath. The reaction was continued 12 hr at room temperature. At that time, the reaction was washed twice with 1 M $KH_2PO_4$ (100 mL), and dried over sodium sulfate. After filtration and evaporation a brown solid was obtained that was used directly.

The brown solid was dissolved in 20 mL dichloromethane and added to a solution of 1d (13.6 g) in dichloromethane (40 mL) containing 2,6-lutidine (5.24 mL) and N-methylimidazole (0.672 mL). After four hr at room temperature, the reaction was washed twice with 1 M citric acid buffer at pH=3. The solution was evaporated to dryness and the product purified by chromatography on silica using an ethyl acetate/heptane gradient. Similar reactions afford the corresponding protected N-methyl-N-methylaminoethyl substituted activated subunits.

Example 5

Morpholino Subunits with Pro-Cationic Linkages Type (b3) (See FIG. 2E)

Oxidation of 1: All glassware was oven dried overnight and cooled under vacuum or with a stream of $N_2$. All solutions were prepared and transferred under $N_2$. The starting alcohol (1) was dried under vacuum at 50° C. for 24 hr prior to use.

A solution of 1 (1 eq; 25 mmol) in DMSO/dichloromethane (1:2 DMSO/dichloromethane (v:v); 5 mL/g 1) was added dropwise over 15 min to the Swern reagent (prepared by adding DMSO (2.2 eq) to a solution of oxalyl chloride (1.1 eq) in dichloromethane (21 mL/g) at −60° C. and stirring for 10 min). After stirring at −60° C. for 25 min, triethylamine (5 eq) was added over 10 min during which time a white precipitate formed. Additional dichloromethane (5 mL/g 1) was added and the reaction mixture stirred in a water bath for 25 min.

The reaction mixture was diluted with isopropanol/dichloromethane (1:15 isopropanol/dichloromethane (v:v); 15 mL/g 1) and washed twice with 1:1 (v:v) water/brine (20 ml/g 1). The solution was dried over $Na_2SO_4$ and concentrated to give the aldehydes 16a-e as pale yellow foams which were used without further purification. Yield=>100%.

Reductive Amination of 16:

A solution of methylamine acetate (10 eq; 1.16 M solution in methanol) was added to a solution of 16a-e (1 eq; 25 mmol) in methanol (8 mL/mmol 16). After adjustment to pH 8 with glacial acetic acid, the reaction mixture was stirred at room temperature for 1 hr and $BH_3$.pyridine (2 eq) was added. After stirring for a further 1 hr, the reaction mixture was concentrated to a viscous oil.

To the crude product dissolved in dichloromethane (10 mL/mmol 16) was added 9-fluorenylmethyl chloroformate (FMOC chloride) (1.5 eq) followed by diisopropylethylamine (2.5 eq) and the solution stirred at room temperature for 30 min. The reaction mixture was diluted with dichloromethane (8 mL/mmol) and washed twice with 1:1 (v:v) water/brine (20 ml/mmol 16). The solution was dried over $Na_2SO_4$, the solvent removed and the crude product was purified by silica gel chromatography (gradient of acetone/chloroform). Yield=40-60% of 18a-e.

A solution of 18 (1 eq; 2.8 mmol) in 1% 1,8-diazabicyclo [5.4.0]undec-7-ene (DBU)/N,N-dimethylformamide (5 mL/g 18) was stirred at room temperature for 30 min. The reaction mixture was diluted with chloroform (15 mL/g 18) and washed with 1:1 (v:v) water/brine (10 mL/g 18). The aqueous phase was re-extracted once with chloroform (10 mL/g 18), the combined organic solutions dried over $Na_2SO_4$ and the solvent removed. The residue was dissolved in N,N-dimethylformamide (15 mL/g 18), washed six times with hexanes (15 mL/g 18) to remove/reduce the dibenzofulvene by-product and the solvent removed to give the product 17a-e as an off-white solid. Yield=85% Freshly distilled ethyl phosphorodichloridate (3 eq) was added dropwise over 3 min to a solution of 17 (1 eq; 2.3 mmol) and diisopropylethylamine (3 eq) in dry dichloromethane (40 mL/g 17) under $N_2$ at 0° C. The cooling bath was removed and the reaction mixture was stirred at room temperature until complete by TLC (30 min). After removal of the solvent, the crude product was purified directly by silica gel chromatography (ethyl acetate/hexane gradient). Yield=50-60%. This subunit is useful for introduction of uncharged linkages of type (a). This general method was applied below for the introduction of charges linkages of type (b3).

Reductive amination with a long chain ethereal diamine with the T subunit:

4-Methoxytriphenylmethyl chloride (15.4 g, 50 mmol) was dissolved in toluene and added dropwise to a stirred solution of 4,7,10-trioxa-1,13-tridecaneamine (150 mmol) in dichloromethane containing 50 mmol triethylamine. Reaction completion was conveniently followed by TLC eluting with ethanol/conc ammonia (4:1, v/v) and visualizing with ninhydrin or UV. When the reaction was done, the solution was washed with water to remove the free amine. The solvent was removed by evaporation and the crude product used without purification in the next step.

Ethyl trifluoroacetate (1.5 eq) was added to a solution of methoxytritylated amine (1 eq; 25 mmol) and triethylamine (1.5 eq) in dichloromethane (12 mL/g amine) at 0° C., the cooling bath was removed and the reaction mixture stirred at room temperature for 4 hr. On reaction completion (TLC), the reaction mixture was diluted with dichloromethane (12 ml/g amine) washed twice with 1:1 (v:v) water/brine (20 ml/g 1), dried over $Na_2SO_4$ and concentrated to a viscous pale yellow oil. The crude methoxytritylated amide product was purified by silica gel chromatography (gradient of ethyl acetate/chloroform). Yield=60-70%.

p-Toluenesulfonic acid (1.5 eq) was added to solution of methoxytritylated amide (3 eq; 7.5 mmol) in methanol/trifluoroethanol/dichloromethane (1:10:89 (v:v:v); 5 ml/g 2) and the yellow-orange solution stirred at room temperature for 30 min when reaction was complete (TLC). The reaction mixture was neutralized to pH 7 with triethylamine and evaporated. The crude product was redissolved in methanol (5 mL/g methoxytritylated amide), the pH adjusted to pH 7 if necessary and re-evaporated. The methanol addition and evaporation was repeated once more and the crude amine used without further purification.

The aldehyde 16d (1 eq; 2.5 mmol) was added to a solution of the crude amine in methanol (5 mL/g crude amine; 12.5 mL/g 16d) and the pH adjusted to pH 8 with acetic acid. The reaction mixture was stirred at room temperature for 1 hr and borane-pyridine (2 eq) added. The pH was adjusted, if necessary, to maintain the starting pH and the reaction mixture stirred for 1 hr or until complete by TLC. The reaction mixture was evaporated, the residue dissolved in dichloromethane (12.5 mL/g 16d) and 9-fluorenylmethyl chloroformate (2 eq) and diisopropylethylamine (3 eq) added and the reaction mixture stirred at room temperature for 45 min. The reaction mixture was partitioned between dichloromethane and 1:1 (v:v) water/brine (12.5 mL/g 16d of each) and the aqueous phase re-extracted with dichloromethane (12.5 mL/g 16d). The combined organics were washed with saturated aqueous sodium chloride (25 mL/g 16d), dried over $Na_2SO_4$ and the solvent removed. The crude product was purified by silica gel chromatography (gradient of methanol/chloroform) to give product 21d as a white foam. Yield=40%.

Deprotection:

A solution of crude 21d (1 eq; 0.9 mmol) in 20% triethylamine/N,N-dimethylformamide (15 mL/mmol 21d) was heated at 50° C. for 30 min when no 21d remained by TLC. The cooled reaction mixture was extracted four times with hexanes (30 mL/mmol 21d) to remove the dibenzofulvene by-product and the solvent removed. The residue was dissolved in isopropanol (15 mL/mmol 21d), evaporated to a foam then dissolved in a minimum volume of dichloromethane and precipitated from hexanes (150 mL/g 21d) to give the product 20d as an off white solid. Yield=90%.

Activation:

A solution of 20d (1 eq; 0.78 mmol) and diisopropylethylamine (3 eq) was prepared in dry dichloromethane (20 mL/g 20d) under nitrogen and added dropwise over ~3 min to a solution of ethyl phosphorodichloridate (3 eq) in dry dichloromethane (20 mL/g 20d) under $N_2$ at 0° C. The cooling bath was removed and the reaction mixture was stirred at room temperature until complete by TLC (20 min). The solution was concentrated to approximately ½ volume and purified directly by silica gel chromatography (acetone/chloroform gradient). Yield=40-50% of 22d.

Reductive amination with a long chain ethereal diamine with the C subunit:

Subunit 1b was oxidized by an alternative method. The subunit (5 g, 1 eq) was added to a solution formed by adding pyridine (9.15 eq) then trifluoroacetic acid (4.58 eq). The solution placed in room temperature water bath and stirred. When the solution was clear, diisopropylcarbodiimide (7.23 eq) was added slowly. After two hr, the solution was added to 800 mL of saturated aqueous sodium chloride solution. After stirring for 20 min, the mixture was filtered. The product was dissolved in acetone and precipitated into de-ionized water. The filtered product was dried under vacuum. The yield was 70-80%. The oxidized subunit may be used as is, but may be purified by chromatography on silica using ethyl acetate/dichloromethane mixtures.

The diamine 4,7,10-trioxa-1,13-tridecaneamine (33 g, 1 eq) was dissolved in 150 mL diethyl ether, cooled to 0° C., and the solution treated slowly with a solution of ethyl trifluoroacetate (32 g, 1.5 eq) in 50 mL ether. TLC indicates reaction completion with only traces of diamine remaining.

A portion of this solution (45 mL, 3 eq amine relative to aldehyde) was added to a stirred solution of 3.42 g 16b in 20 mL methanol. After five min was added p-nitrophenol (2.52 g), and after 20 min was added sodium cyanoborohydride (3.2 g, 8 eq). After 160 min at room temperature additional sodium cyanoborohydride (1.2 g) and nitrophenol (0.8 g) were added. The solution was poured into 800 mL of room temperature water, giving a suspension of solids and viscous oil. The water was removed by decantation and the product dried in vacuo. The entire product was dissolved in ethyl acetate and applied to 250 mL silica gel packed in the same solvent. The column was washed with 2% triethylamine/ethyl acetate and the product eluted with a 1% solution of triethylamine in 6:1 to 10:1 ethyl acetate:ethanol mixture. The fractions containing product were evaporated dried in vacuo to yield 1.95 g, 37% of the amine 20b.

The activated 5'-amino C subunit with the long chain ethereal side chain amine was prepared as described above for the T compound.

Example 6

Morpholino Subunits with Type (b3) Pro-Cationic Linkages by Alkylation (See FIG. 2F)

Hexamethylenediamine (100 g) was dissolved in methanol (1 L) and treated dropwise with a solution of ethyl trifluoroacetate (103 mL) in 150 mL methanol. Very slight warming of the solution occurs. The reaction was stirred for 30 min at room temperature after addition. TLC using chloroform/methanol/conc ammonia (8:3:1) shows the presence of amine. The solvents were removed by rotary evaporation, the residue dissolved in toluene/ethyl acetate (1:3, 1 L) then washed four times with 10% saturated aqueous sodium chloride solution to effect complete removal of excess diamine. Evaporation yields 117 g crude amine which was used directly with the tosylated subunit formed below.

Subunit 1b (20 g) dissolved in dichloromethane (200 mL) was treated with N-methylimidazole (11 mL) and the mixture cooled in an ice bath. p-Toluenesulfonyl chloride (8 g) was added in one step, the solution stirred for 10 min, and the flask placed at 4° C. for 16 hr. TLC (2% methanol in dichloromethane) indicates reaction completion. The reaction was worked up by adding 300 mL dichloromethane and washing with three times 300 mL of 10% saturated aqueous sodium chloride, and evaporating to yield 23b as a foam.

The tosylate 23b (17 g) and the monoprotected amine (46.5 g, containing some bis acylated diamine) were mixed in acetonitrile (200 mL) along with triethylamine (15 mL). Following 16 hr at 45° C., the mixture was evaporated and the residue resuspended in N,N-dimethylformamide (200 mL). The mixture became homogenous at 45° C. The solution was heated for 5 days, at which time it was cooled to ambient temperature, and mixed with 1 L of 10% saturated aqueous sodium chloride and 800 mL ethyl acetate. The organic layer was washed with 1 L 20% saturated aqueous sodium chloride, stirred with sodium sulfate, filtered and evaporated to 48 g of alkylation product, which contains a mixture of benzoylated and debenzoylated heterocyclic base.

A portion of the crude product above (9 g) was suspended in dichloromethane, cooled to 0° C., and treated with a solution of N-(9-fluorenylmethoxycarbonyloxy)succinimide (FMOC-OSu) (Chemical Abstracts number 82911-69-1) in 40 mL dichloromethane. The reaction was complete after 20 minute. To the solution was added 3.3 mL N-methylimidazole then 1.9 mL of benzoyl chloride to re-protect debenzoylated species. After 10 more min at 0° C., the reaction was allowed to warm to room temperature. The reaction was diluted with 150 mL dichloromethane, washed with 250 mL pH=7 phosphate buffer, washed twice with 250 mL 10% saturated aqueous sodium chloride, dried over sodium sulfate, and evaporated. The residue was loaded onto 500 mL silica using dichloromethane (3 L), and eluted with mixtures of ethyl acetate in dichloromethane (1 L each of 5%, 10%, 15%, 2 L of 20%, 2 L of 40%) The last eluent provided 2.9 g of pure benzoylated FMOC protected 5'-amino subunit 24b. Washing the column with 2 L of 5% methanol/dichloromethane allowed the recovery of 5.4 g of the debenzoylated FMOC protected 5'-amino subunit.

The FMOC group was removed from the product above (7.1 g) by treatment with piperidine (28 mL) in DMF (140 mL). After 5 min at room temperature, the reaction was partitioned between dichloromethane (400 mL) and water (30 mL). The organic layer was washed three times with 400 mL 10% saturated aqueous sodium chloride. Evaporation provided 8.8 g crude free amine, purified by chromatography on silica (360 mL), using dichloromethane (1 L), 30% ethyl acetate/dichloromethane (2 L), and 5% methanol/dichloromethane (3 L) to provide 2.5 g of amine product.

One gram of this amine was dissolved in dichloromethane (10 mL) at 0° C. and treated successively with N-ethylmorpholine (500 mL), then ethyl phosphorodichloridate (230 mL). Triethylamine (227 mL) was added and the mixture became homogeneous. The reaction was complete after 4 hr. After the usual aqueous workup the product was purified by silica chromatography (60 mL) using 10-50% ethyl acetate/heptane mixtures to give 800 mg of the activated subunit 25b.

The same process was used to make the activated T subunit with protected hexamethylene diamine side chain at the 5'-position. Subunit 1d (50 g) was reacted with p-toluenesulfonyl chloride (23.7 g) in dichloromethane (500 mL) and N-methylimidazole (16.5 mL). After one hr at 0° C. and 4 hr at room temperature, the reaction was diluted with 400 mL dichloromethane and washed with three times with 1 L of 10% saturated aqueous sodium chloride. After drying over sodium sulfate and evaporation the residue weighed 57 g. The residue (15 g) and 40 g of the crude mono(trifluoroacetylated) hexamethylene diamine were reacted at reflux overnight in 100 mL acetonitrile. The residue after evaporation was dissolved in 2% methanol/dichloromethane and applied to silica. The column was eluted with dichloromethane, 50% ethyl acetate/dichloromethane, ethyl acetate, 80% ethyl acetate/dichloromethane, and finally 5% methanol/dichloromethane to elute the product in >98% purity. One gram of this product was activated and purified as above to yield 300 mg (25%) of the activated subunit 25d.

In a similar fashion, 1a-e were reacted with 3,3'-diamino-N-methyldipropylamine, 26 which affords a side chain with two cationic sites as in 27a-e.

Example 7

Morpholino Subunits with Pro-Cationic Sulfamide Linkages (See FIG. 2G)

The 5'-methylamino subunit 17a-e (1 eq) in dimethylformamide (10 mL/g) was treated with sulfur trioxide/pyridine (4 eq), pyridine (8 eq) followed by triethylamine (6 eq). After 16 hr, the reaction was added to excess saturated aqueous sodium chloride and the dried precipitate chromatographed on silica using 5% methanol/chloroform and containing 2% triethylamine. The triethylammonium salt of the sulfamic acid 28a-e so isolated was dissolved in dichloromethane (20 mL/g). Pyridine (3.2 eq) was added and the mixture cooled under nitrogen in a dry-ice acetone batch. The solution was treated dropwise with 1.1 eq phosgene in toluene solution. After 25 min, the solution was allowed to warm to room temperature over 20 min. The solution was rotary evaporated to an oil that was dissolved in chloroform and directly chromatographed on silica using 40% ethyl acetate and hexane. The product 29a-e obtained in 50% yield, was used for the introduction of sulfamide linkages of type (a). The 5'-amino subunit from hexamethylene diamine (24a-e) was deprotected, sulfated and activated in a similar fashion to provide 30a-e.

Example 8

Preparation of Disulfide Anchor (See FIG. 2H)

Preparation of symmetrical disulfide 32: 1,1'-Carbonyldiimidazole (CDI) (12.402 g; 2.2 eq.) was suspended in dichloromethane (5.25 mL/g) and cooled on an ice bath. Hydroxyethyl disulfide 31 (5.36 g; 1 eq.) was dissolved in dichloromethane (10 mL/g) and tetrahydrofuran (1 mL/g). The diol solution was added to the CDI slowly such that the temperature of the mixture stayed below 4° C. for the duration of the reaction. Upon reaction completion (once addition was complete), de-ionized water (93.8 µL, 0.15 eq.) was added to quench the reaction. Independently, 11 (32.59 g; 2.1 eq.) was dissolved in toluene (8 mL/g 11), dichloromethane (2 mL/g 11), and methanol (2 mL/g 11). $K_2CO_3$ (22.09 g; 4.6 eq.) was dissolved in de-ionized water (10 mL/g). The $K_2CO_3$ solution added to the solution of 11; the mixture was stirred and then separated into two layers. The cloudy organic layer was distilled to remove 90 grams; the resulting water droplets were separated and acetone (8 mL/g 11) was added to the organic layer. The solution of CDI activated disulfide diol was added to the solution of free base 12 and concentrated to 225 mL. Acetone (10 mL/g 11) was added and the mixture was concentrated to 225 mL. The mixture was heated to reflux and solid began crystallizing out of solution. Upon completion, the reaction mixture was cooled and the solid (32) was isolated by filtration. Yield: 27.92 g; 93.1% (based on weight-based assay).

Preparation of disulfide alcohol 33: 32 (36.00 g; 32.1 mmol; 1 eq.) was suspended in acetone (2.8 mL/g 32). Hydroxyethyl disulfide (78.51 mL; 20 eq.) was added followed by acetone (1.7 mL/g 32). 5% NaOH/methanol (2.85 mL; 0.1 eq.) was added; the pH of the mixture was 10 by pH paper. Triphenylphosphine (8.42 g; 1 eq.) was added followed by acetone (1.1 mL/g 32). All solids went into solution and then product began to crystallize out. After sixteen hr, the reaction mixture was neutralized with acetic acid (2.4 g; 0.2 eq.). The crude product was isolated by filtration. The crude solid 33 was subjected to two refluxing acetone reslurries (5 mL/g).

After filtration the crude product was suspended in dichloromethane (7.25 mL/g 32). The mixture was heated until a clear solution formed (35° C.). The solution was extracted five times with an equal volume of de-ionized water and the final organic layer was concentrated to 155 mL. Dichloromethane was added (4.3 mL/g 32), and the solution was again concentrated to 155 mL. CDI (9.17 g; 1.1 eq.) was added and the mixture was stirred at room temperature. Upon reaction completion (~20 min) the reaction mixture was washed twice with an equal volume of de-ionized water, then ethylbenzene (2.1 mL/g 32) was added. The solution was concentrated to 65.2 g, reducing the dichloromethane in the solution to 0.17%, and stirred on an ice bath to crystallize the product. The product 34 was isolated by filtration. Yield: 44%.

Example 9

Triethylene glycol Tail (See FIG. 2I)

Preparation of trityl piperazine phenyl carbamate 35: To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 38 from compound 36. Introduction of the activated "Tail" onto the disulfide anchor-resin was performed in NMP by the procedure used for incorporation of the subunits during solid phase synthesis.

Example 10

Preparation of the Solid Support for Synthesis of Morpholino Oligomers

Example 10a

Preparation of Aminomethylpolystyrene-Disulfide Resin

This procedure was performed in a silanized, jacketed peptide vessel (custom made by ChemGlass, NJ, USA) with a coarse porosity (40-60 µm) glass frit, overhead stirrer, and 3-way Teflon stopcock to allow N$_2$ to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N$_2$ flow up through the frit and the specified resin treatment/wash was added to the reactor and allowed to permeate and completely wet the resin. Mixing was then started and the resin slurry mixed for the specified time. For solvent/solution extraction, mixing and N$_2$ flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N$_2$ substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 was dried under a N$_2$ stream for 1-3 hr and then under vacuum to constant weight (±2%). Yield: 110-150% of the original resin weight.

Example 10b

Determination of the Loading of Aminomethylpolystyrene-Disulfide Resin

The loading of the resin (number of potentially available reactive sites) is determined by a spectrometric assay for the number of triphenylmethyl(trityl) groups per gram of resin. A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 μL) is transferred to a 10 mL volumetric flask and the volume brought up to 10 mL with methanesulfonic acid.

The trityl cation content in the final solution is measured by UV absorbance at 431.7 mm and the resin loading calculated in trityl groups per gram resin (μmol/g) using the appropriate volumes, dilutions, extinction coefficient ($\epsilon$: 41 μmol$^{-1}$cm$^{-1}$) and resin weight. The assay is performed in triplicate and an average loading calculated.

The resin loading procedure in this example will provide resin with a loading of approximately 500 μmol/g. A loading of 300-400 in μmol/g was obtained if the disulfide anchor incorporation step is performed for 24 hr at room temperature.

Example 10c

Tail Loading

Using the same setup and volumes as for the preparation of aminomethylpolystyrene-disulfide resin, the Tail can be introduced into the molecule. For the coupling step, a solution of 38 (0.2 M) in NMP containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Example 11

Preparation of Morpholino Oligomers on an Automated Synthesizer

Example 11a

Solid Phase Synthesis

Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 μmol/g of resin is preferred. For larger oligomers, aminomethylpolystyrene-disulfide resin with loading of 300-400 μmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile;
Neutralization Solution: 5% Diisopropylethylamine in 3:1 dichloromethane/isopropanol;
Coupling Solution: 0.18 M (or 0.24 M for oligomers having grown longer than 20 subunits) activated Morpholino Subunit of the desired base and linkage type and 0.4 M N-ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Example 11b

Cleavage from the Resin and Removal of Bases and Backbone Protecting Groups

After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Example 11c

Initial Oligomer Isolation

The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Example 11d

Demethoxytritylation of Morpholino Oligomers: Methoxytrityl Off Oligomers

The pooled fractions from the Macroprep purification were treated with 1 M $H_3PO_4$ to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% $NH_4OH$/80% acetonitrile; 0.5M NaOH/20% ethanol; water; 50 mM $H_3PO_4$/80% acetonitrile; water; 0.5 NaOH/20% ethanol; water; 0.28% $NH_4OH$.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Example 11e

Analysis of Morpholino Oligomers

MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydroxyacetophenone (THAP) or alpha-cyano-4-hydroxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM $KH_2PO_4$ 25% acetonitrile at pH=3.5 (buffer A) and 25 mM $KH_2PO_4$ 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Example 11f

Purification of Morpholino Oligomers by Cation Exchange Chromatography

The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

The following oligomers exemplify this method:

5'-(EG3)-G+TGC+TCA+TGG+TGCACGG+TC-3'-(H), calculated $[M+H]^+$=6860.9 daltons, found $[M+H]^+$=6861.7 daltons, useful for HCV 5'-(EG3)-GCC+ATGGT+TTT+TTC+TC+AGG-3'-(H), calculated $[M+H]^+$=6825.9 daltons, found $[M+H]^+$=6827.1 daltons, useful for Ebola 5'-(EG3)-+TGGGT+ATG+TTGT+AGCC+AT-3'-(H), calculated $[M+H]^+$=7245.2 daltons, found $[M+H]^+$=7246.8 daltons, useful for Ebola 5'-(EG3)-CC+TGCCC+TTTGT+TCT+AGT+TG-3'-(H), calculated $[M+H]^+$=7092.2 daltons, found $[M+H]^+$=7093.8 daltons, useful for Ebola

Example 11g

3-'-Methoxytrityl and 3'-Trityl Morpholino Oligomers

The Macroprep purified oligomers were directly applied to the solid phase extraction columns, and the 3'-methoxytritylated oligomers were isolated and quantified in the same manner as the demethoxytritylated species.

Example 12

Synthesis of N2,O6-Protected Morpholino G (DPG) for Large Scale Oligomer Synthesis Preparation of 41: To a cooled solution of 1c and imidazole (1.3 eq) in dichloromethane (8 mL/g 1) was added a solution of tert-butyldimethylchlorosilane (1.2 eq) in dichloromethane. After addition, the solution was warmed to 20° C. Upon reaction completion (1-3 hours), this solution was washed successively with 1 M citrate buffer (adjusted to pH 3 with NaOH) and water. The resulting organic solution was distilled to azeotropically remove water and used directly in the next step.

Preparation of 42: To a 0° C. cooled solution of 41 in dichloromethane were added successively triethylamine (1.2 eq), 4-dimethylaminopyridine (0.1 eq), and triisopropylbenzenesulfonyl chloride (1.1 eq). The solution was warmed to 20° C. Upon reaction completion (3-9 hours), the solution was washed successively with 1 M $KH_2PO_4$ and water. The resulting organic solution was distilled to azeotropically remove water and used directly in the preparation of compound 44.

Preparation of 43: To a solution of 4-hydroxybenzaldehyde (1.0 eq) and N-methylimidazole (0.2 eq) in toluene was added a solution of $KHCO_3$ (2.0 eq) in water. To the resulting two-phase mixture was added trimethylacetyl chloride (1.4 eq). Upon reaction completion (1-2 hours), methanol (1.0 eq) was added, and the mixture was stirred for 1 hour. After separation of layers, the organic layer was washed successively with 1 M $KH_2PO_4$ and water. The resulting organic solution was distilled to azeotropically remove water and diluted with THF. To this solution was added 5% Pd/C catalyst (0.004 eq, Johnson Matthey, West Deptford, N.J., USA), and the mixture was hydrogenated under 5-30 psi $H_2$. Upon reaction completion (4-8 hours), the mixture was filtered through a pad of Celite and washed with pH 6.5 phosphate buffer. The product was crystallized from toluene/heptane.

Yield=80%.

Preparation of 44: To a cooled solution of 3 in dichloromethane was added N-methylpyrrolidine (2.0 eq). After 10 minutes, 3a (1.2 eq) was added, followed by DBU (1.2 eq). After reagent addition, the solution was warmed to 20° C. Upon reaction completion (1-9 hours), the solution was washed successively with 1 M $KH_2PO_4$ and water. The resulting organic solution was distilled to azeotropically remove water and used directly in the next step.

Preparation of 45: To the solution of 44 in dichloromethane was added triethylamine trihydrofluoride (2.0 eq). Upon reaction completion (4-20 hours), the solution was washed successively with sodium bicarbonate solution, pH 6.5 phosphate buffer, and water. The resulting solution was distilled to remove dichloromethane, and the product was crystallized from THF/water. Yield=70% from 1c.

Preparation of 46: Compound 45 was dissolved in dichloromethane (6 mL/g 45) and cooled to <5° C. To this solution were added 2,6-lutidine (1.6 eq), N-methylimidazole (0.3 eq), and N,N-dimethylphosphoramidodichloridate (1.6 eq). The solution was warmed to 20° C. Upon reaction completion (6-12 hours), this mixture was washed with a pH 3 citrate buffer. The crude product was isolated by precipitation/reslurry. The doubly protected (DPG) product 46 was purified by silica gel chromatography (gradient of ethyl acetate/heptane) and isolated by precipitation into heptane. Yield=40-60%.

Example 13

Large Scale Synthesis of Morpholino Oligomers

The reactor design for the loading of anchor and Tail on aminomethylpolystyrene resin is used for larger scale synthesis of Morpholino Oligomers. Resin loading guidelines are the same as for the smaller scale synthesis.

Example 13a

Solid Phase Synthesis

Protected oligomers were prepared manually by solid phase oligomer synthesis on aminomethylpolystyrene-disulfide resin (~500 µmol/g loading) at 10 g scale (starting resin weight). Solutions used were as follows: detritylation solution: 2% 4-cyanopyridinium trifluoroacetate (CYTFA) (w/v) in 20% trifluoroethanol/dichloromethane with 1% ethanol; neutralization solution: 5% diisopropylethylamine in 25% isopropanol/dichloromethane; coupling solution: 0.165 M (for 46 (DPG) and 5d or other T subunits) or 0.18 M (for 5a and 5b or other A/C subunits) activated Morpholino Subunit and 0.4 M N-ethylmorpholine in 1,3-dimethylimidazolidinone (DMI).

After transfer of the resin to the synthesis reactor and prior to initiating synthesis cycles, 1-methyl-2-pyrrolidinone (NMP, 20 mL/g resin) was added and allowed to sit for 1-2 hrs. After washing 2 times with dichloromethane (10 mL/g resin), the following synthesis cycle was used with addition of the appropriate coupling solution of activated Morpholino Subunit of the desired base and desired linkage type at each cycle to give the proper sequence.

| Step | Volume (mL/g of starting resin)* | Time (min) |
|---|---|---|
| DCM | 10-30 | 1-2 |
| DCM | 10-30 | 1-2 |
| Detritylation A | 10-30 | 2-3 |
| Detritylation A | 10-30 | 2-3 |
| Detritylation A | 10-30 | 2-3 |
| Detritylation A | 10-30 | 2-3 |
| Detritylation A | 10-30 | 2-3 |
| Neutralization A | 10-30 | 3-4 |
| Neutralization A | 10-30 | 3-4 |
| Neutralization A | 10-30 | 3-4 |
| Neutralization A | 10-30 | 3-4 |
| DCM | 10-30 | 1-2 |
| DCM | 10-30 | 1-2 |
| Coupling | 7-12** | 90 |
| Neutralization A | 10-30 | 1-2 |
| Neutralization A | 10-30 | 1-2 |
| Neutralization A | 10-30 | 1-2 |
| Neutralization A | 10-30 | 1-2 |
| DCM | 10-30 | 1-2 |

*Wash volumes are incremented to account for resin swelling; volume is 10 mL/g of actual resin volume at each cycle
**Coupling volumes are sufficient to maintain good mixing and are incremented to account for resin swelling After incorporation of the final subunit, a final cycle (methoxytritylation) was performed with 0.32 M 4-methoxytriphenylmethyl chloride and 0.4 M N-ethylmorpholine in DMI.

After methoxytritylation, the resin was washed 8 times with NMP and then treated with cleavage solution consisting of 0.1 M 1,4-dithiothreitol (DTT) and 0.73 M triethylamine in NMP (27 mL/g starting resin) for 30 min. After collection of the protected oligomer solution, the resin (significantly reduced in volume) was washed with two additional portions of cleavage solution (13 mL/g starting resin for 15 min each) and the washes were combined with the bulk solution. To the protected oligomer solution in an appropriately sized pressure bottle with Teflon plug (Ace Glass, NJ, USA) was added concentrated aqueous ammonia (106 mL/g starting resin, previously cooled to −20° C.), the bottle sealed, and the contents mixed by swirling. The bottle was placed in a 45° C. oven for 16-20 hr to remove base and backbone protecting groups.

Following ammonolysis, the crude oligomer solution is cooled to room temperature and then diafiltered against 0.28% aqueous ammonia using a PLBC 3 kd Regenerated Cellulose membrane (Millipore) to remove solvents and small molecules prior to ion exchange chromatography.

Example 13b

Purification of Morpholino Oligomers by Anion Exchange Chromatography

The crude oligomer solution obtained from diafiltration is adjusted to pH 11-11.5 and loaded onto a column of ToyoPearl Super-Q 650S anion exchange resin (Tosoh Bioscience.

The methoxytritylated oligomer was eluted with a gradient of 5-35% B over 17 column volume (Buffer A: 10 mM sodium hydroxide; Buffer B: 1 M sodium chloride in 10 mM sodium hydroxide) and fractions of acceptable purity (anion exchange HPLC and mass spec) pooled.

Example 13c

Demethoxytritylation of Morpholino Oligomers

To the pooled fractions from anion exchange chromatography was added acetonitrile (10% by volume) followed by 2 M $H_3PO_4$ to adjust the pH to 3. The solution was mixed for 45 min and then neutralized with concentrated aqueous ammonia to pH 7. The oligomer solution was diafiltered against 20 mM sodium acetate using a PLBC 3 kd Regenerated Cellulose membrane (Millipore) to exchange buffers prior to cation exchange chromatography.

Example 13d

Purification of Morpholino Oligomers by Cation Exchange Chromatography

The oligomer solution was adjusted to pH 4.5 with acetic acid and loaded onto a column of Source 30S cation exchange resin (GE Healthcare). The oligomer was eluted with a gradient of 0-35% B over 17 column volumes (Buffer A: 20 mM sodium acetate, 25% acetonitrile, pH 4.5; Buffer B: 0.5 M sodium chloride, 20 mM sodium acetate, 25% acetonitrile, pH 4.5) and fractions of acceptable purity (cation exchange HPLC and mass spec) pooled.

Example 13e

Isolation of Morpholino Oligomers

The purified oligomer solution was diafiltered against 0.028% aqueous ammonia using a PLBC 3 kd Regenerated Cellulose membrane (Millipore) to remove salt and generate the oligomer free base. The desalted oligomer solution was then frozen and lyophilized to give the oligomer as a white fluffy powder (~12% water content). By this method compounds useful in Ebola treatment were prepared:

```
5'-(EG3)- GCC + ATGGT + TTT + TTC + TC + AGG -3'-(H),   8.4 g

5'-(EG3)- CC + TGCCC + TTTGT + TCT + AGT + TG -3'-(H),  10.0 g
```

Identical to the compounds made by small scale.

Example 13f

Analysis of Morpholino Oligomers by Anion Exchange HPLC

Anion exchange (SAX) HPLC was performed using a Dionex DNAPac, 4×250 mm column (Dionex Corporation; Sunnyvale, Calif.) using 20 mM sodium chloride, 10 mmol sodium hydroxide (Buffer A) and 1 M sodium chloride, 10 mmol sodium hydroxide (buffer B), (Gradient 10-53% B in 20 min).

Example 14

Introduction of a Guanidinium group into a Morpholino Oligomer

Example 14a

By Direct Guanylation of Amines

10 μmol of a Morpholino Oligomer, the backbone of which contained three piperazine secondary amines, were dissolved in 0.5 M $Na_2CO_3$ at 75 mg/mL. 700 μmol of 1-H-pyrazole-1-carboxamidine HCl were added to the Morpholino Oligomer solution and the reaction stirred at room temperature. After three hours had elapsed, the reaction was diluted with water and purified by solid phase extraction (SPE) using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The product, as the HCl salt, was then lyophilized.

Strong cation exchange (SCX) purification at pH=9 of morpholino oligomers containing guanidine backbone moieties may be achieved when the oligomer contains at least three guanidine groups on the backbone and/or termini. Prior to lyophilization, the desalted solution from above was purified by SCX at pH 9 to separate the guanidine-modified product from any remaining underivatized piperazine precursor. The liquid chromatography column had dimensions of 10×62 mm (Bio-Chem Valve/Omnifit, Cambridge, United Kingdom) and contained Source 15S strong cation exchange media (GE Healthcare Bio-Sciences Corp., Piscataway, N.J.). The mobile phase compositions were A) 25 mM Tris HCl, 25% acetonitrile (v/v); pH 9.0 and B) 1.0 M sodium chloride, 25 mM Tris HCl, 25% acetonitrile (v/v); pH 9.0. A linear velocity of 342 cm/hr was used. After equilibration of the column with four column volumes of mobile phase A, the oligomer sample was loaded in mobile phase A at a concentration of approximately 5 mg/mL. The column was then washed for two minutes with mobile phase A, after which fraction collection was initiated concurrently with a linear gradient of 0-20% mobile phase B over twenty-two minutes. Fractions were analyzed individually by MALDI-TOF MS. Selected fractions were pooled and desalted by solid phase extraction. The fraction pool was diluted 5-fold with water and loaded onto an Amberchrom CG300M column. The SPE desalt entailed loading the sample onto the column at 20 mg/mL and washing the column with 3 column volumes of water. The product was then eluted by washing the column with 3 column volumes of acetonitrile/water (1:1 v/v). The product was lyophilized and analyzed by MALDI-TOF MS and SCX HPLC.

The following oligomers exemplify this method:

5'-(EG3)-CTGGG+ATG+AG+ATCC+ATC+ACT-3'-(H) was prepared using resin with Tail. A sample (10000D) was converted by the methods above into: 5'-(EG3)-CTGGG(Gupip)ATG(Gupip)AG(Gupip)ATCC(Gupip)ATC(Gupip)ACT-3'-(Gu) calculated $[M+H]^+$=7421.5 daltons. The crude product (9070D) recovered after SPE, found [M+H]$^+$=7422.6 daltons, was purified on SCX ion exchange at pH=9 to provide 378 OD product, found [M+H]$^+$=7420.9.

Example 14b

Introduction of Guanidinium Groups by Reaction with Guanidino Amino Acid Trifluoroacetate Salts Preparation of Guanidino Acid Trifluoroacetate Salts.

The guanidino acid was dissolved in trifluoroacetic acid at a concentration of 330 mg/mL with gentle heating and stirring. Once fully dissolved, the solution was added dropwise to a tenfold volumetric excess of diethyl ether to precipitate the trifluoroacetate salt of the guanidino acid. The suspension was centrifuged, the supernatant decanted, and the solid triturated in a fresh portion of diethyl ether. The suspension was again centrifuged, the supernatant decanted, and the solid dried under vacuum.

Conjugation of Guanidino Acids (General) to Amines of a Morpholino Oligomer.

The morpholino oligomer, containing free amino groups on the backbone and/or termini, was dissolved in DMSO at 75 mg/mL. Separately, an activated guanidino acid solution was prepared by dissolving the trifluoroacetate or hydrochloride salt of the guanidino acid (2 equivalents with respect to Morpholino Oligomer amines) and HBTU (1.95 equivalents with respect amines) in NMP at 100 mg/mL (with respect to guanidino acid). DIEA (3 equivalents with respect to guanidino acid) was then added to the guanidino acid solution. The activated guanidino acid solution was mixed briefly and immediately added to the Morpholino Oligomer solution. After three hours of stirring at room temperature, the reaction was diluted 2.33-fold with cold concentrated ammonium hydroxide. As required, TFE was added slowly with gentle heating and mixing to redissolve the precipitated solid. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC.

The following oligomers exemplify this method:

5'-(H)—C+TTCGA+TAG+TG-3'-(H) was prepared from using resin with no Tail. A sample (9700D) was converted with 4-guanidinobutanoic acid by the methods above into: 5'-(GuBu)-C(GuBupip)TTCGA(GuBupip)TAG(GuBupip)TG-3'-(GuBu), calculated [M+H]$^+$=4541.2 daltons. The crude product (8200D) recovered after SPE, found [M+H]$^+$=4541.9 daltons, was purified on SCX ion exchange at pH=9 to provide 3560D product, found [M+H]$^+$=4542.1

Conjugation of 6-Guanidinohexanoic Acid to Secondary Amines of a Morpholino Oligomer.

6-Guanidinohexanoic acid was obtained from AlzChem; Trostberg, Germany. The Morpholino Oligomer (20 µmol), an 18-mer with eight secondary amines incorporated into the backbone (160 µmol of amine groups), was dissolved in dimethylsulfoxide (DMSO) at 75 mg/mL. Separately, an activated 6-guanidinohexanoic acid solution was prepared by dissolving 320 µmol (2 molar equivalents with respect to amines) of the trifluoroacetate salt of 6-Guanidinohexanoic acid and 312 µmol of 2-(1-H-benzotriazol-1-yl)-1,1,3,3-tetramethylaminium hexafluorophosphate (HBTU) in 920 µL of 1-methyl-2-pyrrolidinone (NMP) and adding 960 mmol of N,N-diisopropylethylamine (DIEA). Immediately after addition of DIEA, the activated guanidino-acid solution was added to the Morpholino Oligomer solution. After stirring under nitrogen at room temperature for three hours, 4 mL of concentrated ammonium hydroxide were added to the reaction. 7 mL of 2,2,2-trifluoroethanol (TFE) were added with gently heating and mixing to redissolve the precipitated solid and the solution heated at 45° C. for 18 hours. The solution was then diluted to 200 mL with water and purified by solid phase extraction (SPE) using an Amberchrom CG300M column as detailed above. The conjugate was lyophilized and analyzed by MALDI-TOF MS and SCX HPLC.

The following oligomers exemplify this method:

5'-(H)—C+TTCGA+TAG+TG-3'-(H) was prepared using resin with no Tail. A sample (6350D) was converted by the methods above into: 5'-(GuAhx)-C(GuX)TTCGA(GuX)TAG(GuX)TG-3'-(GuAhx), calculated [M+H]$^+$=4681.4 daltons. The crude product (5630D) recovered after SPE, found [M+H]$^+$=4681.2 daltons, was purified on SCX ion exchange at pH=6.5 to provide 4270D product of 93.3% purity by SCX HPLC, found [M+H]$^+$=4682.4.

5'-(EG3)-CTGGG+ATG+AG+ATCC+ATC+ACT-3'-(H) was prepared using resin with Tail. A sample (15000D) was converted by the methods above into: 5'-(EG3)-CTGGG(GuX)ATG(GuX)AG(GuX)ATCC(GuX)ATC(GuX)ACT-3'-(GuAhx), calculated [M+H]$^+$=8100.5 daltons. The crude product (14860D) recovered after SPE, found [M+H]$^+$=8100.4 daltons, was purified on SCX ion exchange at pH=9 to provide 700 OD product, found [M+H]$^+$=8100.6.

This method was also used to add peptide acids such as AcRAhxRAhxB (written more expansively as AcNH-RAhxRAhxB-OH in FIG. 2O) to the backbone amines.

Example 14c

By Conjugation of Aminoalkanoic Acids to Amines of a Morpholino Oligomer Followed by Guanylation The Morpholino Oligomer, containing free amino groups on the backbone and/or termini, was dissolved in DMSO at 75 mg/mL. Separately, an activated Fmoc-aminoalkanoic acid solution was prepared by dissolving the Fmoc-protected amino acid (2 equivalents with respect to Morpholino Oligomer amines) and HBTU (1.95 equivalents with respect amines) in NMP at 100 mg/mL (with respect to amino acid). DIEA (3 equivalents with respect to amino acid) was then added to the amino acid solution. The activated amino acid solution was mixed briefly and immediately added to the Morpholino Oligomer solution. After three hours of stirring at room temperature, the reaction was diluted 2.33-fold with cold concentrated ammonium hydroxide. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC. The product may be guanylated and purified as per the previous examples.

The following oligomers exemplify this method:

5'-(EG3)-CTGGG+ATG+AG+ATCC+ATC+ACT-3'-(H) was prepared using resin with Tail. A sample (20000D) was converted by the methods above into: 5'-(EG3)-CTGGG (Ahxpip)ATG(Ahxpip)AG(Ahxpip)ATCC(G)ATC(Ahxpip)ACT-3'-(Ahx), calculated [M+H]$^+$=7848.3 daltons. The crude product (16720D) recovered after SPE, found [M+H]$^+$=7847.7 daltons. A portion of this material (8000D) was further converted by guanylation into 5'-(EG3)-CTGGG(GuX)ATG(GuX)AG(GuX)ATCC(GuX)ATC(GuX)ACT-3'-(GuAhx), calculated [M+H]$^+$=8100.5 daltons. The crude product recovered after SPE, found [M+H]$^+$=8101.4 daltons, as purified by SCX chromatography to give 3200D of final product.

Example 15

Introduction of Arginine Rich Peptides into a Morpholino Oligomer

The morpholino oligomer, containing free amino groups on the backbone and/or termini, was dissolved in DMSO at 75 mg/mL. Separately, an activated peptide solution was prepared, the peptide being 1-25 amino acid residues in length, containing an N-terminal blocking group, preferably acetyl, and comprised of amino acids with guanidinium, hydrocarbon, or other non-nucleophilic side chains. The peptide (2 equivalents with respect to morpholino oligomer amines) and HBTU (1.95 equivalents with respect to amine groups) were dissolved in NMP at 100 mg/mL (with respect to peptide). DIEA (2 equivalents with respect to peptide) was then added to the peptide solution. The activated peptide solution was mixed briefly and immediately added to the morpholino oligomer solution. After three hours of stirring at room temperature, the reaction was diluted 2.33-fold with cold concentrated ammonium hydroxide. As required, TFE was added slowly with gentle heating and mixing to redissolve the precipitated solid. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC. The product may be purified as per the pervious examples.

Example 16

Preparation of Morpholino Oligomers Having an Arginine Rich Peptide and Backbone Guanidinium Groups Morpholino oligomers with backbone guanidinium groups, as prepared in Example 14, were reacted with arginine rich peptides as in Example 15. The products were purified on Source 15S SCX cation exchange resin as described in Example 13.

Example 17

Preparation of Morpholino Oligomers Having an Arginine Rich Peptide and Backbone Amine Groups

Example 17a

Protection of Morpholino Oligomer Secondary Amines as Trifluoroacetamides 41 mg of the Morpholino oligomer, an 11-mer with three backbone secondary amines and 3'-trityl or methoxytrityl, were dissolved in 0.500 mL of dimethylsulfoxide (DMSO). To the oligomer solution were added 8.2 μL (5 eq) N,N-diisopropylethylamine (DIEA) followed by 44 μL (5 eq.) of a 250 mg/mL solution of 4-nitrophenyl trifluoroacetate in N-methylpyrrolidinone (NMP). The additions of DIEA and 4-nitrophenyl trifluoroacetate were repeated four more times at 90 min intervals and the reaction then stirred for 15 hr at room temperature. The 3'-trityl or methoxytrityl group was then removed by adding 3.76 mL (20 eq.) of a 50 mM solution of 4-cyanopyridinium trifluoroacetate in 2,2,2-trifluoroethanol (TFE) and stirring for 40 min. The reaction was then diluted to 40 mL with water and the pH adjusted to 7.5 by adding 0.5 M sodium phosphate buffer, pH 7.5, dropwise. The product was isolated by solid phase extraction using a 2 mL Amberchrom CG300M column. After loading the crude reaction mixture onto the column, the column was rinsed with two column volumes of water, four column volumes of 15% acetonitrile/water (v/v), and four column volumes of 20% acetonitrile/water (v/v). The backbone-protected product with free 3'-morpholine amine was then eluted with three column volumes of 1:1 acetonitrile/water (v/v) and lyophilized.

Example 17b

Conjugation of Arginine Rich Peptides to Morpholino Oligomer Followed by Unmasking of Oligomer Backbone Amines An activated peptide solution was prepared by dissolving the peptide-acid (22.6 μmol) and HBTU (22.3 lμmol) in 300111 NMP and adding DIEA (40.8 μmol). Immediately after addition of DIEA, the peptide solution was added to a solution of the backbone-protected Morpholino oligomer with free 3'-morpholino amine in 0.550 mL DMSO. After 180 minutes at room temperature, 2 mL of concentrated ammonium hydroxide were added to the reaction. The resulting precipitate was redissolved with the addition of 4 mL TFE and gentle heating and mixing. The reaction was placed in a 45° C. oven for 15 hours. Water was then added, diluting the reaction to 40 mL. Then the solution was neutralized by adding 2 M phosphoric acid dropwise with stirring. The product was isolated by solid phase extraction using a 2 mL Amberchrom CG300M column. After loading the crude reaction mixture onto the column, the column was rinsed with four column volumes of water. The product was then eluted with three column volumes of 1:1 acetonitrile/water (v/v) and lyophilized.

The following oligomers exemplify this method:

5'-(EG3)-G+TGC+TCA+TGG+TGCACGG+TC-3'-(Ac(RAhxR)$_4$AhxB-), calculated [M+H]$^+$=8789.3 daltons, found [M+H]$^+$=8789.9 daltons, useful for Ebola 5'-(EG3)-C+TTCGA+TAG+TG-3'-(trityl) was prepared using resin with Tail. A sample (9940D) was converted by the methods above into: 5'-(EG3)-C(TFApip)TTCGA(TFApip)TAG(TFApip)TG-3'-(H), calculated [M+H]$^+$=4368.6 daltons. The crude product recovered after SPE, found [M+H]$^+$=4371.1 daltons. This sample was further converted by acylation with Ac(RAhxR)$_4$AhxB to give 5'-(EG3)-C+TTCGA+TAG+TG-3'-(Ac(RAhxR)$_4$AhxB-), calculated [M+H]$^+$=6010.0 daltons. The crude product (7700D) recovered after SPE, found [M+H]$^+$=6011.6 daltons. This was purified on SCX ion exchange at pH=6.5 to provide 4780D product, found [M+H]$^+$=6010.7 daltons, with SCX HPLC purity of 84.7%.

Example 18

Reductive Methylation of Morpholino Oligomer Amines

A formaldehyde solution was prepared by dissolving 0.52 g paraformaldehyde in 17 mL of 200 mM pH 8.5 sodium borate buffer with heating and stirring. The solution was heated to a gentle boil, with a reflux condenser attached, for 1 hour. Heating was then ceased, the reaction mixture cooled to room temperature, and the solution continued to stir for the duration of the methylation reaction.

A 1 M solution of sodium borohydride was prepared by cooling 10 mL of 200 mM pH 8.5 sodium borate buffer on an ice bath and then dissolving 0.378 g of sodium borohydride in it. The solution was kept cold on ice for the duration of the methylation reaction.

33 mg (4.6 µmol) of a 20-mer Morpholino oligomer with five secondary amines incorporated into the backbone and a free morpholine secondary amine at the 3'-terminus was weighed into a glass vial. The oligomer was then dissolved in 1 mL of 200 mM pH 8.5 sodium borate buffer and cooled to 0° C. on an ice bath with stirring. 200 µL of the formaldehyde solution (~43 eq.) prepared above were added to the stirring Morpholino oligomer solution. Immediately after the formaldehyde addition, 40 µL of the 1 M sodium borohydride solution (8.7 eq.) were added. The formaldehyde and sodium borohydride additions were repeated five times at 30 min. intervals. After the final additions, the reaction was stirred for 30 min. and then 4 mg of sodium borohydride added. The reaction was then stirred for another 2 hours. Water was added to dilute the reaction to 5 mL and the pH adjusted to 6.5 by adding 1 M phosphoric acid dropwise.

The product was isolated by solid phase extraction using a 2 mL Amberchrom CG300M column. After loading the crude reaction mixture onto the column, the column was rinsed with four column volumes of water. The product was then eluted with three column volumes of 1:1 acetonitrile/water (v/v) and lyophilized.

The following oligomers exemplify this method:
5'-(EG3)-CTGGG+ATG+AG+ATCC+ATC+ACT-3'-(H) was prepared using resin with Tail. A sample (8850D) was converted by the methods above into: 5'-(EG3)-CTGGG(Mepip)ATG(Mepip)AG(Mepip)ATCC(Mepip)ATC(Mepip)ACT-3'-(Methyl) calculated [M+H]$^+$=7253.5 daltons. The crude product (6250D) recovered after SPE, found [M+H]$^+$ =7250.5 daltons.

Example 19

Cell Free In Vitro Translation Assay (General Method)

The protein coding sequence for firefly luciferase, without the initiator-Met codon ATG, was subcloned into the multiple cloning site of plasmid pCiNeo (Promega). Subsequently, complementary oligonucleotides for Ebola virus (GenBank Accession No. AF086833) VP35 (−98 to +39 bases 3020 to 3157), Ebola virus VP24 (−84 to +43 or bases 10261 to 10390), or Ebola virus L (−80 to +49 or bases 11501 to 11632) start codon regions were duplexed and subcloned into Nhe 1 and Sal 1 sites. RNA was generated from the T7 promoter with T7 Mega script (Ambion, Inc., Austin, Tex.).

For experiments targeting CYP3A2 gene mRNA, oligonucleotides for the rat CYP3A2 gene start codon region were prepared (GenBank Accession No. U09742; −25 to +22 or bases 44 to 90) and cloned into pCiNeo as described above.

For experiments targeting the hepatitis C virus start codon region, oligonucleotides encoding the HCV start codon region were prepared (GenBank Accession No. AF009606; −20 to +31 or bases 322 to 372) and cloned into pCiNeo as described above.

The cell free in vitro translation assays were carried out by mixing different concentrations of PMO with 6 nM RNA. The mixture was then added to a rabbit reticulocyte translation system (Promega, Inc.), and the amount of luciferase protein produced was determined by light emission measured in a luminometer. A sigmoidal curve to determine the $EC_{50}$ values was generated from the plot of the observed luciferase light emission (n=3 per PMO concentration) versus the PMO concentration, e.g. as shown in FIG. 4.

Example 20

Splice Correction Translation Assay in Cell Culture (General Method)

HeLa cells were stably transfected with plasmid pLuc/705, which has a luciferase gene interrupted by a human β-globin intron mutated at nucleotide 705, thus causing incorrect splicing. Because the mis-spliced transcripts do not produce functional reporter proteins, no reporter signals are observed unless wild-type splicing is induced with a splice-correcting oligomer. An antisense oligomer targeting the 705 splice site (having SEQ ID NO: 286), when delivered effectively, corrects splicing and allows luciferase expression.

This assay measures the ability of oligomers to enter cells and nuclei, block incorrect splicing of pre-mRNA, and thus cause expression of a reporter gene. Because oligomers must enter cells and cell nuclei to produce a signal in the assay, it is useful for measuring uptake and effectiveness of delivery moieties as well as antisense activity of the binding oligomers.

The uptake and activity of various oligomers and transporter-oligomer conjugates, as described above, in HeLa pLuc/705 cells was studied by fluorescence spectroscopy. Experiments were generally run in triplicate. According to the general procedure, culture medium containing the test substance at a specified concentration was added to HeLa pLuc/705 cells plated in a 48-well plate. After incubation, the cells were washed with PBS three times, and the cell lysate was collected. The amount of functional luciferase produced was determined by mixing 30 μl of cell lysate and 50 μl of Luciferase Assay Reagent (LAR) (Promega, WI) and measuring the light production using a Flx 800 microplate fluorescence/luminescence reader (Bio-tek, Vermont). The relative light units were normalized to μg of protein determined by the bicinchoninic acid (BCA) method, following the manufacturer's procedure (Pierce, Ill.).

Example 21

Increased Antisense of Activity Using PMO with Cationic Linkages

Two PMOs were synthesized using cationic linkages for a subset of the oligomer linkages as shown in Sequence Listing for SEQ ID NOs: 9 (+T+TCAACC+T+TG AAACC+T+TGCG) and 10 (GCCA+TGG+T+T+T+T+T+TC+TCAGG). These oligomers incorporated a cationic linkage (1-piperazino phosphoramidate), as shown in FIG. 1B, at the positions indicated with a "+". These two PMOs target the EBOV VP24 mRNA. A cell free translation assay was performed using the VP24:luciferase mRNA as the input RNA. PMO with and without cationic linkages were compared for their ability to inhibit luciferase expression and the results are shown in FIG. 3. Compared to the uncharged PMO with the same base sequence, the PMOs with between 6 and 8 cationic linkages demonstrated between 10 and 100-fold increased antisense activity in this assay.

Example 22

Ebola Virus Infection of Oligomer-Treated Animals

C57B1/6 mice, aged 8-10 weeks of both sexes, were obtained from National Cancer Institute, Frederick Cancer Research and Development Center (Frederick, Md.). Mice were housed in microisolator cages and provided autoclaved water and chow ad libitum. Mice were challenged by intraperitoneal injection with ~1000 pfu of mouse-adapted Ebola virus diluted in phosphate buffered saline (PBS) (Bray, Davis et al. 1998). Mice were treated with a total of 100 μg of either PMO or +PMO, split between two equivalent doses at 24 and 4 hours prior to Ebola virus challenge. C57B1/6 mice were challenged intraperitoneally with 1000 plaque-forming units of mouse-adapted Ebola virus (Bray, Davis et al. 1998). Results are described above and displayed graphically in FIG. 6.

Hartley guinea pigs were treated intraperitoneally with up to 20 mg/kg of each of the VP24-AUG, L-AUG and VP35 PMO or +PMO (SEQ ID NOs: 1, 5 and 11 or 287, 288 and 289, respectively) 24 hours before or 24 or 96 hours after subcutaneous challenge with 1000 pfu of guinea-pig adapted Ebola virus (Connolly, Steele et al. 1999).

The non-human primate model for lethal Ebola virus challenge used female rhesus macaques of 3-4 kg in weight that were challenged with 1,000 pfu of EBOV-Zaire (1995 strain) by intramuscular injection prior to PMO treatment. The monkeys were treated from days 1 through day 10 via parenteral routes. The dose of the PMO was 20 mg/kg for each of the two PMO in the two drug combination (SEQ ID NOs: 288 and 289).

Sequence Listing Table

| AVI Ref. No. | Name | Sequence (5'→ 3') | SEQ ID NO. |
|---|---|---|---|
| Ebola Virus Targeting Sequences | | | |
| 4539 | VP35-AUG | CCTGCCCTTTGTTCTAGTTG | 1 |
| 06-131 | VP35-2+ | CCTGCCCTTTGTTCTAG + T + TG | 2 |
| 06-132 | VP35-4a+ | CCTGCCCTTTG + T + TCTAG + T + TG | 3 |
| 06-133 | VP35-4b+ | CC + TGCCC + TTTGT + TCTAGT + TG | 4 |
| 537 | VP24-AUG | GCCATGGTTTTTCTCAGG | 5 |
| 06-125 | VP24-2+ | GCCATGGTTTTT + TC + TCAGG | 6 |
| 06-126 | VP24-4a+ | GCCA + TGGT + TTT + TTC + TCAGG | 7 |
| 06-127 | VP24-4b+ | GCCATGGT + TT + TT + TC + TCAGG | 8 |
| 05-166 | VP24 5'trm6+ | +T + TCAACC + T + TGAAACC + T + TGCG | 9 |
| 05-164 | VP24-8+ | GCCA + TGG + T + T + T + T + T + TC + TCAGG | 10 |
| 4538 | L-AUG | TGGGTATGTTGTGTAGCCAT | 11 |
| 06-125 | L-2+ | TGGGTATGTTGTG + TAGCCA + T | 12 |
| 06-126 | L-4a+ | +TGGGTA + TGTTGTG + TAGCCA + T | 13 |
| 06-127 | L-4b+ | TGGGTATG + TTG + TG + TAGCCA + T | 14 |
| 05-165 | VP24 5'trm | TTCAACCTTGAAACCTTGCG | 15 |
| Control Sequences | | | |
| 183 | DSscr | AGTCTCGACTTGCTACCTCA | 16 |
| 542 | Scr | TGTGCTTACTGTTATACTACTC | 17 |
| Hepatitis C Virus Targeting Sequences | | | |
| 4065 | HCV-AUG | GTGCTCATGGTGCACGGTC | 18 |
| 06-0143 | HCV-2a+ | G + TGC + TCATGGTGCACGGTC | 19 |
| 06-0144 | HCV-2b+ | GTGCTCATGGTGC + ACGG + TC | 20 |
| 06-0145 | HCV-2c+ | G + TGCTCATGGTGCACGG + TC | 21 |
| 06-0146 | HCV-2d+ | GTGCTC + ATGGTGC + ACGGTC | 22 |

-continued

Sequence Listing Table

| AVI Ref. No. | Name | Sequence (5'→ 3') | SEQ ID NO. |
|---|---|---|---|
| 06-0147 | HCV-2e+ | GTGCTCA + TGG + TGCACGGTC | 23 |
| 06-0148 | HCV-2f+ | GTGCTC + A + TGGTGCACGGTC | 24 |
| 06-0149 | HCV-3g+ | GTGCTCATGG + TGC + ACGG + TC | 25 |
| 06-0150 | HCV-3h+ | GTGCTC + ATGGTGC + ACGG + TC | 26 |
| 06-0151 | HCV-3i+ | G + TGCTCATGG + TGCACGG + TC | 27 |
| 06-0152 | HCV-4j+ | GTGCTCA + TGG + TGC + ACGG + TC | 28 |
| 06-0153 | HCV-4k+ | G + TGCTCA + TGG + TGCACGG + TC | 29 |
| 06-0154 | HCV-4l+ | G + TGCTC + ATGGTGC + ACGG + TC | 30 |
| 06-0155 | HCV-5m+ | G + TGC + TCA + TGG + TGCACGG + TC | 31 |
| 06-0156 | HCV-5n+ | G + TGCTC + ATGG + TGC + ACGG + TC | 32 |
| 06-0157 | HCV-6o+ | G + TGC + TCA + TGG + TGC + ACGG + TC | 33 |
| 06-0158 | HCV-7p+ | G + TGC + TC + A + TGG + TGC + ACGG + TC | 34 |
| CYP3A2 Targeting Sequences | | | |
| 4472 | CYP3A2 | GAGCTGAAAGCAGGTCCATCCC | 35 |
| 06-0136 | CYP3A2-3a+ | GAGCTGAAAGCAGG + TCC + A + TCCC | 36 |
| 06-0137 | CYP3A2-3b+ | G + AGC + TG + AAAGCAGGTCCATCCC | 37 |
| 06-0138 | CYP3A2-3c+ | GAGCTG + AAAGC + AGGTCC + ATCCC | 38 |
| 06-0139 | CYP3A2-3d+ | GAGC + TGAAAGCAGG + TCCA + TCCC | 39 |
| 06-0140 | CYP3A2-3e+ | GAGCTG + A + A + AGCAGGTCCATCCC | 40 |
| 06-0141 | CYP3A2-4f+ | G + AGCTGA + AAGC + AGGTCC + ATCCC | 41 |
| 06-0142 | CYP3A2-6g+ | G + AGCTG + A + A + AGC + AGGTCC + ATCCC | 42 |
| 4126 | c-Myc | ACGTTGAGGGGCATCGTCGC | 43 |
| 4SA2ex | huCTLA | GCAGGCTGGGCCACGTGCATTG | 44 |
| 4SA2sj | huCTLA | CACGTGCATTGCTAGCATGG | 45 |
| 4SA2bp | huCTLA | CTAGCATGGAAAAGCCAAAG | 46 |
| 4SA2in | huCTLA | GGAACTCAGTGAACTCATGC | 47 |
| AUG1 | huCD86 | GTTACTCAGTCCCATAGTGCTG | 48 |
| AUG2 | huCD86 | CCATAGTGCTGTCACAAATG | 49 |
| AUG3 | huCD86 | GAATGTTACTCAGTCCCATAG | 50 |
| Ex6sa | huCD86 | GAGGCTGAGGGTCCTCAAGCT | 51 |
| Ex6sd | huCD86 | CACATTTATAAGAGTTGCGAGGC | 52 |
| Ex7sa | huCD86 | TCCCTCTCCATTGTGTTGGTTC | 53 |
| Ex7sd | huCD86 | CTTTTCTTGGTCTGTTCACTC | 54 |
| 3'32 | Picornaviridae | RYGGRACCRACTACTTTGGGTGTCCGTGTTTC | 55 |
| 5'32 | Picornaviridae | TCCTCCGGCCCCTGAATGYGGCTAAYCYYAAC | 56 |
| 3'-CS | Flaviviridae | CATATTGA | 57 |
| mFlav | Flaviviridae | TCCCAGGTGTCAATATGCTGTT | 58 |

-continued

Sequence Listing Table

| AVI Ref. No. | Name | Sequence (5'→ 3') | SEQ ID NO. |
|---|---|---|---|
| c-Myc target | human c-Myc | CGCCGCTGCCAGGACCCGCTTCTCTGAA AGGCTCTCCTTGCAGCTGCTTAGACGCT GGATTTTTTTCGGGTAGTGGAAAACCAG CAGCCTCCCGCGACGATGCCCCTCAACG TTAGCTTCACCAA | 59 |
| c-MycB | hu-c-Myc | GGAGGCTGCTGGTTTTCCAC | 60 |
| c-MycC | hu-c-Myc | GGCATCGTCGCGGGAGGCTC | 61 |
| PV | Poliovirus | CCTGAGCACCCATTATGATAC | 62 |
| HAV | Hepatitis A | CCTTGTCTAGACATGTTCATTATT | 63 |
| HRV-14 | Rhinovirus 14 | TTGAGCGCCCATGATAACAA | 64 |
| HRV-16 | Rhinovirus 16 | TTGAGCGCCCATGATAACAA | 65 |
| HRV-1B | Rhinovirus 1B | CTGGGCACCCATGATGCCAA | 66 |
| Pan-1a | Vesivirus | GAGCCATAGCTCAAATTCTC | 67 |
| Pan-1b | Vesivirus | TAGCTCAAATTCTCATTTAC | 68 |
| Pan-1b | Vesivirus | GAGCGTTTGAGCCATAGCTC | 69 |
| PEC | Porcine calicivirus | GACGGCAATTAGCCATCACG | 70 |
| NV | Norovirus | CGACGCCATCATCATTCAC | 71 |
| FCV | Feline calicivirus | CAGAGTTTGAGACATTGTCTC | 72 |
| HEVa | Hepatitis C virus | CCTTAATAAACTGATGGGCCTCC | 73 |
| HEVb | Hepatitis C virus | CTGATGGGCCTCCATGGC | 74 |
| HCV | HCV target | AAGACTGCTAGCCGAGTAGTGTTGGGTC GCGAAAGGCCTTGTGGTACTGCCTGATA GGGTGCTTGCGAGTGCCCCGGGAGGTCT CGTAGACCGTGCACCATGAGCACGAATC CTAAACCTCAAAG | 75 |
| HCV-IRES 8070 | HCV | GGCCTTTCGCGACCCAACAC | 76 |
| SLEV | St. Louis Encephalitis virus | AGATGTTCGCGTCGGTGAGCGGAGAGGA AACAGATTTCCT | 77 |
| JEV | Japanese Encephalitis virus | AGAAGTTTATCTGTGTGAACTTCTTGGC TTAGTATCGTTG | 78 |
| MVEV | Murray Valley Encephalitis virus | AGACGTTCATCTGCGTGAGCTTCCGATC TCAGTATTGTTT | 79 |
| WNV | West Nile Virus | AGTAGTTCGCCTGTGTGAGCTGACAAAC TTAGTAGTGTTT | 80 |
| YFV | Yellow Fever virus | AGTAAATCCTGTGTGCTAATTGAGGTGC ATTGGTCTGCAA | 81 |
| DEN2 | Dengue Type 2 | AGTTGTTAGTCTACGTGGACCGACAAAG ACAGATTCTTTG | 82 |
| HCV | Hepatitis C virus | GCCAGCCCCTGATGGGGCGACACTCC ACCATGAATCAC | 83 |
| TVEV | Tick Borne Encephalitis virus | AGATTTTCTTGCACGTGCATGCGTTTGC TTCGGACAGCAT | 84 |
| OHFV | Omsk Hemorrhagic Fever virus | AGATTTCTTGCACGTGCGTGCGCTTGC TTCAGACAGCAA | 85 |
| POW | Powassan virus | AGATTTCTTGCACGTGTGTGCGGGTGC TTTAGTCAGTGT | 86 |

-continued

Sequence Listing Table

| AVI Ref. No. | Name | Sequence (5'→ 3') | SEQ ID NO. |
|---|---|---|---|
| SLEVa | St. Louis Encephalitis virus | ACCGACGCGAACATCNNC | 87 |
| SLEVb | St. Louis Encephalitis virus | TCCTCTCCGCTCACCGACGC | 88 |
| JEVa | Japanese Encephalitis virus | TCACACAGATAAACTTCT | 89 |
| JEVb | Japanese Encephalitis virus | AAGCCAAGAAGTTCACACAG | 90 |
| MVEVa | Murray Valley Encephalitis virus | TCACGCAGATGAACGTCT | 91 |
| MVEVb | Murray Valley Encephalitis virus | GAGATCGGAAGCTCACGCAG | 92 |
| WNVa | West Nile Virus | GCTCACACAGGCGAACTACT | 93 |
| WNVb | West Nile Virus | TAAGTTTGTCAGCTCACACAG | 94 |
| YFVa | Yellow Fever virus | CAATTAGCACACAGGATTTACT | 95 |
| YFVb | Yellow Fever virus | TTGCAGACCAATGCACCTCA | 96 |
| DEN2a | Dengue Type 2 | GTCCACGTAGACTAACAACT | 97 |
| DEN2b | Dengue Type 2 | GTCTTTGTCGGTCCACGTAG | 98 |
| HCVa | Hepatitis C virus | CCCATCAGGGGGCTGGC | 99 |
| HCVb | Hepatitis C virus | TGGAGTGTCGCCCCCATCAG | 100 |
| TVEVa | Tick Borne Encephalitis virus | ATGCACGTGCAAGAAAATCT | 101 |
| TBEVb | Tick Borne Encephalitis virus | ATGCTGTCCGAAGCAAACGC | 102 |
| OHFVa | Omsk Hemorrhagic Fever virus | CACGCACGTGCAAGAAAATCT | 103 |
| OHFVb | Omsk Hemorrhagic Fever virus | TGAAGCAAGCGCACGCACGT | 104 |
| POWa | Powassan virus | ACACACGTGCAAGAAAATCT | 105 |
| POWb | Powassan virus | ACACTGACTAAAGCACCCGC | 106 |
| PV | Poliovirus | TTAAAACAGCTCTGGGGTTGTACCCACCCCAGAGGCCCAC | 107 |
| HEV-A | Human enterovirus A | TTAAAACAGCCTGTGGGTTGTACCCACCCACAGGGCCCAC | 108 |
| HEV-B | Human enterovirus B | TTAAAACAGCCTGTGGGTTGTTCCCACCCACAGGCCCATT | 109 |
| HEV-C | Human enterovirus C | TTAAAACAGCTCTGGGGTTGCTCCCACCCCAGAGGCCCAC | 110 |
| HEV-D | Human enterovirus D | TTAAAACAGCTCTGGGGTTGTTCCCACCCCAGAGGCCCAC | 111 |
| HEV-E | Human enterovirus E | GAGTGTTCCCACCCAACAGGCCCACTGGGTGTTGTACTCT | 112 |
| BEV | Bovine enterovirus | TTAAAACAGCCTGGGGGTTGTACCCACCCCTGGGGCCCAC | 113 |
| HRV-89 | Human rhinovirus 89 | TTAAAACTGGGAGTGGGTTGTTCCCACTCACTCCACCCAT | 114 |
| HRV-B | Human rhinovirus B | TTAAAACAGCGGATGGGTATCCCACCATTCGACCCATTGG | 115 |

-continued

Sequence Listing Table

| AVI Ref. No. | Name | Sequence (5'→ 3') | SEQ ID NO. |
|---|---|---|---|
| FMDV | Foot-and-mouth disease virus | TTGAAAGGGGGCGCTAGGGTTTCACCCC TAGCATGCCAAC | 116 |
| HAV | Hepatitis A | TTCAAGAGGGGTCTCCGGGAATTTCCGG AGTCCCTCTTGG | 117 |
| PVa | Poliovirus | GGTACAACCCCAGAGCTGTTTTAA | 118 |
| PVb | Poliovirus | GTGGGCCTCTGGGGTGGGTA | 119 |
| HEV-A1 | Human enterovirus A | CAACCCACAGGCTGTTTTAA | 120 |
| HEV-A2 | Human enterovirus A | GTGGGCCCTGTGGGTGGGTA | 121 |
| HEV-B1 | Human enterovirus B | CAACCCACAGGCTGTTTTAA | 122 |
| HEV-B2 | Human enterovirus B | AATGGGCCTGTGGGTGGGAA | 123 |
| HEV-C1 | Human enterovirus C | CAACCCCAGAGCTGTTTTAA | 124 |
| HEV-C2 | Human enterovirus C | GTGGGCCTCTGGGGTGGGAG | 125 |
| HEV-D1 | Human enterovirus D | CAACCCCAGAGCTGTTTTAA | 126 |
| HEV-D2 | Human enterovirus D | GTGGGCCTCTGGGGTGGGAA | 127 |
| HEV-E | Human enterovirus E | CCTGTTGGGTGGGAACACTC | 128 |
| HEV-E | Human enterovirus E | AGAGTACAACACCCAGTGGG | 129 |
| BEVa | Bovine enterovirus | CAACCCCCAGGCTGTTTTAA | 130 |
| BEVb | Bovine enterovirus | GTGGGCCCCAGGGGTGGGTA | 131 |
| HRV-89a | Human rhinovirus 89 | CAACCCACTCCCAGTTTTAA | 132 |
| HRV-89b | Human rhinovirus 89 | ATGGGTGGAGTGAGTGGGAA | 133 |
| HRV-B1 | Human rhinovirus B | ATACCCATCCGCTGTTTTAA | 134 |
| HRV-B2 | Human rhinovirus B | CCAATGGGTCGAATGGTGGG | 135 |
| FMDVa | Foot-and-mouth disease virus | AACCCTAGCGCCCCCTTTCAA | 136 |
| FMDVb | Foot-and-mouth disease virus | GTTGGCATGCTAGGGGTGAA | 137 |
| HAVa | Hepatitis A | TCCCGGAGACCCCTCTTGAA | 138 |
| HAVb | Hepatitis A | CCAAGAGGGACTCCGGAAAT | 139 |
| FCV | Feline calicivirus | GTAAAAGAAATTTGAGACAATGTCTCAA ACTCTGAGCTTC | 140 |
| CaCV | Canine calicivirus | GTTAATGAGAAATGGCTTCTGCCATCGC TCTCTCGAGCTC | 141 |
| PoCV | Porcine enteric calicivirus | GTGATCGTGATGGCTAATTGCCGTCCGT TGCCTATTGGGC | 142 |

-continued

Sequence Listing Table

| AVI Ref. No. | Name | Sequence (5'→ 3') | SEQ ID NO. |
|---|---|---|---|
| CVNB | Calicivirus strain NB | GTGATTTAATTATAGAGAGATAGTGACT TTCACTTTTCTT | 143 |
| NV | Norwalk virus | GTGAATGATGATGGCGTCAAAAGACGTC GTTCCTACTGCT | 144 |
| FCVa | Feline calicivirus | TTGTCTCAAATTTCTTTTAC | 145 |
| FCVb | Feline calicivirus | GAAGCTCAGAGTTTGAGACA | 146 |
| CaCVa | Canine calicivirus | AGAAGCCATTTCTCATTAAC | 147 |
| CaCVb | Canine calicivirus | GAGCTCGAGAGAGCGATGGC | 148 |
| PoCVa | Porcine enteric calicivirus | CAATTAGCCATCACGATCAC | 149 |
| PoCVb | Porcine enteric calicivirus | GGCAACGGACGGCAATTAGC | 150 |
| CVNBa | Calicivirus strain NB | TCTCTCTATAATTAAATCAC | 151 |
| CVNBb | Calicivirus strain NB | AAAGTCACTATCTCTCTATA | 152 |
| NVa | Norwalk virus | TTGACGCCATCATCATTCAC | 153 |
| NVb | Norwalk virus | AGCAGTAGGAACGACGTCTT | 154 |
| HEV | Hebatitis E virus | GCCATGGAGGCCCATCAGTTTATTAAGG CTCCTGGCATCA | 155 |
| HEVa | Hebatitis E virus | AACTGATGGGCCTCCATGGC | 156 |
| HEVb | Hebatitis E virus | TGATGCCAGGAGCCTTAATA | 157 |
| RUBV | Rubella virus | ATGGAAGCTATCGGACCTCGCTTAGGAC TCCCATTCCCAT | 158 |
| EEEV | Eastern equine encephalitis | ATAGGGTACGGTGTAGAGGCAACCACCC TATTTCCACCTA | 159 |
| WEEV | Western equine encephalomyelits | ACCCTACAAACTAATCGATCCAATATGG AAAGAATTCACG | 160 |
| VEEV | Venezuelan equine encephalitis | ATGGGCGGCGCAAGAGAGAAGCCCAAAC CAATTACCTACC | 161 |
| RUBVa | Rubella virus | CGAGGTCCGATAGCTTCCAT | 162 |
| RUBVb | Rubella virus | ATGGGAATGGGAGTCCTAAG | 163 |
| EEEVa | Eastern equine encephalitis | GCCTCTACACCGTACCCTAT | 164 |
| EEEVb | Eastern equine encephalitis | TAGGTGGAAATAGGGTGGTT | 165 |
| WEEVa | Western equine encephalomyelits | GATCGATTAGTTTGTAGGGT | 166 |
| WEEVb | Western equine encephalomyelits | CGTGAATTCTTTCCATATTG | 167 |
| VEEVa | Venezuelan equine encephalitis | TTCTCTCTTGCGCCGCCCAT | 168 |
| VEEVb | Venezuelan equine encephalitis | GGTAGGTAATTGGTTTGGGC | 169 |
| SARS-CoV | SARS coronavirus | ATATTAGGTTTTTACCTACCCAGGAAAA GCCAACCAACCT | 170 |
| PEDV | Porcine epidemic diarrhea virus | ACTTAAAAAGATTTTCTATCTACGGATA GTTAGCTCTTTT | 171 |

-continued

| Sequence Listing Table | | | |
|---|---|---|---|
| AVI Ref. No. | Name | Sequence (5'→ 3') | SEQ ID NO. |
| TGEV | Transmissible gastroenteritis | ACTTTTAAAGTAAAGTGAGTGTAGCGTG GCTATATCTCTT | 172 |
| BCoV | Bovine coronavirus | GATTGCGAGCGATTTGCGTGCGTGCATC CCGCTTCACTGA | 173 |
| HCoV-229E | Human corona-virus 229E | ACTTAAGTACCTTATCTATCTACAGATA GAAAAGTTGCTT | 174 |
| MHV | Murine Hepatitis | TATAAGAGTGATTGGCGTCCGTACGTAC CCTCTCAACTCT | 175 |
| PRRSV | Porcine reproductive & respiratory syndrome virus | ATGACGTATAGGTGTTGGCTCTATGCCT TGGCATTTGTAT | 176 |
| SARS-CoVa | SARS coronavirus | GGTAGGTAAAAACCTAATAT | 177 |
| SARS-CoVb | SARS coronavirus | AGGTTGGTTGGCTTTTCCTG | 178 |
| PEDVa | Porcine epidemic diarrhea virus | GATAGAAAATCTTTTTAAGT | 179 |
| PEDVb | Porcine epidemic diarrhea virus | AAAAGAGCTAACTATCCGTA | 180 |
| TGEVa | Transmissible gastroenteritis | ACTCACTTTACTTTAAAAGT | 181 |
| TGEVb | Transmissible gastroenteritis | GCCACGCTACACTCACTTTA | 182 |
| BCoVa | Bovine coronavirus | CACGCAAATCGCTCGCAATC | 183 |
| BCoVb | Bovine coronavirus | TCAGTGAAGCGGGATGCACG | 184 |
| HCoV-229Ea | Human coronavirus 229E | GATAGATAAGGTACTTAAGT | 185 |
| HCoV-229Eb | Human coronavirus 229E | AAGCAACTTTTCTATCTGTA | 186 |
| MHVa | Murine Hepatitis | CGGACGCCAATCACTCTTATA | 187 |
| MHVb | Murine Hepatitis | GAGTTGAGAGGGTACGTACGGA | 188 |
| PRRSVa | Porcine reproductive & respiratory syndrome virus | CATAGAGCCAACACCTATACG | 189 |
| PRRSVb | Porcine reproductive & respiratory syndrome virus | ATACAAATGCCAAGGCATAG | 190 |
| HAstV | Human astrovirus | CCAAGAGGGGGGTGGTGATTGGCCTTTG GCTTATCAGTGT | 191 |
| EAV | Equine arteritis | GCTCGAAGTGTGTATGGTGCCATATACG GCTCACCACCAT | 192 |
| HAstVa | Human astrovirus | AATCACCACCCCCCTCTTGG | 193 |
| HAstVb | Human astrovirus | GCCAAAGGCCAATCACCACC | 194 |
| EAVa | Equine arteritis | GCACCATACACACTTCGAGC | 195 |
| EAVb | Equine arteritis | ATGGTGGTGAGCCGTATATG | 196 |
| 8063 | | | |
| Vif-AUGc | HIV-1 Vif target | GACTATGGAAAACAGATGGCAGGTGAT GATTGT | 197 |

Sequence Listing Table

| AVI Ref. No. | Name | Sequence (5'→ 3') | SEQ ID NO. |
|---|---|---|---|
| TARc | HIV-1 TAR target | GACCAGATCTGAGCCTGGGAGCTCTCTGGCTAAC | 198 |
| U3Rc | HIV-1 U3R target | CCTGTACTGGGTCTCTCTGG | 199 |
| Vif-AUG4 | HIV-1 | CCTGCCATCTGTTTTCCATAATC | 200 |
| Vif-AUG56 | HIV-1 | CACCTGCCATCTGTTTTCCATA | 201 |
| Vif-AUG4+ | HIV-1 | CCTGCC + ATC + TGT + TTTCC + ATA + ATC | 202 |
| Vif-AUG56+ | HIV-1 | CACCTGCCATCTGT + T + TTCC + A + TA | 203 |
| Tar1 | HIV-1 | GCTCCCAGGCTCAGATCTGGTC | 204 |
| Tar2 | HIV-1 | GTTAGCCAGAGAGCTCCCAGGC | 205 |
| U3R | HIV-1 | CCAGAGAGACCCAGTACAGG | 206 |
| 8064 | | | |
| HCoV-229Ec | HCoV-229E target | CUACUUUCUCAACUAAACGAAAU | 207 |
| HCoV-OC43c | HCoV-OC43 target | GAUCUUUUGUAAUCUAAACUUUA | 208 |
| SARS-CoVc | SARS-CoV target | GAUCUGUUCUCUAAACGAACUUUA | 209 |
| HCoV-229Ea | HCoV-229E TRS | ATTTCGTTTAGTTGAGAAAAG | 210 |
| HCoV-229Eb | HCoV-229E TRS | GTTTAGTTGAGAAAAGTAG | 211 |
| HCoV-OC43 | HCoV-OC43 TRS | TAAAGTTTAGATTACAAAAG | 212 |
| SARS-CoVa | SARS-CoV TRS | TAAAGTTCGTTTAGAGAACAG | 213 |
| SARS-CoVb | SARS-CoVTRS | GTTCGTTTAGAGAACAGATC | 214 |
| 8065 | | | |
| CD86 mRNA | Human CD86 | AGGAGCCTTAGGAGGTACGGGGAGCTCGCAAATACTCCTTTTGGTTTATTCTTACCACCTTGCTTCTGTGTTCCTTGGGAATGCTGCTGTGCTTATGCATCTGGTCTCTTTTTGGAGCTACAGTGGACAGGCATTTGTGACAGCACTATGGGACTGAGTAACATTCTCTTTGTGATGGCCTTCCTGCTCTCTGGTGCTGCTCCTCTGAAGATTCAAGCTTATTTCAATGAGACTGCAGACCTGCCATGCCAATTTGCAAACTCTCAAAACCAAAGCCTGAGTGAGCTAGTAGTATTTTGGCAGGACCAGGAAAACTTGGTTCTGAATGAGGTATACTTAGGCAAAGAGAAATTTGACAGTGTTCATTCCAAGTATATGGGCCGCACAAGTTTTGATTCGGACAGTTGGACCCTGAGACTTCACAATCTTCAGATCAAGGACAAGGGCTTGTATCAATGTATCATCCATCACAAAAAGCCCACAGGAATGATTCGCATCCACCAGATGAATTCTGAACTGTCAGTGCTTGCTAACTTCAGTCAACCTGAAATAGTACCAATTTCTAATATAACAGAAAATGTGTACATAAATTTGACCTGCTCATCTATACACGGTTACCCAGAACCTAAGAAGATGAGTGTTTTGCTAAGAACCAAGAATTCAACTATCGAGTATGATGGTATTATGCAGAAATCTCAAGATAATGTCACAGAACTGTACGACGTTTCCATCAGCTTGTCTGTTTCATTCCCTGATGTTACGAGCAATATGACCATCTTCTGTATTCTGGAAACTGACAAGACGCGGCTTTTATCTTCACCTTTCTCTATAGAGCTTGAGGACCCTCAGCCTCCCCCAGACCACATTCCTTGGATTACAGCTGTACTTCCAACAGTTATTATATGTGTGATGGTTTTCTGTCTAATTCTATGGAAATGGAAGAAGAAGAAGCGGCCTCGCAACTCTTATAAATGTGGAACCAACACAATGGAGAGGGAAGAGAGTGAA | 215 |

Sequence Listing Table

| AVI Ref. No. | Name | Sequence (5'→ 3') | SEQ ID NO. |
|---|---|---|---|
| | | CAGACCAAGAAAAGAGAAAAAATCCATA<br>TACCTGAAAGATCTGATGAAGCCCAGCG<br>TGTTTTTAAAAGTTCGAAGACATCTTCA<br>TGCGACAAAAGTGATACATGTTTTTAAT<br>TAAAGAGTAAAGCCCATACAAGTATTCA<br>TTTTTTCTACCCTTTCCTTTGTAAGTTC<br>CTGGGCAACCTTTTTGATTTCTTCCAGA<br>AGGCAAAAAGACATTACCATGAGTAATA<br>AGGGGGCTCCAGGACTCCCTCTAAGTGG<br>AATAGCCTCCCTGTAACTCCAGCTCTGC<br>TCCGTATGCCAAGAGGAGACTTTAATTC<br>TCTTACTGCTTCTTTTCACTTCAGAGCA<br>CACTTATGGGCCAAGCCCAGCTTAATGG<br>CTCATGACCTGGAAATAAAATTTAGGAC<br>CAATACCTCCTCCAGATCAGATTCTTCT<br>CTTAATTTCATAGATTGTGTTTTTTTTT<br>AAATAGACCTCTCAATTTCTGGAAAACT<br>GCCTTTTATCTGCCCAGAATTCTAAGCT<br>GGTGCCCCACTGAATCTTGTGTACCTGT<br>GACTAAACAACTACCTCCTCAGTCTGGG<br>TGGGACTTATGTATTTATGACCTTATAG<br>TGTTAATATCTTGAAACATAGAGATCTA<br>TGTACTGTAATAGTGTGATTACTATGCT<br>CTAGAGAAAAGTCTACCCCTGCTAAGGA<br>GTTCTCATCCCTCTGTCAGGGTCAGTAA<br>GGAAAACGGTGGCCTAGGGTACAGGCAA<br>CAATGAGCAGACCAACCTAAATTTGGGG<br>AAATTAGGAGAGGCAGAGATAGAACCTG<br>GAGCCACTTCTATCTGGGCTGTTGCTAA<br>TATTGAGGAGGCTTGCCCCACCCAACAA<br>GCCATAGTGGAGAGAACTGAATAAACAG<br>GAAAATGCCAGAGCTTGTGAACCCTGTT<br>TCTCTTGAAGAACTGACTAGTGAGATGG<br>CCTGGGGAAGCTGTGAAAGAACCAAAAG<br>AGATCACAATACTCAAAAGAGAGAGAGA<br>GAGAAAAAAGAGAGATCTTGATCCACAG<br>AAATACATGAAATGTCTGGTCTGTCCAC<br>CCCATCAACAAGTCTTGAAACAAGCAAC<br>AGATGGATAGTCTGTCCAAATGGACATA<br>AGACAGACAGCAGTTTCCCTGGTGGTCA<br>GGGAGGGGTTTTGGTGATACCCAAGTTA<br>TTGGGATGTCATCTTCCTGGAAGCAGAG<br>CTGGGGAGGGAGAGCCATCACCTTGATA<br>ATGGGATGAATGGAAGGAGGCTTAGGAC<br>TTTCCACTCCTGGCTGAGAGAGGAAGAG<br>CTGCAACGGAATTAGGAAGACCAAGACA<br>CAGATCACCCGGGGCTTACTTAGCCTAC<br>AGATGTCCTACGGGAACGTGGGCTGGCC<br>CAGCATAGGGCTAGCAAATTTGAGTTGG<br>ATGATTGTTTTGCTCAAGGCAACCAGA<br>GGAAACTTGCATACAGAGACAGATATAC<br>TGGGAGAAATGACTTTGAAAACCTGGCT<br>CTAAGGTGGGATCACTAAGGGATGGGC<br>AGTCTCTGCCCAAACATAAAGAGAACTC<br>TGGGGAGCCTGAGCCACAAAAATGTTCC<br>TTTATTTTATGTAAACCCTCAAGGGTTA<br>TAGACTGCCATGCTAGACAAGCTTGTCC<br>ATGTAATATTCCCATGTTTTTACCCTGC<br>CCCTGCCTTGATTAGACTCCTAGCACCT<br>GGCTAGTTTCTAACATGTTTTGTGCAGC<br>ACAGTTTTAATAAATGCTTGTTACATT<br>C | |
| CD86 AUG | Human CD86 AUG target | CATTTGTGACAGCACTATGGGACTGAGT<br>AACATTCTCTTTGTGATG | 216 |
| Ex6sa | huCD86 Ex6 target | AGCTTGAGGACCCTCAGCCTC | 217 |
| Ex6sd | huCD86 Ex6 target | GCCTCGCAACTCTTATAAATGTG | 218 |
| Ex7sa | huCD86 Ex7 target | GAACCAACACAATGGAGAGGGA | 219 |
| Ex7sd | huCD86 Ex7 target | GAGTGAACAGACCAAGAAAAG | 220 |

-continued

Sequence Listing Table

| AVI Ref. No. | Name | Sequence (5'→ 3') | SEQ ID NO. |
|---|---|---|---|
| 8071 | | | |
| PB1-AUG | FluA PB1-AUG target | AGCGAAAGCAGGCAAACCAUUUGAAUGG AUGUCAAUCCGACCUUACUUUU | 221 |
| NP-v3' | FluA NP-3'term target | AGTGATTATCTACCCTGCTTTTGCT | 222 |
| AVI-4164 | NP-3'-Term | AGCAAAAGCAGGGTAGATAATC | 223 |
| AVI-4235 | PB1-AUG | GACATCCATTCAAATGGTTTG | 224 |
| 8073 | | | |
| Myostatin mRNA | Human Myostatin mRNA | AGATTCACTGGTGTGGCAAGTTGTCTCT CAGACTGTACATGCATTAAAATTTTGCT TGGCATTACTCAAAAGCAAAGAAAAGT AAAAGGAAGAAACAAGAACAAGAAAAAA GATTATATTGATTTTAAAATCATGCAAA AACTGCAACTCTGTGTTTATATTTACCT GTTTATGCTGATTGTTGCTGGTCCAGTG GATCTAAATGAGAACAGTGAGCAAAAAG AAAATGTGGAAAAAGAGGGGCTGTGTAA TGCATGTACTTGGAGACAAAACACTAAA TCTTCAAGAATAGAAGCCATTAAGATAC AAATCCTCAGTAAACTTCGTCTGGAAAC AGCTCCTAACATCAGCAAAGATGTTATA AGACAACTTTTACCCAAAGCTCCTCCAC TCCGGGAACTGATTGATCAGTATGATGT CCAGAGGGATGACAGCAGCGATGGCTCT TTGGAAGATGACGATTATCACGCTACAA CGGAAACAATCATTACCATGCCTACAGA GTCTGATTTTCTAATGCAAGTGGATGGA AAACCCAAATGTTGCTTCTTTAAATTTA GCTCTAAAATACAATACAATAAAGTAGT AAAGGCCCAACTATGGATATATTTGAGA CCCGTCGAGACTCCTACAACAGTGTTTG TGCAAATCCTGAGACTCATCAAACCTAT GAAAGACGGTACAAGGTATACTGGAATC CGATCTCTGAAACTTGACATGAACCCAG GCACTGGTATTTGGCAGAGCATTGATGT GAAGACAGTGTTGCAAAATTGGCTCAAA CAACCTGAATCCAACTTAGGCATTGAAA TAAAAGCTTTAGATGAGAATGGTCATGA TCTTGCTGTAACCTTCCCAGGACCAGGA GAAGATGGGCTGAATCCGTTTTTAGAGG TCAAGGTAACAGACACACCAAAAAGATC CAGAAGGGATTTTGGTCTTGACTGTGAT GAGCACTCAACAGAATCACGATGCTGTC GTTACCCTCTAACTGTGGATTTTGAAGC TTTTGGATGGGATTGGATTATCGCTCCT AAAAGATATAAGGCCAATTACTGCTCTG GAGAGTGTGAATTTGTATTTTTACAAAA ATATCCTCATACTCATCTGGTACACCAA GCAAACCCCAGAGGTTCAGCAGGCCCTT GCTGTACTCCCACAAAGATGTCTCCAAT TAATATGCTATATTTTAATGGCAAAGAA CAAATAATATATGGGAAAATTCCAGCGA TGGTAGTAGACCGCTGTGGGTGCTCATG AGATTTATATTAAGCGTTCATAACTTCC TAAAACATGGAAGGTTTTCCCCTCAACA ATTTTGAAGCTGTGAAATTAAGTACCAC AGGCTATAGGCCTAGAGTATGCTACAGT CACTTAAGCATAAGCTACAGTATGTAAA CTAAAAGGGGAATATATGCAATGGTTG GCATTTAACCATCCAAACAAATCATACA AGAAAGTTTTATGATTTCCAGAGTTTTT GAGCTAGAAGGAGATCAAATTACATTTA TGTTCCTATATATTACAACATCGGCGAG GAAATGAAAGCGATTCTCCTTGAGTTCT GATGAATTAAAGGAGTATGCTTTAAAGT CTATTTCTTTAAAGTTTTGTTTAATATT TACAGAAAAATCCACATACAGTATTGGT AAAATGCAGGATTGTTATATACCATCAT TCGAATCATCCTTAAACACTTGAATTTA TATTGTATGGTAGTATACTTGGTAAGAT | 225 |

Sequence Listing Table

| AVI Ref. No. | Name | Sequence (5'→ 3') | SEQ ID NO. |
|---|---|---|---|
| | | AAAATTCCACAAAAATAGGGATGGTGCA<br>GCATATGCAATTTCCATTCCTATTATAA<br>TTGACACAGTACATTAACAATCCATGCC<br>AACGGTGCTAATACGATAGGCTGAATGT<br>CTGAGGCTACCAGGTTTATCACATAAAA<br>AACATTCAGTAAATAGTAAGTTTCTCT<br>TTTCTTCAGGGGCATTTTCCTACACCTC<br>CAAATGAGGAATGGATTTTCTTTAATGT<br>AAGAAGAATCATTTTTCTAGAGGTTGGC<br>TTTCAATTCTGTAGCATACTTGGAGAAA<br>CTGCATTATCTTAAAAGGCAGTCAAATG<br>GTGTTTGTTTTTATCAAAATGTCAAAAT<br>AACATACTTGGAGAAGTATGTAATTTTG<br>TCTTTGGAAAATTACAACACTGCCTTTG<br>CAACACTGCAGTTTTTATGGTAAAATAA<br>TAGAAATGATCGACTCTATCAATATTGT<br>ATAAAAAGACTGAAACAATGCATTTATA<br>TAATATGTATACAATATTGTTTTGTAAA<br>TAAGTGTCTCCTTTTTTATTTACTTTGG<br>TATATTTTTACACTAAGGACATTTCAAA<br>TTAAGTACTAAGGCACAAAGACATGTCA<br>TGCATCACAGAAAAGCAACTACTTATAT<br>TTCAGAGCAAATTAGCAGATTAAATAGT<br>GGTCTTAAAACTCCATATGTTAATGATT<br>AGATGGTTATATTACAATCATTTTATAT<br>TTTTTTACATGATTAACATTCACTTATG<br>GATTCATGATGGCTGTATAAAGTGAATT<br>TGAAATTTCAATGGTTTACTGTCATTGT<br>GTTTAAATCTCAACGTTCCATTATTTTA<br>ATACTTGCAAAAACATTACTAAGTATAC<br>CAAAATAATTGACTCTATTATCTGAAAT<br>GAAGAATAAACTGATGCTATCTCAACAA<br>TAACTGTTACTTTTATTTTATAATTTGA<br>TAATGAATATATTTCTGCATTTATTTAC<br>TTCTGTTTTGTAAATTGGGATTTTGTTA<br>ATCAAATTTATTGTACTATGACTAAATG<br>AAATTATTTCTTACATCTAATTTGTAGA<br>AACAGTATAAGTTTATATTAAAGTGTTTT<br>CACATTTTTTTGAAAGACAAAAA | |
| MSTN-SD1 trgt | Human Myostatin SD1 target | ACAATCATTACCATGCCTACAGAGT/GT<br>AAGTAGTCCTATTAGTGTATATC | 226 |
| MSTN-SD2 trgt | Human Myostatin SD2 target | CTTTTCTTTTCTTATTCATTTATAG/CT<br>GATTTTCTAATGCAAGTGGATGG | 227 |
| MSTN-SA2 trgt | Human Myostatin SA2 target | CCCAGGACCAGGAGAAGATGGGCTG/GT<br>AAGTGATAACTGAAAATAACATT | 228 |
| MSTN-SA3 trgt | Human Myostatin SA3 | TGATTGTTCTTTCCTTTTCAAACAG/AA<br>TCCGTTTTTAGAGGTCAAGGTAA | 229 |
| MSTN-SD1 | Human Myostatin SD1 | ACTCTGTAGGCATGGTAATG | 230 |
| MSTN-SD2 | Human Myostatin SD2 | CAGCCCATCTTCTCCTGG | 231 |
| MSTN-SA2 | Human Myostatin SA2 | CACTTGCATTAGAAAATCAG | 232 |
| MSTN-SA3 | Human Myostatin SA3 | CTTGACCTCTAAAAACGGATT | 233 |
| 8077 & 8078 | | | |
| 5'-32 | 5'32 IRES target | GTTGGGRTTRGCCGCATTCAGGGGCCGG<br>AGGA | 234 |
| PV444 | 5'-32 IRES PMO | CCGCATTCAGGGGCCGGAGG | 235 |
| PV449 | 5'-32 IRES PMO | GGATTAGCCGCATTCAGGGCC | 236 |
| PV454 | 5'-32 IRES PMO | GTTGGGATTAGCCGCATTCAG | 237 |

-continued

Sequence Listing Table

| AVI Ref. No. | Name | Sequence (5'→ 3') | SEQ ID NO. |
|---|---|---|---|
| 3'-37 | 3'37 IRES target | AAAANGAAACACGGACACCCAAAGTAGT CGGTTCCGC | 238 |
| PV533 | 5'37 IRES PMO | CACCCAAAGTAGTCGGTTCC | 239 |
| PV539 | 5'37 IRES PMO | CACGGACACCCAAAGTAGTC | 240 |
| PV544 | 5'37 IRES PMO | GGAAACACGGACACCCAAAG | 241 |
| PV548 | 5'37 IRES PMO | AAAAGGAAACACGGACACCC | 242 |
| CVB3-548 | 5'37 IRES PMO | ATGAAACACGGACACCCAAAG | 243 |
| EnteroX | 5'37 IRES PMO | GAAACACGGACACCCAAAGTAG | 244 |
| HRV14-IRES | 5'37 IRES PMO | GAGAAACACGGACACCCAAAGTAG | 245 |
| 8079 | | | |
| huCTLA-4SA2sj | Human CTLA-4 splice junction target region | GCATGAGTTCACTGAGTTCCCTTTGGCT TTTCCATGCTAGCAATGCACGTGGCCCA GCCTGCTGTGGTACTGGCCAGCAGCCGA GGCATCGCCAGCTTTG | 246 |
| TGF-β [8039] | | | |
| | | GAGGGCGGCA TGGGGAGGC | 247 |
| | | GACCGATGGC AGCCCCCGTC G | 248 |
| | | GCAGCAGTTC TTCTCCGTGG | 249 |
| 8072 | | | |
| EBOV VP35-AUG | VP35-AUG target | AAUGAUGAAGAUUAAAACCUUCAUCAUC CUUACGUCAAUUGAAUUCUCUAGCACUC GAAGCUUAUUGUCUUCAAUGUAAAAGAA AAGCUGGUCUAACAAGAUGACAACUAGA ACAAAGGGCAGGG | 250 |
| EBOV VP24-AUG | VP24-AUG target | CGUUCCAACAAUCGAGCGCAAGGUUUCA AGGUUGAACUGAGAGUGUCUAGACAACA AAAUAUUGAUACUCCAGACACCAAGCAA GACCUGAGAAAAACCAUGGCUAAAGCU ACGGGACGAUACA | 251 |
| EBOV L-AUG | L-AUG target | GUAGAUUAAGAAAAAGCCUGAGGAAGA UUAAGAAAACUGCUUAUUGGGUCUUUC CGUGUUUUAGAUGAAGCAGUUGAAAUUC UUCCUCUUGAUAUUAAAUGGCUACACAA CAUACCCAAUAC | 252 |
| MARV VP35-AUG | VP35-AUG target | CUAAAAAUCGAAGAAUAUUAAAGGUUUU CUUUAAUAUUCAGAAAAGGUUUUUUAUU CUCUUCUUUCUUUUUGCAAACAUAUUGA AAUAAUAAUUUCACAAUGUGGGACUCA UCAUAUAUGCAAC | 253 |
| MARV VP24-AUG | VP24-AUG target | UUCAUUCAAACACCCCAAAUUUUCAAUC AUACACAUAAUAACCAUUUUAGUAGCGU UACCUUUCAAUACAAUCUAGGUGAUUGU GAAAAGACUUCCAAACAUGGCAGAAUUA UCAACGCGUUACA | 254 |
| MARV L-AUG | L-AUG target | UCAUUCUCUUCGAUACACGUUAUAUCUU UAGCAAAGUAAUGAAAAUAGCCUUGUCA UGUUAGACGCCAGUUAUCCAUCUUAAGU GAAUCCUUUCUUCAAUAUGCAGCAUCCA ACUCAAUAUCCUG | 255 |
| VP35-AUG | MARV 2932-2952 | GTCCCACATTGTGAAAATTAT | 256 |
| VP35 + 7-AUG | MARV 2950-2971 | CTTGTTGCATATATGATGAGTC | 257 |
| VP24 + 5-AUG | MARV 10209-10231 | GTTGTAACGCGTTGATAATTCTG | 258 |

-continued

Sequence Listing Table

| AVI Ref. No. | Name | Sequence (5'→ 3') | SEQ ID NO. |
|---|---|---|---|
| L-AUG | 11467-11485 | GCTGCATATTGAAGAAAGG | 259 |
| L + 7-AUG | 11485-11506 | CATCAGGATATTGAGTTGGATG | 260 |
| Arenavirus [8080] | | | |
| Arenavirus vRNA | | CGC ACM GDG GAT CCT AGG C | 261 |
| CL-trm | NC_005080 | CGC CTA GGA TCC CCG GTG CG | 262 |
| LS-trm | NC_005080 | CGC CTA GGA TCC CCG GTG CGC | 263 |
| SS-trm | NC_005081 | GCC TAG GAT CCA CTG TGC GC | 264 |
| PanCL | N/A | GCC TAG GAT CCI CIG TGC G | 265 |
| PanLS | N/A | CGC CTA GGA TCC ICI GTG CG | 266 |
| 8059: Flavivirus | 5'CS and 3'CS | | |
| St. Louis encephalitis Murray Valley encephalitis; West Nile; Kunjin | | GUCAAUAUGCUAAACGCGG | 267 |
| Japanese encephalitis | | AUCAAUAUGCUGAAACGCGG | 268 |
| Yellow fever | | GUCAAUAUGGUACGACGAGG | 269 |
| Dengue Type 1 Dengue Type 2 Dengue Type 4 | | CUUUCAAUAUGCUGAAACGCG | 270 |
| Dengue Type 3 | | CUAUCAAUAUGCUGAAACGCG | 271 |
| Tick borne encephalitis | | CAGCUUAGGAGAACAAGAGCUG | 272 |
| West Nile | | GGCUGUCAAUAUGCUAAAAC | 273 |
| St. Louis encephalitis; Japanese encephalitis; Murray Valley encephalitis; West Nile; Kunjin | | AACAGCAUAUUGACACCUGGGA | 274 |
| Yellow fever | | UGGGACCAUAUUGACGCCAGGGA | 275 |
| Dengue Type 1 Dengue Type 2 Dengue Type 3 Dengue Type 4 | | AAACAGCAUAUUGACGCUGGGA | 276 |
| Tick borne encephalitis | | CGGUUCUUGUUCUCCCUGAGCC | 277 |
| Peptide Transporters | | | |
| | (RRAhx)₄B | RRAhxRRAhxRRAhxRRAhxB | 278 |
| | (RAhxR)₄AhxB | RAhxRRAhxRRAhxRRAhxRAhxB | 279 |
| | (AhxRR)₄AhxB | AhxRRAhxRRAhxRRAhxRRAhxB | 280 |
| | (RAhx)₆B | RAhxRAhxRAhxRAhxRAhxRAhxB | 281 |

Sequence Listing Table

| AVI Ref. No. | Name | Sequence (5'→ 3') | SEQ ID NO. |
|---|---|---|---|
| | (RAhx)$_8$B | RAhxRAhxRAhxRAhxRAhxRAhxRAhxRAhxB | 282 |
| | (RAhxR)$_3$AhxB | RAhxRRAhxRRAhxR AhxB | 283 |
| | (RAhxRRBR)$_2$AhxB | RAhxRRBRRAhxRRBRAhxB | 284 |
| | ((RB)$_3$RAhx)$_2$XB | RBRBRBRAhxRBRBRBRAhxB | 285 |
| Splice Correction Assay Sequence | 705 | CCTCTTACCTCAGTTACA | 286 |
| 06-0648 | EBOV-L(+5) | +TGGGT + ATG + TTGTGT + AGCC + AT | 287 |
| 06-0649 | EBOV-VP35'(+5) | CC + TGCCC + TTTGT + TCT + AGT + TG | 288 |
| 06-0647 | EBOV-VP24(+5) | G

```
<213> ORGANISM: Artificial Sequence
<220> FEATURE:
<223> OTHER INFORMATION: Synthetic oligomer

<400> SEQUENCE: 4
cctgcccttt gttctagttg                                                      20

<210> SEQ ID NO 5
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 5
gccatggttt tttctcagg                                                       19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 6
gccatggttt tttctcagg                                                       19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 7
gccatggttt tttctcagg                                                       19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 8
gccatggttt tttctcagg                                                       19

<210> SEQ ID NO 9
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 9
ttcaaccttg aaaccttgcg                                                      20

<210> SEQ ID NO 10
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 10
gccatggttt tttctcagg                                                       19
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 11
tgggtatgtt gtgtagccat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 12
tgggtatgtt gtgtagccat                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 13
tgggtatgtt gtgtagccat                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 14
tgggtatgtt gtgtagccat                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 15
ttcaaccttg aaaccttgcg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 16
agtctcgact tgctacctca                                               20

<210> SEQ ID NO 17
<211> LENGTH: 22
<212> TYPE: DNA
<213> ORGANISM: Artificial Sequence
<220> FEATURE:
<223> OTHER INFORMATION: Synthetic oligomer
```

-continued

```
<400> SEQUENCE: 17
tgtgcttact gttatactac tc                                              22

<210> SEQ ID NO 18
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 18
gtgctcatgg tgcacggtc                                                  19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 19
gtgctcatgg tgcacggtc                                                  19

<210> SEQ ID NO 20
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 20
gtgctcatgg tgcacggtc                                                  19

<210> SEQ ID NO 21
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 21
gtgctcatgg tgcacggtc                                                  19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 22
gtgctcatgg tgcacggtc                                                  19

<210> SEQ ID NO 23
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 23
gtgctcatgg tgcacggtc                                                  19

<210> SEQ ID NO 24
<211> LENGTH: 19
<212> TYPE: DNA
```

<213> ORGANISM: Artificial Sequence
<220> FEATURE:
<223> OTHER INFORMATION: Synthetic oligomer

<400> SEQUENCE: 24
gtgctcatgg tgcacggtc                                                      19

<210> SEQ ID NO 25
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 25
gtgctcatgg tgcacggtc                                                      19

<210> SEQ ID NO 26
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 26
gtgctcatgg tgcacggtc                                                      19

<210> SEQ ID NO 27
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 27
gtgctcatgg tgcacggtc                                                      19

<210> SEQ ID NO 28
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 28
gtgctcatgg tgcacggtc                                                      19

<210> SEQ ID NO 29
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 29
gtgctcatgg tgcacggtc                                                      19

<210> SEQ ID NO 30
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 30
gtgctcatgg tgcacggtc                                                      19

```
<210> SEQ ID NO 31
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 31
gtgctcatgg tgcacggtc                                                    19

<210> SEQ ID NO 32
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 32
gtgctcatgg tgcacggtc                                                    19

<210> SEQ ID NO 33
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 33
gtgctcatgg tgcacggtc                                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 34
gtgctcatgg tgcacggtc                                                    19

<210> SEQ ID NO 35
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 35
gagctgaaag caggtccatc cc                                                22

<210> SEQ ID NO 36
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 36
gagctgaaag caggtccatc cc                                                22

<210> SEQ ID NO 37
<211> LENGTH: 22
<212> TYPE: DNA
<213> ORGANISM: Artificial Sequence
<220> FEATURE:
<223> OTHER INFORMATION: Synthetic oligomer
```

```
<400> SEQUENCE: 37
gagctgaaag caggtccatc cc                                             22

<210> SEQ ID NO 38
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 38
gagctgaaag caggtccatc cc                                             22

<210> SEQ ID NO 39
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 39
gagctgaaag caggtccatc cc                                             22

<210> SEQ ID NO 40
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 40
gagctgaaag caggtccatc cc                                             22

<210> SEQ ID NO 41
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 41
gagctgaaag caggtccatc cc                                             22

<210> SEQ ID NO 42
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 42
gagctgaaag caggtccatc cc                                             22

<210> SEQ ID NO 43
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 43
acgttgaggg gcatcgtcgc                                                20

<210> SEQ ID NO 44
<211> LENGTH: 22
<212> TYPE: DNA
```

```
<213> ORGANISM: Artificial Sequence
<220> FEATURE:
<223> OTHER INFORMATION: Synthetic oligomer

<400> SEQUENCE: 44
gcaggctggg ccacgtgcat tg                                           22

<210> SEQ ID NO 45
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 45
cacgtgcatt gctagcatgg                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 46
ctagcatgga aaagccaaag                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 47
ggaactcagt gaactcatgc                                              20

<210> SEQ ID NO 48
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 48
gttactcagt cccatagtgc tg                                           22

<210> SEQ ID NO 49
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 49
ccatagtgct gtcacaaatg                                              20

<210> SEQ ID NO 50
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 50
gaatgttact cagtcccata g                                            21
```

```
<210> SEQ ID NO 51
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 51
gaggctgagg gtcctcaagc t                                           21

<210> SEQ ID NO 52
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 52
cacatttata agagttgcga ggc                                         23

<210> SEQ ID NO 53
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 53
tccctctcca ttgtgttggt tc                                          22

<210> SEQ ID NO 54
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 54
cttttcttgg tctgttcact c                                           21

<210> SEQ ID NO 55
<211> LENGTH: 32
<212> TYPE: DNA
<213> ORGANISM: Picornavirus

<400> SEQUENCE: 55
ryggraccra ctactttggg tgtccgtgtt tc                               32

<210> SEQ ID NO 56
<211> LENGTH: 32
<212> TYPE: DNA
<213> ORGANISM: Picornavirus

<400> SEQUENCE: 56
tcctccggcc cctgaatgyg gctaaycyya ac                               32

<210> SEQ ID NO 57
<211> LENGTH: 8
<212> TYPE: DNA
<213> ORGANISM: Flavivirus

<400> SEQUENCE: 57 catattga                                                          8

<210> SEQ ID NO 58
```

```
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 58
tcccaggtgt caatatgctg tt                                              22

<210> SEQ ID NO 59
<211> LENGTH: 125
<212> TYPE: DNA
<213> ORGANISM: Homo sapiens

<400> SEQUENCE: 59
cgccgctgcc aggacccgct tctctgaaag gctctccttg cagctgctta gacgctggat     60 tttttcggg tagtggaaaa ccagcagcct cccgcgacga tgcccctcaa cgttagcttc     120
accaa                                                                 125

<210> SEQ ID NO 60
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 60
ggaggctgct ggttttccac                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 61
ggcatcgtcg cgggaggctc                                                 20

<210> SEQ ID NO 62
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 62
cctgagcacc cattatgata c                                               21

<210> SEQ ID NO 63
<211> LENGTH: 24
<212> TYPE: DNA
<213> ORGANISM: Artificial Sequence
<220> FEATURE:
<223> OTHER INFORMATION: Synthetic oligomer

<400> SEQUENCE: 63
ccttgtctag acatgttcat tatt                                            24

<210> SEQ ID NO 64
<211> LENGTH: 20
<212> TYPE: DNA
<213> ORGANISM: Artificial Sequence
<220> FEATURE:
<223> OTHER INFORMATION: Synthetic oligomer
```

```
<400> SEQUENCE: 64
ttgagcgccc atgataacaa                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 65
ttgagcgccc atgataacaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 66
ctgggcaccc atgatgccaa                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 67
gagccatagc tcaaattctc                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 68
tagctcaaat tctcatttac                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 69
gagcgtttga gccatagctc                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 70
gacggcaatt agccatcacg                                              20

<210> SEQ ID NO 71
<211> LENGTH: 19
<212> TYPE: DNA
```

<213> ORGANISM: Artificial Sequence
<220> FEATURE:
<223> OTHER INFORMATION: Synthetic oligomer

<400> SEQUENCE: 71
cgacgccatc atcattcac                                                      19

<210> SEQ ID NO 72
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 72
cagagtttga gacattgtct c                                                   21

<210> SEQ ID NO 73
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 73
ccttaataaa ctgatgggcc tcc                                                 23

<210> SEQ ID NO 74
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 74
ctgatgggcc tccatggc                                                       18

<210> SEQ ID NO 75
<211> LENGTH: 125
<212> TYPE: DNA
<213> ORGANISM: Hepatitis C virus

<400> SEQUENCE: 75
aagactgcta gccgagtagt gttgggtcgc gaaaggcctt gtggtactgc ctgatagggt         60
gcttgcgagt gccccgggag gtctcgtaga ccgtgcacca tgagcacgaa tcctaaacct        120
caaag                                                                   125

<210> SEQ ID NO 76
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 76
ggcctttcgc gacccaacac                                                     20

<210> SEQ ID NO 77
<211> LENGTH: 40
<212> TYPE: DNA
<213> ORGANISM: St. Louis Encephalitis virus

<400> SEQUENCE: 77
agatgttcgc gtcggtgagc ggagaggaaa cagatttcct                               40

```
<210> SEQ ID NO 78
<211> LENGTH: 40
<212> TYPE: DNA
<213> ORGANISM: Japanese Encephalitis virus

<400> SEQUENCE: 78
agaagtttat ctgtgtgaac ttcttggctt agtatcgttg                              40

<210> SEQ ID NO 79
<211> LENGTH: 40
<212> TYPE: DNA
<213> ORGANISM: Murray Valley Encephalitis virus

<400> SEQUENCE: 79
agacgttcat ctgcgtgagc ttccgatctc agtattgttt                              40

<210> SEQ ID NO 80
<211> LENGTH: 40
<212> TYPE: DNA
<213> ORGANISM: West Nile Virus

<400> SEQUENCE: 80
agtagttcgc ctgtgtgagc tgacaaactt agtagtgttt                              40

<210> SEQ ID NO 81
<211> LENGTH: 40
<212> TYPE: DNA
<213> ORGANISM: Yellow Fever virus

<400> SEQUENCE: 81
agtaaatcct gtgtgctaat tgaggtgcat tggtctgcaa                              40

<210> SEQ ID NO 82
<211> LENGTH: 40
<212> TYPE: DNA
<213> ORGANISM: Dengue Type 2

<400> SEQUENCE: 82
agttgttagt ctacgtggac cgacaaagac agattctttg                              40

<210> SEQ ID NO 83
<211> LENGTH: 40
<212> TYPE: DNA
<213> ORGANISM: Hepatitis C virus

<400> SEQUENCE: 83
gccagccccc tgatgggggc gacactccac catgaatcac                              40

<210> SEQ ID NO 84
<211> LENGTH: 40
<212> TYPE: DNA
<213> ORGANISM: Tick Bone Encephalitis virus

<400> SEQUENCE: 84
agattttctt gcacgtgcat gcgtttgctt cggacagcat                              40

<210> SEQ ID NO 85
<211> LENGTH: 40
<212> TYPE: DNA
<213> ORGANISM: Omsk Hemorrhagic Fever virus

<400> SEQUENCE: 85
agattttctt gcacgtgcgt gcgcttgctt cagacagcaa                              40
```

<210> SEQ ID NO 86
<211> LENGTH: 40
<212> TYPE: DNA
<213> ORGANISM: Powassan virus

<400> SEQUENCE: 86
agattttctt gcacgtgtgt gcgggtgctt tagtcagtgt                                40

<210> SEQ ID NO 87
<211> LENGTH: 18
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)...(18)
<223> OTHER INFORMATION: n = A,T,C or G

<400> SEQUENCE: 87
accgacgcga acatcnnc                                                       18

<210> SEQ ID NO 88
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 88
tcctctccgc tcaccgacgc                                                     20

<210> SEQ ID NO 89
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 89
tcacacagat aaacttct                                                       18

<210> SEQ ID NO 90
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 90
aagccaagaa gttcacacag                                                     20

<210> SEQ ID NO 91
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 91
tcacgcagat gaacgtct                                                       18

<210> SEQ ID NO 92
<211> LENGTH: 20
<212> TYPE: DNA
<213> ORGANISM: Artificial Sequence
<220> FEATURE:

```
<223> OTHER INFORMATION: Synthetic oligomer

<400> SEQUENCE: 92
gagatcggaa gctcacgcag                                                    20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 93
gctcacacag gcgaactact                                                    20

<210> SEQ ID NO 94
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 94
taagtttgtc agctcacaca g                                                  21

<210> SEQ ID NO 95
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 95
caattagcac acaggattta ct                                                 22

<210> SEQ ID NO 96
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 96
ttgcagacca atgcacctca                                                    20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 97
gtccacgtag actaacaact                                                    20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 98
gtctttgtcg gtccacgtag                                                    20

<210> SEQ ID NO 99
```

```
<211> LENGTH: 17
<212> TYPE: DNA
<213> ORGANISM: Artificial Sequence
<220> FEATURE:
<223> OTHER INFORMATION: Synthetic oligomer

<400> SEQUENCE: 99
cccatcaggg ggctggc                                                        17

<210> SEQ ID NO 100
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 100
tggagtgtcg cccccatcag                                                     20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 101
atgcacgtgc aagaaaatct                                                     20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 102
atgctgtccg aagcaaacgc                                                     20

<210> SEQ ID NO 103
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 103
cacgcacgtg caagaaaatc t                                                   21

<210> SEQ ID NO 104
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 104
tgaagcaagc gcacgcacgt                                                     20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 105
```

```
acacacgtgc aagaaaatct                                                     20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 106
acactgacta aagcacccgc                                                     20

<210> SEQ ID NO 107
<211> LENGTH: 40
<212> TYPE: DNA
<213> ORGANISM: Poliovirus

<400> SEQUENCE: 107
ttaaaacagc tctggggttg tacccacccc agaggcccac                               40

<210> SEQ ID NO 108
<211> LENGTH: 40
<212> TYPE: DNA
<213> ORGANISM: Human enterovirus A

<400> SEQUENCE: 108
ttaaaacagc ctgtgggttg tacccaccca cagggcccac                               40

<210> SEQ ID NO 109
<211> LENGTH: 40
<212> TYPE: DNA
<213> ORGANISM: Human enterovirus B

<400> SEQUENCE: 109
ttaaaacagc ctgtgggttg ttcccaccca caggcccatt                               40

<210> SEQ ID NO 110
<211> LENGTH: 40
<212> TYPE: DNA
<213> ORGANISM: Human enterovirus C

<400> SEQUENCE: 110
ttaaaacagc tctggggttg ctcccacccc agaggcccac                               40

<210> SEQ ID NO 111
<211> LENGTH: 40
<212> TYPE: DNA
<213> ORGANISM: Human enterovirus D

<400> SEQUENCE: 111
ttaaaacagc tctggggttg ctcccacccc agaggcccac                               40

<210> SEQ ID NO 112
<211> LENGTH: 40
<212> TYPE: DNA
<213> ORGANISM: Human enterovirus E

<400> SEQUENCE: 112
gagtgttccc acccaacagg cccactgggt gttgtactct                               40

<210> SEQ ID NO 113
<211> LENGTH: 40
<212> TYPE: DNA
<213> ORGANISM: Bovine enterovirus
```

```
<400> SEQUENCE: 113
ttaaaacagc ctgggggttg tacccacccc tggggcccac                              40

<210> SEQ ID NO 114
<211> LENGTH: 40
<212> TYPE: DNA
<213> ORGANISM: Human rhinovirus 89

<400> SEQUENCE: 114
ttaaaactgg gagtgggttg ttcccactca ctccacccat                              40

<210> SEQ ID NO 115
<211> LENGTH: 40
<212> TYPE: DNA
<213> ORGANISM: Human rhinovirus B

<400> SEQUENCE: 115
ttaaaacagc ggatgggtat cccaccattc gacccattgg                              40

<210> SEQ ID NO 116
<211> LENGTH: 40
<212> TYPE: DNA
<213> ORGANISM: Foot-and-mouth disease virus

<400> SEQUENCE: 116
ttgaaagggg gcgctagggt ttcaccccta gcatgccaac                              40

<210> SEQ ID NO 117
<211> LENGTH: 40
<212> TYPE: DNA
<213> ORGANISM: Hepatitis A

<400> SEQUENCE: 117
ttcaagaggg gtctccggga atttccggag tccctcttgg                              40

<210> SEQ ID NO 118
<211> LENGTH: 24
<212> TYPE: DNA
<213> ORGANISM: Artificial Sequence
<220> FEATURE:
<223> OTHER INFORMATION: Synthetic oligomer

<400> SEQUENCE: 118
ggtacaaccc cagagctgtt ttaa                                               24

<210> SEQ ID NO 119
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 119
gtgggcctct ggggtgggta                                                    20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 120
caacccacag gctgttttaa                                                    20
```

```
<210> SEQ ID NO 121
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 121
gtgggcsctg tgggtgggta                                           20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 122
caacccacag gctgttttaa                                           20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 123
aatgggcctg tgggtgggaa                                           20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 124
caaccccaga gctgttttaa                                           20

<210> SEQ ID NO 125
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 125
gtgggcctct ggggtgggag                                           20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 126
caaccccaga gctgttttaa                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic oligomer
```

<400> SEQUENCE: 127
gtgggcctct ggggtgggaa                                         20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 128
cctgttgggt gggaacactc                                         20

<210> SEQ ID NO 129
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 129
agagtacaac acccagtggg                                         20

<210> SEQ ID NO 130
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 130 caaccccag gctgttttaa                                          20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 131
gtgggcccca ggggtgggta                                         20

<210> SEQ ID NO 132
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 132
caacccactc ccagttttaa                                         20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 133
atgggtggag tgagtgggaa                                         20

<210> SEQ ID NO 134
<211> LENGTH: 20
<212> TYPE: DNA

```
<213> ORGANISM: Artificial Sequence
<220> FEATURE:
<223> OTHER INFORMATION: Synthetic oligomer

<400> SEQUENCE: 134
atacccatcc gctgttttaa                                              20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 135
ccaatgggtc gaatggtggg                                              20

<210> SEQ ID NO 136
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 136
aaccctagcg cccccttca a                                             21

<210> SEQ ID NO 137
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 137
gttggcatgc tagggtgaa                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 138
tcccggagac ccctcttgaa                                              20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 139
ccaagaggga ctccggaaat                                              20

<210> SEQ ID NO 140
<211> LENGTH: 40
<212> TYPE: DNA
<213> ORGANISM: Feline calicivirus

<400> SEQUENCE: 140
gtaaaagaaa tttgagacaa tgtctcaaac tctgagcttc                        40

<210> SEQ ID NO 141
```

-continued

```
<211> LENGTH: 40
<212> TYPE: DNA
<213> ORGANISM: Canine calicivirus

<400> SEQUENCE: 141
gttaatgaga aatggcttct gccatcgctc tctcgagctc                              40

<210> SEQ ID NO 142
<211> LENGTH: 40
<212> TYPE: DNA
<213> ORGANISM: Porcine enteric calicivirus

<400> SEQUENCE: 142
gtgatcgtga tggctaattg ccgtccgttg cctatgggc                               40

<210> SEQ ID NO 143
<211> LENGTH: 40
<212> TYPE: DNA
<213> ORGANISM: Calicivirus strain NB

<400> SEQUENCE: 143
gtgatttaat tatagagaga tagtgacttt cacttttctt                              40

<210> SEQ ID NO 144
<211> LENGTH: 40
<212> TYPE: DNA
<213> ORGANISM: Norwalk virus

<400> SEQUENCE: 144
gtgaatgatg atggcgtcaa aagacgtcgt tcctactgct                              40

<210> SEQ ID NO 145
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 145
ttgtctcaaa tttcttttac                                                    20

<210> SEQ ID NO 146
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 146
gaagctcaga gtttgagaca                                                    20

<210> SEQ ID NO 147
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 147
agaagccatt tctcattaac                                                    20

<210> SEQ ID NO 148
<211> LENGTH: 20
<212> TYPE: DNA
<213> ORGANISM: Artificial Sequence
<220> FEATURE:
```

<223> OTHER INFORMATION: Synthetic oligomer

<400> SEQUENCE: 148
gagctcgaga gagcgatggc                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 149
caattagcca tcacgatcac                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 150
ggcaacggac ggcaattagc                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 151
tctctctata attaaatcac                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 152
aaagtcacta tctctctata                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 153
ttgacgccat catcattcac                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 154
agcagtagga acgacgtctt                                               20

<210> SEQ ID NO 155

```
<211> LENGTH: 40
<212> TYPE: DNA
<213> ORGANISM: Hepatitis E virus

<400> SEQUENCE: 155
gccatggagg cccatcagtt tattaaggct cctggcatca                              40

<210> SEQ ID NO 156
<211> LENGTH: 20
<212> TYPE: DNA
<213> ORGANISM: Hepatitis E virus

<400> SEQUENCE: 156
aactgatggg cctccatggc                                                   20

<210> SEQ ID NO 157
<211> LENGTH: 20
<212> TYPE: DNA
<213> ORGANISM: Hepatitis E virus

<400> SEQUENCE: 157
tgatgccagg agccttaata                                                   20

<210> SEQ ID NO 158
<211> LENGTH: 40
<212> TYPE: DNA
<213> ORGANISM: Rubella virus

<400> SEQUENCE: 158
atggaagcta tcggacctcg cttaggactc ccattcccat                              40

<210> SEQ ID NO 159
<211> LENGTH: 40
<212> TYPE: DNA
<213> ORGANISM: Eastern equine encephalitis

<400> SEQUENCE: 159
atagggtacg gtgtagaggc aaccacccta tttccaccta                              40

<210> SEQ ID NO 160
<211> LENGTH: 40
<212> TYPE: DNA
<213> ORGANISM: Western equine encephalomyelitis

<400> SEQUENCE: 160
accctacaaa ctaatcgatc caatatggaa agaattcacg                              40

<210> SEQ ID NO 161
<211> LENGTH: 40
<212> TYPE: DNA
<213> ORGANISM: Venezuelan equine encephalitis

<400> SEQUENCE: 161
atgggcggcg caagagagaa gcccaaacca attacctacc                              40

<210> SEQ ID NO 162
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 162
cgaggtccga tagcttccat                                                   20
```

-continued

```
<210> SEQ ID NO 163
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 163
atgggaatgg gagtcctaag                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 164
gcctctacac cgtaccctat                                              20

<210> SEQ ID NO 165
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 165
taggtggaaa tagggtggtt                                              20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 166
gatcgattag tttgtagggt                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 167
cgtgaattct ttccatattg                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 168
ttctctcttg cgccgcccat                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 169
```

-continued

```
ggtaggtaat tggtttgggc                                              20

<210> SEQ ID NO 170
<211> LENGTH: 40
<212> TYPE: DNA
<213> ORGANISM: SARS coronavirus

<400> SEQUENCE: 170
atattaggtt tttacctacc caggaaaagc caaccaacct                         40

<210> SEQ ID NO 171
<211> LENGTH: 40
<212> TYPE: DNA
<213> ORGANISM: Porcine epidemic diarrhea virus

<400> SEQUENCE: 171
acttaaaaag attttctatc tacggatagt tagctctttt                         40

<210> SEQ ID NO 172
<211> LENGTH: 40
<212> TYPE: DNA
<213> ORGANISM: Transmissible gastroenteritis

<400> SEQUENCE: 172
acttttaaag taaagtgagt gtagcgtggc tatatctctt                         40

<210> SEQ ID NO 173
<211> LENGTH: 40
<212> TYPE: DNA
<213> ORGANISM: Bovine coronavirus

<400> SEQUENCE: 173
gattgcgagc gatttgcgtg cgtgcatccc gcttcactga                         40

<210> SEQ ID NO 174
<211> LENGTH: 40
<212> TYPE: DNA
<213> ORGANISM: Human corona-virus 229E

<400> SEQUENCE: 174
acttaagtac cttatctatc tacagataga aaagttgctt                         40

<210> SEQ ID NO 175
<211> LENGTH: 40
<212> TYPE: DNA
<213> ORGANISM: Murine Hepatitis

<400> SEQUENCE: 175
tataagagtg attggcgtcc gtacgtaccc tctcaactct                         40

<210> SEQ ID NO 176
<211> LENGTH: 40
<212> TYPE: DNA
<213> ORGANISM: Porcine reproductive and Respiratory virus

<400> SEQUENCE: 176
atgacgtata ggtgttggct ctatgccttg gcatttgtat                         40

<210> SEQ ID NO 177
<211> LENGTH: 20
<212> TYPE: DNA
<213> ORGANISM: Artificial Sequence
<220> FEATURE:
<223> OTHER INFORMATION: Synthetic oligomer
```

```
<400> SEQUENCE: 177
ggtaggtaaa aacctaatat                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 178
aggttggttg gcttttcctg                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 179
gatagaaaat cttttttaagt                                             20

<210> SEQ ID NO 180
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 180
aaaagagcta actatccgta                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 181
actcacttta ctttaaaagt                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 182
gccacgctac actcacttta                                              20

<210> SEQ ID NO 183
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 183
cacgcaaatc gctcgcaatc                                              20

<210> SEQ ID NO 184
<211> LENGTH: 20
<212> TYPE: DNA
```

```
<213> ORGANISM: Artificial Sequence
<220> FEATURE:
<223> OTHER INFORMATION: Synthetic oligomer

<400> SEQUENCE: 184
tcagtgaagc gggatgcacg                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 185
gatagataag gtacttaagt                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 186
aagcaacttt tctatctgta                                               20

<210> SEQ ID NO 187
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 187
cggacgccaa tcactcttat a                                             21

<210> SEQ ID NO 188
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 188
gagttgagag ggtacgtacg ga                                            22

<210> SEQ ID NO 189
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 189
catagagcca acacctatac g                                             21

<210> SEQ ID NO 190
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 190
atacaaatgc caaggcatag                                               20
```

```
<210> SEQ ID NO 191
<211> LENGTH: 40
<212> TYPE: DNA
<213> ORGANISM: Human astrovirus

<400> SEQUENCE: 191
ccaagagggg ggtggtgatt ggcctttggc ttatcagtgt                              40

<210> SEQ ID NO 192
<211> LENGTH: 40
<212> TYPE: DNA
<213> ORGANISM: Equine arteritis virus

<400> SEQUENCE: 192
gctcgaagtg tgtatggtgc catatacggc tcaccaccat                              40

<210> SEQ ID NO 193
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 193
aatcaccacc ccctcttgg                                                     20

<210> SEQ ID NO 194
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 194
gccaaaggcc aatcaccacc                                                    20

<210> SEQ ID NO 195
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 195
gcaccataca cacttcgagc                                                    20

<210> SEQ ID NO 196
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 196
atggtggtga gccgtatatg                                                    20

<210> SEQ ID NO 197
<211> LENGTH: 33
<212> TYPE: DNA
<213> ORGANISM: HIV-1

<400> SEQUENCE: 197
gactatggaa aacagatggc aggtgatgat tgt                                     33

<210> SEQ ID NO 198
```

-continued

```
<211> LENGTH: 34
<212> TYPE: DNA
<213> ORGANISM: HIV-1

<400> SEQUENCE: 198
gaccagatct gagcctggga gctctctggc taac                                    34

<210> SEQ ID NO 199
<211> LENGTH: 20
<212> TYPE: DNA
<213> ORGANISM: HIV-1

<400> SEQUENCE: 199
cctgtactgg gtctctctgg                                                    20

<210> SEQ ID NO 200
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 200
cctgccatct gttttccata atc                                                23

<210> SEQ ID NO 201
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 201
cacctgccat ctgttttcca ta                                                 22

<210> SEQ ID NO 202
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 202
cctgccatct gttttccata atc                                                23

<210> SEQ ID NO 203
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 203
cacctgccat ctgttttcca ta                                                 22

<210> SEQ ID NO 204
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 204
gctcccaggc tcagatctgg tc                                                 22

<210> SEQ ID NO 205
```

```
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 205
gttagccaga gagctcccag gc                                              22

<210> SEQ ID NO 206
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 206
ccagagagac ccagtacagg                                                 20

<210> SEQ ID NO 207
<211> LENGTH: 24
<212> TYPE: RNA
<213> ORGANISM: Nidovirus

<400> SEQUENCE: 207
cuacuuuucu caacuaaacg aaau                                            24

<210> SEQ ID NO 208
<211> LENGTH: 24
<212> TYPE: RNA
<213> ORGANISM: Nidovirus

<400> SEQUENCE: 208 gaucuuuug uaaucuaaac uuua                                             24

<210> SEQ ID NO 209
<211> LENGTH: 24
<212> TYPE: RNA
<213> ORGANISM: Nidovirus

<400> SEQUENCE: 209
gaucuguucu cuaaacgaac uuua                                            24

<210> SEQ ID NO 210
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 210
atttcgttta gttgagaaaa g                                               21

<210> SEQ ID NO 211
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 211
gtttagttga gaaaagtag                                                  19

<210> SEQ ID NO 212
<211> LENGTH: 21
<212> TYPE: DNA
```

```
<213> ORGANISM: Artificial Sequence
<220> FEATURE:
<223> OTHER INFORMATION: Synthetic oligomer

<400> SEQUENCE: 212
taaagtttag attacaaaaa g                                              21

<210> SEQ ID NO 213
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 213
taaagttcgt ttagagaaca g                                              21

<210> SEQ ID NO 214
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 214
gttcgtttag agaacagatc                                                20

<210> SEQ ID NO 215
<211> LENGTH: 2717
<212> TYPE: DNA
<213> ORGANISM: Homo sapiens

<400> SEQUENCE: 215
aggagcctta ggaggtacgg ggagctcgca aatactcctt ttggtttatt cttaccacct    60
tgcttctgtg ttccttggga atgctgctgt gcttatgcat ctggtctctt tttggagcta   120
cagtggacag gcatttgtga cagcactatg ggactgagta acattctctt tgtgatggcc   180
ttcctgctct ctggtgctgc tcctctgaag attcaagctt atttcaatga gactgcagac   240
ctgccatgcc aatttgcaaa ctctcaaaac caaagcctga gtgagctagt agtattttgg   300
caggaccagg aaaacttggt tctgaatgag gtatacttag caaagagaa atttgacagt   360 gttcattcca gtatatgggc cgcacaagt ttttgattcgg acagttggac cctgagactt   420
cacaatcttc agatcaagga caagggcttg tatcaatgta tcatccatca caaaaagccc   480
acaggaatga ttcgcatcca ccagatgaat tctgaactgt cagtgcttgc taacttcagt   540
caacctgaaa tagtaccaat ttctaatata acagaaaatg tgtacataaa tttgacctgc   600
tcatctatac acgggttaccc agaacctaag aagatgagtg ttttgctaag aaccaagaat   660
tcaactatcg agtatgatgg tattatgcag aaatctcaag ataatgtcac agaactgtac   720
gacgtttcca tcagcttgtc tgtttcattc cctgatgtta cgagcaatat gaccatcttc   780
tgtattctgg aaactgacaa gacgcggctt ttatcttcac cttctctat agagcttgag   840 gaccctcagc ctccccccaga ccacattcct tggattacag ctgtacttcc aacagttatt   900
atatgtgtga tggttttctg tctaattcta tggaaatgga agaagaagaa gcggcctcgc   960
aactcttata aatgtggaac caacacaatg gagagggaag agagtgaaca gaccaagaaa  1020
agagaaaaaa tccatatacc tgaaagatct gatgaagccc agcgtgtttt taaagttcg  1080 aagacatctt catgcgacaa aagtgataca tgttttttaat taaagagtaa agcccataca  1140
agtattcatt ttttctaccc tttcctttgt aagttcctgg gcaaccttt tgatttcttc  1200
```

```
cagaaggcaa aaagacatta ccatgagtaa taagggggct ccaggactcc ctctaagtgg   1260
aatagcctcc ctgtaactcc agctctgctc cgtatgccaa gaggagactt taattctctt   1320
actgcttctt ttcacttcag agcacactta tgggccaagc ccagcttaat ggctcatgac   1380
ctggaaataa aatttaggac caatacctcc tccagatcag attcttctct taatttcata   1440
gattgtgttt ttttttaaat agacctctca atttctggaa aactgccttt tatctgccca   1500
gaattctaag ctggtgcccc actgaatctt gtgtacctgt gactaaacaa ctacctcctc   1560
agtctgggtg ggacttatgt atttatgacc ttatagtgtt aatatcttga aacatagaga   1620
tctatgtact gtaatagtgt gattactatg ctctagagaa aagtctaccc ctgctaagga   1680
gttctcatcc ctctgtcagg gtcagtaagg aaaacggtgg cctagggtac aggcaacaat   1740
gagcagacca acctaaattt ggggaaatta ggagaggcag agatagaacc tggagccact   1800
tctatctggg ctgttgctaa tattgaggag gcttgcccca cccaacaagc catagtggag   1860
agaactgaat aaacaggaaa atgccagagc ttgtgaaccc tgtttctctt gaagaactga   1920
ctagtgagat ggcctgggga agctgtgaaa gaaccaaaag agatcacaat actcaaaaga   1980
gagagagaga gaaaaaagag agatcttgat ccacagaaat acatgaaatg tctggtctgt   2040
ccaccccatc aacaagtctt gaaacaagca acagatggat agtctgtcca aatggacata   2100
agacagacag cagtttccct ggtggtcagg gaggggtttt ggtgataccc aagttattgg   2160
gatgtcatct tcctggaagc agagctgggg agggagagcc atcaccttga taatgggatg   2220
aatggaagga ggcttaggac tttccactcc tggctgagag aggaagagct gcaacggaat   2280
taggaagacc aagacacaga tcacccgggg cttacttagc ctacagatgt cctacgggaa   2340
cgtgggctgg cccagcatag ggctagcaaa tttgagttgg atgattgttt ttgctcaagg   2400
caaccagagg aaacttgcat acagagacag atatactggg agaaatgact ttgaaaacct   2460
ggctctaagg tgggatcact aagggatggg gcagtctctg cccaaacata aagagaactc   2520
tggggagcct gagccacaaa aatgttcctt tattttatgt aaaccctcaa gggttataga   2580
ctgccatgct agacaagctt gtccatgtaa tattcccatg ttttacccct gcccctgcct   2640
tgattagact cctagcacct ggctagtttc taacatgttt tgtgcagcac agttttaat   2700 aaatgcttgt tacattc                                                 2717

<210> SEQ ID NO 216
<211> LENGTH: 46
<212> TYPE: DNA
<213> ORGANISM: Homo sapiens

<400> SEQUENCE: 216
catttgtgac agcactatgg gactgagtaa cattctcttt gtgatg                  46

<210> SEQ ID NO 217
<211> LENGTH: 21
<212> TYPE: DNA
<213> ORGANISM: Homo sapiens

<400> SEQUENCE: 217
agcttgagga ccctcagcct c                                             21

<210> SEQ ID NO 218
<211> LENGTH: 23
<212> TYPE: DNA
<213> ORGANISM: Homo sapiens

<400> SEQUENCE: 218
```

```
gcctcgcaac tcttataaat gtg                                              23
```

<210> SEQ ID NO 219
<211> LENGTH: 22
<212> TYPE: DNA
<213> ORGANISM: Homo sapiens

<400> SEQUENCE: 219

```
gaaccaacac aatggagagg ga                                               22
```

<210> SEQ ID NO 220
<211> LENGTH: 21
<212> TYPE: DNA
<213> ORGANISM: Homo sapiens

<400> SEQUENCE: 220

```
gagtgaacag accaagaaaa g                                                21
```

<210> SEQ ID NO 221
<211> LENGTH: 50
<212> TYPE: RNA
<213> ORGANISM: Influenza A virus

<400> SEQUENCE: 221

```
agcgaaagca ggcaaaccau uugaauggau gucaauccga ccuuacuuuu                 50
```

<210> SEQ ID NO 222
<211> LENGTH: 25
<212> TYPE: DNA
<213> ORGANISM: Influenza A virus

<400> SEQUENCE: 222

```
agtgattatc taccctgctt ttgct                                            25
```

<210> SEQ ID NO 223
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 223

```
agcaaaagca gggtagataa tc                                               22
```

<210> SEQ ID NO 224
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 224

```
gacatccatt caaatggttt g                                                21
```

<210> SEQ ID NO 225
<211> LENGTH: 2823
<212> TYPE: DNA
<213> ORGANISM: Homo sapiens

<400> SEQUENCE: 225

```
agattcactg gtgtggcaag ttgtctctca gactgtacat gcattaaaat tttgcttggc      60
attactcaaa agcaaagaa  aagtaaaagg aagaaacaag aacaagaaaa aagattatat     120
tgattttaaa atcatgcaaa aactgcaact ctgtgtttat atttacctgt ttatgctgat    180
```

```
tgttgctggt ccagtggatc taaatgagaa cagtgagcaa aaagaaaatg tggaaaaaga    240
ggggctgtgt aatgcatgta cttggagaca aaacactaaa tcttcaagaa tagaagccat    300
taagatacaa atcctcagta aacttcgtct ggaaacagct cctaacatca gcaaagatgt    360
tataagacaa cttttacccc aagctcctcc actccgggaa ctgattgatc agtatgatgt    420
ccagagggat gacagcagcg atggctcttt ggaagatgac gattatcacg ctacaacgga    480
aacaatcatt accatgccta cagagtctga ttttctaatg caagtggatg aaaacccaa     540 atgttgcttc tttaaattta gctctaaaat acaatacaat aaagtagtaa aggcccaact    600
atggatatat ttgagacccg tcgagactcc tacaacagtg tttgtgcaaa tcctgagact    660
catcaaacct atgaaagacg gtacaaggta tactggaatc cgatctctga aacttgacat    720
gaacccaggc actggtattt ggcagagcat tgatgtgaag acagtgttgc aaaattggct    780
caaacaacct gaatccaact taggcattga aataaaagct ttagatgaga atggtcatga    840
tcttgctgta accttcccag gaccaggaga agatgggctg aatccgtttt tagaggtcaa    900
ggtaacagac acaccaaaaa gatccagaag ggattttggt cttgactgtg atgagcactc    960
aacagaatca cgatgctgtc gttaccctct aactgtggat tttgaagctt ttggatggga   1020
ttggattatc gctcctaaaa gatataaggc caattactgc tctggagagt gtgaatttgt   1080 attttacaa aaatatcctc atactcatct ggtacaccaa gcaaacccca gaggttcagc    1140
aggcccttgc tgtactccca caaagatgtc tccaattaat atgctatatt ttaatggcaa   1200
agaacaaata atatatggga aaattccagc gatggtagta daccgctgtg ggtgctcatg   1260
agatttatat taagcgttca taacttccta aaacatggaa ggttttcccc tcaacaattt   1320
tgaagctgtg aaattaagta ccacaggcta taggcctaga gtatgctaca gtcacttaag   1380
cataagctac agtatgtaaa ctaaaagggg gaatatatgc aatggttggc atttaaccat   1440
ccaaacaaat catacaagaa agttttatga tttccagagt ttttgagcta gaaggagatc   1500
aaattacatt tatgttccta tatattacaa catcggcgag gaaatgaaag cgattctcct   1560
tgagttctga tgaattaaag gagtatgctt taaagtctat ttctttaaag ttttgtttaa   1620
tatttacaga aaaatccaca tacagtattg gtaaaatgca ggattgttat ataccatcat   1680
tcgaatcatc cttaaacact tgaatttata ttgtatggta gtatacttgg taagataaaa   1740
ttccacaaaa ataqggatgg tgcagcatat gcaatttcca ttcctattat aattgacaca   1800
gtacattaac aatccatgcc aacggtgcta atacgatagg ctgaatgtct gaggctacca   1860
ggtttatcac ataaaaaaca ttcagtaaaa tagtaagttt ctcttttctt caggggcatt   1920
ttcctacacc tccaaatgag gaatggattt tctttaatgt aagaagaatc attttttctag  1980 aggttggctt tcaattctgt agcatacttg gagaaactgc attatcttaa aaggcagtca   2040
aatggtgttt gttttatca aaatgtcaaa ataacatact tggagaagta tgtaattttg    2100
tctttggaaa attacaacac tgcctttgca acactgcagt ttttatggta aaataataga   2160
aatgatcgac tctatcaata ttgtataaaa agactgaaac aatgcattta taatatatgt   2220
atacaatatt gttttgtaaa taagtgtctc ctttttttatt tactttggta tatttttaca   2280
ctaaggacat ttcaaattaa gtactaaggc acaaagacat gtcatgcatc acagaaaagc   2340
aactacttat atttcagagc aaattagcag attaaatagt ggtcttaaaa ctccatatgt   2400
taatgattag atggttatat tacaatcatt ttatatttt ttacatgatt aacattcact    2460 tatgggattca tgatggctgt ataaagtgaa tttgaaattt caatggttta ctgtcattgt  2520
gtttaaatct caacgttcca ttattttaat acttgcaaaa acattactaa gtataccaaa   2580
```

-continued

```
ataattgact ctattatctg aaatgaagaa taaactgatg ctatctcaac aataactgtt    2640 actttttattt tataatttga taatgaatat atttctgcat ttatttactt ctgttttgta    2700
aattgggatt ttgttaatca aatttattgt actatgacta aatgaaatta tttcttacat    2760
ctaatttgta gaaacagtat aagttatatt aaagtgtttt cacatttttt tgaaagacaa    2820
aaa                                                                  2823
```

<210> SEQ ID NO 226
<211> LENGTH: 50
<212> TYPE: DNA
<213> ORGANISM: Homo sapiens

<400> SEQUENCE: 226

```
acaatcatta ccatgcctac agagtgtaag tagtcctatt agtgtatatc                50
```

<210> SEQ ID NO 227
<211> LENGTH: 50
<212> TYPE: DNA
<213> ORGANISM: Homo sapiens

<400> SEQUENCE: 227

```
cttttctttt cttattcatt tatagctgat tttctaatgc aagtggatgg                50
```

<210> SEQ ID NO 228
<211> LENGTH: 50
<212> TYPE: DNA
<213> ORGANISM: Homo sapiens

<400> SEQUENCE: 228

```
cccaggacca ggagaagatg ggctggtaag tgataactga aaataacatt                50
```

<210> SEQ ID NO 229
<211> LENGTH: 50
<212> TYPE: DNA
<213> ORGANISM: Homo sapiens

<400> SEQUENCE: 229

```
tgattgttct ttccttttca aacagaatcc gttttttagag gtcaaggtaa                50
```

<210> SEQ ID NO 230
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 230

```
actctgtagg catggtaatg                                                 20
```

<210> SEQ ID NO 231
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 231

```
cagcccatct tctcctgg                                                   18
```

<210> SEQ ID NO 232
<211> LENGTH: 20
<212> TYPE: DNA
<213> ORGANISM: Artificial Sequence
<220> FEATURE:

<223> OTHER INFORMATION: Synthetic oligomer

<400> SEQUENCE: 232
cacttgcatt agaaaatcag                                           20

<210> SEQ ID NO 233
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 233
cttgacctct aaaaacggat t                                         21

<210> SEQ ID NO 234
<211> LENGTH: 32
<212> TYPE: DNA
<213> ORGANISM: Artificial Sequence
<220> FEATURE:
<223> OTHER INFORMATION: Synthetic oligomer

<400> SEQUENCE: 234
gttgggrttr gccgcattca ggggccggag ga                             32

<210> SEQ ID NO 235
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 235
ccgcattcag gggccggagg                                           20

<210> SEQ ID NO 236
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 236
ggattagccg cattcagggg cc                                        22

<210> SEQ ID NO 237
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 237
gttgggatta gccgcattca g                                         21

<210> SEQ ID NO 238
<211> LENGTH: 37
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)...(37)
<223> OTHER INFORMATION: n = A,T,C or G

<400> SEQUENCE: 238
aaaangaaac acggacaccc aaagtagtcg gttccgc                                37

<210> SEQ ID NO 239
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 239
cacccaaagt agtcggttcc                                                   20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 240
cacggacacc caaagtagtc                                                   20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 241
ggaaacacgg acacccaaag                                                   20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 242
aaaaggaaac acggacaccc                                                   20

<210> SEQ ID NO 243
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 243
atgaaacacg gacacccaaa g                                                 21

<210> SEQ ID NO 244
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 244
gaaacacgga cacccaaagt ag                                                22

<210> SEQ ID NO 245
<211> LENGTH: 24
<212> TYPE: DNA
<213> ORGANISM: Artificial Sequence
<220> FEATURE:

<223> OTHER INFORMATION: Synthetic oligomer

<400> SEQUENCE: 245
gagaaacacg gacacccaaa gtag                                          24

<210> SEQ ID NO 246
<211> LENGTH: 100
<212> TYPE: DNA
<213> ORGANISM: Homo sapiens

<400> SEQUENCE: 246
gcatgagttc actgagttcc ctttggcttt tccatgctag caatgcacgt ggcccagcct   60
gctgtggtac tggccagcag ccgaggcatc gccagctttg                        100

<210> SEQ ID NO 247
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 247
gagggcggca tgggggaggc                                               20

<210> SEQ ID NO 248
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 248
gacccatggc agcccccgtc g                                             21

<210> SEQ ID NO 249
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 249
gcagcagttc ttctccgtgg                                               20

<210> SEQ ID NO 250
<211> LENGTH: 125
<212> TYPE: RNA
<213> ORGANISM: Ebola virus

<400> SEQUENCE: 250
aaugaugaag auuaaaaccu ucaucauccu uacgucaauu gaauucucua gcacucgaag   60
cuuauugucu ucaauguaaa agaaaagcug gucuaacaag augacaacua gaacaaaggg  120
caggg                                                              125

<210> SEQ ID NO 251
<211> LENGTH: 125
<212> TYPE: RNA
<213> ORGANISM: Ebola virus

<400> SEQUENCE: 251
cguuccaaca aucgagcgca agguuucaag guugaacuga gagugucuag acaacaaaau   60
auugauacuc cagacaccaa gcaagaccug agaaaaaacc auggcuaaag cuacgggacg  120

```
                                  -continued
auaca                                                                125

<210> SEQ ID NO 252
<211> LENGTH: 124
<212> TYPE: RNA
<213> ORGANISM: Ebola virus

<400> SEQUENCE: 252
guagauuaag aaaaaagccu gaggaagauu aagaaaaacu gcuuauuggg ucuuuccgug     60
uuuuagauga agcaguugaa auucuuccuc uugauauuaa auggcuacac aacauaccca    120
auac                                                                124

<210> SEQ ID NO 253
<211> LENGTH: 125
<212> TYPE: RNA
<213> ORGANISM: Marburg virus

<400> SEQUENCE: 253
cuaaaaaucg aagaauauua aagguuuucu uuaauauuca gaaagguuuu uuauucucu      60 ucuuucuuuu ugcaaacaua uugaaauaau aauuuucaca auguggacu caucauauau    120 gcaac                                                               125

<210> SEQ ID NO 254
<211> LENGTH: 125
<212> TYPE: RNA
<213> ORGANISM: Marburg virus

<400> SEQUENCE: 254
uucauucaaa caccccaaau uuucaaucau acacauaaua accauuuuag uagcguuacc     60
uuucaauaca aucuagguga uugugaaaag acuuccaaac auggcagaau uaucaacgcg    120
uuaca                                                               125

<210> SEQ ID NO 255
<211> LENGTH: 125
<212> TYPE: RNA
<213> ORGANISM: Marburg virus

<400> SEQUENCE: 255
ucauucucuu cgauacacgu uauaucuuua gcaaaguaau gaaaauagcc uugucauguu     60
agacgccagu uaccaucuu aagugaaucc uuucuucaau augcagcauc caacucaaua    120
uccug                                                               125

<210> SEQ ID NO 256
<211> LENGTH: 21
<212> TYPE: DNA
<213> ORGANISM: Artificial Sequence
<220> FEATURE:
<223> OTHER INFORMATION: Synthetic oligomer

<400> SEQUENCE: 256
gtcccacatt gtgaaaatta t                                              21

<210> SEQ ID NO 257
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 257
```
cttgttgcat atatgatgag tc                                       22

<210> SEQ ID NO 258
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 258
gttgtaacgc gttgataatt ctg                                      23

<210> SEQ ID NO 259
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 259
gctgcatatt gaagaaagg                                           19

<210> SEQ ID NO 260
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 260
catcaggata ttgagttgga tg                                       22

<210> SEQ ID NO 261
<211> LENGTH: 19
<212> TYPE: DNA
<213> ORGANISM: Arenavirus

<400> SEQUENCE: 261
cgcacmgdgg atcctaggc                                           19

<210> SEQ ID NO 262
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 262
cgcctaggat ccccggtgcg                                          20

<210> SEQ ID NO 263
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 263
cgcctaggat ccccggtgcg c                                        21

<210> SEQ ID NO 264
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 264
gcctaggatc cactgtgcgc 20

<210> SEQ ID NO 265
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: modified_base
<222> LOCATION: (12), (14)
<223> OTHER INFORMATION: n = Inosine

<400> SEQUENCE: 265
gcctaggatc cncngtgcg 19

<210> SEQ ID NO 266
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: modified_base
<222> LOCATION: (13), (15)
<223> OTHER INFORMATION: n = Inosine

<400> SEQUENCE: 266
cgcctaggat ccncngtgcg 20

<210> SEQ ID NO 267
<211> LENGTH: 20
<212> TYPE: RNA
<213> ORGANISM: Flavivirus

<400> SEQUENCE: 267
gucaauaugc uaaaacgcgg 20

<210> SEQ ID NO 268
<211> LENGTH: 20
<212> TYPE: RNA
<213> ORGANISM: Flavivirus

<400> SEQUENCE: 268
aucaauaugc ugaaacgcgg 20

<210> SEQ ID NO 269
<211> LENGTH: 20
<212> TYPE: RNA
<213> ORGANISM: Flavivirus

<400> SEQUENCE: 269
gucaauaugg uacgacgagg 20

<210> SEQ ID NO 270
<211> LENGTH: 21
<212> TYPE: RNA
<213> ORGANISM: Flavivirus

<400> SEQUENCE: 270
cuuucaauau gcugaaacgc g 21

<210> SEQ ID NO 271
<211> LENGTH: 21
<212> TYPE: RNA

```
<213> ORGANISM: Flavivirus

<400> SEQUENCE: 271
cuaucaauau gcugaaacgc g                                                 21

<210> SEQ ID NO 272
<211> LENGTH: 22
<212> TYPE: RNA
<213> ORGANISM: Flavivirus

<400> SEQUENCE: 272
cagcuuagga gaacaagagc ug                                                22

<210> SEQ ID NO 273
<211> LENGTH: 20
<212> TYPE: RNA
<213> ORGANISM: Flavivirus

<400> SEQUENCE: 273
ggcugucaau augcuaaaac                                                   20

<210> SEQ ID NO 274
<211> LENGTH: 22
<212> TYPE: RNA
<213> ORGANISM: Flavivirus

<400> SEQUENCE: 274
aacagcauau ugacaccugg ga                                                22

<210> SEQ ID NO 275
<211> LENGTH: 23
<212> TYPE: RNA
<213> ORGANISM: Flavivirus

<400> SEQUENCE: 275
ugggaccaua uugacgccag gga                                               23

<210> SEQ ID NO 276
<211> LENGTH: 22
<212> TYPE: RNA
<213> ORGANISM: Flavivirus

<400> SEQUENCE: 276
aaacagcaua uugacgcugg ga                                                22

<210> SEQ ID NO 277
<211> LENGTH: 22
<212> TYPE: RNA
<213> ORGANISM: Flavivirus

<400> SEQUENCE: 277
cgguucuugu ucucccugag cc                                                22

<210> SEQ ID NO 278
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(12)
<223> OTHER INFORMATION: Xaa = 6-amino hexanoic acid
<220> FEATURE:
<221> NAME/KEY: MISC_FEATURE
<222> LOCATION: (13)
```

<223> OTHER INFORMATION: Xaa = beta-alanine

<400> SEQUENCE: 278

Arg Arg Xaa Arg Arg Xaa Arg Xaa Arg Arg Xaa Xaa
1               5                   10

<210> SEQ ID NO 279
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(13)
<223> OTHER INFORMATION: Xaa = 6-amino hexanoic acid
<220> FEATURE:
<221> NAME/KEY: MISC_FEATURE
<222> LOCATION: (14)
<223> OTHER INFORMATION: Xaa = beta-alanine

<400> SEQUENCE: 279

Arg Xaa Arg Arg Xaa Arg Arg Xaa Arg Xaa Arg Xaa Xaa
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(13)
<223> OTHER INFORMATION: Xaa = 6-amino hexanoic acid
<220> FEATURE:
<221> NAME/KEY: MISC_FEATURE
<222> LOCATION: (14)
<223> OTHER INFORMATION: Xaa = beta-alanine

<400> SEQUENCE: 280

Xaa Arg Arg Xaa Arg Arg Xaa Arg Arg Xaa Arg Xaa Xaa
1               5                   10

<210> SEQ ID NO 281
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(12)
<223> OTHER INFORMATION: Xaa = 6-amino hexanoic acid
<220> FEATURE:
<221> NAME/KEY: MISC_FEATURE
<222> LOCATION: (13)
<223> OTHER INFORMATION: Xaa = beta-alanine

<400> SEQUENCE: 281

Arg Xaa Arg Xaa Arg Xaa Arg Xaa Arg Xaa Arg Xaa Xaa
1               5                   10

<210> SEQ ID NO 282
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(14)

```
<223> OTHER INFORMATION: Xaa = 6-amino hexanoic acid
<220> FEATURE:
<221> NAME/KEY: MISC_FEATURE
<222> LOCATION: (15)
<223> OTHER INFORMATION: Xaa = beta-alanine

<400> SEQUENCE: 282

Arg Xaa Arg Xaa Arg Xaa Arg Xaa Arg Xaa Arg Xaa Arg Xaa Xaa
1               5                   10                  15

<210> SEQ ID NO 283
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)...(10)
<223> OTHER INFORMATION: Xaa = 6-amino hexanoic acid
<220> FEATURE:
<221> NAME/KEY: MISC_FEATURE
<222> LOCATION: (11)
<223> OTHER INFORMATION: Xaa = beta-alanine

<400> SEQUENCE: 283

Arg Xaa Arg Arg Xaa Arg Arg Xaa Arg Xaa Xaa
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2), (8), (13)
<223> OTHER INFORMATION: Xaa = 6-amino hexanoic acid
<220> FEATURE:
<221> NAME/KEY: MISC_FEATURE
<222> LOCATION: (5), (11), (14)
<223> OTHER INFORMATION: Xaa = beta-alanine

<400> SEQUENCE: 284

Arg Xaa Arg Arg Xaa Arg Arg Xaa Arg Arg Xaa Arg Xaa Xaa
1               5                   10

<210> SEQ ID NO 285
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8), (16)
<223> OTHER INFORMATION: Xaa = 6-amino hexanoic acid
<220> FEATURE:
<221> NAME/KEY: MISC_FEATURE
<222> LOCATION: (2), (4), (6), (10), (12), (14), (17)
<223> OTHER INFORMATION: Xaa = beta-alanine

<400> SEQUENCE: 285

Arg Xaa Arg Xaa Arg Xaa Arg Xaa Arg Xaa Arg Xaa Arg Xaa Arg Xaa
1               5                   10                  15

Xaa

<210> SEQ ID NO 286
<211> LENGTH: 18
<212> TYPE: DNA
```

```
<213> ORGANISM: Artificial Sequence
<220> FEATURE:
<223> OTHER INFORMATION: Synthetic Oligomer

<400> SEQUENCE: 286
cctcttacct cagttaca                                              18

<210> SEQ ID NO 287
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 287
tgggtatgtt gtgtagccat                                            20

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 288
cctgcccttt gttctagttg                                            20

<210> SEQ ID NO 289
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 289
gccatggttt tttctcagg                                             19

<210> SEQ ID NO 290
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 290
gtctgggatg agagccatca c                                          21

<210> SEQ ID NO 291
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 291
ctgggatgag agccatcac                                             19

<210> SEQ ID NO 292
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 292
ctgggatgag agccatcact                                            20
```

The invention claimed is:

1. An oligomer comprising a sequence of morpholino subunits, each morpholino subunit comprising a base-pairing moiety, such that the oligomer can bind in a sequence-specific manner to a target nucleic acid, wherein the morpholino subunits are each joined by a phosphorus-containing intersubunit linkage having the structure:

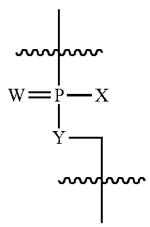

wherein:
W is S or O;
X is $NR^1R^2$ or $OR^6$;
Y is O or $NR^7$;
and the intersubunit linkage is, at each occurrence, independently:
linkage (a), where each of $R^1$, $R^2$, $R^6$ and $R^7$ is independently hydrogen or lower alkyl; or
linkage (b1), where X is $NR^1R^2$, Y is O and $NR^1R^2$ is a piperazino group, such that $R^1R^2$ is —CHRCHRN($R^3$)($R^4$)CHRCHR—, wherein:
each R is, at each occurrence, independently H or $CH_3$;
$R^4$ is H, $CH_3$ or an electron pair; and
$R^3$ is H, lower alkyl, —C(=NH)$NH_2$, —Z-L-NHC(=NH)$NH_2$ or —[C(O)CHR'NH]$_m$H, where Z is carbonyl (C(O)) or a direct bond, L is an optional linker up to 18 atoms in length comprising alkyl, alkoxy or alkylamino groups, or combinations thereof, R' is a side chain of a naturally occurring amino acid or a one- or two-carbon homolog thereof, and m is 1 to 6;
and at least one intersubunit linkage is linkage (b1).

2. The oligomer of claim 1, wherein each of the morpholino subunits have the structure (i):

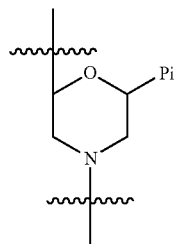

where each Pi is, at each occurrence, independently a base-pairing moiety, and the intersubunit linkage connects the nitrogen atom of (i) to the 5' carbon of an adjacent morpholino subunit.

3. The oligomer of claim 1, wherein each linkage (b1) in the oligomer has the same W, X and Y groups.

4. The oligomer of claim 1, wherein 5% to 50% of the intersubunit linkages in the oligomer are linkage (b1).

5. The oligomer of claim 4, wherein 10% to 35% of the intersubunit linkages in the oligomer are linkage (b1).

6. The oligomer of claim 1, wherein for each occurrence of linkage (a), X is $NR^1R^2$, and each of $R^1$ and $R^2$ is methyl.

7. The oligomer of claim 1, wherein the oligomer comprises at least two consecutive intersubunit linkages of linkage (a).

8. The oligomer of claim 1 having a length of 10 to 40 subunits.

9. The oligomer of claim 1 having a length of 15 to 25 subunits.

10. The oligomer of claim 1, wherein each R is H, $R^4$ is H, $CH_3$ or an electron pair, and $R^3$ is H, $CH_3$, —C(=NH)$NH_2$ or —C(O)-L-NHC(=NH)$NH_2$.

11. The oligomer of claim 1, wherein each R is H, $R^3$ is H or $CH_3$ and $R^4$ is an electron pair, H or $CH_3$.

12. The oligomer of claim 11, wherein each of $R^3$ and $R^4$ is H, and linkage (b1) has the following structure (iv):

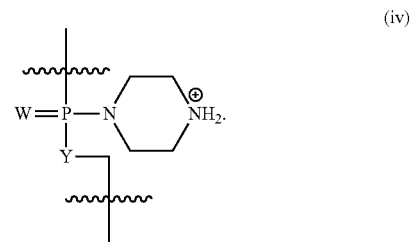

13. The oligomer of claim 1, wherein each of W and Y are O.

14. The oligomer of claim 11, wherein $R^3$ is H, $R^4$ is an electron pair and linkage (b1) has the following structure (v):

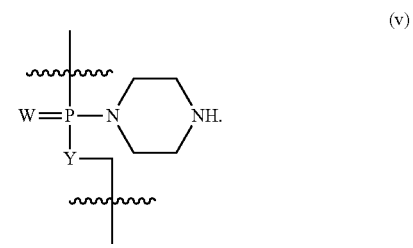

15. The oligomer of claim 14, wherein each of W and Y are O.

16. The oligomer of claim 1, wherein Z is a direct bond and L has the structure —(CH$_2$)$_n$— where n is 1-12.

* * * * *